(12) United States Patent
Roy et al.

(10) Patent No.: US 10,934,359 B2
(45) Date of Patent: Mar. 2, 2021

(54) ANTI-BMPR1B ANTIBODIES AND METHODS OF USE

(71) Applicant: ABBVIE STEMCENTRX LLC, North Chicago, IL (US)

(72) Inventors: Somdutta Roy, San Bruno, CA (US); Laura Saunders, San Francisco, CA (US); Casey Franklin, Pacifica, CA (US); Kevin Martinez, Davis, CA (US); Sarah Fong, Oakland, CA (US); Zhao Huang, Burlingame, CA (US); Silvia Juarez, Millbrae, CA (US); Alina He, San Francisco, CA (US); Kathryn A. Loving, Berkeley, CA (US); Sandro Vivona, Emerald Hills, CA (US)

(73) Assignee: AbbVie Stemcentrx LLC, North Chicago, IL (US)

( * ) Notice: Subject to any disclaimer, the term of this patent is extended or adjusted under 35 U.S.C. 154(b) by 223 days.

(21) Appl. No.: 16/095,057

(22) PCT Filed: Apr. 21, 2017

(86) PCT No.: PCT/US2017/028772
§ 371 (c)(1),
(2) Date: Oct. 19, 2018

(87) PCT Pub. No.: WO2017/184942
PCT Pub. Date: Oct. 26, 2017

(65) Prior Publication Data
US 2019/0153103 A1 May 23, 2019

Related U.S. Application Data

(60) Provisional application No. 62/486,140, filed on Apr. 17, 2017, provisional application No. 62/443,404, (Continued)

(51) Int. Cl.
*C07K 16/28* (2006.01)
*C07K 16/32* (2006.01)
(Continued)

(52) U.S. Cl.
CPC ........ *C07K 16/2863* (2013.01); *A61K 39/395* (2013.01); *A61K 47/6803* (2017.08);
(Continued)

(58) Field of Classification Search
None
See application file for complete search history.

(56) References Cited

U.S. PATENT DOCUMENTS

| 5,122,368 A | 6/1992 | Greenfield et al. |
| 5,622,929 A | 4/1997 | Willner et al. |

(Continued)

FOREIGN PATENT DOCUMENTS

| WO | WO 1997/034631 | 9/1997 |
| WO | WO 2000/042072 | 7/2000 |

(Continued)

OTHER PUBLICATIONS

Accession No. NM_001203.3, "*Homo sapiens* bone morphogenetic protein receptor type 1B (BMPR1B), transcript variant 2, mRNA".
(Continued)

*Primary Examiner* — Karl J Puttlitz
(74) *Attorney, Agent, or Firm* — Womble Bond Dickinson (US) LLP

(57) ABSTRACT

Provided are novel anti-BMPR1B antibodies and antibody drug conjugates, and methods of using such anti-BMPR1B antibodies and antibody drug conjugates to treat cancer.

9 Claims, 49 Drawing Sheets

Specification includes a Sequence Listing.

Schematic Diagram of hBMPR1B

1 TM: Single pass trans membrane domain
ECD: Extracellular domain
N': N terminus
C': C terminus
GS: GS domain (glycine and serine rich sequence)
TK: Tyrosine kinase domain

Related U.S. Application Data filed on Jan. 6, 2017, provisional application No. 62/325,981, filed on Apr. 21, 2016.

(51) Int. Cl.

| | | |
|---|---|---|
| *A61K 47/68* | (2017.01) | |
| *A61K 39/395* | (2006.01) | |
| *A61P 35/00* | (2006.01) | |
| *A61K 45/06* | (2006.01) | |

(52) U.S. Cl.
CPC ...... *A61K 47/6849* (2017.08); *A61K 47/6855* (2017.08); *A61K 47/6869* (2017.08); *A61P 35/00* (2018.01); *C07K 16/32* (2013.01); *A61K 45/06* (2013.01); *C07K 2317/33* (2013.01); *C07K 2317/77* (2013.01); *C07K 2317/92* (2013.01)

(56) References Cited

U.S. PATENT DOCUMENTS

| | | | |
|---|---|---|---|
| 5,714,350 | A | 2/1998 | Co et al. |
| 5,824,805 | A | 10/1998 | King et al. |
| 6,214,345 | B1 | 4/2001 | Firestone et al. |
| 6,350,861 | B1 | 2/2002 | Co et al. |
| 6,362,331 | B1 | 3/2002 | Kamal et al. |
| 6,737,056 | B1 | 5/2004 | Presta |
| 7,049,311 | B1 | 5/2006 | Thurston et al. |
| 7,189,710 | B2 | 3/2007 | Kamal et al. |
| 7,407,951 | B2 | 8/2008 | Thurston et al. |
| 7,422,739 | B2 | 9/2008 | Anderson et al. |
| 7,429,658 | B2 | 9/2008 | Howard et al. |
| 7,521,541 | B2 | 4/2009 | Eigenbrot et al. |
| 7,557,099 | B2 | 7/2009 | Howard et al. |
| 7,619,068 | B2 | 11/2009 | Pilkington et al. |
| 7,632,678 | B2 | 12/2009 | Hansford et al. |
| 7,741,319 | B2 | 6/2010 | Howard et al. |
| 8,034,808 | B2 | 10/2011 | Delavault et al. |
| 8,163,736 | B2 | 4/2012 | Gauzy et al. |
| 8,426,402 | B2 | 4/2013 | Li et al. |
| 2003/0190311 | A1 | 10/2003 | Dall'acqua et al. |
| 2007/0292414 | A1 | 12/2007 | Duntsch et al. |
| 2007/0292424 | A1 | 12/2007 | Akerblom |
| 2008/0138313 | A1 | 6/2008 | Frankel |
| 2008/0175870 | A1 | 7/2008 | Mather et al. |
| 2010/0111932 | A1 | 5/2010 | Skerry et al. |
| 2010/0162416 | A1 | 6/2010 | Krtolica et al. |
| 2010/0184119 | A1 | 7/2010 | Bright et al. |
| 2010/0273160 | A1 | 10/2010 | Donahoe et al. |
| 2010/0275280 | A1 | 10/2010 | Clevers et al. |
| 2011/0020221 | A1 | 1/2011 | Berman et al. |
| 2011/0145937 | A1 | 6/2011 | MacDonald et al. |
| 2011/0182904 | A1 | 7/2011 | Zimmerman et al. |
| 2011/0256157 | A1 | 10/2011 | Howard et al. |
| 2013/0061340 | A1 | 3/2013 | Dylla et al. |
| 2013/0061342 | A1 | 3/2013 | Dylla et al. |
| 2013/0260385 | A1 | 10/2013 | Dylla et al. |
| 2015/0030636 | A1 | 1/2015 | Dylla et al. |

FOREIGN PATENT DOCUMENTS

| | | |
|---|---|---|
| WO | WO 2004/029207 | 4/2004 |
| WO | WO 2011/128650 | 10/2011 |
| WO | WO 2011/130613 | 10/2011 |
| WO | WO 2011/130616 | 10/2011 |
| WO | WO 2012/012801 | 1/2012 |
| WO | WO 2012/031280 | 3/2012 |
| WO | WO 2012/117002 | 9/2012 |
| WO | WO 2012/128868 | 9/2012 |
| WO | WO 2013/119964 | 8/2013 |
| WO | WO 2014/031566 | 2/2014 |
| WO | WO 2014/057073 | 4/2014 |
| WO | WO 2014/057074 | 4/2014 |
| WO | WO 2014/130879 | 8/2014 |
| WO | WO 2015/031698 | 3/2015 |
| WO | WO 2015/127407 | 8/2015 |
| WO | WO 2016/064749 | 4/2016 |

OTHER PUBLICATIONS

Accession No. NM_001256792.1, "*Homo sapiens* bone morphogenetic protein receptor type 1B (BMPR1B), transcript variant 3, mRNA".

Accession No. NM_001256793.2, "*Homo sapiens* bone morphogenetic protein receptor type 1B (BMPR1B), transcript variant 1, mRNA)".

Accession No. NM_001256794.1, "*Homo sapiens* bone morphogenetic protein receptor type 1B (BMPR1B), transcript variant 4, mRNA".

Accession No. NP_001194.1, "bone morphogenetic protein receptor type-1B isoform b precurs".

Accession No. NP_031586.1, "bone morphogenetic protein receptor type-1B isoform a precursor [Mus musculus]".

Accession No. NP_001019430.1, "bone morphogenetic protein receptor type-1B [Rattus norvegicus]".

Accession No. NP_001243722.1, "bone morphogenetic protein receptor type-1B isoform a precursor [*Homo sapiens*]".

Accession No. NP_001253192.1, "bone morphogenetic protein receptor type-1B [Macaca mulatta]".

Accession No. XM_006233398.1, "PREDICTED: Rattus norvegicus bone morphogenetic protein receptor, type IB (Bmpr1b), transcript variant X2, mRNA".

Accession No. XP_005555526.1, "PREDICTED: bone morphogenetic protein receptor type-1B isoform X2 [Macaca fascicularis]".

Abir et al., "Expression of bone morphogenetic proteins 4 and 7 and their receptors IA, IB, and II in human ovaries from fetuses and adults," Fertility and Sterility, May 2008, 89(Supp 3):1430-1440, PMID:17624341.

Banerji et al., "Sequence analysis of mutations and translocations across breast cancer subtypes," Nature, 2012, 486(7403):405-409, PMID:22722202.

Capel et al., "Heterogeneity of Human IgG Fc Receptors," Immunomethods, 1994, 4:25-34.

Cejalvo et al., "Bone morphogenetic protein-2/4 signalling pathway components are expressed in the human thymus and inhibit early T-cell developoment," Immunology, 2007, 121:94-104, PMID:17425602.

Chapellier et al., "Disequilibrium of BMP2 Levels in the Breast Stem Cell Niche Launches Epithelial Transformation by Overamplifying BMPR IB Cell Response," Stem Cell Reports, Feb. 10, 2015, 4:239-254.

Curtis et al., "The genomic and transcriptomic architecture of 2,000 breast tumours reveals novel subgroups," Nature, 2012, 486(7403):346-352, PMID:22522925.

De Haas et al., "Fc gamma receptors of phagocytes," Oct. 1995, J Lab Clin Med, 126(4):330-341, PMID:7561440.

Dylla et al., "Colorectal Cancer Stem Cells Are Enriched in Xenogeneic Tumors Following Chemotherapy," PLoS One, Jun. 2008, 3(6):e2428 (13 pp), PMC2413402.

Fazekas et al., "The Evaluation of Limiting Dilution Assays," J Immunol Methods, 1982, 49:R11-R23, PMID:7040548.

Fuhrmann et al., "Abstract 5625: In vitro and in vivo pharmacology of MEDI-565 (MT111), a novel CEA/CD3-bispecific single-chain BiTE antibody in development for the treatment of gastrointestinal adenocarcinomas," Cancer Research, Apr. 15, 2010, 70(8)(Supp 1):1-2, AACR 101st Annual Meeting 2010.

Haÿ et al., "Bone Morphogenetic Protein Receptor IB Signaling Mediates Apoptosis Independently of Differentiation in Osteoblastic Cells," J Biol Chem, 2004, 279(3):1650-1658, PMID:14576167.

Hoey et al., "DLL4 Blockade Inhibits Tumor Growth and Reduces Tumor-Initiating Cell Frequency," Cell Stem Cell, Aug. 7, 2009, 5:168-177, PMID:19664991.

Hurley et al., "Covalent Binding of Antitumor Antibiotics in the Minor Groove of DNA. Mechanism of Action of CC-1065 and the Pyrrolo(1,4)benzodiazepines," Acc. Chem. Res., 1986, 19(8):230-237.

(56) References Cited

OTHER PUBLICATIONS

Johnson et al., "Anti-Tumor Activity of CC49-Doxorubicin Immunoconjugates," Anticancer Res., 1995, 15(4):1387-1394, PMID:7654026.

Kjaer et al., "A mutation in the receptor binding site of GDF5 cuases Mohr-Wriedt brachydactyly type A2," J Med Genet, 2006, 43:225-231, PMID:16014698.

Kohn, "Anthramycin," Antibiotics III, Springer-Verlag, New York, 1975, pp. 3-11.

Laperrousaz et al., "Primitive CML cell expansion relies on abnormal levels of BMPs provided by the niche and on BMPRIb overexpression," Blood, Nov. 18, 2013, 122(23):3767-3777, PMID:24100446.

Lau et al., "Conjugation of Doxorubicin to Monoclonal Anti-carcinoembryonic Antigen Antibody via Novel Thiol-directed Cross-linked Reagents," Bioorg Med Chem, 1995, 3(10):1299-1304, PMID:8564395.

Lau et al., "Novel Doxorubicin-Monoclonal Anti-carcinoembryonic Antigen Antibody Immunoconjugate Activity in vitro," Bioorg Med Chem, 1995, 3(10):1305-1312, PMID:8564396.

Lee et al., "Epigenetic-Mediated Dysfunction of the Bone Morphogenetic Protein Pathway Inhibits Differentiation of Glioblastoma-Initiating Cells," Cancer Cell, Jan. 2008, 13:69-80.

Lim et al., "Aberrant luminal progenitors as the candidate target population for basal tumor development in BRCA1 mutation carriers," Nature Medicine, 2009, 15:907-913, PMID:19648928.

Macke et al., "Bone Morphogenetic Protein Receptor, Type IB; BMPR1B," 1998, 10 pp, http://omim.org/entry/603248.

Miller et al., "Epitope binning of murine monoclonal antibodies by a multiplexed pairing assay," J Immunol Methods, 2011, 365:118-125, PMID:21223970.

Ravetch et al., "Fc Receptors," Annu Rev Immunol, 1991, 9:457-492.

Schulenburg et al., "Neoplastic stem cells: Current concepts and clinical perspectives," Clinical Reviews in Oncology/Hematology, 2010, 76:79-98, PMID:20185329.

Shields et al., "High Resolution Mapping of the Binding Site on Human IgG1 for FcγRI, FcγRII, FcγRIII, and FcRn and Design of IgG1 Variants with Improved Binding to the FcγR," J Biol Chem, 2001, 276(9):6591-6604.

Shields et al., "Lack of Fucose on Human IgG1 N-Linked Oligosaccharide Improves Binding to H uman FcγRIII and Antibody-dependent Cellular Toxicity," J Biol Chem, 2002, 277(30):26733-26740.

Visvader et al., "Cancer stem cells in solid tumours: accumulating evidence and unresolved questions," Nature Reviews Cancer, Oct. 2008, 8:755-768, PMID:18784658.

International Search Report and Written Opinion dated Sep. 22, 2017 in International Application No. PCT/US2017/028772.

Human BMPR1B Amino Acid Sequence

```
  1  MLLRSAGKLN  VGTKKEDGES  TAPTPRPKVL  RCKCHHHCPE  DSVNNICSTD
 51  GYCFTMIEED  DSGLPVVTSG  CLGLEGSDFQ  CRDTPIPHQR  RSIECCTERN
101  ECNKDLHPTL  PPLKNRDFVD  GPIHHRALLI  SVTVCSLLLV  LILFCYFRY
151  KRQETRPRYS  IGLEQDETYI  PPGESLRDLI  EQSQSSGSGS  GLPLLVQRTI
201  AKQIQMVKQI  GKGRYGEVWM  GKWRGEKVAV  KVFFTTEEAS  WFRETEIYQT
251  VLMRHENILG  FIAADIKGTG  SWTQLYLITD  YHENGSLYDY  LKSTTLDAKS
301  MLKLAYSSVS  GLCHLHTEIF  STQGKPAIAH  RDLKSKNILV  KKNGTCCIAD
351  LGLAVKFISD  TNEVDIPPNT  RVGTKRYMPP  EVLDESLNRN  HFQSYIMADM
401  YSFGLIIWEV  ARRCVSGGIV  EEYQLPYHDL  VPSDPSYEDM  REIVCIKKLR
451  PSFPNRWSSD  ECLRQMGKLM  TECWAHNPAS  RLTALRVKKT  LAKMSESQDI
501  KL          SEQ ID NO. 1
```

FIG. 1A

Anti-BMPR1B Antibody Characteristic (Screen 1)

| Clone | Biacore | | | In vitro killing | | Luminex Binning | Flow cytometry | |
|---|---|---|---|---|---|---|---|---|
| | Cyno-his KD (nM) | human-his KD (nM) | rat-his KD (nM) | Human % Live cells 100pM | Rat % Live cells 100pM | | HU | RAT |
| SC91.1 | 5.1 | 2.34 | 3.34 | 9.53 | 15.59 | A | 5521 | 5080 |
| SC91.2 | 18.3 | 1.71 | + | 63.42 | 79.48 | B | 1010 | 864 |
| SC91.3 | 0.503 | 0.163 | ++ | 9.34 | 16.04 | A | 6845 | 5837 |
| SC91.4 | + | + | + | 71.45 | 87.77 | B | 213 | 135 |
| SC91.5 | 7.51 | 3.77 | + | 114.94 | 112.24 | B | 470 | 280 |
| SC91.6 | 21.5 | 0.387 | + | 16.24 | 94.79 | C | 7042 | 2655 |
| SC91.7 | 1.72 | 0.614 | +++ | 11.04 | 18.12 | A | 5483 | 4762 |
| SC91.9 | 0.153 | 0.322 | 0.181 | 9.44 | 14.69 | E | 5484 | 5270 |
| SC91.10 | + | 4.07 | + | 15.77 | 85.4 | C | 7260 | 2687 |
| SC91.11 | 11.1 | 1.15 | + | 15.5 | 68.68 | C | 7328 | 4659 |
| SC91.12 | 1.06 | 0.571 | + | 77.73 | 99.28 | D | 2426 | 1683 |
| SC91.13 | + | + | + | 67.99 | 90.4 | B | 204 | 178 |
| SC91.14 | 6.18 | 3.41 | ++ | 19.43 | 33.3 | E | 7619 | 6581 |
| SC91.15 | 0.947 | 0.922 | 1.5 | 11.94 | 18.52 | A | 5607 | 4586 |
| SC91.16 | 19.8 | 15.9 | + | 51.45 | 79.18 | B | 312 | 222 |
| SC91.17 | 22.7 | 16.5 | + | 66.17 | 82.31 | E | 5238 | 4943 |
| SC91.19 | + | 8.46 | 2.14 | 14.28 | 101.71 | C | 7251 | 470 |
| SC91.20 | 2.3 | 0.934 | 1.91 | 10.4 | 18.2 | A | 7483 | 5945 |
| SC91.21 | 10.8 | 5.77 | + | 62.83 | 72.12 | B | 1154 | 1048 |
| SC91.22 | 6 | 13.9 | 12.1 | 113.05 | 111.23 | D | 331 | 264 |
| SC91.23 | + | + | + | 62.11 | 76.11 | B | 266 | 211 |
| SC91.24 | 21.3 | 8.4 | + | 21.9 | 41.38 | A | 4882 | 4069 |
| SC91.25 | 5.36 | + | + | 111.93 | 107.37 | B | 1570 | 1042 |
| SC91.26 | 1.23 | 0.714 | + | 14.36 | 24.6 | A | 6372 | 5506 |
| SC91.27 | 2.56 | 1.98 | + | 11.91 | 17.9 | A | 6878 | 5968 |
| SC91.28 | 3.33 | 5.09 | + | 112.25 | 99.16 | D | 1549 | 1336 |
| SC91.33 | + | + | + | 110.39 | 101.76 | F | 1004 | 800 |
| SC91.34 | + | + | + | 98.19 | 97.59 | B | 206 | 137 |
| SC91.35 | + | + | + | 77.63 | 98.88 | B | 2725 | 1592 |
| SC91.43 | 3.52 | 0.98 | + | 64.38 | 83.42 | A | 4548 | 3546 |
| SC91.44 | 5.64 | 1.36 | + | 37.88 | 59.4 | A | 5352 | 4201 |
| SC91.45 | 28.7 | 8.34 | + | 14.15 | 27.1 | A | 5681 | 4067 |
| SC91.46 | + | 4.39 | + | 20.77 | 91.02 | C | 7946 | 805 |
| SC91.47 | 27.6 | 9.13 | + | 17.63 | 37.39 | A | 4874 | 4119 |
| SC91.48 | + | + | + | 110.7 | 102.72 | F | 69 | 68 |
| SC91.50 | 20.6 | 9.64 | + | 21.89 | 38.23 | A | 4946 | 4161 |
| SC91.79 | 2.72 | 2.15 | + | 87.92 | 84.42 | D | 2723 | 2216 |
| SC91.82 | 10.3 | 0.593 | + | 80.19 | 109.2 | B | 958 | 180 |
| SC91.83 | 3 | 1.51 | + | 103.45 | 97.39 | D | 1386 | 1218 |
| SC91.84 | + | + | + | 121.23 | 105.2 | F | nd | nd |

FIG. 7A

Anti-BMPR1B Antibody Characteristics (Screen 2)

FIG. 7B

| antibody | Biacore hSCRx91-his KD(nM) | Biacore cSCRx91-his KD (nM) | Biacore rSCRx91-his KD (nM) | In vitro killing Hx91, 250pM, fz, % live | In vitro killing Cx91, 250pM, fz, % live | In vitro killing Rx91, 250pM, fz, % live | Luminex Binning | Flowcytometry Purified Ab Cx91 APC gMFI | Flowcytometry Purified Ab Hx91 APC gMFI | Flowcytometry Purified Ab Rx91 APC gMFI |
|---|---|---|---|---|---|---|---|---|---|---|
| SC91.101 | 2.707 | 2.507 | no binding | 85.5 | 100.7 | 107.8 | C | 12031 | 19449 | 1906 |
| SC91.102 | 0.959 | <2nM | 2.18 | 19.5 | 25.9 | 38.3 | A | 11685 | 15717 | 7045 |
| SC91.103 | 8.651 | 11.38 | 10.97 | 33.1 | 32.8 | 52.9 | E | 17435 | 23362 | 11567 |
| SC91.104 | 12.9 | 18.8 | 19.6 | 28.5 | 36.4 | 49.7 | X | 15295 | 21837 | 8506 |
| SC91.105 | 0.0611 | 4.11 | 1.31 | 18.7 | 27.8 | 34.4 | A | 13848 | 22083 | 9153 |
| SC91.106 | 62.1 | biphasic | biphasic | 28.1 | 53.8 | 55.2 | A | 10791 | 20547 | 7231 |
| SC91.107 | 15.6 | 70.8 | 61.5 | 25.5 | 32.7 | 39.8 | A | 11051 | 19889 | 8099 |
| SC91.108 | 0.987 | 3.77 | 1.63 | 16.1 | 20.2 | 36.8 | A | 14738 | 22013 | 9227 |
| SC91.109 | 2.31 | 3.77 | <5nM | 24.4 | 28.2 | 41.3 | A | 13701 | 18664 | 8848 |
| SC91.110 | poor biphasic | poor biphasic | no binding | 78.6 | 109 | 109.9 | B | 766 | 5137 | 460 |
| SC91.111 | 6.665 | poor biphasic | poor biphasic | 20.3 | 52.9 | 87.1 | C | 9117 | 25180 | 3807 |
| SC91.112 | 4.456 | poor biphasic | no binding | 74.4 | 102.6 | 136.4 | B | 668 | 4468 | 296 |
| SC91.113 | 1.25 | 3.71 | 2.21 | 17.5 | 20 | 28.6 | A | 16201 | 25715 | 10577 |
| SC91.114 | 1.8 | 4.27 | 2.59 | 17.6 | 24.5 | 30.6 | A | 14854 | 24185 | 9700 |
| SC91.115 | 26.5 | 109 | 67.3 | 25.2 | 48.4 | 51.8 | A | 11631 | 20807 | 8137 |
| SC91.116 | 5.796 | poor biphasic | poor biphasic | 69 | 100.8 | 108.4 | B | 991 | 7001 | 434 |
| SC91.117 | 3.978 | poor biphasic | poor biphasic | 21.9 | 53.2 | 96.8 | C | 11263 | 25832 | 4763 |
| SC91.118 | 11 | no binding | no binding | 30.8 | 94.1 | 100.3 | C | 2264 | 24248 | 1102 |
| SC91.119 | 6.441 | 5.522 | 5.354 | 24.9 | 34.7 | 40.8 | E | 11530 | 17303 | 7513 |
| SC91.121 | 1.91 | 2.51 | 1.12 | 24.4 | 29.4 | 40.4 | A | 15248 | 21683 | 9565 |
| SC91.122 | 37.68 | no binding | no binding | 34.5 | 101 | 128.5 | C | 5358 | 23938 | 189 |
| SC91.123 | 2.37 | 4.21 | 3 | 20 | 23.7 | 33.9 | A | 14617 | 24155 | 9003 |
| SC91.124 | 6.138 | low affinity | low affinity | 25.2 | 58 | 106.1 | C | 9975 | 26361 | 3361 |
| SC91.125 | 1.48 | 3.82 | 2.59 | 19.4 | 17.9 | 35.9 | A | 16136 | 25948 | 9974 |
| SC91.126 | 1.13 | <1nM | <1nM | 23.2 | 21.1 | 45.8 | A | 11361 | 16921 | 7330 |
| SC91.127 | 1.5 | 3.4 | 2.28 | 17.2 | 21.9 | 35.6 | A | 14878 | 22039 | 8875 |
| SC91.128 | 3.657 | 4.514 | 2.683 | 23.9 | 18.4 | 38.1 | A | 14732 | 24299 | 9045 |
| SC91.129 | 0.564 | 1.62 | 0.561 | 23.1 | 18.5 | 39.2 | A | 16029 | 26882 | 10229 |
| SC91.130 | 1.01 | 2.11 | 0.0663 | 21.2 | 23.4 | 39.5 | A | 16439 | 24535 | 10347 |
| SC91.131 | 4.38 | no binding | no binding | 26.4 | 23.1 | 45.9 | A | 14083 | 23114 | 9799 |
| SC91.132 | no binding | no binding | no binding | 31.6 | 32.2 | 46.3 | E | 15390 | 22907 | 9794 |
| SC91.133 | 12.27 | 11.18 | no binding | 107.4 | 92.1 | 110.5 | B | 504 | 866 | 367 |
| SC91.134 | 11.45 | no binding | no binding | 27.7 | 86.6 | 114.6 | C | 3832 | 26535 | 914 |
| SC91.135 | 3.31 | 14.6 | 6.99 | 21.6 | 26.9 | 45.5 | A | 13027 | 22884 | 9407 |
| SC91.136 | biphasic | biphasic | biphasic | 29.1 | 38.5 | 47.7 | E | 10336 | 15878 | 7449 |
| SC91.137 | no binding | no binding | no binding | 19.7 | 18 | 31.7 | A | 15316 | 22935 | 9507 |
| SC91.138 | 0.658 | 0.937 | 1.84 | 21 | 17.6 | 37.3 | A | 15969 | 24492 | 9655 |
| SC91.139 | 0.641 | <0.1nM | <0.1nM | 22 | 22.9 | 37.5 | A | 15891 | 24435 | 9197 |
| SC91.140 | 1.4 | 1.41 | 4.87 | 21.7 | 21.4 | 40.7 | A | 10825 | 17277 | 7195 |
| SC91.141 | 1.72 | 3.95 | 2.43 | 24 | 18.5 | 40.7 | A | 14526 | 22637 | 8845 |
| SC91.142 | 31.3 | 28.5 | 23.7 | 35.7 | 32.5 | 60.2 | E | 15730 | 23924 | 11366 |
| SC91.143 | no binding | no binding | no binding | 28.3 | 31 | 70 | C | 11011 | 19833 | 5197 |
| SC91.144 | 1.96 | 5.07 | 3.76 | 20.5 | 19.8 | 35.4 | A | 14329 | 23849 | 9187 |
| SC91.145 | 1.24 | 2.31 | 1.18 | 20.9 | 21.9 | 27.4 | A | 14847 | 25097 | 8652 |
| SC91.146 | 1.21 | <0.1nM | <2nM | 20.5 | 25.4 | 38.8 | A | 10897 | 15788 | 6215 |
| SC91.147 | biphasic | biphasic | biphasic | 108.5 | 125.8 | 125.4 | B | 3105 | 6493 | 1526 |
| SC91.148 | 1.587 | 2.2 | 1.822 | 19.4 | 22.3 | 38.9 | A | 15302 | 24703 | 10387 |
| SC91.149 | 1.03 | 2 | <0.1nM | 18.3 | 20.7 | 29.1 | A | 15441 | 26958 | 10598 |
| SC91.150 | biphasic | biphasic | biphasic | 26.9 | 39.2 | 59.4 | A | 11460 | 21230 | 8137 |
| SC91.151 | 51.2 | 70.4 | 178 | 38.9 | 43.7 | 80.9 | A | 12416 | 18844 | 5998 |
| SC91.152 | 10.49 | 9.685 | 9.955 | 23.3 | 27.4 | 40.1 | A | 13723 | 20322 | 8888 |
| SC91.153 | 2.07 | 4.48 | 2.88 | 18.9 | 22.4 | 37 | A | 14848 | 24537 | 9338 |
| SC91.154 | 30.3 | 26.5 | biphasic | 33.1 | 34.4 | 53.5 | E | 16475 | 22608 | 11250 |
| SC91.155 | 1.124 | biphasic | biphasic | 29.3 | 45.1 | 81.1 | C | 14647 | 25306 | 7688 |
| SC91.156 | no binding | no binding | no binding | 87.6 | 87.8 | 110.5 | X | 369 | 379 | 286 |
| SC91.157 | 3.02 | 4.464 | 3.428 | 18.4 | 22.3 | 34.7 | A | 16183 | 24579 | 9940 |
| SC91.158 | no binding | no binding | no binding | 31.8 | 82.4 | 119.2 | C | 3267 | 25912 | 1304 |
| SC91.159 | 1.5 | 4.25 | 4.05 | 21.8 | 23 | 37.7 | A | 13957 | 23277 | 9387 |
| SC91.160 | 3.116 | 38.82 | biphasic | 24.3 | 34.6 | 77.9 | C | 15761 | 26983 | 117 |
| SC91.161 | 2.01 | 4.38 | 2.67 | 15.5 | 17.8 | 29.1 | A | 14906 | 23211 | 9770 |
| SC91.162 | 4.514 | 8.635 | 6.209 | 21.6 | 21.5 | 34.9 | A | 15808 | 23591 | 9422 |
| SC91.163 | 0.799 | 0.761 | 1.47 | 20 | 18.7 | 32.7 | A | 14856 | 24388 | 7731 |
| SC91.164 | 5.34 | <20nM | <20nM | 24.7 | 22.1 | 45.3 | A | 13315 | 18577 | 8402 |
| SC91.165 | 3.98 | poor biphasic | poor biphasic | 25.8 | 47 | 91.9 | C | 10685 | 26119 | 4662 |
| SC91.166 | biphasic | biphasic | biphasic | 63.5 | 58.3 | 86.4 | E | 12627 | 24086 | 9153 |
| SC91.167 | 1.74 | 3.71 | 2.23 | 18.8 | 16.9 | 34.6 | A | 13862 | 24410 | 8871 |
| SC91.169 | 1.43 | 1.83 | 0.459 | 19.9 | 19.3 | 27.1 | A | 18197 | 30822 | 10059 |
| SC91.170 | 1.658 | 2.899 | 1.775 | 20.8 | 22.5 | 42.6 | A | 14766 | 22886 | 9929 |
| SC91.171 | 0.765 | 1.07 | 1.75 | 19.3 | 23.9 | 38 | A | 14549 | 23347 | 9263 |
| SC91.172 | 1.96 | 4.47 | 1.18 | 19.6 | 18 | 34.1 | A | 14964 | 23986 | 9506 |
| SC91.173 | 4.793 | low affinity | low affinity | 23.3 | 44.3 | 97.4 | C | 9808 | 27887 | 4270 |
| SC91.174 | 4.6 | 13 | 1.93 | 23.1 | 25.7 | 43.4 | A | 14473 | 26835 | 10254 |
| SC91.175 | biphasic | biphasic | biphasic | 29.6 | 45.6 | 63.6 | A | 11332 | 20835 | 8173 |
| SC91.176 | 1.202 | 3.11 | 1.729 | 19.9 | 20.6 | 37.1 | A | 14027 | 24300 | 9172 |
| SC91.177 | 1.243 | 1.546 | 0.9561 | 21 | 22.8 | 40.4 | A | 15818 | 24624 | 9324 |
| SC91.178 | 12.78 | 19.69 | no binding | 22.1 | 29.4 | 55.6 | C | 16779 | 24735 | 9177 |
| SC91.179 | 3.43 | poor biphasic | poor biphasic | 27.1 | 64.4 | 93.9 | C | 9571 | 24300 | 3836 |
| SC91.180 | 4.01 | biphasic | biphasic | 29.9 | 62 | 98.9 |  | 11130 | 25544 | 5181 |
| SC91.181 | 3.379 | 3.834 | 3.34 | 19.1 | 23 | 28.1 | A | 14372 | 22512 | 9068 |
| SC91.182 | 5.201 | 4.753 | 1.577 | 19.2 | 22.8 | 35.7 | A | 13560 | 24587 | 8714 |
| SC91.183 | 4.127 | 3.932 | 3.51 | 18.8 | 22.1 | 30.1 | A | 15428 | 23601 | 9183 |
| SC91.184 | 1.08 | 2.02 | 3.71 | 17.1 | 21.2 | 37.1 | A | 15316 | 21648 | 2685 |
| SC91.185 | 0.921 | <2nM | <1nM | 17.2 | 18.9 | 32.2 | A | 14672 | 25910 | 10458 |
| SC91.186 | 22.1 | biphasic | biphasic | 28.3 | 32 | 46.9 | E | 10891 | 17801 | 7071 |
| SC91.187 | 2.857 | 5.582 | 3.245 | 19.1 | 24.2 | 36.7 | A | 14845 | 25852 | 9680 |
| SC91.188 | 1.04 | <0.1nM | 0.535 | 24 | 22.7 | 44.1 | A | 10495 | 16206 | 7412 |
| SC91.189 | 1.51 | 3.19 | 1.87 | 20.5 | 22.9 | 41.9 | A | 13684 | 24834 | 10271 |
| SC91.190 | 5.219 | poor biphasic | 140.4 | 30.1 | 45.6 | 82.6 | C | 13466 | 25143 | 7579 |
| SC91.191 | 5.07 | 28 | 7.37 | 21.5 | 23.6 | 37.7 | A | 12657 | 25310 | 9730 |
| SC91.192 | 5.16 | 153.5 | low affinity | 23.4 | 65.3 | 111.1 | C | 9439 | 25199 | 3178 |
| SC91.193 | 0.476 | <0.1nM | <0.1nM | 18.2 | 21.8 | 33.3 | A | 15931 | 24749 | 9407 |
| SC91.195 | 1.88 | 4.1 | 2.25 | 18.2 | 19.3 | 35.6 | A | 14719 | 24181 | 9224 |

Anti-BMPR1B Antibody Cross Reactivity with BMPR1A
(Screen 1)

| Antibody | hBMPR1B-his | hBMPR1B-Fc | BMPR1A-Fc | Control-Fc |
|---|---|---|---|---|
| SC91.1 | 1.170 | 0.483 | 0.031 | 0.039 |
| SC91.2 | 1.331 | 1.160 | 0.042 | 0.040 |
| SC91.3 | 0.883 | 0.423 | 0.035 | 0.039 |
| SC91.4 | 0.900 | 0.598 | 0.047 | 0.037 |
| SC91.5 | 1.222 | 0.987 | 0.043 | 0.039 |
| SC91.6 | 0.819 | 0.327 | 0.044 | 0.040 |
| SC91.7 | 1.143 | 0.726 | 0.156 | 0.296 |
| SC91.9 | 1.410 | 0.551 | 0.056 | 0.042 |
| SC91.10 | 0.805 | 0.450 | 0.585 | 0.136 |
| SC91.11 | 0.791 | 0.387 | 0.117 | 0.040 |
| SC91.12 | 1.228 | 0.767 | 0.045 | 0.041 |
| SC91.13 | 0.975 | 0.647 | 0.042 | 0.042 |
| SC91.14 | 1.303 | 0.814 | 0.114 | 0.106 |
| SC91.15 | 1.189 | 0.829 | 0.055 | 0.050 |
| SC91.16 | 1.057 | 0.712 | 0.051 | 0.042 |
| SC91.17 | 0.640 | 0.131 | 0.044 | 0.047 |
| SC91.19 | 1.461 | 0.737 | 0.121 | 0.050 |
| SC91.20 | 1.010 | 0.462 | 0.116 | 0.041 |
| SC91.21 | 1.483 | 1.417 | 0.122 | 0.116 |
| SC91.22 | 1.208 | 0.892 | 0.044 | 0.040 |
| SC91.23 | 0.973 | 0.605 | 0.043 | 0.046 |
| SC91.24 | 0.760 | 0.239 | 0.046 | 0.042 |
| SC91.25 | 1.502 | 1.532 | 0.057 | 0.068 |
| SC91.26 | 1.254 | 0.689 | 0.046 | 0.043 |
| SC91.27 | 0.855 | 0.417 | 0.043 | 0.042 |
| SC91.28 | 1.038 | 0.829 | 0.052 | 0.043 |
| SC91.33 | 0.431 | 0.520 | 0.208 | 0.358 |
| SC91.34 | 0.757 | 0.400 | 0.044 | 0.043 |
| SC91.35 | 0.885 | 0.248 | 0.048 | 0.042 |
| SC91.43 | 0.678 | 0.289 | 0.129 | 0.334 |
| SC91.44 | 0.953 | 0.214 | 0.049 | 0.113 |
| SC91.45 | 1.224 | 0.306 | 0.052 | 0.085 |
| SC91.46 | 0.921 | 0.219 | 0.043 | 0.046 |
| SC91.47 | 0.883 | 0.272 | 0.047 | 0.044 |
| SC91.48 | N/A | N/A | N/A | N/A |
| SC91.50 | 0.918 | 0.275 | 0.049 | 0.046 |
| SC91.79 | 1.193 | 1.194 | 0.049 | 0.044 |
| SC91.82 | 1.516 | 1.374 | 0.068 | 0.049 |
| SC91.83 | 1.233 | 1.320 | 0.045 | 0.043 |
| SC91.84 | 0.453 | 0.098 | 0.052 | 0.107 |

FIG. 8A

Anti-BMPR1B Antibody Cross Reactivity with BMPR1A (Screen 2)

| antibody | ELISA rhBMPR-1A-Fc Chimera | antibody | ELISA rhBMPR-1A-Fc Chimera |
|---|---|---|---|
| SC91.101 | 0.062 | SC91.148 | 0.074 |
| SC91.102 | 0.072 | SC91.149 | 0.066 |
| SC91.103 | 1.921 | SC91.150 | 0.083 |
| SC91.104 | 0.071 | SC91.151 | 0.056 |
| SC91.105 | 0.104 | SC91.152 | 0.060 |
| SC91.106 | 0.092 | SC91.153 | 0.069 |
| SC91.107 | 0.096 | SC91.154 | 2.138 |
| SC91.108 | 0.061 | SC91.155 | 0.059 |
| SC91.109 | 0.063 | SC91.156 | 0.055 |
| SC91.110 | 0.314 | SC91.157 | 0.057 |
| SC91.111 | 0.077 | SC91.158 | 0.057 |
| SC91.112 | 0.302 | SC91.159 | 0.077 |
| SC91.113 | 0.074 | SC91.160 | 0.061 |
| SC91.114 | 0.074 | SC91.161 | 0.279 |
| SC91.115 | 0.066 | SC91.162 | 0.105 |
| SC91.116 | 0.243 | SC91.163 | 0.098 |
| SC91.117 | 0.112 | SC91.164 | 0.064 |
| SC91.118 | 0.062 | SC91.165 | 0.071 |
| SC91.119 | 0.122 | SC91.166 | 0.095 |
| SC91.121 | 0.056 | SC91.167 | 0.182 |
| SC91.122 | 0.082 | SC91.169 | 0.062 |
| SC91.123 | 0.078 | SC91.170 | 0.057 |
| SC91.124 | 0.105 | SC91.171 | 0.066 |
| SC91.125 | 0.069 | SC91.172 | 0.062 |
| SC91.126 | 0.078 | SC91.173 | 0.091 |
| SC91.127 | 0.251 | SC91.174 | 0.068 |
| SC91.128 | 0.068 | SC91.175 | 0.076 |
| SC91.129 | 0.063 | SC91.176 | 0.057 |
| SC91.130 | 0.080 | SC91.177 | 0.057 |
| SC91.131 | 0.058 | SC91.178 | 0.253 |
| SC91.132 | 0.095 | SC91.179 | 0.098 |
| SC91.133 | 0.081 | SC91.180 | 0.074 |
| SC91.134 | 0.057 | SC91.181 | 0.073 |
| SC91.135 | 0.081 | SC91.182 | 0.074 |
| SC91.136 | 0.109 | SC91.183 | 0.056 |
| SC91.137 | 0.087 | SC91.184 | 0.280 |
| SC91.138 | 0.065 | SC91.185 | 0.232 |
| SC91.139 | 0.434 | SC91.186 | 0.105 |
| SC91.140 | 0.069 | SC91.187 | 0.092 |
| SC91.141 | 0.070 | SC91.188 | 0.063 |
| SC91.142 | 2.423 | SC91.189 | 0.067 |
| SC91.143 | 0.157 | SC91.190 | 0.064 |
| SC91.144 | 0.067 | SC91.191 | 0.063 |
| SC91.145 | 0.065 | SC91.192 | 0.127 |
| SC91.146 | 0.081 | SC91.193 | 0.073 |
| SC91.147 | 0.081 | SC91.195 | 0.155 |

FIG. 8B

Anti-BMPR1B Murine Light Chain Antibody Variable Region Amino Acid Sequences

| Name | FR1 | CDR1 | FR2 | CDR2 | FR3 | CDR3 | FR4 | SEQ ID NO |
|---|---|---|---|---|---|---|---|---|
| SC91.1 | DVVMTQTPLSLPVSLGDQASIFC | RSSQSLVHSTGNTYLH | WYLQKPGQSPKLLIY | KVSNRFS | GVPDRFSGSGSGTDFTLKISRVEAEDLGVVFC | SQSTHVPFT | FGSGTKLEIK | 21 |
| SC91.3 | DVVMTQTPLSLPVSLGDQASISC | RSSQSLVHSTGNTYLH | WYLQKPGQSPKLLIY | KVSNRFS | GVPDRFSGSGSGTDFTLKISRVEAEDLGVVFC | SQSTHVPFT | FGSGTKLEIK | 25 |
| SC91.9 | DIQMTQTTSSLSASLGDRVTISC | RASQDISNFLN | WYQQKPDGTIKFLIY | YTSRLHS | GVPSRFSGSGSGTDYSLTIRNLEQEDIATYFC | QQGNTLPYT | FGGGTKLEIK | 29 |
| SC91.11 | DIVMTQSQKFMSTSVGDRVSVTC | KASQNVGTNVF | WYQQKPGQSPKALIY | AASYRYS | GVPDRFTGSGSGTDFTLTISNVQSEDLADYFC | QQYDSYPLT | FGDGTKLELR | 33 |
| SC91.14 SC91.186 | DIVMSQSPSSLAVSVGEKVTMSC | KSSQSLLYSSNQKNYLA | WYQQKPGQSPQLLIY | WASTRES | GVPDRFTGSGSGTDFTLTISSVKAEDLAVYYC | QQYVSYPLT | FGAGTKLELK | 37 |
| SC91.15 | DIVMSQSPSSLAMSVGQKVTMSC | KSSQSLLKSSNQKNYLA | WYQQKPGQSPKLLVY | FASTRES | GVPDRFIGSGSGTDFTLTISSVQAEDLADYFC | QQYVRIPWT | FGGGTKLEIK | 41 |
| SC91.19 | SFVMTQTPKFLLVSAGDRVTITC | KASQSVGNDVA | WYQQKPGQSPKLLIY | YASNRYT | GVPDRFTGSGYGTDFTFTISTVQAEDLAVYFC | QQDYSSPFT | FGSGTKLEMK | 45 |
| SC91.111 | SFVMTQTPKFLLVSAGDRVTITC | KASQNMGHNVA | WYQQKPGQSPKLLIY | YASNRYT | GVPDRFTGSGYGTDFTFTISTVQAEDLAVYFC | QQDYSSPFT | FGSGTKLEIK | 49 |
| SC91.119 | DIVMSQSPSSLAVSVGEKVTMSC | KSSQSLLYSNNQKNYLA | WYQQKPGQSPKLLIY | WASTRES | GVPDRFTGSGSGTDFTLTISSVKAEDLAVYYC | QQYVSFPLT | FGAGTKLELK | 53 |
| SC91.129 | DAVMTQSPLSLPVSLGDQASISC | RSSQSLVHSTGNTYLH | WYLQKPGQSPKLLIY | KVSNRFS | GVPDRFSGSGSGTDFTLKISRVEAEDLGVVFC | SQTTHVPFT | FGSGTKLEIK | 57 |

FIG. 9A

Anti-BMPR1B Murine Light Chain Antibody Variable Region Amino Acid Sequences

| Name | FR1 | CDR1 | FR2 | CDR2 | FR3 | CDR3 | FR4 | SEQ ID NO |
|---|---|---|---|---|---|---|---|---|
| SC91.138 | DIVMTQSPSSLAMSVGQKVTMSC | KSSQSLLKSNNQKNYLA | WYQQKPGQSPKLLVY | FASTRES | GVPDRFIGSGSGTDFTLTISSVQAEDLADYFC | QQYYSTPWT | FGGGTKLEIK | 61 |
| SC91.146 | DIVMTQSPSSLAMSVGQKVTMSC | KSSQSLLKSSNQKNYLA | WYQQKPGQSPKLLVY | FASTRES | GVPDRFIGSGSGTDFTLTISSVQAEDLADYFC | QQHYNIPLT | FGAGTKLELK | 65 |
| SC91.149 | DVVMTQTPLSLPVSLGDQASISC | RSSQSLVHSTGNTYFH | WYLQKPGQSPELLIY | KVSNRFS | GVPDRFRGSGSGTDFTLKISRVEAEDLGVYFC | SQSTHVPFT | FGSGTKLEIK | 69 |
| SC91.155 | SFVMTQTPKFLLVSAGDRVTITC | KASQNLGNDVA | WYQQKPGQSPRLLIY | FASNRYT | GVPDRFTGSGYGTDFTFTISTVQAEDLAVYFC | QQDYSSPFT | FGSGTKLEIK | 73 |
| SC91.160 | SFVMTQTPKFLLVSAGDRVTITC | KASQNMGHDVA | WYQQKPGQSPKLLIY | SASNRYT | GVPDRFTGSGYGTDFTFTISTVQAEDLAVYFC | QQDYSSPFT | FGSGTKLEMK | 77 |
| SC91.172 | DVVMTQTPLSLPVSLGDQASISC | RSSQSLVHSTGNTYLH | WYLQKAGQSPKLLIY | KVSNRFS | GVPDRFSGSGSGTDFTLKISRVEAEDLGVYFC | SQSTHVPFT | FGSGTKLEIK | 81 |
| SC91.187 | DVVMTQTPLSLPVSLGEQASISC | RSSQSLVHSTGNTYLH | WYLQKPGQSPKLLIY | KVSNRFS | GVPDRFSGSGSGTDFTLKISRVEAEDLGVYFC | SQSTHVPFT | FGSGTKLEIK | 85 |
| SC91.20 SC91.27 | DVVMTQTPLSLPVSLGDQASISC | RSSQSLVHSTGNTYLH | WYLQKPGQSPNLLIY | KVSNRFS | GVPDRFSGSGSGTDFTLKISRVEAEDLGVYFC | SQSTHVPFT | FGSGTKLEIK | 89 |

FIG. 9A (Cont.)

Anti-BMPR1B Murine Heavy Chain Antibody Variable Region Amino Acid Sequences

| Name | FR1 | CDR1 | FR2 | CDR2 | FR3 | CDR3 | FR4 | SEQ ID NO |
|---|---|---|---|---|---|---|---|---|
| SC91.1 | QVQLQQPGAELVKPGASVKLSCKASGYTFT | SYWMQ | WVKQRPGQGLEWIG | EIDPSDNYTLYNQKFKG | KATLTVDTSSSTAYMQLSSLTSEDSAVYYCAR | FGYYVDY | WGLGTTLTVSS | 23 |
| SC91.3 | QVQLQQPGAELVKPGASVKLSCKASGYTFT | SYWMQ | WVKQRPGQGLEWIG | EIDPSDSYTLYNQKFKG | KATLTVDTSSSTAYMQLSSLTSEDSAVYFCAR | FGYYIEY | WGQGTTLTVSS | 27 |
| SC91.9 | QVQLQQPGAELVKPGASVKLSCKASGYTFI | SYWMH | WVKQRPGQGLEWIG | MIHPNSGSTNYNESFKS | KATLTVDKSSSTAYMQLSSLTSEDSAVYYCAR | DLLIATVVTPYFAY | WGQGTTLTVSS | 31 |
| SC91.11 | QVQLQQPGAELVKPGASVKLSCKASGYTFT | TYWMH | WVKQRPGRGLEWIG | RIDPNSGGTKYNEKFKS | KATLTVDKPSSTACMQLSSLTSEDSAVYYCAS | RRGDIDV | WGTGTTVTVSS | 35 |
| SC91.14 | QVTLKESGPGTIQPSQTLSLTCSFSGFSLR | TSGMNIG | WIRQPSGKGLEWLT | HIWWNDDKSYNPALKS | RLTISKDTSNNQVFLKIASVVTADTATYYCVR | GDRFPY | WGQGTLVTVSA | 39 |
| SC91.15 | QVQLQQPGAELVMPGASVKLSCKASGYTLT | NYWMH | WVKQRPGQGLEWIG | DIDPSDTYTNYNHKFKG | KATLTVDKSSSTAYMQLSSLTSEDSAVYYCAR | SGWDYFDS | WGQGTTLTVSS | 43 |
| SC91.19 | QIQLVQSGPELKKPGETVKISCKASGYTFT | TYGMN | WVKQAPGKGLKWMG | WINTYSGVPSSANDFKG | RFAFSLETSASTAYLQINNLKNEDTATYFCAR | SELRNWYFDV | WGTGTTVTVSS | 47 |
| SC91.111 | QIQLVQSGPELKKPGETVKISCKASGYTLT | TYGMN | WVKQAPGKGLKWMG | WINTYSGVPAYADDFKG | RFAFSLETSASTAYLQINNFKNEDTATYFCAR | SELRNWYFDV | WGTGTTVTVSS | 51 |
| SC91.119 | QVTLKESGPGTLQPSQTLSLTCSFSGLSLS | TPGMSVG | WIRQPSGKGLEWLA | HIWWNDDKSYNPALKS | RLTISKDTSNNQVFLKIASVVTADTATYYCAR | GDRFAY | WGQGTLVTVSA | 55 |
| SC91.129 | QVQLQQPGAELVKPGASVKLSCKASGYTFT | NYWMQ | WVKQRPGQGLEWIG | EIDPSDRYTLYNQKFKD | KATLTVDTSSSTAYMQLSSLTSEDSAVYYCAR | FGYYVDY | WGQGTTLTVSS | 59 |

FIG. 9B

Anti-BMPR1B Murine Heavy Chain Antibody Variable Region Amino Acid Sequences

| Name | FR1 | CDR1 | FR2 | CDR2 | FR3 | CDR3 | FR4 | SEQ ID NO |
|---|---|---|---|---|---|---|---|---|
| SC91.138 | QVQLQQPGAELVMPGASVKLSCKASGYTFT | NYWMH | WVKQRPGQGLEWIG | EIDPSDVVTYNQKFKD | KATLTVDKSSSTAYMQLINLTSEDSAVYYCAR | SGWDYFDY | WGQGTALTVSS | 63 |
| SC91.146 | QVQLQQPGAELVKPGASVKLSCKASGYTFT | SYWMH | WVKQRPGQGLEWIG | DIDPSDRYTNVNQKFKG | KATLTVDTTSSTAYMQLSSLTSEDSAVYYCAI | SGWDYFDY | WGQGTTLTVSS | 67 |
| SC91.149 | QVQLLQPGAELVKPGSSVKVSCKASGYTFT | NYWMQ | WVKQRPGQGLEWIG | EIDPSDTYTLYNQKFKG | KATLTVDTSSSTAYMQLSSLTSEDSAVYYCAR | FGYYVDY | WGQGTTLTVSS | 71 |
| SC91.155 | QIQLVQSGPELKKPGETVKISCKASGYTFT | TYGMN | WVKQAPGKGLKWMG | WINSYSGVPAYADDFKG | RFAFSLETFASTAYLQINNLRDEDTATYFCAR | SELRNWYFDV | WGTGTTVTVSS | 75 |
| SC91.160 | QIQLVQSGPELKKPGETVKISCKASGYTFT | TYGMN | WVKQAPGKGLKWMG | WINTYSGVPSSADDFKG | RFAFSLETSASTAVLLINNLKNEDTATYFCAR | SELRNWYFDV | WGTGTTVTVSS | 79 |
| SC91.172 | QVQLQQPGADLVKPGTSVKLSCKASGYTFT | SYWMQ | WVKQRPGQGLEWIG | EIDPSDTYTMYNQKFKG | KATLTVDTSSSTAYMQLSSLTSEDSAVYYCAR | FGYYVDY | WGQGTTLTVSS | 83 |
| SC91.187 | QVQLQQPGPEFVKPGASVKLSCKASGYTFT | SYWVQ | WVKQRPGQGLEWIG | EIDPSDNYTLYNQNFKG | KATLTVDTSSSTAYMQLSSLTSEDSAVYYCAR | FGFYVDY | WGQGTTLTVSS | 87 |
| SC91.20 | QVQLQQPGAEVVRPGASLKLSCKASGYTFT | SYWMQ | WIKQRPGQGLEWIG | EIDPSDNYTMYNQKFKG | KATLTVDTSSSTAYMQLSSLTSEDSAVFCAR | FGFYVDY | WGQGTTLTVSS | 91 |
| SC91.27 | QVQLQQPGAEVVKPGASVKLSCKASGYTFT | NYWMQ | WVKQRPGQGLEWIG | EIDPSDRYTMYNQKFKG | KATLIVDTSSSTAYMQLSSLTSEDSAVYFCAR | FGYYVDY | WGQGTTLTVSS | 93 |
| SC91.186 | QVTLKESGPGILQPSQTLSLTCSFSGFSLR | TSGMNIG | WIRQPSGKGLEWLT | HIWWNDDKSYNPALKS | RLTISKDTSNNQVFLKIASVVTADTATYYCVR | GDRFAY | WGQGTLVTVSA | 95 |

FIG. 9B (Cont.)

Anti-BMPR1B Murine Antibody Variable Region Nucleotide Sequences

| Name | Chain | Nucleic Acid Sequence | SEQ ID NO |
|---|---|---|---|
| SC91.1 | Light Chain | GATGTTGTGATGACCCAAACTCCACTCTCCCTGCCTGTCAGTCTTGGAGATCAAGCCTCCATCTTTTGCAGATCTAGTCAGAGCCTTGTACACAGTACTGGAAACACCTATTTACATTGGTACCT GCAGAAGCCAGGCCAGTCTCCAAAGCTCCTGATCTACAAAGTTTCCAACCGATTTTCTGGGGTCCCAGACAGGTTCAGTGGCAGTGGATCAGGGACAGATTTCACACTCAAGATCAGCAGAGTGG AGGCTGAGGATCTGGGAGTTTATTTCTGCTCTCAAAGTACACATGTTCCATTCACGTTCGGCTCGGGGACAAAGTTGGAAATAAAA | 20 |
| SC91.1 | Heavy Chain | CAGGTCCAACTGCAGCAGCCTGGGGCTGAACTTGTGAAGCCTGGGGCTTCAGTGAAGCTGTCCTGCAAGGCTTCTGGCTACACCTTCACCAGCTACTGGATGCAGTGGGTAAAACAGAGGCCTGG ACAGGGCCTTGAGTGGATCGGAGAGATTGATCCTTCTGATAACTATACTCTACAATGCAAAAGTTCAAGGGCAAGGCCACGTTGACTGTAGACACATCCTCCAGCACAGCCTACATGCAGCTCA GCAGCCTGACATCTGAGGACTCTGCGGTCTATTACTGTGCAAGGTTTGGTTACTATGTGACTACTGGGGCCAAGGGACCACGGTCTCCTCA | 22 |
| SC91.3 | Light Chain | GATGTTGTGATGACCCAAACTCCACTCTCCCTGCCTGTCAGTCTTGGAGATCAAGCCTCCATCTCTTGCAGATCTAGTCAGAGCCTTGTACACAGTACTGGAAACACCTATTTACATTGGTACCT GCAGAAGCCAGGCCAGTCTCCAAACTCCTGATCTACAAAGTTTCCAACCAGATTTTCTGGGGTCCCAGACAGGTTCAGTGGCAGTGGATCAGGGACAGATTTCACACTCAAGATCAGCAGAGTGG AGGCTGAGGATCTGGGAGTTTATTTCTGCTCTCAAAGTACACATGTTCCATTCACGTTCGGCTCGGGGACAAAGTTGGAAATAAAA | 24 |
| SC91.3 | Heavy Chain | CAGGTCCAACTGCAGCAGCCTGGGGCTGAGCTGGTGAAGCCTGGGGCTTGTGAAGCTGTCCTGCAAGGCTTCTGATAGCTACACTCTCTACAATGCAAAATTCAAGGGCAAGGCCACATTGACTGTAGACACATCCTCCAGCACAGCCTACATGCAGCTCA GCAGCCTGACATCTGAGGACTCTGCGGTCTATTCTGTGCAAGATTTGGTTACTATATTGAGTACTGGGGCCAAGGCACCACTCTCACAGTCTCCTCA | 26 |
| SC91.9 | Light Chain | GATATCCAGATGACACAGACTACATCTCCCTGTCTGCCTCTGGGAGACAGAGTCACCATCAGTTGCAGGGCAAGTCAGGGCATTAGCAATTATTTAAACTGGTATCAGCAGAAACCAGATGG AACTATTAAATTCCTGATCTACTACACATCAAGATTACACTCAGGAGTCCCATCAGGTTCAGTGGCAGTGGGTCTGGAACAGAGATTACTCTCACCATTCGCAACCTGGAGCAAGAAGATATTG CCACTTACTTTTGCCAACAGGGTAATACGCTTCCGTACACGTTCGGAGGGGACCAAGCTGGAAATAAAA | 28 |
| SC91.9 | Heavy Chain | CAGGTCCAACTGCAGCAGCCTGGGGCTGAGCTGGTAAAGCCTGGGGCTTCAGTGAAGTTGTCCTGCAAGGCTTCTGGCTACACCTTTCATCAGTTACTGGATGCACTGGGTGAAGCAGAGGCCTGG AAAGGGCCTTGAGTGGATTGGAATGATTCATCCTAATAGTGGTAGTACTAACTACAATGAGAGTTTCAAGAGCAAGGCCACACTGACTGTAGACAAATCTCCAGTACAGCCTACATGCAACTCA GCAGCCTGACATCTGAGGACTCTGCGGTCTATTACTGTGCAGGACTTACTTATTGCCTACTGGGGCCAAGGCACTATTCTCACAGTCTCCTCA | 30 |
| SC91.11 | Light Chain | GACATTGTGATGACCCAGTCTCAAAAATTCATGTCCACATCAGTAGGAGACAGGGTCAGCCTCACCTGCAAGGCCAGTCAGAATGTGGGTACTAATGTATTCTGGTATCAACAGAAACCAGGGCA ATCTCCTAAAGCACTGATTTACGCGGCATCTTACCGGTACAGTGGAGTCCCTGATCGCTTCACAGGCAGTGGATCTGGGACAGATTTCACTCTCACCATCAGCAGTGTGGTGCAGGACTTGG CAGATTATTTCTGTCAGCAATATGACAGCTATCCTCTCACGTTCGGTGATGGGACCAAGCTGGAGCTGAGA | 32 |
| SC91.11 | Heavy Chain | CAGGTCCAACTGCAGCAGCCTGGGGCTGAGCTTGTGAAGCCTGGGGCTTGTGAAGCTGTCCTGCAAGGCTTCTGGGTACACCTTCACCAGCTACTGGATGCACTGGGTGAAGCAGAGGCCTGG ACGAGGCCTTGAGTGGATTGGAAGGATTGATCCTAATAGTGGTACTAAGTACAATGAGAAGTTCAAGAGCAAGGCCACACTGACTGTAGACAAACCCTCCAGCACAGCCTACATGCAGCTCA GCAGCCTGACCTCTGAGGACTCTGCGGTCTATTATTGTGCAAGCAGGAGGGGGACATCGATGTCTGGGGCCACAGGGACCACGGTCACCGTCTCCTCA | 34 |

FIG. 9C

Anti-BMPR1B Murine Antibody Variable Region Nucleotide Sequences

| Name | Chain | Nucleic Acid Sequence | SEQ ID NO |
|---|---|---|---|
| SC91.14 | Light Chain | GACATTGTGATGTCACAGTCTCCATCCTCCCTAGCTGTGTCAGTTGGAGAGAAGGTTACTATGAGCTGCAAGTCCAGTCAGAGCCTTTTATATAGTAGCAATCAAAAGAACTACTTGGCTGGTACCAGCAGAAACCAGGGCAGTCTCCTCAACTGCTGATTTACTGGGCATCCACTAGGGAATCTGGGGTCCCTGATCGCTTCACAGGCAGTGGATCTGGGACAGATTTCACTCTCACCATCAGCAGTGTGAAGGCTGAAGACCTGGCAGTTTATTACTGTCAGCAATATTATAGCTATCCGCTCACGTTCGGTGCTGGGACCAAGCTGGAGCTGAAA | 36 |
| SC91.14 | Heavy Chain | CAAGTTACTCTGAAAGAGTCTGGCCCTGGGATATTGCAGCCCTCCCAGACCCTCAGTCACTTGTTCTTTCTCTGGGTTTTCACTGCGCACATCTGGTATGAATATAGGCTGGATTCGTCAGCCTTCAGGGAAGGGTCTGGAGTGGCTGACACACATTTGGTGGAATGATGATAAGTCCTACAACCCAGCCTCACAATCTCCAAAAGCCGGCTCACAATCTCCAACAACCAGGTATTCCTCAAGCTCGCCAGTGTGGTCACTGCAGATACCGCCACATACTGTGTTGAGGTGACCGGTTTCCTTACTGGGGCCAAGGGACTCTGGTCACTGTCTCTGCA | 38 |
| SC91.15 | Light Chain | GACATTGTGATGACACAGTCTCCATCCTCCCTGGCTATGTCAGTAGGAGACAGAAGGTCACTATGAGCTGCAAGTCCAGTGCAAGTGAAGGAATCTAGGGAATCTGGGGTCCCTGATCGCTTCATAGGCAGTGGATCTGGGACAGATTCACTCTTACCATCAGCAGTGTGCAGGCTGAAGACCTGGCAGATTACTTCTGTCAGCAATATTATAGGATTCCTTGGACGTTCGGTGGAGGCACCAAGCTGGAAATCAAA | 40 |
| SC91.15 | Heavy Chain | CAGGTCCAACTGCAGCAGCCTGGGGCTGAGCTTGTGATGCCTGGGGCTTCAGTGAAGCTGTCCTGCAAGGCTTCTGGCTACACCCTCACCAACTACTGGATGCACTGGGTGAAGCAGAGGCCTGGACAAGGCCTTGAGTGGATCGGAGTGATTGATCCTTCTGATACTTATACTAACTACAATCAAAATTCAAGGCAAGGCCACATTCAGTGACTGTAGACAAATCTTCCAGCAGCCTACATGCAGCTCAGCAGCCTGACATCTGAGGACTCTGCGGTCTATTACTGTGCAAGATCGGGATTGGGAGATGGGAGATGGGACAAAGTTGGAAATGAAA | 42 |
| SC91.19 | Light Chain | AGTTTTGTGATGACCCAGACTCCACTCCCAATTCCTGTCTGTATCAGCAGGAGACAGGGTTACCATAACCTGCAAGGCCAGTCAGAGTGTGGGTAATGATGTTGCCTGGTACCAACTGCAGCAGTCTCCAGGACAGTCTCCTAAATTGCATCATCTGATACTGCATACTGGAATCCGGAAACTGGTACTTCTGCAAGACCGGGTCCACCGTCACCAGGACACTTCGATGCACAGGGCACAGGGCACTGCCATCAGCAGCCTCAGCAGCCTCTAGCAGCAGCCTGGTACAGCAGTCCTGATGTCTGGGGACAAAGTTGGAATATAAA | 44 |
| SC91.19 | Heavy Chain | CAGATCCAGTTGGTACAGTCTGGACCTGAGCTGAAGAAGCCTGGAGAGAGACTTCCCTGAAGACTTCCTGAAGGCTTCTGGATACACCTTCACCGAGTGCCATCATCCTGGAGCTTCAAGGAACCCCATGGAGTGCCATCATCCTGGAGTGCCAAGGCTTCAAGCAGCCTGATCATGGACACCTGGAGACTCTGCAGCATCCTGCCTGCAGCATGCACACCTGCCTCCAACTCCACAACAAGGAGCACCTGCGGCAGGGCACCAGGGACCATCACCGTCTCCTCA | 46 |
| SC91.111 | Light Chain | AGTTTTGTGATGACCCAGACTCCACTCCCAGATTCCTGTTGTATCAGCAGGAGACAGGGGTTACCATAACCTGCAAGGCCAGTCAGAATATGGGTACTAATGTAGCTTGGTACCAACAGAAGCCAGGGCAGTCTCCTAAATTGCATCATCTGATATACTGCATCCAATGCATCAACTACTGGAATCCGGAAACTGGTACTGGTGGAATCCGAAGCATCAGCAGGTATCTGAATCAGAATATGGGAGTCCTGATATACTCCCTGATATGGAGCCTCAGCAGCCTCTCTACTTTCACCATCAGCAGCCTGCAGGCTGAAGACCTGG | 48 |
| SC91.111 | Heavy Chain | CAGATCCAGTTGGTACAGTCTGGACCTGAGCTGAAGAAGCCTGGAGAGACAGTCAAGATCTCCTGCAAGGCTTCTGGGTATACCTTCACAACCTATGGAATGAACTGGGTGAAACAGGCTCCAGGAAAGGGTTTAAAGTGGATGGGCTGGATAAACACCTACTCTGGAGTGCCATCATCCTGCAGCACTGCCTATTTGCAGATCAAAGGCACTTCAAGGACGGTTTGCCTTCTGCCAGCACTGCCTATTTGCAGATCAACAACCTCAAAAAATGAGGACACGGCTACACATATTTCTGTGCAAGATCGAAACTACGAAACTGGTACTCGATGTCTGGGGCACAGGGACCACGGTCACCGTCTCCTCA | 50 |

FIG. 9C (Cont.)

Anti-BMPR1B Murine Antibody Variable Region Nucleotide Sequences

| Name | Chain | Nucleic Acid Sequence | SEQ ID NO |
|---|---|---|---|
| SC91.119 | Light Chain | GACATTGTGATGTCACAGTCTCCATCCTCCCTAGCTGTGTCAGTTGGAGAGAAGGTTACTATGAGCTGCAAGTCCAGTCAGAGCCTTTTATATAGTAACAATCAAAAGAACTACTTGGCCTGGTA CCAGCAGAAACCAGGGCAGTCTCCTAAACTGCTGATTTACTGGGCATCCACTAGGGAATCTGGGGTCCCTGATCGCTTCACAGGCAGTGGATCTGGGACGAGATTTCACTCTCACCATCAGCAGTG TGAAGGCTGAAGACCTGGCAGTTTATTACTGTCAGCAATATTATAGCTTTCCGCTCACGTTCGGTGCTGGGACCAAGCTGGAGCTAAAA | 52 |
| SC91.119 | Heavy Chain | CAGGTTACTCTGAAAGAGTCTGGCCCTGGGATATTGCAGCCCTCCCAGACCCTCAGTCAGTTGTTCTTTCTCTGGGCTTTCACTGAGCACACCTGGTATGAGTGTAGGCTGGATTCGTCAGCC TTCAGGGAAGGGTCTGGAGTGGCTGGCACACATTTGGTGGACATGATAAGTCCTATAACCAGCCTGGCTACAATCTCCAAGACTACCTCCAAGATACCTCCAACAATCAGGTATTCCTCAAGA TCGCCAGTGTGTTCACTGCAGATACTGCCACATACTGTGCGAGGTGACCGGTTTGCTTACTGGGGCCAAGGGACTCTGGTCACTGTCTCTGCA | 54 |
| SC91.129 | Light Chain | GATGCTGTGATGACCCAATCTCCACTCTCCCTGCCTGTCAGTCTTGGAGATCAAGCCTCCATCTCCTGCAGATCTAGTCAGAGCCTTGTACAGAGTACTGGAAACACCTATTTACATTGGTACCT GCAAAAGCCAGGCCAGTCTCCAAAATCCTGATCTATAAAGTTTCCAACCGATTTTCTGGGGTCCCAGACAGGTTCAGTGGCAGTGGATCAGGGACAGAGATTTCACACTCAAGATCAGCAGAGTGG AGGCTGAGGATCTGGGAGTTTATTTCTGCTCTCAAACTACACATGTTCCATTCACGTTCGGCTCGGGGACAAAGTTGGAAATAAAA | 56 |
| SC91.129 | Heavy Chain | CAGGTCCAACTGCAGCAGCCTGGGGCTGAACTTGTGAAGCCTGGGGCTTCAGTGAAGCTGTCCTGCAAGGCTTCTGGCTACACCTTCACCAACTACTGGATGCAGTGGGTAAAACAGAGGCCTGG ACAGGGCCTTGAGTGGATCGGATCGGAGAGATTGATCCTTCTGATAGGTACACTCTGATAGGTACACTTGCATCCACTAGGGAATCTAAATTCAAAGGCCACAGGCCACATTGACTGTAGACAATGTCCTCAGCACAGCCTACATGTGCAGCTCA GCAGCCTGACATCTGAGGACTCTGCGGTCTATTATTGTGCAAGATTTGGTTACTATGTTGACTACTGGGGCCAAGGCACCACTCTCACAGTCTCTCA | 58 |
| SC91.138 | Light Chain | GACATTGTGATGACACAGTCTCCATCCTCCCTGGCTATGTCAGTAGGACAGAAGGTCACTATGAGCTGCAGCTCCAGTTCAAGGTCCTCCATCCGTATCTTGGATATACTTTGCATCCACTAGGGAATCTGGGGTCCCT GATCGCTTCATAGGCAGTGGATCTGGGACGGATTTCACTCTTCACCATCAGCAGTGTGCAGGCTGAAGACCTGGCAGTTTATTACTGTCAGCAGATTTATAGCTGGGACAATCGGGACGTTCGGTGGAGGCACCAAGCTGGAAATCAAA | 60 |
| SC91.138 | Heavy Chain | CAGGTCCAACTGCAGCAGCCTGGGGCTGAGCTTGTGATGCCTGGGGCTTCAGTGAAGCTGTCCTGCAAGGCTTCTGAAGCCTCTGGCTACACCTTCACCAACTACTGGATGCACTGGGTGAAGCAGAGGCCTGG ACAAGGCCTTGAGTGGATCGGAGAGATTGATCCTTCTGATGTTTATACTACCTACAATCAAATGTTCAAGGACAAGGCCACGTTGACTGTAGACAAATCCTCAGCACAGCCTACATGCAACTCA TCAACCTGACATCTGAGGACTCTGCGGTCTATTATTGTGCAAGATCGGGAATACTGGGACTACTTTGACTACTGGGGCCAAGGGACCACGGTCACCGTCTCCTCA | 62 |
| SC91.146 | Light Chain | GACATTGTGATGACACAGTCTCCATCCTCCCTGCTATGTCAGTAGGACAGAAGGTCACTATGAGCTGCAAGTCCAGTCAGAGCCTTGTCATCAGCTTCATCAGCCTTGATCGCTTCATAGGCAGTGGATCTGGGACAGATTCACTCTTACCATCAGCAGTG TGCAGGCTGAAGACCTGGCAGTTTATTACTGTCAGCAAACCATCGTCTGGTCGTCGGTGGAGGCACCAAGCTGGAGCTGAAA | 64 |
| SC91.146 | Heavy Chain | CAAGTCCAACTGCAGCAGCCTGGGGCTGAGCTTGTGAAGCCTGGGGCTTCAGTGAAGGTGTCCTGCAAGGCTTCTGGCTACACCTTCACCAGCTACTGGATGCACTGGGTAAAACAGAGGCCTGG ACAGGGCCTTGAGTGGATCGGAGAGATTGATCCTTCTGATCGTTATACTAACTACAATCAAAAGTTCAAGGACAAGGCGACATTGACTGTAGACAACCTCCAGCACAGCCTACATGCAGCTCA GCAGCCTGACATCTGAGGACTCTGCGGTCTATTATTGTGCAATATCGGGCTGGGACTACTTTGACTACTGGGGCCAAGGGACCACCTCCTCACAGTCTCCTCA | 66 |

FIG. 9C (Cont.)

Anti-BMPR1B Murine Antibody Variable Region Nucleotide Sequences

| Name | Chain | Nucleic Acid Sequence | SEQ ID NO |
|---|---|---|---|
| SC91.149 | Light Chain | GATGTTGTGATGACCCAGACTCCACTCTCCCTGCCTGTCAGTCTTGGAGATCAAGCCTCCATCTCTTGCAGATCGAGTCAGAGCCTTGTACACAGTACTGGAAACACCTATTTCCATTGGTACCT GCAGAAGCCAGGCCAGTCTCCAAAGCTCCTGATCTACAAAGTTTCCAACCGATTTTCTGCTCTCAAAGTACACATGTTCCATTCACGTTCGGCTCGGGGACAAAGTTGGAAATAAAA AGGCTGAGGATCTGGGAGTTTATTTCTGCTCTCAAAGTACACATGTTCCATTCACGTTCGGCTCGGGGACAAAGTTGGAAATAAAA | 68 |
| SC91.149 | Heavy Chain | CAGGTCCAACTGCTCGAGCCTGGGGCTGAGCTTGTGAAGCCTGGGCTTCTTCAGTGAAGGTGTCCTGCAAGGTCTTCACCAACTACTGGATGCAGTGGGTGAAACAGAGGCCTGG ACAGGGCCTTGAGTGATCGGAGAGATTGATCCTTCTGATACAATCAAAGTTCAAGGCAAGGCCACATTGACTGTAGACACATCCTCAGCACCGCCTACACTGCAGCTCA GCAGCCTGACATCTGAGGACTCTGCGGTCTATTACTGTGCAAGATTTGGTTACTACTGGGGCCAAGGCACCACTCTCACAGTCTCCTCA | 70 |
| SC91.155 | Light Chain | AGTTTTGTGATGACCCAGACTCCCAGACTCCCTGCTTGTATCAGCAGGAGACAGGGTTACCATAACCTGCAAGGCCAGTCAGAATTTGGGTAATGATGTCGCTTGGTACCAACAGAAGCCAGGCCA GTCTCCTAGACTGCTGATATACTTTGCATCCAATCGCTACACTGGAGTCCCTGATCGCTTCACTGGCAGTGGATATGGGACGGATTTCACTTTCACCATCAGCAGTGCAGCTGAAGACCTGG CAGTTTATTTCTGCAGCAGGATTATAGCCTCTCCATTCACGTTCGGCTCGGGGACAAAGTTGGAAATAAAA | 72 |
| SC91.155 | Heavy Chain | CAGATCCAGTTGGTACAGTCTGGACCTGAGCTGAAGAAGCCTGGAGAGACAGTCAAGATCTCCTGCAAGGCTTCTGGGTATACCTTCACAACCTATGAATGAACTGGGTGAAACAGGCTCCAGG AAAGGGTTTAAAGTGGATGGGCTGGATAAACACCTACTCTGGAGTTGCCATATCCGGAAGCCTTCAAGGGACGGTTTGCCTTCTCTTTGCCAGACTTTGCCAGCACTGCCTATTTGCAGATCA ACAACCTCAGAGATGAGGACACGGCTACATATTTCTGTGCAAGATCCGAAACTGGTACTTCTGTGTCTGGGCACAGGGACCACGGTCACCGTCTCCTCA | 74 |
| SC91.160 | Light Chain | AGTTTTGTGATGACCCAGACTCCACTCTCCCTGCTTGTTTCAGCAGGAGACAGGGTTACCATAACCTGCAAGGCCAGTCAGAATATGGGTCATGATGTAGCTTGGTACCAACAGAAGCCAGGGCA GTCTCCTAAACTCCTGATACTCTGCATCCAATCGCTACACTGGAGTCCCTGATCGCTTCACTGGCAGTGGATATGGGACGGATTTCACTTTCACCATCAGCAGTGTGCAGGCTGAAGACCTGG CAGTTTATTTCTGCAGCAGGATTATAGCCTCTCCATTCACGTTCGGCTCGGGGACAAAGTTGGAAATGAAA | 76 |
| SC91.160 | Heavy Chain | CAGATCCAGTTGGTACAGTCTGGACCTGAGCTGAAGAAGCCTGGAGAGACAGTCAAGATCTCCTGCAAGGCTTCAGGGTATACCTTCACAACCTATGGAATGAACTGGGTGAAACAGGCTCCAGG AAAGGGTTTAAAGTGGATGGGCTGGATAAACACCTACTCTGGAGTGCCATATCCGGAAGCTTCAAGGGACGGTTTGCCTTCTCTGTATGACTTCAAGGGACGGTTTGCCTTCTCTCTATGACTTGCCAGCACTGCCTATTTGCTGTGATCA ACAACCTCAAAAATGAGGACACGGCTACATATTTCTGTGCAAGATCCGAAACTGGTACTTCTGTGTCTGGGCACAGGGACCACGGTCACCGTCTCCTCA | 78 |
| SC91.172 | Light Chain | GATGTTGTGATGACCCAGACTCCACTCTCCCTGCCTGTCAGTCTTGGAGATCAAGCCTCCATCTCTTGCAGATCTAGTCAGAGCCTTGTACACAGTACTGGAAACACCTATTTACATTGGTACCT GCAGAAGCCAGGCCAGTCTCCAAAGCTCCTGATCTACAAAGTTTCCAACCGATTTTCTGGGGTCCCAGACAGGTTCAGTGGCAGTGGATCAGGGACAGATTTCACACTCAAGATCAGCAGAGTGG AGGCTGAGGATCTGGGAGTTTATTTCTGCTCTCAAAGTACACATGTTCCATTCACGTTCGGCTCGGGGACAAAGTTGGAAATAAAA | 80 |
| SC91.172 | Heavy Chain | CAGGTCCAACTGCTCGAGCCTGGGGCTGAGCTTGTGAAGCCTGGACTTCTCAGTGAAGGTCTCTGCAAGGCTTCTGGCTACACCTTCACCAGTTATTGGATGCAGTGGGTAAAACAGAGGCCTGG ACAGGGCCTTGAGTGATCGGAGAGATTGATCCTTCTGATACCTATACTAAAAAGTTCAAGGGCAAGGCCACATTGACTGTTGACACATCCTCAGCACAGCCTACATGCAGCTCA GCAGCCTGACATCTGAGGACTCTGCGGTCTATTACTGTGCAAGATTTGGTTACTACTGGGGCCAAGGCACCACTCTCACAGTCTCTTCA | 82 |

FIG. 9C (Cont.)

Anti-BMPR1B Murine Antibody Variable Region Nucleotide Sequences

| Name | Chain | Nucleic Acid Sequence | SEQ ID NO |
|---|---|---|---|
| SC91.187 | Light Chain | GATGTTGTGATGACCCAAACTCCACTCTCCCTGCCTGTCAGTCTTGGAGAGCAAGCCTTCCATCTCTGCAGATCTAGTCAGAGCCTTGTACACAGTACTGAAACACCTATTTACATTGGTACCTGCAGAAGCCAGGCCAGTCTCCAAAGCTCCTGATCTACAAAGTTTCCAACCGATTTTCTGGGGTCCCAGACAGGTTCAGTGGCAGTGGATCAGGGACAGATTTCACACTCAAGATCAGCAGAGTGGAGGCTGAGGATCTGGGAGTTTATTTCTGCTCTCAAAGTACACATGTTCCATTCACGTTCGGCTCGGGGACAAAGTTGGAAATAAAA | 84 |
| SC91.187 | Heavy Chain | CAGGTCCAACTGCAGCAGCCTGGGGCTGAGTTGTGAAGCCTGGGGCTTCAGTGAAGCTGTCCTGCAAGGCTTCTGGCTACACCTTCACCAGCTACTGGGTGCAGTGGGTAAAACAGAGGCCTGGACAGGGCCTTGAGTGGATCGGAGAGATTGATCCTTCTGATAACTACTCTCTACAATCAAAATTTCAAGGGCAAGGCCACATTGACTGTGACACAGCCTACACAGCTCAGCCTCAGCTCAGCCTCAGCCTCAGCCTGACATCTGAGGACTCTGCGGTCTATTACTGTGCAAGATTGGTTTCTATGTTGACTACTGGGGCCAAGGCACCACTCTCACAGTCTCCTCA | 86 |
| SC91.20 | Light Chain | GATGTTGTGATGACCCAAACTCCACTCTCCCTGCCTGTCAGTCTTGGGGATCAAGCCTCCATCTCTGCAGATCTAGTCAGAGCCTTGTACACAGTACTGAAACACCTATTTACATTGGTACCTGCAGAAGCCAGGCCAGTCTCCAAACCTCCTGATCTACAAAGTTTCCAACCGATTTTCTGGGGTCCCAGACAGGTTCAGTGGCAGTGGATCAGGGACAGATTTCACACTCAAGATCAGCAGAGTGGAGGCTGAGGATCTGGGAGTTTATTTCTGCTCTCAAAGTACACATGTTCCATTCACGTTCGGCTCGGGGACAAAGTTGGAAATAAAA | 88 |
| SC91.20 | Heavy Chain | CAGGTCCAACTGCAGCAGCCTGGGGCTGAGGTTGTGAGGCCTGGGGCTTCTGTGAAGCTGTCCTGCAAGGCTTCTGGCTACACCTTCACCAGCTACTGGATGCAGTGGATAAAACAGAGGCCTGGACAGGGCCTTGAATGGATCGGAGAAATTGATCCTTCTGATAACTACTATACTATACAATCAGAAGTTCAAGGGCAAGGCCACATTGACTGTAGACACATCCTCCAGCAGCCTACATGCAGCTCAGCCTGACATCTGAGGACTCTGCGGTCTATTACTGTGCAAGATTGGTTTCTATGTTGACTACTGGGGCCAAGGCACCACTCTCACAGTCTCCTCA | 90 |
| SC91.27 | Light Chain | GATGTTGTGATGACCCAAACTCCACTCTCCCTGCCTGTCAGTCTTGGAGATCAAGCCTCTAGTCAGAGCCTTGTACACAGTACTGAAACACCTATTTACATTGGTACCTGCAGAAGCCAGGCCAGTCTCCAAACCTCCTGATCTACAAAGTTTCCAACCGATTTTCTGGGGTCCCAGACAGGTTCAGTGGCAGTGGATCAGGGACAGATTTCACACTCAAGATCAGCAGAGTGGAGGCTGAGGATCTGGGAGTTTATTTCTGCTCTCAAAGTACACATGTTCCATTCACGTTCGGCTCGGGGACAAAGTTGGAAATAAAA | 88 |
| SC91.27 | Heavy Chain | CAGGTCCAACTGCAGCAGCCTGGGGCTGAGGTTGTGAAGCCTGGGGCTTCAGTGAAGCTGTCCTGCAAGGCTTCTGGCTACACCTTCACCAACTACTGGATGCAGTGGATCAGTCAGAGCCTACAGCTCCAGCAGCCTACATGCAGCTCAGCCTGACATCTGAGGACTCTGCGGTCTATTACTGTGCAAGATTGGTTTCTATGTTGACTACTGGGGCCAAGGCACCACTCTCACAGTCTCCTCA | 92 |
| SC91.186 | Light Chain | GACATTGTGATGTCACAGTCTCCATCCTCCCTAGCTGTGTCAGTTGGAGAGAAGGTTACTATGAGCTGCAAGTCCAGTGAGTGCAGTTATATAGTAGCAATCAAAAGAACTACTTGGCCTGGTACCAGCAGAAACCAGGGCAGTCTCCTAAACTGCTGATTTACTGGGCATCCACTAGGGAATCTGGGGTCCCTGATCGCTTCACAGGCAGTGGATCTGGGACAGATTCACTCTCACCATCAGCAGTGTGAAGGCTGAAGACCTGGCAGTTTATTACTGTCAGCAATATTATAGCTATCCGCTCACGTTCGGTGCTGGGACCAAGCTGGAGCTGAAA | 36 |
| SC91.186 | Heavy Chain | CAAGTTACTCTGAAAGAGTCTGGCCTGGACCTGGTGAAACCTCCACAGTCCCTCAGTGACCTCAGTCTTCTTTCTCTGGGTTTTCACTGCGCACATCTGGTATGAATATAGGCTGGATTCGTCAGCCTTCAGGAAAGGGTCTGGAGTGGCTGACACATATTGGTGGAATGATGATAAGTCCTACAACCCAGCCGCACAATCTCAAGGATACCTCCAAGGAGTCCAAGCAGGTATTCCTCAAGATCGCCCAGTGTGTTGGTCACTGCAGATACCGCCACATACTACTGTGTTCGAGGTGACCGGTTTGCTTACTGGGGCCAAGGGACTCTGGTCACTGTCTCTGCA | 94 |

FIG. 9C (Cont.)

Anti-BMPR1B Humanized Antibody Variable Region Amino Acid Sequences

| Name | FR1 | CDR1 | FR2 | CDR2 | FR3 | CDR3 | FR4 | SEQ ID NO |
|---|---|---|---|---|---|---|---|---|
| hSC91.1 Light Chain | DIVMTQSPDSLAVSLGERATINC | RSSQSLVHSTGNTYLH | WYQQKPGQPPKLLIY | KVSNRFS | GVPDRFSGSGSGTDFTLTISSLQAEDVAVYYC | SQSTHVPFT | FGQGTKLEIK | 101 |
| hSC91.1 Heavy Chain | EVQLVQSGAEVKKPGESLKISCKGSGYSFT | SYWMQ | WVRQMPGKGLEWMG | EIDPSDNYTLYNQKFKG | QVTISADKSISTAYLQWSSLKASDTAMYYCAR | FGYYVDY | WGQGTTVTVSS | 103 |
| hSC91.1 N55Q Heavy Chain | EVQLVQSGAEVKKPGESLKISCKGSGYSFT | SYWMQ | WVRQMPGKGLEWMG | EIDPSDQYTLYNQKFKG | QVTISADKSISTAYLQWSSLKASDTAMYYCAR | FGYYVDY | WGQGTTVTVSS | 105 |
| hSC91.9 Light Chain | DIQMTQSPSSLSASVGDRVTITC | RASQDISNFLN | WYQQKPGKAPKLLIY | YTSRLHS | GVPSRFSGSGSGTDFTLTISSLQPEDFATYYC | QQGNTLPYT | FGGGTKVEIK | 107 |
| hSC91.9 Heavy Chain | QVQLVQSGAEVKKPGASVKVSCKASGYTFI | SYWMH | WVRQAPGQGLEWMG | MIHPNSGSTNYMENFKS | RVTMTRDTSTSTVYMELSSLRSEDTAVYYCAR | DLLIATVVTPYFAY | WGQGTLLTVSS | 109 |
| hSC91.1v2 N55Q Heavy Chain | QVQLQQPGAELVKPGASVKLSCKASGYTFT | SYWMQ | WVKQRPGQGLEWIG | EIDPSDQYTLYNQKFKG | KATLTVDTSSSTAYMQLSSLTSEDSAVYYCAR | FGYYVDY | WGLGTTLTVSS | 127 |

FIG. 9D

Anti-BMPR1B Humanized Antibody Full Length Amino Acid Sequences

| Name | Chain | Full Sequence | SEQ ID NO |
|---|---|---|---|
| hSC91.1 | Light Chain | DIVMTQSPDSLAVSLGERATINCRSSQSLVHSTGNTYLHWYQQKPGQPPKLLIYKVSNRFSGVPDRFSGSGSGTDFTLTISSLQAEDVAVYYCSQSTHVPFTFGQGTKLEIKRTVAAPSVFIFPPSDEQLKSGTASVVCL LNNFYPREAKVQWKVDNALQSGNSQESVTEQDSKDSTYSLSSTLTLSKADYEKHKVYACEVTHQGLSSPVTKSFNRGEC | 110 |
| hSC91.1 | Heavy Chain | EVQLVQSGAEVKKPGESLKISCKGSGYSFTSYWMQWVRQMPGKGLEWMGEIDPSDQYTLYNQKFKGQVTISADKSISTAYLQWSSLKASDTAMYYCARFGYYVDYWGQGTTVTVSSASTKGPSVFPLAPSSKSTSGGTAA LGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGN VFSCSVMHEALHNHYTQKSLSLSPG | 111 |
| hSC91.1M3 | Light Chain | DIVMTQSPDSLAVSLGERATINCRSSQSLVHSTGNTYLHWYQQKPGQPPKLLIYKVSNRFSGVPDRFSGSGSGTDFTLTISSLQAEDVAVYYCSQSTHVPFTFGQGTKLEIKRTVAAPSVFIFPPSDEQLKSGTASVVCL LNNFYPREAKVQWKVDNALQSGNSQESVTEQDSKDSTYSLSSTLTLSKADYEKHKVYACEVTHQGLSSPVTKSFNRGEC | 110 |
| hSC91.1M3 | Heavy Chain | EVQLVQSGAEVKKPGESLKISCKGSGYSFTSYWMQWVRQMPGKGLEWMGEIDPSDQYTLYNQKFKGQVTISADKSISTAYLQWSSLGTQTYICNVNHKPSNTKVDKKVEPKSCDKTHTCPPCPAPELLGGPSVFLFPPKPKDTLMISRTPEVTCVVVDVSHEDPEVKFNWYVDG VEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGN VFSCSVMHEALHNHYTQKSLSLSPG | 113 |
| hSC91.1ss1 | Light Chain | DIVMTQSPDSLAVSLGERATINCRSSQSLVHSTGNTYLHWYQQKPGQPPKLLIYKVSNRFSGVPDRFSGSGSGTDFTLTISSLQAEDVAVYYCSQSTHVPFTFGQGTKLEIKRTVAAPSVFIFPPSDEQLKSGTASVVCL LNNFYPREAKVQWKVDNALQSGNSQESVTEQDSKDSTYSLSSTLTLSKADYEKHKVYACEVTHQGLSSPVTKSFNRGEC | 110 |
| hSC91.1ss1 (N55Q) | Heavy Chain | EVQLVQSGAEVKKPGESLKISCKGSGYSFTSYWMQWVRQMPGKGLEWMGEIDPSDQYTLYNQKFKGQVTISADKSISTAYLQWSSLKASDTAMYYCARFGYYVDYWGQGTTVTVSSASTKGPSVFPLAPSSKSTSGGTAA LGCLVKDYFPEPVTVSWNSGALTSGVHTFPAVLQSSGLYSLSSVVTVPSSSLGTQTYICNVNHKPSNTKVDKKVEPKSSDKTHTCPPCPAPELLGGPSVFLFPPKPKDTLMISRTPEVTCVVVDVSHEDPEVKFNWYVDS VEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGN VFSCSVMHEALHNHYTQKSLSLSPG | 115 |
| hSC91.1ss1M3 | Light Chain | DIVMTQSPDSLAVSLGERATINCRSSQSLVHSTGNTYLHWYQQKPGQPPKLLIYKVSNRFSGVPDRFSGSGSGTDFTLTISSLQAEDVAVYYCSQSTHVPFTFGQGTKLEIKRTVAAPSVFIFPPSDEQLKSGTASVVCL LNNFYPREAKVQWKVDNALQSGNSQESVTEQDSKDSTYSLSSTLTLSKADYEKHKVYACEVTHQGLSSPVTKSFNRGEC | 110 |
| hSC91.1ss1M3 (N55Q) | Heavy Chain | EVQLVQSGAEVKKPGESLKISCKGSGYSFTSYWMQWVRQMPGKGLEWMGEIDPSDQYTLYNQKFKGQVTISADKSISTAYLQWSSLKASDTAMYYCARFGYYVDYWGQGTTVTVSSASTKGPSVFPLAPSSKSTSGGTAA LGCLVKDYFPEPVTVSWNSGALTSGVHTFPAVLQSSGLYSLSSVVTVPSSSLGTQTYICNVNHKPSNTKVDKKVEPKSSDKTHTCPPCPAPELLGGPSVFLFPPKPKDTLMISRTPEVTCVVVDVSHEDPEVKFNWYVDG VEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGN VFSCSVMHEALHNHYTQKSLSLSPG | 117 |

FIG. 9E

Anti-BMPR1B Humanized Antibody Full Length Amino Acid Sequences

| Name | Chain | Full Sequence | SEQ ID NO |
|---|---|---|---|
| hSC91.9 | Light Chain | DIQMTQSPSSLSASVGDRVTITCRASQDISNFLNWYQQKPGKAPKLLIYYTSRLHSGVPSRFSGSGSGTDFTLTISSLQPEDFATYYCQQGNTLPYTFPPSDEQLKSGTASVVCLLNNFY PREAKVQWKVDNALQSGNSQESVTEQDSKDSTYSLSSTLTLSKADYEKHKVYACEVTHQGLSSPVTKSFNRGEC | 120 |
| hSC91.9 | Heavy Chain | QVQLVQSGAEVKKPGASVKVSCKASGYTFISYWMHWVRQAPGQGLEWMGMIHPNSGSTNYNENFKSRVTMTRDTSTSTVYMELSSLRSEDTAVYYCARDLLIATVVTPYFAYWGQGTLVTVSSASTKGPSVFPLAPSSK STSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNKALPAPIEKTISKAKGQPREPQVVTLPPSRDELTKNQVSLTCLVKGFYPSDIAVEWESNGQPENNYKTTPPVLDSDGSFFLYSKLTVD KSRWQQGNVFSCSVMHEALHNHYTQKSLSLSPG | 121 |
| hSC91.9MJ | Light Chain | DIQMTQSPSSLSASVGDRVTITCRASQDISNFLNWYQQKPGKAPKLLIYYTSRLHSGVPSRFSGSGSGTDFTLTISSLQPEDFATYYCQQGNTLPYTFGGGTKVEIKRTVAAPSVFIFPPSDEQLKSGTASVVCLLNNFY PREAKVQWKVDNALQSGNSQESVTEQDSKDSTYSLSSTLTLSKADYEKHKVYACEVTHQGLSSPVTKSFNRGEC | 120 |
| hSC91.9MJ | Heavy Chain | QVQLVQSGAEVKKPGASVKVSCKASGYTFISYWMHWVRQAPGQGLEWMGMIHPNSGSTNYNENFKSRVTMTRDTSTSTVYMELSSLRSEDTAVYYCARDLLIATVVTPYFAYWGQGTLVTVSSASTKGPSVFPLAPSSK STSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEV KFNWYVDGVEVHNAKTKPREEQYASTYRVVSVLTVLHQDWLNGKEYKCKVSNKALPAPIEKTISKAKGQPREPQVVTLPPSRDELTKNQVSLTCLVKGFYPSDIAVEWESNGQPENNYKTTPPVLDSDGSFFLYSKLTVD KSRWQQGNVFSCSVMHEALHNHYTQKSLSLSPG | 123 |
| hSC91.9ss1MJ | Light Chain | DIQMTQSPSSLSASVGDRVTITCRASQDISNFLNWYQQKPGKAPKLLIYYTSRLHSGVPSRFSGSGSGTDFTLTISSLQPEDFATYYCQQGNTLPYTFGGGTKVEIKRTVAAPSVFIFPPSDEQLKSGTASVVCLLNNFY PREAKVQWKVDNALQSGNSQESVTEQDSKDSTYSLSSTLTLSKADYEKHKVYACEVTHQGLSSPVTKSFNRGEC | 120 |
| hSC91.9ss1MJ | Heavy Chain | QVQLVQSGAEVKKPGASVKVSCKASGYTFISYWMHWVRQAPGQGLEWMGMIHPNSGSTNYNENFKSRVTMTRDTSTSTVYMELSSLRSEDTAVYYCARDLLIATVVTPYFAYWGQGTLVTVSSASTKGPSVFPLAPSSK STSGGTAALGCLVKDYFPEPVTVSWNSGALTSGVHTFPAVLQSSGLYSLSSVVTVPSSSLGTQTYICNVNHKPSNTKVDKKVEPKSSDKTHTCPPCPAPELLGGPSVFLFPPKPKDTLMISRTPEVTCVVVDVSHEDPEV KFNWYVDGVEVHNAKTKPREEQYASTYRVVSVLTVLHQDWLNGKEYKCKVSNKALPAPIEKTISKAKGQPREPQVVTLPPSRDELTKNQVSLTCLVKGFYPSDIAVEWESNGQPENNYKTTPPVLDSDGSFFLYSKLTVD KSRWQQGNVFSCSVMHEALHNHYTQKSLSLSPG | 125 |

FIG. 9E (Cont.)

CDRs of SC91.1
Light and Heavy Chain Variable Regions

*Displaying 1 - 112 of 112 residues:*

| Query protein sequence | D | V | V | M | T | Q | T | P | L | S | L | P | V | S | L | G | D | Q | A | S |
|---|---|---|---|---|---|---|---|---|---|---|---|---|---|---|---|---|---|---|---|---|
| Chothia numbering | L1 | L2 | L3 | L4 | L5 | L6 | L7 | L8 | L9 | L10 | L11 | L12 | L13 | L14 | L15 | L16 | L17 | L18 | L19 | L20 |
| Chothia + numbering | L1 | L2 | L3 | L4 | L5 | L6 | L7 | L8 | L9 | L10 | L11 | L12 | L13 | L14 | L15 | L16 | L17 | L18 | L19 | L20 |
| Kabat numbering | L1 | L2 | L3 | L4 | L5 | L6 | L7 | L8 | L9 | L10 | L11 | L12 | L13 | L14 | L15 | L16 | L17 | L18 | L19 | L20 |

REGIONS:
- CHOTHIA: LFR1
- ABM: LFR1
- KABAT: LFR1
- CONTACT: LFR1

| | I | F | C | R | S | S | Q | S | L | V | H | S | T | G | N | T | Y | L | H | W | Y | L | Q |
|---|---|---|---|---|---|---|---|---|---|---|---|---|---|---|---|---|---|---|---|---|---|---|---|
| Chothia | L21 | L22 | L23 | L24 | L25 | L26 | L27 | L28 | L29 | L30 | L30A | L30B | L30C | L30D | L30E | L31 | L32 | L33 | L34 | L35 | L36 | L37 | L38 |
| Chothia+ | L21 | L22 | L23 | L24 | L25 | L26 | L27 | L28 | L29 | L30 | L30A | L30B | L30C | L30D | L30E | L31 | L32 | L33 | L34 | L35 | L36 | L37 | L38 |
| Kabat | L21 | L22 | L23 | L24 | L25 | L26 | L27 | L27A | L27B | L27C | L27D | L27E | L28 | L29 | L30 | L31 | L32 | L33 | L34 | L35 | L36 | L37 | L38 |

- CHOTHIA: CDR-L1 / LFR2
- ABM: CDR-L1 / LFR2
- KABAT: CDR-L1 / LFR2
- CONTACT: CDR-L1 / LFR2

| K | P | G | Q | S | P | K | L | L | I | Y | K | V | S | N | R | F | S | G | V | P | D | R |
|---|---|---|---|---|---|---|---|---|---|---|---|---|---|---|---|---|---|---|---|---|---|---|
| L39 | L40 | L41 | L42 | L43 | L44 | L45 | L46 | L47 | L48 | L49 | L50 | L51 | L52 | L53 | L54 | L55 | L56 | L57 | L58 | L59 | L60 | L61 |

- CHOTHIA: CDR-L2 / LFR3
- ABM: CDR-L2 / LFR3
- KABAT: CDR-L2 / LFR3
- CONTACT: CDR-L2 / LFR3

| F | S | G | S | G | S | G | T | D | F | T | L | K | I | S | R | V | E | A | E | D | L | G |
|---|---|---|---|---|---|---|---|---|---|---|---|---|---|---|---|---|---|---|---|---|---|---|
| L62 | L63 | L64 | L65 | L66 | L67 | L68 | L69 | L70 | L71 | L72 | L73 | L74 | L75 | L76 | L77 | L78 | L79 | L80 | L81 | L82 | L83 | L84 |

| V | Y | F | C | S | Q | S | T | H | V | P | F | T | F | G | S | G | T | K | L | E | I | K | SEQ ID NO: 21 |
|---|---|---|---|---|---|---|---|---|---|---|---|---|---|---|---|---|---|---|---|---|---|---|---|
| L85 | L86 | L87 | L88 | L89 | L90 | L91 | L92 | L93 | L94 | L95 | L96 | L97 | L98 | L99 | L100 | L101 | L102 | L103 | L104 | L105 | L106 | L107 | |

- CHOTHIA: CDR-L3 / LFR4
- ABM: CDR-L3 / LFR4
- KABAT: CDR-L3 / LFR4
- CONTACT: CDR-L3 / LFR4

LIGHT CHAIN

FIG. 9F

CDRs of SC91.1
Light and Heavy Chain Variable Regions

*Displaying 1 - 116 of 116 residues:*

| Query protein sequence | Q | V | Q | L | Q | Q | P | G | A | E | L | V | K | P | G | A | S | V | K | L |
|---|---|---|---|---|---|---|---|---|---|---|---|---|---|---|---|---|---|---|---|---|
| Chothia numbering | H1 | H2 | H3 | H4 | H5 | H6 | H7 | H8 | H9 | H10 | H11 | H12 | H13 | H14 | H15 | H16 | H17 | H18 | H19 | H20 |
| Chothia + numbering | H1 | H2 | H3 | H4 | H5 | H6 | H7 | H8 | H9 | H10 | H11 | H12 | H13 | H14 | H15 | H16 | H17 | H18 | H19 | H20 |
| Kabat numbering | H1 | H2 | H3 | H4 | H5 | H6 | H7 | H8 | H9 | H10 | H11 | H12 | H13 | H14 | H15 | H16 | H17 | H18 | H19 | H20 |

REGIONS:
- CHOTHIA: HFR1
- ABM: HFR1
- KABAT: HFR1
- CONTACT: HFR1

| S | C | K | A | S | G | Y | T | F | T | S | Y | W | M | Q | W | V | K | Q | R | P | G | Q |
|---|---|---|---|---|---|---|---|---|---|---|---|---|---|---|---|---|---|---|---|---|---|---|
| H21 | H22 | H23 | H24 | H25 | H26 | H27 | H28 | H29 | H30 | H31 | H32 | H33 | H34 | H35 | H36 | H37 | H38 | H39 | H40 | H41 | H42 | H43 |

CDR-H1 / HFR2 regions indicated.

| G | L | E | W | I | G | E | I | D | P | S | D | N | Y | T | L | Y | N | Q | K | F | K | G |
|---|---|---|---|---|---|---|---|---|---|---|---|---|---|---|---|---|---|---|---|---|---|---|
| H44 | H45 | H46 | H47 | H48 | H49 | H50 | H51 | H52 | H52A | H53 | H54 | H55 | H56 | H57 | H58 | H59 | H60 | H61 | H62 | H63 | H64 | H65 |

CDR-H2 / HFR3 regions indicated.

| K | A | T | L | T | V | D | T | S | S | S | T | A | Y | M | Q | L | S | S | L | T | S | E |
|---|---|---|---|---|---|---|---|---|---|---|---|---|---|---|---|---|---|---|---|---|---|---|
| H66 | H67 | H68 | H69 | H70 | H71 | H72 | H73 | H74 | H75 | H76 | H77 | H78 | H79 | H80 | H81 | H82 | H82A | H82B | H82C | H83 | H84 | H85 |
| H66 | H67 | H68 | H69 | H70 | H71 | H72 | H72A | H72B | H72C | H73 | H74 | H75 | H76 | H77 | H78 | H79 | H80 | H81 | H82 | H83 | H84 | H85 |

HFR3

| D | S | A | V | Y | Y | C | A | R | F | G | Y | Y | V | D | Y | W | G | L | G | T | T | L |
|---|---|---|---|---|---|---|---|---|---|---|---|---|---|---|---|---|---|---|---|---|---|---|
| H86 | H87 | H88 | H89 | H90 | H91 | H92 | H93 | H94 | H95 | H96 | H97 | H98 | H99 | H101 | H102 | H103 | H104 | H105 | H106 | H107 | H108 | H109 |

CDR-H3 / HFR4 regions indicated.

| T | V | S | S | SEQ ID NO: 23 |
|---|---|---|---|---|
| H110 | H111 | H112 | H113 | |

HEAVY CHAIN

FIG. 9F (CONT.)

CDRs of SC91.9
Light and Heavy Chain Variable Regions

*Displaying 1 - 107 of 107 residues:*

| Query protein sequence | D | I | Q | M | T | Q | T | T | S | S | L | S | A | S | L | G | D | R | V | T |
|---|---|---|---|---|---|---|---|---|---|---|---|---|---|---|---|---|---|---|---|---|
| Chothia numbering | L1 | L2 | L3 | L4 | L5 | L6 | L7 | L8 | L9 | L10 | L11 | L12 | L13 | L14 | L15 | L16 | L17 | L18 | L19 | L20 |
| Chothia + numbering | L1 | L2 | L3 | L4 | L5 | L6 | L7 | L8 | L9 | L10 | L11 | L12 | L13 | L14 | L15 | L16 | L17 | L18 | L19 | L20 |
| Kabat numbering | L1 | L2 | L3 | L4 | L5 | L6 | L7 | L8 | L9 | L10 | L11 | L12 | L13 | L14 | L15 | L16 | L17 | L18 | L19 | L20 |

REGIONS: CHOTHIA — LFR1
ABM — LFR1
KABAT — LFR1
CONTACT — LFR1

| I | S | C | R | A | S | Q | D | I | S | N | F | L | N | W | Y | Q | Q | K | P | D | G | T |
|---|---|---|---|---|---|---|---|---|---|---|---|---|---|---|---|---|---|---|---|---|---|---|
| L21 | L22 | L23 | L24 | L25 | L26 | L27 | L28 | L29 | L30 | L31 | L32 | L33 | L34 | L35 | L36 | L37 | L38 | L39 | L40 | L41 | L42 | L43 |

CDR-L1 / LFR2 (Chothia, ABM, Kabat, Contact variations)

| I | K | L | L | I | Y | Y | T | S | R | L | H | S | G | V | P | S | R | F | S | G | S | G |
|---|---|---|---|---|---|---|---|---|---|---|---|---|---|---|---|---|---|---|---|---|---|---|
| L44 | L45 | L46 | L47 | L48 | L49 | L50 | L51 | L52 | L53 | L54 | L55 | L56 | L57 | L58 | L59 | L60 | L61 | L62 | L63 | L64 | L65 | L66 |

CDR-L2 / LFR3

| S | G | T | D | Y | S | L | T | I | R | N | L | E | Q | E | D | I | A | T | Y | F | C | Q |
|---|---|---|---|---|---|---|---|---|---|---|---|---|---|---|---|---|---|---|---|---|---|---|
| L67 | L68 | L69 | L70 | L71 | L72 | L73 | L74 | L75 | L76 | L77 | L78 | L79 | L80 | L81 | L82 | L83 | L84 | L85 | L86 | L87 | L88 | L89 |

CDR-L3

| Q | G | N | T | L | P | Y | T | F | G | G | G | T | K | L | E | I | K | SEQ ID NO: 29 |
|---|---|---|---|---|---|---|---|---|---|---|---|---|---|---|---|---|---|---|
| L90 | L91 | L92 | L93 | L94 | L95 | L96 | L97 | L98 | L99 | L100 | L101 | L102 | L103 | L104 | L105 | L106 | L107 | |

LFR4

▲ Unusual residue (<1% of sequences)

LIGHT CHAIN

FIG. 9G

CDRs of SC91.9
Light and Heavy Chain Variable Regions

*Displaying 1 - 124 of 124 residues:*

| Query protein sequence | Q | V | Q | L | Q | Q | P | G | A | E | L | V | K | P | G | A | S | V | K | L |
|---|---|---|---|---|---|---|---|---|---|---|---|---|---|---|---|---|---|---|---|---|
| Chothia numbering | H1 | H2 | H3 | H4 | H5 | H6 | H7 | H8 | H9 | H10 | H11 | H12 | H13 | H14 | H15 | H16 | H17 | H18 | H19 | H20 |
| Chothia + numbering | H1 | H2 | H3 | H4 | H5 | H6 | H7 | H8 | H9 | H10 | H11 | H12 | H13 | H14 | H15 | H16 | H17 | H18 | H19 | H20 |
| Kabat numbering | H1 | H2 | H3 | H4 | H5 | H6 | H7 | H8 | H9 | H10 | H11 | H12 | H13 | H14 | H15 | H16 | H17 | H18 | H19 | H20 |

REGIONS:
- CHOTHIA: HFR1
- ABM: HFR1
- KABAT: HFR1
- CONTACT: HFR1

| | S | C | K | A | S | G | Y | T | F | I | S | Y | W | M | H | W | V | K | Q | R | P | G | Q |
|---|---|---|---|---|---|---|---|---|---|---|---|---|---|---|---|---|---|---|---|---|---|---|---|
| | H21 | H22 | H23 | H24 | H25 | H26 | H27 | H28 | H29 | H30 | H31 | H32 | H33 | H34 | H35 | H36 | H37 | H38 | H39 | H40 | H41 | H42 | H43 |
| | H21 | H22 | H23 | H24 | H25 | H26 | H27 | H28 | H29 | H30 | H31 | H32 | H33 | H34 | H35 | H36 | H37 | H38 | H39 | H40 | H41 | H42 | H43 |
| | H21 | H22 | H23 | H24 | H25 | H26 | H27 | H28 | H29 | H30 | H31 | H32 | H33 | H34 | H35 | H36 | H37 | H38 | H39 | H40 | H41 | H42 | H43 |

Regions: CDR-H1 / HFR2 (with varying boundaries per numbering scheme)

| G | L | E | W | I | G | M | I | H | P | N | S | G | S | T | N | Y | N | E | S | F | K | S |
|---|---|---|---|---|---|---|---|---|---|---|---|---|---|---|---|---|---|---|---|---|---|---|
| H44 | H45 | H46 | H47 | H48 | H49 | H50 | H51 | H52 | *H52A* | H53 | H54 | H55 | H56 | H57 | H58 | H59 | H60 | H61 | H62 | H63 | H64 | H65 |

Regions: CDR-H2 / HFR3

| K | A | T | L | T | V | D | K | S | S | S | T | A | Y | M | Q | L | S | S | L | T | S | E |
|---|---|---|---|---|---|---|---|---|---|---|---|---|---|---|---|---|---|---|---|---|---|---|
| H66 | H67 | H68 | H69 | H70 | H71 | H72 | H73 | H74 | H75 | H76 | H77 | H78 | H79 | H80 | H81 | H82 | *H82A* | *H82B* | *H82C* | H83 | H84 | H85 |
| H66 | H67 | H68 | H69 | H70 | H71 | H72 | *H72A* | *H72B* | *H72C* | H73 | H74 | H75 | H76 | H77 | H78 | H79 | H80 | H81 | H82 | H83 | H84 | H85 |
| H66 | H67 | H68 | H69 | H70 | H71 | H72 | H73 | H74 | H75 | H76 | H77 | H78 | H79 | H80 | H81 | H82 | *H82A* | *H82B* | *H82C* | H83 | H84 | H85 |

HFR3

| D | S | A | V | Y | Y | C | A | R | D | L | L | I | A | T | V | V | V | T | P | Y | F | A |
|---|---|---|---|---|---|---|---|---|---|---|---|---|---|---|---|---|---|---|---|---|---|---|
| H86 | H87 | H88 | H89 | H90 | H91 | H92 | H93 | H94 | H95 | H96 | H97 | H98 | H99 | H100 | *H100A* | *H100B* | *H100C* | *H100D* | *H100E* | *H100F* | *H100G* | H101 |

Regions: CDR-H3

| Y | W | G | Q | G | T | L | T | V | S | S | SEQ ID NO: 31 |
|---|---|---|---|---|---|---|---|---|---|---|---|
| H102 | H103 | H104 | H105 | H106 | H107 | H108 | H109 | H110 | H111 | H112 | H113 |

HFR4

HEAVY CHAIN

FIG. 9G (CONT.)

Anti-BMPR1B Antibodies Detect BMPR1B Protein on Luminal B Breast PDX Tumors

| Annotation Name | H-Score For Membrane Staining | % of Cells Positive |
|---|---|---|
| BR153 | 80 | 60 |
| BR154 | 0 | 0 |
| BR155 | 0 | 0 |
| BR156 | 95 | 70 |
| BR158 | 30 | 70 |
| BR159 | 35 | 35 |
| BR160 | 0 | 0 |
| BR162 | 90 | 70 |
| BR163 | 20 | 20 |
| BR164 | 60 | 60 |
| BR165 | 30 | 30 |
| BR166 | 0 | 0 |
| BR167 | 85 | 50 |

FIG. 11A

BMPR1B ADC Modulators Suppress Tumor Initiating Cell Frequency *In Vivo*

Anti-BMPR1B Antibodies Exhibit the Ability to Modulate the Interactions of BMPR1B and BMP2/4

| antibody | % inhibition of BMP4 ligand receptor interaction | % inhibition of BMP2 ligand receptor interaction | antibody | % inhibition of BMP4 ligand receptor interaction | % inhibition of BMP2 ligand receptor interaction | antibody | % inhibition of BMP4 ligand receptor interaction | % inhibition of BMP2 ligand receptor interaction |
|---|---|---|---|---|---|---|---|---|
| SC91.101 | 72% | 36% | SC91.133 | 0% | 5% | SC91.165 | 62% | 32% |
| SC91.102 | 80% | 35% | SC91.134 | 44% | 10% | SC91.166 | 27% | 22% |
| SC91.103 | 32% | 25% | SC91.135 | 64% | 26% | SC91.167 | 81% | 47% |
| SC91.104 | 56% | 24% | SC91.136 | 16% | 15% | SC91.9 | 93% | 50% |
| SC91.105 | 80% | 44% | SC91.137 | 85% | 19% | SC91.169 | 79% | 47% |
| SC91.106 | 38% | 20% | SC91.138 | 79% | 10% | SC91.170 | 82% | 51% |
| SC91.107 | 56% | 21% | SC91.139 | 83% | 25% | SC91.171 | 89% | 51% |
| SC91.108 | 79% | 43% | SC91.140 | 79% | 17% | SC91.172 | 81% | 51% |
| SC91.109 | 77% | 49% | SC91.141 | 74% | 23% | SC91.173 | 67% | 32% |
| SC91.110 | 12% | 30% | SC91.142 | 30% | 3% | SC91.174 | 61% | 27% |
| SC91.111 | 69% | 36% | SC91.143 | 5% | 5% | SC91.175 | 25% | 10% |
| SC91.112 | 22% | 28% | SC91.144 | 77% | 31% | SC91.176 | 69% | 27% |
| SC91.113 | 79% | 37% | SC91.145 | 79% | 32% | SC91.177 | 74% | 32% |
| SC91.114 | 78% | 28% | SC91.146 | 79% | 29% | SC91.178 | 49% | 32% |
| SC91.115 | 25% | 12% | SC91.147 | 8% | 11% | SC91.179 | 68% | 40% |
| SC91.116 | 28% | N/A | SC91.148 | 79% | 35% | SC91.180 | 69% | 35% |
| SC91.117 | 63% | 27% | SC91.149 | 84% | 47% | SC91.181 | 81% | 43% |
| SC91.118 | 63% | 10% | SC91.150 | 26% | 26% | SC91.182 | 81% | 42% |
| SC91.119 | 65% | 35% | SC91.151 | 25% | 20% | SC91.183 | 81% | 40% |
| SC91.1 | 75% | 38% | SC91.152 | 66% | 62% | SC91.184 | 79% | 43% |
| SC91.121 | 80% | 37% | SC91.153 | 73% | 42% | SC91.185 | 71% | 34% |
| SC91.122 | 36% | 20% | SC91.154 | 48% | 27% | SC91.186 | 26% | 13% |
| SC91.123 | 73% | 37% | SC91.155 | 79% | 49% | SC91.187 | 83% | 37% |
| SC91.124 | 64% | 34% | SC91.156 | 27% | 35% | SC91.188 | 16% | 35% |
| SC91.125 | 68% | 28% | SC91.157 | 86% | 53% | SC91.189 | 61% | 38% |
| SC91.126 | 78% | 26% | SC91.158 | 61% | 46% | SC91.190 | 68% | 29% |
| SC91.127 | 52% | 32% | SC91.159 | 77% | 51% | SC91.191 | 58% | 32% |
| SC91.128 | 61% | 31% | SC91.160 | 79% | 47% | SC91.192 | 65% | 28% |
| SC91.129 | 83% | 40% | SC91.161 | 79% | 47% | SC91.193 | 85% | 42% |
| SC91.130 | 78% | 32% | SC91.162 | 68% | 25% | SC91.19 | 61% | 32% |
| SC91.131 | 77% | 29% | SC91.163 | 76% | 41% | SC91.195 | 81% | 41% |
| SC91.132 | 36% | 15% | SC91.164 | 63% | 30% | SC91.15 | 92% | 11% |

FIG. 19A

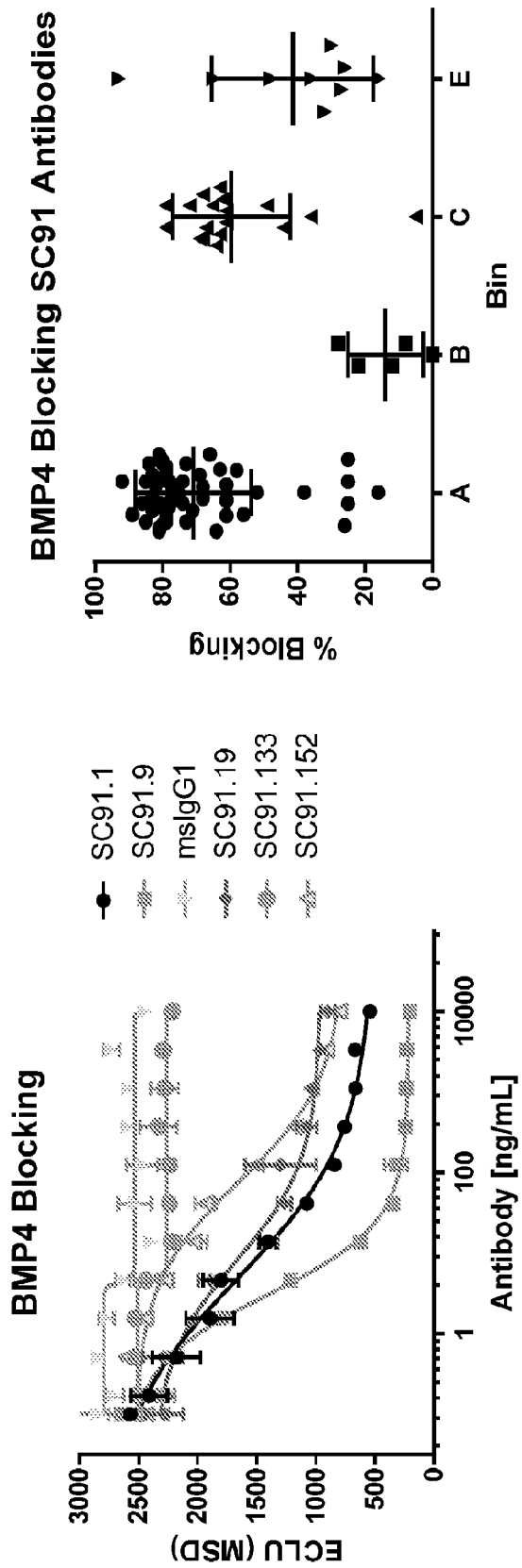

SEQUENCE LISTING

<160> NUMBER OF SEQ ID NOS: 127

<210> SEQ ID NO 1
<211> LENGTH: 502
<212> TYPE: PRT
<213> ORGANISM: Homo sapiens
<220> FEATURE:
<221> NAME/KEY: MISC_FEATURE
<223> OTHER INFORMATION: Human BMPR1B Amino Acid Sequence

<400> SEQUENCE: 1

Met Leu Leu Arg Ser Ala Gly Lys Leu Asn Val Gly Thr Lys Lys Glu
1               5                   10                  15

Asp Gly Glu Ser Thr Ala Pro Thr Pro Arg Pro Lys Val Leu Arg Cys
            20                  25                  30

Lys Cys His His His Cys Pro Glu Asp Ser Val Asn Asn Ile Cys Ser
        35                  40                  45

Thr Asp Gly Tyr Cys Phe Thr Met Ile Glu Asp Asp Ser Gly Leu
    50                  55                  60

Pro Val Val Thr Ser Gly Cys Leu Gly Leu Glu Gly Ser Asp Phe Gln
65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
            100                 105                 110

Leu Lys Asn Arg Asp Phe Val Asp Gly Pro Ile His His Arg Ala Leu
        115                 120                 125

Leu Ile Ser Val Thr Val Cys Ser Leu Leu Leu Val Leu Ile Ile Leu
    130                 135                 140

Phe Cys Tyr Phe Arg Tyr Lys Arg Gln Glu Thr Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
        195                 200                 205

Gln Ile Gly Lys Gly Arg Tyr Gly Glu Val Trp Met Gly Lys Trp Arg
    210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
        275                 280                 285

Asp Tyr Leu Lys Ser Thr Thr Leu Asp Ala Lys Ser Met Leu Lys Leu
    290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
                325                 330                 335

Asn Ile Leu Val Lys Lys Asn Gly Thr Cys Cys Ile Ala Asp Leu Gly
            340                 345                 350

```
Leu Ala Val Lys Phe Ile Ser Asp Thr Asn Glu Val Asp Ile Pro Pro
            355                 360                 365

Asn Thr Arg Val Gly Thr Lys Arg Tyr Met Pro Pro Glu Val Leu Asp
370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Val Ala Arg Arg Cys Val Ser
                405                 410                 415

Gly Gly Ile Val Glu Glu Tyr Gln Leu Pro Tyr His Asp Leu Val Pro
                420                 425                 430

Ser Asp Pro Ser Tyr Glu Asp Met Arg Glu Ile Val Cys Ile Lys Lys
                435                 440                 445

Leu Arg Pro Ser Phe Pro Asn Arg Trp Ser Ser Asp Glu Cys Leu Arg
450                 455                 460

Gln Met Gly Lys Leu Met Thr Glu Cys Trp Ala His Asn Pro Ala Ser
465                 470                 475                 480

Arg Leu Thr Ala Leu Arg Val Lys Lys Thr Leu Ala Lys Met Ser Glu
                485                 490                 495

Ser Gln Asp Ile Lys Leu
                500

<210> SEQ ID NO 2
<211> LENGTH: 329
<212> TYPE: PRT
<213> ORGANISM: Homo sapiens
<220> FEATURE:
<221> NAME/KEY: MISC_FEATURE
<223> OTHER INFORMATION: IgG1 heavy chain constant region protein

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205
```

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 3
<211> LENGTH: 329
<212> TYPE: PRT
<213> ORGANISM: Homo sapiens
<220> FEATURE:
<221> NAME/KEY: MISC_FEATURE
<223> OTHER INFORMATION: C220S IgG1 heavy chain constant region protein

<400> SEQUENCE: 3

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
```

```
                225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 4
<211> LENGTH: 328
<212> TYPE: PRT
<213> ORGANISM: Homo sapiens
<220> FEATURE:
<221> NAME/KEY: MISC_FEATURE
<223> OTHER INFORMATION: C220delta IgG1 heavy chain constant region
      protein

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255
```

```
Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 5
<211> LENGTH: 107
<212> TYPE: PRT
<213> ORGANISM: Homo sapiens
<220> FEATURE:
<221> NAME/KEY: MISC_FEATURE
<223> OTHER INFORMATION: kappa light chain constant region protein

<400> SEQUENCE: 5

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 6
<211> LENGTH: 107
<212> TYPE: PRT
<213> ORGANISM: Homo sapiens
<220> FEATURE:
<221> NAME/KEY: MISC_FEATURE
<223> OTHER INFORMATION: C214S kappa light chain constant region protein

<400> SEQUENCE: 6

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105
```

```
<210> SEQ ID NO 7
<211> LENGTH: 106
<212> TYPE: PRT
<213> ORGANISM: Homo sapiens
<220> FEATURE:
<221> NAME/KEY: MISC_FEATURE
<223> OTHER INFORMATION: C214delta kappa light chain constant region

<400> SEQUENCE: 7

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu
            100                 105

<210> SEQ ID NO 8
<211> LENGTH: 105
<212> TYPE: PRT
<213> ORGANISM: Homo sapiens
<220> FEATURE:
<221> NAME/KEY: MISC_FEATURE
<223> OTHER INFORMATION: lambda light chain constant region protein

<400> SEQUENCE: 8

Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Gly Ser Pro Val
        35                  40                  45

Lys Ala Gly Val Glu Thr Thr Lys Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 9
<211> LENGTH: 105
<212> TYPE: PRT
<213> ORGANISM: Homo sapiens
<220> FEATURE:
<221> NAME/KEY: MISC_FEATURE
<223> OTHER INFORMATION: C214S lambda light chain constant region
      protein

<400> SEQUENCE: 9

Gln Pro Lys Ala Asn Pro Thr Val Thr Leu Phe Pro Pro Ser Ser Glu
1               5                   10                  15
```

```
Glu Leu Gln Ala Asn Lys Ala Thr Leu Val Cys Leu Ile Ser Asp Phe
             20                  25                  30

Tyr Pro Gly Ala Val Thr Val Ala Trp Lys Ala Asp Gly Ser Pro Val
         35                  40                  45

Lys Ala Gly Val Glu Thr Thr Lys Pro Ser Lys Gln Ser Asn Asn Lys
 50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
             85                  90                  95

Lys Thr Val Ala Pro Thr Glu Ser Ser
            100                 105

<210> SEQ ID NO 10
<211> LENGTH: 104
<212> TYPE: PRT
<213> ORGANISM: Homo sapiens
<220> FEATURE:
<221> NAME/KEY: MISC_FEATURE
<223> OTHER INFORMATION: C214delta lambda light chain constant region
      protein

<400> SEQUENCE: 10

Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
             20                  25                  30

Tyr Pro Gly Ala Val Thr Val Ala Trp Lys Ala Asp Gly Ser Pro Val
         35                  40                  45

Lys Ala Gly Val Glu Thr Thr Lys Pro Ser Lys Gln Ser Asn Asn Lys
 50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
             85                  90                  95

Lys Thr Val Ala Pro Thr Glu Ser
            100

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000
```

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20
<211> LENGTH: 336
<212> TYPE: DNA
<213> ORGANISM: Mus musculus
<220> FEATURE:
<221> NAME/KEY: misc_feature
<223> OTHER INFORMATION: SC91.1 Light Chain Variable Region

<400> SEQUENCE: 20

```
gatgttgtga tgacccaaac tccactctcc ctgcctgtca gtcttggaga tcaagcctcc      60
atcttttgca gatctagtca gagccttgta cacagtactg gaaacaccta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttcca     300
ttcacgttcg gctcggggac aaagttggaa ataaaa                               336
```

<210> SEQ ID NO 21
<211> LENGTH: 112
<212> TYPE: PRT
<213> ORGANISM: Mus musculus
<220> FEATURE:
<221> NAME/KEY: MISC_FEATURE
<223> OTHER INFORMATION: SC91.1 Light Chain Variable Region

<400> SEQUENCE: 21

Asp Val Val Met Thr Gln Thr Pro Leu Ser Leu Pro Val Ser Leu Gly
1               5                   10                  15

Asp Gln Ala Ser Ile Phe Cys Arg Ser Ser Gln Ser Leu Val His Ser
            20                  25                  30

Thr Gly Asn Thr Tyr Leu His Trp Tyr Leu Gln Lys Pro Gly Gln Ser
        35                  40                  45

```
Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
 65              70                  75                      80

Ser Arg Val Glu Ala Glu Asp Leu Gly Val Tyr Phe Cys Ser Gln Ser
                 85                  90                  95

Thr His Val Pro Phe Thr Phe Gly Ser Gly Thr Lys Leu Glu Ile Lys
            100                 105                 110

<210> SEQ ID NO 22
<211> LENGTH: 348
<212> TYPE: DNA
<213> ORGANISM: Mus musculus
<220> FEATURE:
<221> NAME/KEY: misc_feature
<223> OTHER INFORMATION: SC91.1 Heavy Chain Variable Region

<400> SEQUENCE: 22
caggtccaac tgcagcagcc tggggctgaa cttgtgaagc ctggggcttc agtgaagctg      60
tcctgcaagg cttctggcta caccttcacc agctactgga tgcagtgggt aaaacagagg     120
cctggacagg gccttgagtg gatcggagag attgatcctt ctgataacta tactctctac     180
aatcaaaagt tcaagggcaa ggccacgttg actgtagaca catcctccag cacagcctac     240
atgcagctca gcagcctgac atctgaggac tctgcggtct attactgtgc aaggtttggt     300
tactatgttg actactgggg cctaggcacc actctcacag tctcctca                  348

<210> SEQ ID NO 23
<211> LENGTH: 115
<212> TYPE: PRT
<213> ORGANISM: Mus musculus
<220> FEATURE:
<221> NAME/KEY: MISC_FEATURE
<223> OTHER INFORMATION: SC91.1 Heavy Chain Variable Region

<400> SEQUENCE: 23

Gln Val Gln Leu Gln Gln Pro Gly Ala Glu Leu Val Lys Pro Gly Ala
  1               5                  10                  15

Ser Val Lys Leu Ser Cys Lys Ala Ser Gly Tyr Thr Phe Thr Ser Tyr
             20                  25                  30

Trp Met Gln Trp Val Lys Gln Arg Pro Gly Gln Gly Leu Glu Trp Ile
         35                  40                  45

Gly Glu Ile Asp Pro Ser Asp Asn Thr Leu Tyr Asn Gln Lys Phe Lys
 50                  55                  60

Gly Lys Ala Thr Leu Thr Val Asp Thr Ser Ser Ser Thr Ala Tyr Met
 65                  70                  75                  80

Gln Leu Ser Ser Leu Thr Ser Glu Asp Ser Ala Val Tyr Tyr Cys Ala
                 85                  90                  95

Arg Phe Gly Tyr Tyr Val Asp Tyr Trp Gly Leu Gly Thr Thr Leu Thr
            100                 105                 110

Val Ser Ser
        115

<210> SEQ ID NO 24
<211> LENGTH: 336
<212> TYPE: DNA
<213> ORGANISM: Mus musculus
<220> FEATURE:
<221> NAME/KEY: misc_feature
<223> OTHER INFORMATION: SC91.3 Light Chain Variable Region
```

<400> SEQUENCE: 24

```
gatgttgtga tgacccaaac tccactctcc ctgcctgtca gtcttggaga tcaagcctcc    60
atctcttgca gatctagtca gagccttgta cacagtactg gaaacaccta tttacattgg   120
tacctgcaga agccaggcca gtctccaaaa ctcctgatct acaaagtttc caaccgattt   180
tctggggtcc cagacaggtt cagtggcagt ggatcaggga cagatttcac actcaagatc   240
agcagagtgg aggctgagga tctgggagtt tatttctgct ctcaaagtac acatgttcca   300
ttcacgttcg gctcggggac aaagttggaa ataaaa                             336
```

<210> SEQ ID NO 25
<211> LENGTH: 112
<212> TYPE: PRT
<213> ORGANISM: Mus musculus
<220> FEATURE:
<221> NAME/KEY: MISC_FEATURE
<223> OTHER INFORMATION: SC91.3 Light Chain Variable Region

<400> SEQUENCE: 25

```
Asp Val Val Met Thr Gln Thr Pro Leu Ser Leu Pro Val Ser Leu Gly
1               5                   10                  15
Asp Gln Ala Ser Ile Ser Cys Arg Ser Ser Gln Ser Leu Val His Ser
            20                  25                  30
Thr Gly Asn Thr Tyr Leu His Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Phe Cys Ser Gln Ser
                85                  90                  95
Thr His Val Pro Phe Thr Phe Gly Ser Gly Thr Lys Leu Glu Ile Lys
            100                 105                 110
```

<210> SEQ ID NO 26
<211> LENGTH: 348
<212> TYPE: DNA
<213> ORGANISM: Mus musculus
<220> FEATURE:
<221> NAME/KEY: misc_feature
<223> OTHER INFORMATION: SC91.3 Heavy Chain Variable Region

<400> SEQUENCE: 26

```
caggtccaac tgcagcagcc tggggctgag cttgtgaagc ctggggcttc agtgaagctg    60
tcctgcaagg cttctggcta caccttcacc agctactgga tgcagtgggt aaaacagagg   120
cctggacagg gccttgaatg gatcggagag attgatcctt ctgatagcta cactctctac   180
aatcaaaaat tcaagggcaa ggccacattg actgtagaca tcctccag  cacagcctac    240
atgcagctca gcagcctgac atctgaggac tctgcggtct atttctgtgc aagatttggt   300
tactatattg agtactgggg ccaaggcacc actctcacag tctcctca                348
```

<210> SEQ ID NO 27
<211> LENGTH: 116
<212> TYPE: PRT
<213> ORGANISM: Mus musculus
<220> FEATURE:
<221> NAME/KEY: MISC_FEATURE
<223> OTHER INFORMATION: SC91.3 Heavy Chain Variable Region

<400> SEQUENCE: 27

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Glu Ile Asp Pro Ser Asp Ser Tyr Thr Leu Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Phe Gly Tyr Tyr Ile Glu Tyr Trp Gly Gln Gly Thr Thr Leu
            100                 105                 110

Thr Val Ser Ser
        115

<210> SEQ ID NO 28
<211> LENGTH: 321
<212> TYPE: DNA
<213> ORGANISM: Mus musculus
<220> FEATURE:
<221> NAME/KEY: misc_feature
<223> OTHER INFORMATION: SC91.9 Light Chain Variable Region

<400> SEQUENCE: 28
gatatccaga tgacacagac tacatcctcc ctgtctgcct ctctgggaga cagagtcacc      60
atcagttgca gggcaagtca ggacattagc aattttttaa actggtatca gcagaaacca     120
gatggaacta ttaaattcct gatctactac acatcaagat acactcagg agtcccatca      180 aggttcagtg gcagtgggtc tggaacagat tattctctca ccattcgcaa cctggagcaa     240
gaagatattg ccacttactt ttgccaacag ggtaatacgc ttccgtacac gttcggaggg     300
gggaccaagc tggaaataaa a                                               321

<210> SEQ ID NO 29
<211> LENGTH: 107
<212> TYPE: PRT
<213> ORGANISM: Mus musculus
<220> FEATURE:
<221> NAME/KEY: MISC_FEATURE
<223> OTHER INFORMATION: SC91.9 Light Chain Variable Region

<400> SEQUENCE: 29

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Phe
            20                  25                  30

Leu Asn Trp Tyr Gln Gln Lys Pro Asp Gly Thr Ile Lys Phe Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Arg Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105
```

<210> SEQ ID NO 30
<211> LENGTH: 372
<212> TYPE: DNA
<213> ORGANISM: Mus musculus
<220> FEATURE:
<221> NAME/KEY: misc_feature
<223> OTHER INFORMATION: SC91.9 Heavy Chain Variable Region

<400> SEQUENCE: 30

```
caggtccaac tgcagcagcc tggggctgag ctggtaaagc ctggggcttc agtgaagttg      60
tcctgcaagg cttctggcta cactttcatc agttactgga tgcactgggt gaagcagagg     120
cctggacaag gccttgagtg gattggaatg attcatccta atagtggtag tactaactac     180
aatgagagtt tcaagagcaa ggccacactg actgtagaca atcctccag  tacagcctac     240
atgcaactca gcagcctgac atctgaggac tctgcggtct attactgtgc aagggactta    300
cttattgcta cggtagtagt tactccttac tttgcctact ggggccaagg cactattctc    360
acagtctcct ca                                                         372
```

<210> SEQ ID NO 31
<211> LENGTH: 124
<212> TYPE: PRT
<213> ORGANISM: Mus musculus
<220> FEATURE:
<221> NAME/KEY: MISC_FEATURE
<223> OTHER INFORMATION: SC91.9 Heavy Chain Variable Region

<400> SEQUENCE: 31

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ile Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr Asn Tyr Asn Glu Ser Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Leu Leu Ile Ala Thr Val Val Thr Pro Tyr Phe Ala
            100                 105                 110

Tyr Trp Gly Gln Gly Thr Ile Leu Thr Val Ser Ser
        115                 120

<210> SEQ ID NO 32
<211> LENGTH: 321
<212> TYPE: DNA
<213> ORGANISM: Mus musculus
<220> FEATURE:
<221> NAME/KEY: misc_feature
<223> OTHER INFORMATION: SC91.11 Light Chain Variable Region

<400> SEQUENCE: 32

```
gacattgtga tgacccagtc tcaaaaattc atgtccacat cagtaggaga cagggtcagc      60
gtcacctgca aggccagtca gaatgtgggt actaatgtat tctggtatca acagaaacca    120
gggcaatctc ctaaagcact gatttacgcg gcatcttacc ggtacagtgg agtccctgat    180
cgcttcacag gcagtggatc tgggacagat ttcactctca ccatcagcaa tgtgcagtct    240
```

```
gaagacttgg cagattattt ctgtcagcaa tatgacagct atcctctcac gttcggtgat    300
gggaccaagc tggagctgag a                                              321
```

<210> SEQ ID NO 33
<211> LENGTH: 107
<212> TYPE: PRT
<213> ORGANISM: Mus musculus
<220> FEATURE:
<221> NAME/KEY: MISC_FEATURE
<223> OTHER INFORMATION: SC91.11 Light Chain Variable Region

<400> SEQUENCE: 33

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Phe Trp Tyr Gln Gln Lys Pro Gly Gln Ser Pro Lys Ala Leu Ile
        35                  40                  45

Tyr Ala Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asp Ser Tyr Pro Leu
                85                  90                  95

Thr Phe Gly Asp Gly Thr Lys Leu Glu Leu Arg
            100                 105
```

<210> SEQ ID NO 34
<211> LENGTH: 348
<212> TYPE: DNA
<213> ORGANISM: Mus musculus
<220> FEATURE:
<221> NAME/KEY: misc_feature
<223> OTHER INFORMATION: SC91.11 Heavy Chain Variable Region

<400> SEQUENCE: 34

```
caggtccaac tgcagcagcc tggggctgag cttgtgaagc ctggggcttc agtgaagctg    60
tcctgcaagg cttctgggta caccttcacc acctactgga tgcactgggt gaagcagagg    120
cctggacgag ccttgagtg gattggaagg attgatccta atagtggtgg tactaagtac    180
aatgagaagt tcaagagcaa ggccacactg actgtagaca aaccctccag cacagcctgc    240
atgcagctca gcagcctgac ctctgaggac tctgcggtct attattgtgc aagcaggagg    300
ggggacatcg atgtctgggg cacagggacc acggtcaccg tctcctca              348
```

<210> SEQ ID NO 35
<211> LENGTH: 116
<212> TYPE: PRT
<213> ORGANISM: Mus musculus
<220> FEATURE:
<221> NAME/KEY: MISC_FEATURE
<223> OTHER INFORMATION: SC91.11 Heavy Chain Variable Region

<400> SEQUENCE: 35

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Lys Gln Arg Pro Gly Arg Gly Leu Glu Trp Ile
        35                  40                  45
```

Gly Arg Ile Asp Pro Asn Ser Gly Gly Thr Lys Tyr Asn Glu Lys Phe
            50                  55                  60

Lys Ser Lys Ala Thr Leu Thr Val Asp Lys Pro Ser Ser Thr Ala Cys
 65                  70                  75                  80

Met Gln Leu Ser Ser Leu Thr Ser Glu Asp Ser Ala Val Tyr Tyr Cys
                85                  90                  95

Ala Ser Arg Arg Gly Asp Ile Asp Val Trp Gly Thr Gly Thr Thr Val
            100                 105                 110

Thr Val Ser Ser
        115

<210> SEQ ID NO 36
<211> LENGTH: 339
<212> TYPE: DNA
<213> ORGANISM: Mus musculus
<220> FEATURE:
<221> NAME/KEY: misc_feature
<223> OTHER INFORMATION: SC91.14 and SC 91.186 Light Chain Variable
      Region

<400> SEQUENCE: 36
gacattgtga tgtcacagtc tccatcctcc ctagctgtgt cagttggaga aaaggttact    60
atgagctgca agtccagtca gagccttta tatagtagca atcaaaagaa ctacttggcc   120
tggtaccagc agaaaccagg gcagtctcct caactgctga tttactgggc atccactagg   180
gaatctgggg tccctgatcg cttcacaggc agtggatctg ggacagattt cactctcacc   240
atcagcagtg tgaaggctga agacctggca gtttattact gtcagcaata ttatagctat   300
ccgctcacgt tcggtgctgg gaccaagctg gagctgaaa                          339

<210> SEQ ID NO 37
<211> LENGTH: 112
<212> TYPE: PRT
<213> ORGANISM: Mus musculus
<220> FEATURE:
<221> NAME/KEY: MISC_FEATURE
<223> OTHER INFORMATION: SC91.14 and SC91.186 Light Chain Variable
      Region

<400> SEQUENCE: 37

Asp Ile Val Met Ser Gln Ser Pro Ser Ser Leu Ala Val Ser Val Gly
 1               5                  10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Gln Leu Leu Ile Tyr Trp Ala Ser Arg Glu Ser Gly Val Pro
     50                  55                  60

Asp Arg Phe Thr Gly Ser Gly Ser Gly Thr Asp Phe Thr Leu Thr Ile
 65                  70                  75                  80

Ser Ser Val Lys Ala Glu Asp Leu Ala Val Tyr Tyr Cys Gln Gln Tyr
                85                  90                  95

Tyr Ser Tyr Pro Leu Thr Phe Gly Ala Gly Thr Lys Leu Glu Leu Lys
            100                 105                 110

<210> SEQ ID NO 38
<211> LENGTH: 348
<212> TYPE: DNA
<213> ORGANISM: Mus musculus
<220> FEATURE:

<221> NAME/KEY: misc_feature
<223> OTHER INFORMATION: SC91.14 Heavy Chain Variable Region

<400> SEQUENCE: 38

```
caagttactc tgaaagagtc tggccctggg atattgcagc cctcccagac cctcagtcta    60
acttgttctt tctctgggtt ttcactgcgc acatctggta tgaatatagg ctggattcgt   120
cagccttcag ggaagggtct ggagtggctg acacacattt ggtggaatga tgataagtcc   180
tacaacccag ccctgaaaag ccggctcaca atctccaagg atacctccaa caaccaggta   240
ttcctcaagc tcgccagtgt ggtcactgca gataccgcca catactactg tgttcgaggt   300
gaccggtttc cttactgggg ccaagggact ctggtcactg tctctgca                348
```

<210> SEQ ID NO 39
<211> LENGTH: 116
<212> TYPE: PRT
<213> ORGANISM: Mus musculus
<220> FEATURE:
<221> NAME/KEY: MISC_FEATURE
<223> OTHER INFORMATION: SC91.14 Heavy Chain Variable Region

<400> SEQUENCE: 39

```
Gln Val Thr Leu Lys Glu Ser Gly Pro Gly Ile Leu Gln Pro Ser Gln
  1               5                  10                  15

Thr Leu Ser Leu Thr Cys Ser Phe Ser Gly Phe Ser Leu Arg Thr Ser
             20                  25                  30

Gly Met Asn Ile Gly Trp Ile Arg Gln Pro Ser Gly Lys Gly Leu Glu
         35                  40                  45

Trp Leu Thr His Ile Trp Trp Asn Asp Asp Lys Ser Tyr Asn Pro Ala
     50                  55                  60

Leu Lys Ser Arg Leu Thr Ile Ser Lys Asp Thr Ser Asn Asn Gln Val
 65                  70                  75                  80

Phe Leu Lys Leu Ala Ser Val Val Thr Ala Asp Thr Ala Thr Tyr Tyr
                 85                  90                  95

Cys Val Arg Gly Asp Arg Phe Pro Tyr Trp Gly Gln Gly Thr Leu Val
            100                 105                 110

Thr Val Ser Ala
        115
```

<210> SEQ ID NO 40
<211> LENGTH: 339
<212> TYPE: DNA
<213> ORGANISM: Mus musculus
<220> FEATURE:
<221> NAME/KEY: misc_feature
<223> OTHER INFORMATION: SC91.15 Light Chain Variable Region

<400> SEQUENCE: 40

```
gacattgtga tgacacagtc tccatcctcc ctggctatgt cagtaggaca gaaggtcact    60
atgagctgca gtccagtca gagccttta aaaagtagca atcaaaagaa ctatttggcc   120
tggtaccagc agaaaccagg acagtctcct aaacttctgg tatattttgc atccactagg   180
gaatctgggg tccctgatcg cttcataggc agtggatctg ggacagattt cactcttacc   240
atcagcagtg tgcaggctga agacctggca gattacttct gtcagcaata ttataggatt   300
ccttggacgt tcggtggagg caccaagctg gaaatcaaa                          339
```

<210> SEQ ID NO 41
<211> LENGTH: 113
<212> TYPE: PRT

```
<213> ORGANISM: Mus musculus
<220> FEATURE:
<221> NAME/KEY: MISC_FEATURE
<223> OTHER INFORMATION: SC91.15 Light Chain Variable Region

<400> SEQUENCE: 41

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Lys Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

Tyr Tyr Arg Ile Pro Trp Thr Phe Gly Gly Gly Thr Lys Leu Glu Ile
                100                 105                 110

Lys

<210> SEQ ID NO 42
<211> LENGTH: 351
<212> TYPE: DNA
<213> ORGANISM: Mus musculus
<220> FEATURE:
<221> NAME/KEY: misc_feature
<223> OTHER INFORMATION: SC91.15 Heavy Chain Variable Region

<400> SEQUENCE: 42
caggtccaac tgcagcagcc tggggctgag cttgtgatgc ctggggcttc agtgaagctg    60
tcctgcaagg cttctggcta caccctcacc aactactgga tgcactgggt gaagcagagg   120
cctggacaag gccttgagtg gatcggagac attgatcctt ctgatactta tactaactac   180
aatcataaat tcaagggcaa ggccacattg actgtagaca atcttccag cacagcctac    240
atgcagctca gcagcctgac atctgaggac tctgcggtct attactgtgc aagatcggga   300
tgggactact ttgactcctg gggccaaggc accactctca cagtctcctc a            351

<210> SEQ ID NO 43
<211> LENGTH: 115
<212> TYPE: PRT
<213> ORGANISM: Mus musculus
<220> FEATURE:
<221> NAME/KEY: MISC_FEATURE
<223> OTHER INFORMATION: SC91.15 Heavy Chain Variable Region

<400> SEQUENCE: 43

Gln Val Gln Leu Gln Gln Pro Gly Ala Glu Leu Val Met Pro Gly Ala
1               5                   10                  15

Ser Val Lys Leu Ser Cys Lys Ala Ser Gly Tyr Thr Leu Thr Asn Tyr
            20                  25                  30

Trp Met His Trp Val Lys Gln Arg Pro Gly Gln Gly Leu Glu Trp Ile
        35                  40                  45

Gly Asp Ile Asp Pro Ser Asp Thr Thr Asn Tyr Asn His Lys Phe Lys
    50                  55                  60

Gly Lys Ala Thr Leu Thr Val Asp Lys Ser Ser Ser Thr Ala Tyr Met
65                  70                  75                  80
```

Gln Leu Ser Ser Leu Thr Ser Glu Asp Ser Ala Val Tyr Tyr Cys Ala
            85                  90                  95

Arg Ser Gly Trp Asp Tyr Phe Ser Trp Gly Gln Gly Thr Thr Leu
            100                 105                 110

Val Ser Ser
        115

<210> SEQ ID NO 44
<211> LENGTH: 321
<212> TYPE: DNA
<213> ORGANISM: Mus musculus
<220> FEATURE:
<221> NAME/KEY: misc_feature
<223> OTHER INFORMATION: SC91.19 Light Chain Variable Region

<400> SEQUENCE: 44
agttttgtga tgacccagac tcccaaattc ctgcttgtat cagcaggaga cagggttacc     60
ataacctgca aggccagtca gagtgtgggt aatgatgtag cttggtacca acagaagcca    120
gggcagtctc ctaaactcct gatatactat gcatccaatc gctacactgg agtccctgat    180
cgcttcactg gcagtggata tgggacggat ttcactttca ccatcagcac tgtgcaggct    240
gaagacctgg cagtttattt ctgtcagcag gattatagct ctccattcac gttcggctcg    300
gggacaaagt tggaaatgaa a                                              321

<210> SEQ ID NO 45
<211> LENGTH: 107
<212> TYPE: PRT
<213> ORGANISM: Mus musculus
<220> FEATURE:
<221> NAME/KEY: MISC_FEATURE
<223> OTHER INFORMATION: SC91.19 Light Chain Variable Region

<400> SEQUENCE: 45

Ser Phe Val Met Thr Gln Thr Pro Lys Phe Leu Leu Val Ser Ala Gly
1               5                   10                  15

Asp Arg Val Thr Ile Thr Cys Lys Ala Ser Gln Ser Val Gly Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Phe
                85                  90                  95

Thr Phe Gly Ser Gly Thr Lys Leu Glu Met Lys
            100                 105

<210> SEQ ID NO 46
<211> LENGTH: 357
<212> TYPE: DNA
<213> ORGANISM: Mus musculus
<220> FEATURE:
<221> NAME/KEY: misc_feature
<223> OTHER INFORMATION: SC91.19 Heavy Chain Variable Region

<400> SEQUENCE: 46
cagatccagt tggtacagtc tggacctgag ctgaagaagc ctggagagac agtcaagatc     60
tcctgcaagg cttctgggta taccttcaca acctatggaa tgaactgggt gaaacaggct    120

```
ccaggaaagg gtttaaagtg gatgggctgg ataaacacct actctggagt gccatcatct      180
gctaatgact tcaagggacg gtttgccttc tctttggaaa cctctgccag cactgcctat      240
ttgcagatca acaacctcaa aaatgaggac acggctacat atttctgtgc aagatccgaa      300
ctacgaaact ggtacttcga tgtctggggc acagggacca cggtcaccgt ctcctca        357
```

<210> SEQ ID NO 47
<211> LENGTH: 119
<212> TYPE: PRT
<213> ORGANISM: Mus musculus
<220> FEATURE:
<221> NAME/KEY: MISC_FEATURE
<223> OTHER INFORMATION: SC91.19 Heavy Chain Variable Region

<400> SEQUENCE: 47

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Asn Trp Val Lys Gln Ala Pro Gly Lys Gly Leu Lys Trp Met
        35                  40                  45

Gly Trp Ile Asn Thr Tyr Ser Gly Val Pro Ser Ala Asn Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Ser Glu Leu Arg Asn Trp Tyr Phe Asp Val Trp Gly Thr Gly
            100                 105                 110

Thr Thr Val Thr Val Ser Ser
        115
```

<210> SEQ ID NO 48
<211> LENGTH: 321
<212> TYPE: DNA
<213> ORGANISM: Mus musculus
<220> FEATURE:
<221> NAME/KEY: misc_feature
<223> OTHER INFORMATION: SC91.111 Light Chain Variable Region

<400> SEQUENCE: 48

```
agttttgtga tgacccagac tcccaaattc ctgcttgtat cagcaggaga cagggttacc      60
ataacctgca aggccagtca gaatatgggt cataatgtag cttggtacca acagaagcca     120
gggcagtctc ctaaattgct gatatactat gcatccaatc gctacactgg agtccctgat     180
cgcttcactg gcagtggata tgggacggat ttcactttca ccatcagcac tgtgcaggct     240
gaagacctgg cagtttattt ctgtcagcag gattatagct ctccattcac gttcggctcg     300
gggacaaagt tggaaataaa a                                               321
```

<210> SEQ ID NO 49
<211> LENGTH: 107
<212> TYPE: PRT
<213> ORGANISM: Mus musculus
<220> FEATURE:
<221> NAME/KEY: MISC_FEATURE
<223> OTHER INFORMATION: SC91.111 Light Chain Variable Region

<400> SEQUENCE: 49

```
Ser Phe Val Met Thr Gln Thr Pro Lys Phe Leu Leu Val Ser Ala Gly
1               5                   10                  15
```

Asp Arg Val Thr Ile Thr Cys Lys Ala Ser Gln Asn Met Gly His Asn
            20                  25                  30

Val Ala Trp Tyr Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
 50                  55                  60

Ser Gly Tyr Gly Thr Asp Phe Thr Phe Thr Ile Ser Thr Val Gln Ala
 65                  70                  75                  80

Glu Asp Leu Ala Val Tyr Phe Cys Gln Gln Asp Tyr Ser Ser Pro Phe
                85                  90                  95

Thr Phe Gly Ser Gly Thr Lys Leu Glu Ile Lys
            100                 105

<210> SEQ ID NO 50
<211> LENGTH: 357
<212> TYPE: DNA
<213> ORGANISM: Mus musculus
<220> FEATURE:
<221> NAME/KEY: misc_feature
<223> OTHER INFORMATION: SC91.111 Heavy Chain Variable Region

<400> SEQUENCE: 50
cagatccagt tggtacagtc tggacctgag ctgaagaagc ctggagagac agtcaagatc      60
tcctgcaagg cttctgggta taccttaaca acctatggaa tgaactgggt gaaacaggct     120
ccaggaaagg gtttaaagtg gatgggctgg ataaacacct actctggagt gccagcatat     180
gctgatgact tcaagggacg gtttgccttc tctttggaaa cctctgccag cactgcctat     240
ttgcagatca caaacttcaa aaatgaggac acggctacat atttctgtgc aagatccgaa     300
ctacgaaact ggtacttcga tgtctggggc acagggacca cggtcaccgt ctcctca       357

<210> SEQ ID NO 51
<211> LENGTH: 117
<212> TYPE: PRT
<213> ORGANISM: Mus musculus
<220> FEATURE:
<221> NAME/KEY: MISC_FEATURE
<223> OTHER INFORMATION: SC91.111 Heavy Chain Variable Region

<400> SEQUENCE: 51

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Leu Thr Thr Tyr
            20                  25                  30

Gly Met Asn Trp Val Lys Gln Ala Pro Gly Lys Gly Leu Lys Trp Met
        35                  40                  45

Gly Trp Ile Asn Thr Tyr Ser Gly Val Pro Ala Tyr Ala Asp Asp Phe
    50                  55                  60

Lys Gly Arg Phe Ala Phe Ser Leu Glu Thr Ser Ala Ser Thr Ala Tyr
 65                  70                  75                  80

Leu Gln Ile Asn Asn Phe Lys Asn Glu Asp Thr Ala Thr Tyr Phe Cys
                85                  90                  95

Ala Arg Ser Glu Leu Arg Asn Trp Tyr Phe Asp Val Trp Gly Thr Gly
            100                 105                 110

Thr Thr Val Ser Ser
        115

<210> SEQ ID NO 52

<211> LENGTH: 339
<212> TYPE: DNA
<213> ORGANISM: Mus musculus
<220> FEATURE:
<221> NAME/KEY: misc_feature
<223> OTHER INFORMATION: SC91.119 Light Chain Variable Region

<400> SEQUENCE: 52

```
gacattgtga tgtcacagtc tccatcctcc ctagctgtgt cagttggaga gaaggttact    60
atgagctgca agtccagtca gagccttta tatagtaaca atcaaaagaa ctacttggcc   120
tggtaccagc agaaaccagg gcagtctcct aaactgctga tttactgggc atccactagg   180
gaatctgggg tccctgatcg cttcacaggc agtggatctg gacagattt cactctcacc    240
atcagcagtg tgaaggctga agacctggca gtttattact gtcagcaata ttatagcttt   300
ccgctcacgt tcggtgctgg gaccaagctg gagctaaaa                          339
```

<210> SEQ ID NO 53
<211> LENGTH: 113
<212> TYPE: PRT
<213> ORGANISM: Mus musculus
<220> FEATURE:
<221> NAME/KEY: MISC_FEATURE
<223> OTHER INFORMATION: SC91.119 Light Chain Variable Region

<400> SEQUENCE: 53

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Asn Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Phe Pro Leu Thr Phe Gly Ala Gly Thr Lys Leu Glu Leu
            100                 105                 110

Lys

<210> SEQ ID NO 54
<211> LENGTH: 348
<212> TYPE: DNA
<213> ORGANISM: Mus musculus
<220> FEATURE:
<221> NAME/KEY: misc_feature
<223> OTHER INFORMATION: SC91.119 Heavy Chain Variable Region

<400> SEQUENCE: 54

```
caggttactc tgaaagagtc tggccctggg atattgcagc cctcccagac cctcagtcta    60
acttgttctt tctctgggct ttcactgagc acacctggta tgagtgtagg ctggattcgt   120
cagccttcag ggaagggtct ggagtggctg gcacacattt ggtggaatga tgataagtcc   180
tataacccag ccctgaaaag ccggctcaca atctccaagg atacctccaa caatcaggta   240
ttcctcaaga tcgccagtgt ggtcactgca gatactgcca catactactg tgctcgaggt   300
gaccggtttg cttactgggg ccaagggact ctggtcactg tctctgca                348
```

```
<210> SEQ ID NO 55
<211> LENGTH: 116
<212> TYPE: PRT
<213> ORGANISM: Mus musculus
<220> FEATURE:
<221> NAME/KEY: MISC_FEATURE
<223> OTHER INFORMATION: SC91.119 Heavy Chain Variable Region

<400> SEQUENCE: 55

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Leu Ser Leu Ser Thr Pro
            20                  25                  30

Gly Met Ser Val Gly Trp Ile Arg Gln Pro Ser Gly Lys Gly Leu Glu
        35                  40                  45

Trp Leu Ala His Ile Trp Trp Asn Asp Asp Lys Ser Tyr Asn Pro Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Val Thr Ala Asp Thr Ala Thr Tyr Tyr
                85                  90                  95

Cys Ala Arg Gly Asp Arg Phe Ala Tyr Trp Gly Gln Gly Thr Leu Val
            100                 105                 110

Thr Val Ser Ala
        115

<210> SEQ ID NO 56
<211> LENGTH: 336
<212> TYPE: DNA
<213> ORGANISM: Mus musculus
<220> FEATURE:
<221> NAME/KEY: misc_feature
<223> OTHER INFORMATION: SC91.129 Light Chain Variable Region

<400> SEQUENCE: 56
gatgctgtga tgacccaatc tccactctcc ctgcctgtca gtcttggaga tcaagcctcc      60
atctcctgca gatctagtca gagccttgta cacagtactg aaacaccta tttacattgg      120 tacctgcaaa agccaggcca gtctccaaaa ctcctgatct ataaagtttc caaccgattt     180
tctggggtcc cagacaggtt cagtggcagt ggatcaggga cagatttcac actcaagatc     240
agcagagtgg aggctgagga tctgggagtt tatttctgct ctcaaactac acatgttcca     300
ttcacgttcg gctcggggac aaagttggaa ataaaa                               336

<210> SEQ ID NO 57
<211> LENGTH: 111
<212> TYPE: PRT
<213> ORGANISM: Mus musculus
<220> FEATURE:
<221> NAME/KEY: MISC_FEATURE
<223> OTHER INFORMATION: SC91.129 Light Chain Variable Region

<400> SEQUENCE: 57

Asp Ala Val Met Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Thr Gly Asn Thr Tyr Leu His Trp Tyr Leu Gln Lys Pro Gly Gln Ser
        35                  40                  45

Pro Lys Leu Leu Ile Tyr Lys Val Ser Asn Arg Ser Gly Val Pro Asp
    50                  55                  60
```

```
Arg Phe Ser Gly Ser Gly Ser Gly Thr Asp Phe Thr Leu Lys Ile Ser
 65                  70                  75                  80

Arg Val Glu Ala Glu Asp Leu Gly Val Tyr Phe Cys Ser Gln Thr Thr
                 85                  90                  95

His Val Pro Phe Thr Phe Gly Ser Gly Thr Lys Leu Glu Ile Lys
            100                 105                 110
```

<210> SEQ ID NO 58
<211> LENGTH: 348
<212> TYPE: DNA
<213> ORGANISM: Mus musculus
<220> FEATURE:
<221> NAME/KEY: misc_feature
<223> OTHER INFORMATION: SC91.129 Heavy Chain Variable Region

<400> SEQUENCE: 58

```
caggtccaac tgcagcagcc tggggctgaa cttgtgaagc ctggggcttc agtgaagctg    60
tcctgcaagg cttctggcta caccttcacc aactactgga tgcagtgggt aaaacagagg   120
cctggacagg gccttgagtg gatcggagag attgatcctt ctgataggta cactctctac   180
aatcaaaagt tcaagacaa ggccacattg actgtagaca tcctccag cacagcctac    240 atgcagctca gcagcctgac atctgaggac tctgcggtct attactgtgc aagatttggt   300
tactatgttg actactgggg ccaaggcacc actctcacag tctcctca               348
```

<210> SEQ ID NO 59
<211> LENGTH: 116
<212> TYPE: PRT
<213> ORGANISM: Mus musculus
<220> FEATURE:
<221> NAME/KEY: MISC_FEATURE
<223> OTHER INFORMATION: SC91.129 Heavy Chain Variable Region

<400> SEQUENCE: 59

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met Gln Trp Val Lys Gln Arg Pro Gly Gln Gly Leu Glu Trp Ile
        35                  40                  45

Gly Glu Ile Asp Pro Ser Asp Arg Tyr Thr Leu Tyr Asn Gln Lys Phe
    50                  55                  60

Lys Asp Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Phe Gly Tyr Tyr Val Asp Tyr Trp Gly Gln Gly Thr Thr Leu
            100                 105                 110

Thr Val Ser Ser
            115
```

<210> SEQ ID NO 60
<211> LENGTH: 339
<212> TYPE: DNA
<213> ORGANISM: Mus musculus
<220> FEATURE:
<221> NAME/KEY: misc_feature
<223> OTHER INFORMATION: SC91.138 Light Chain Variable Region

<400> SEQUENCE: 60

-continued

```
gacattgtga tgacacagtc tccatcctcc ctggctatgt cagtaggaca gaaggtcact      60
atgagctgca agtccagtca gagccttta aagagtaaca atcaaaagaa ctatttggcc      120
tggtaccagc agaaaccagg acagtctcct aaacttctgg tatactttgc atccactagg     180
gaatctgggg tccctgatcg cttcataggc agtggatctg ggacagattt cactcttacc     240
atcagcagtg tgcaggctga agacctggca gattacttct gtcagcaata ttatagcact     300
ccttggacgt tcggtggagg caccaagctg gaaatcaaa                            339
```

<210> SEQ ID NO 61
<211> LENGTH: 113
<212> TYPE: PRT
<213> ORGANISM: Mus musculus
<220> FEATURE:
<221> NAME/KEY: MISC_FEATURE
<223> OTHER INFORMATION: SC91.138 Light Chain Variable Region

<400> SEQUENCE: 61

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Lys Ser
            20                  25                  30

Asn Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

Tyr Tyr Ser Thr Pro Trp Thr Phe Gly Gly Gly Thr Lys Leu Glu Ile
            100                 105                 110

Lys

<210> SEQ ID NO 62
<211> LENGTH: 351
<212> TYPE: DNA
<213> ORGANISM: Mus musculus
<220> FEATURE:
<221> NAME/KEY: misc_feature
<223> OTHER INFORMATION: SC91.138 Heavy Chain Variable Region

<400> SEQUENCE: 62

```
caggtccaac tgcagcagcc tggggctgag cttgtgatgc ctggggcttc agtgaagctg      60
tcctgcaagg cttctggcta caccttcacc aactactgga tgcactgggt gaagcagagg     120
cctggacaag gccttgagtg gatcggagag attgatcctt ctgatgttta tactacctac     180
aatcaaaagt tcaaggacaa ggccacgttg actgtagaca atcctccag cacagcctac     240 atgcaactca tcaacctgac atctgaggac tctgcggtct attactgtgc aagatcggga     300
tgggactact ttgactactg gggccaaggc accgctctca cagtctcctc a              351
```

<210> SEQ ID NO 63
<211> LENGTH: 117
<212> TYPE: PRT
<213> ORGANISM: Mus musculus
<220> FEATURE:
<221> NAME/KEY: MISC_FEATURE
<223> OTHER INFORMATION: SC91.138 Heavy Chain Variable Region

<400> SEQUENCE: 63

Gln Val Gln Leu Gln Gln Pro Gly Ala Glu Leu Val Met Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Val Tyr Thr Thr Tyr Asn Gln Lys Phe
    50                  55                  60

Lys Asp Lys Ala Thr Leu Thr Val Asp Lys Ser Ser Thr Ala Tyr
65                  70                  75                  80

Met Gln Leu Ile Asn Leu Thr Ser Glu Asp Ser Ala Val Tyr Tyr Cys
                85                  90                  95

Ala Arg Ser Gly Trp Asp Tyr Phe Asp Tyr Trp Gly Gln Gly Thr Ala
            100                 105                 110

Leu Thr Val Ser Ser
        115

<210> SEQ ID NO 64
<211> LENGTH: 339
<212> TYPE: DNA
<213> ORGANISM: Mus musculus
<220> FEATURE:
<221> NAME/KEY: misc_feature
<223> OTHER INFORMATION: SC91.146 Light Chain Variable Region

<400> SEQUENCE: 64
gacattgtga tgacacagtc tccatcctcc ctggctatgt cagtaggaca gaaggtcact      60
atgagctgca agtccagtca gagccttta aaaagtagca atcaaagaa ctatttggcc      120 tggtaccagc agaaaccagg acagtctcct aaacttctgg tatactttgc atccactagg    180
gaatctgggg tccctgatcg cttcataggc agtggatctg ggacagattt cactcttacc    240
atcagcagtg tgcaggctga agacctggca gattacttct gtcagcaaca ttataacatt    300
ccgctcacgt tcggtgctgg gaccaagctg gagctgaaa                           339

<210> SEQ ID NO 65
<211> LENGTH: 113
<212> TYPE: PRT
<213> ORGANISM: Mus musculus
<220> FEATURE:
<221> NAME/KEY: MISC_FEATURE
<223> OTHER INFORMATION: SC91.146 Light Chain Variable Region

<400> SEQUENCE: 65

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Lys Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Asn Ile Pro Leu Thr Phe Gly Ala Gly Thr Lys Leu Glu Leu
            100                 105                 110

Lys

```
<210> SEQ ID NO 66
<211> LENGTH: 351
<212> TYPE: DNA
<213> ORGANISM: Mus musculus
<220> FEATURE:
<221> NAME/KEY: misc_feature
<223> OTHER INFORMATION: SC91.146 Heavy Chain Variable Region

<400> SEQUENCE: 66
caagtccaac tgcagcagcc tggggctgag cttgtgaagc ctggggcttc agtgaagctg      60
tcctgcaagg cttctggcta caccttcacc agctactgga tgcactgggt aaaacagagg     120
cctggacagg ccttgagtg gatcggagac attgatcctt ctgatcgtta tactaactac     180
aatcaaaagt tcaagggcaa ggcgacattg actgtagaca acctccag cacagcgtac      240 atgcagctca gcagcctgac atctgaggac tctgcagtct attactgtgc aatatcgggc     300
tgggactact ttgactactg gggccaaggc accactctca cagtctcctc a              351

<210> SEQ ID NO 67
<211> LENGTH: 117
<212> TYPE: PRT
<213> ORGANISM: Mus musculus
<220> FEATURE:
<221> NAME/KEY: MISC_FEATURE
<223> OTHER INFORMATION: SC91.146 Heavy Chain Variable Region

<400> SEQUENCE: 67

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asp Ile Asp Pro Ser Asp Arg Tyr Thr Asn Tyr Asn Gln Lys Phe
    50                  55                  60

Lys Gly Lys Ala Thr Leu Thr Val Asp Thr Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ile Ser Gly Trp Asp Tyr Phe Asp Tyr Trp Gly Gln Gly Thr Thr
            100                 105                 110

Leu Thr Val Ser Ser
        115

<210> SEQ ID NO 68
<211> LENGTH: 336
<212> TYPE: DNA
<213> ORGANISM: Mus musculus
<220> FEATURE:
<221> NAME/KEY: misc_feature
<223> OTHER INFORMATION: SC91.149 Light Chain Variable Region

<400> SEQUENCE: 68
gatgttgtga tgacccaaac tcctctctcc ctgcctgtca gtcttggaga tcaagcctcc      60
atctcttgca gatcgagtca gagccttgta cacagtactg aaacaccta tttccattgg     120 tacctgcaga agccaggcca gtctccagag ctcctgatct acaaagtttc caaccgattt     180
tctggggtcc cagacaggt ccgtggcagt ggatcaggga cagatttcac actcaagatc     240
```

```
agcagagtgg aggctgagga tctgggagtt tatttctgct ctcaaagtac acatgttcca    300
ttcacgttcg gctcggggac aaagttggaa ataaaa                              336
```

<210> SEQ ID NO 69
<211> LENGTH: 112
<212> TYPE: PRT
<213> ORGANISM: Mus musculus
<220> FEATURE:
<221> NAME/KEY: MISC_FEATURE
<223> OTHER INFORMATION: SC91.149 Light Chain Variable Region

<400> SEQUENCE: 69

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Thr Gly Asn Thr Tyr Phe His Trp Tyr Leu Gln Lys Pro Gly Gln Ser
        35                  40                  45

Pro Glu Leu Leu Ile Tyr Lys Val Ser Asn Arg Phe Ser Gly Val Pro
    50                  55                  60

Asp Arg Phe Arg Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110
```

<210> SEQ ID NO 70
<211> LENGTH: 348
<212> TYPE: DNA
<213> ORGANISM: Mus musculus
<220> FEATURE:
<221> NAME/KEY: misc_feature
<223> OTHER INFORMATION: SC91.149 Heavy Chain Variable Region

<400> SEQUENCE: 70

```
caggtccaac tgctgcagcc tggggctgag cttgtgaagc ctgggtcttc agtgaaggtg    60
tcctgcaagg cttctggcta caccttcacc aactactgga tgcagtgggt gaaacagagg   120
cctggacagg ccttgagtg gatcggagag attgatcctt ctgatacctg tactctgtac   180
aatcaaaagt tcaagggcaa ggccacattg actgtagaca catcctccag caccgcctac   240
atgcagctca gcagcctgac atctgaggac tctgcggtct attactgtgc aagatttggt   300
tactatgttg actactgggg ccaaggcacc actctcacag tctcctca                348
```

<210> SEQ ID NO 71
<211> LENGTH: 116
<212> TYPE: PRT
<213> ORGANISM: Mus musculus
<220> FEATURE:
<221> NAME/KEY: MISC_FEATURE
<223> OTHER INFORMATION: SC91.149 Heavy Chain Variable Region

<400> SEQUENCE: 71

```
Gln Val Gln Leu Leu Gln Pro Gly Ala Glu Leu Val Lys Pro Gly Ser
1               5                   10                  15

Ser Val Lys Val Ser Cys Lys Ala Ser Gly Tyr Thr Phe Thr Asn Tyr
            20                  25                  30

Trp Met Gln Trp Val Lys Gln Arg Pro Gly Gln Gly Leu Glu Trp Ile
        35                  40                  45
```

Gly Glu Ile Asp Pro Ser Asp Thr Tyr Thr Leu Tyr Asn Gln Lys Phe
        50                  55                  60

Lys Gly Lys Ala Thr Leu Thr Val Asp Thr Ser Ser Thr Ala Tyr
 65                  70                  75                  80

Met Gln Leu Ser Ser Leu Thr Ser Glu Asp Ser Ala Val Tyr Tyr Cys
                    85                  90                  95

Ala Arg Phe Gly Tyr Tyr Val Asp Tyr Trp Gly Gln Gly Thr Thr Leu
                100                 105                 110

Thr Val Ser Ser
        115

<210> SEQ ID NO 72
<211> LENGTH: 321
<212> TYPE: DNA
<213> ORGANISM: Mus musculus
<220> FEATURE:
<221> NAME/KEY: misc_feature
<223> OTHER INFORMATION: SC91.155 Light Chain Variable Region

<400> SEQUENCE: 72
agttttgtga tgacccagac tcccaaattc ctgcttgtat cagcaggaga cagggttacc      60
ataacctgca aggccagtca gaatttgggt aatgatgtcg cttggtacca acagaagcca     120
ggccagtctc ctagactgct gatatacttt gcatccaatc gctacactgg agtccctgat     180
cgcttcactg gcagtggata tgggacggat ttcactttca ccatcagcac tgtgcaggct     240
gaagacctgg cagtttattt ctgtcagcag gattatagct ctccattcac gttcggctcg     300
gggacaaagt tggaaataaa a                                               321

<210> SEQ ID NO 73
<211> LENGTH: 107
<212> TYPE: PRT
<213> ORGANISM: Mus musculus
<220> FEATURE:
<221> NAME/KEY: MISC_FEATURE
<223> OTHER INFORMATION: SC91.155 Light Chain Variable Region

<400> SEQUENCE: 73

Ser Phe Val Met Thr Gln Thr Pro Lys Phe Leu Leu Val Ser Ala Gly
 1               5                  10                  15

Asp Arg Val Thr Ile Thr Cys Lys Ala Ser Gln Asn Leu Gly Asn Asp
                20                  25                  30

Val Ala Trp Tyr Gln Gln Lys Pro Gly Gln Ser Pro Arg Leu Leu Ile
            35                  40                  45

Tyr Phe Ala Ser Asn Arg Tyr Thr Gly Val Pro Asp Arg Phe Thr Gly
        50                  55                  60

Ser Gly Tyr Gly Thr Asp Phe Thr Phe Thr Ile Ser Thr Val Gln Ala
 65                  70                  75                  80

Glu Asp Leu Ala Val Tyr Phe Cys Gln Gln Asp Tyr Ser Ser Pro Phe
                85                  90                  95

Thr Phe Gly Ser Gly Thr Lys Leu Glu Ile Lys
                100                 105

<210> SEQ ID NO 74
<211> LENGTH: 357
<212> TYPE: DNA
<213> ORGANISM: Mus musculus
<220> FEATURE:
<221> NAME/KEY: misc_feature
<223> OTHER INFORMATION: SC91.155 Heavy Chain Variable Region

<400> SEQUENCE: 74

```
cagatccagt tggtacagtc tggacctgag ctgaagaagc ctggagagac agtcaagatc     60
tcctgcaagg cttctgggta taccttcaca acctatggaa tgaactgggt gaaacaggct    120
ccaggaaagg gtttaaagtg gatgggctgg ataaacagct actctggagt gccagcatat    180
gctgatgact tcaagggacg gtttgccttc tctttggaaa cctttgccag cactgcctat    240
ttgcagatca acaacctcag agatgaggac acggctacat atttctgtgc aagatccgaa    300
ctacgaaact ggtacttcga tgtctggggc acagggacca cggtcaccgt ctcctca       357
```

<210> SEQ ID NO 75
<211> LENGTH: 119
<212> TYPE: PRT
<213> ORGANISM: Mus musculus
<220> FEATURE:
<221> NAME/KEY: MISC_FEATURE
<223> OTHER INFORMATION: SC91.155 Heavy Chain Variable Region

<400> SEQUENCE: 75

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Asn Trp Val Lys Gln Ala Pro Gly Lys Gly Leu Lys Trp Met
        35                  40                  45

Gly Trp Ile Asn Ser Tyr Ser Gly Val Pro Ala Tyr Ala Asp Asp Phe
    50                  55                  60

Lys Gly Arg Phe Ala Phe Ser Leu Glu Thr Phe Ala Ser Thr Ala Tyr
65                  70                  75                  80

Leu Gln Ile Asn Asn Leu Arg Asp Glu Asp Thr Ala Thr Tyr Phe Cys
                85                  90                  95

Ala Arg Ser Glu Leu Arg Asn Trp Tyr Phe Asp Val Trp Gly Thr Gly
            100                 105                 110

Thr Thr Val Thr Val Ser Ser
        115
```

<210> SEQ ID NO 76
<211> LENGTH: 321
<212> TYPE: DNA
<213> ORGANISM: Mus musculus
<220> FEATURE:
<221> NAME/KEY: misc_feature
<223> OTHER INFORMATION: SC91.160 Light Chain Variable Region

<400> SEQUENCE: 76

```
agttttgtga tgacccagac tcccaaattc ctgcttgttt cagcaggaga cagggttacc     60
ataacctgca aggccagtca gaatatgggt catgatgtag cttggtacca acagaagcca    120
gggcagtctc ctaaactcct gatatactct gcatccaatc gctacactgg agtccctgat    180
cgcttcactg gcagtggata tgggacggat ttcactttca ccatcagcac tgtgcaggct    240
gaagacctgg cagtttattt ctgtcagcag gattatagct ctccattcac gttcggctcg    300
gggacaaagt tggaaatgaa a                                              321
```

<210> SEQ ID NO 77
<211> LENGTH: 107
<212> TYPE: PRT
<213> ORGANISM: Mus musculus
<220> FEATURE:

-continued

```
<221> NAME/KEY: MISC_FEATURE
<223> OTHER INFORMATION: SC91.160 Light Chain Variable Region

<400> SEQUENCE: 77

Ser Phe Val Met Thr Gln Thr Pro Lys Phe Leu Leu Val Ser Ala Gly
1               5                   10                  15

Asp Arg Val Thr Ile Thr Cys Lys Ala Ser Gln Asn Met Gly His Asp
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Phe
                85                  90                  95

Thr Phe Gly Ser Gly Thr Lys Leu Glu Met Lys
            100                 105

<210> SEQ ID NO 78
<211> LENGTH: 357
<212> TYPE: DNA
<213> ORGANISM: Mus musculus
<220> FEATURE:
<221> NAME/KEY: misc_feature
<223> OTHER INFORMATION: SC91.160 Heavy Chain Variable Region

<400> SEQUENCE: 78
cagatccagt tggtacagtc tggacctgag ctgaagaagc ctggagagac agtcaagatc      60
tcctgcaagg cttcaggtta taccttcaca acctatggaa tgaactgggt gaaacaggct     120
ccaggaaagg gtttaaagtg gatgggctgg ataaacacct actctggagt gccatcatct     180
gctgatgact tcaagggacg gtttgccttc tctttggaaa cctctgccag cactgcctat     240
ttgctgatca acaacctcaa aaatgaggac acggctacat atttctgtgc aagatccgaa     300
ctacgaaact ggtacttcga tgtctggggc acagggacca cggtcaccgt ctcctca        357

<210> SEQ ID NO 79
<211> LENGTH: 119
<212> TYPE: PRT
<213> ORGANISM: Mus musculus
<220> FEATURE:
<221> NAME/KEY: MISC_FEATURE
<223> OTHER INFORMATION: SC91.160 Heavy Chain Variable Region

<400> SEQUENCE: 79

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Asn Trp Val Lys Gln Ala Pro Gly Lys Gly Leu Lys Trp Met
        35                  40                  45

Gly Trp Ile Asn Thr Tyr Ser Gly Val Pro Ser Ser Ala Asp Asp Phe
50                  55                  60

Lys Gly Arg Phe Ala Phe Ser Leu Glu Thr Ser Ala Ser Thr Ala Tyr
65                  70                  75                  80

Leu Leu Ile Asn Asn Leu Lys Asn Glu Asp Thr Ala Thr Tyr Phe Cys
                85                  90                  95

Ala Arg Ser Glu Leu Arg Asn Trp Tyr Phe Asp Val Trp Gly Thr Gly
```

```
                100               105               110
Thr Thr Val Thr Val Ser Ser
         115

<210> SEQ ID NO 80
<211> LENGTH: 336
<212> TYPE: DNA
<213> ORGANISM: Mus musculus
<220> FEATURE:
<221> NAME/KEY: misc_feature
<223> OTHER INFORMATION: SC91.172 Light Chain Variable Region

<400> SEQUENCE: 80
gatgttgtga tgacccaaac tccactctcc ctgcctgtca gtcttggaga tcaagcctcc      60
atctcttgca gatctagtca gagccttgta cacagtactg gaaacaccta tttacattgg    120
tacctgcaga aggcaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttcca    300
ttcacgttcg gctcggggac aaagttggaa ataaaa                              336

<210> SEQ ID NO 81
<211> LENGTH: 112
<212> TYPE: PRT
<213> ORGANISM: Mus musculus
<220> FEATURE:
<221> NAME/KEY: MISC_FEATURE
<223> OTHER INFORMATION: SC91.172 Light Chain Variable Region

<400> SEQUENCE: 81

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Thr Gly Asn Thr Tyr Leu His Trp Tyr Leu Gln Lys Ala Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

<210> SEQ ID NO 82
<211> LENGTH: 348
<212> TYPE: DNA
<213> ORGANISM: Mus musculus
<220> FEATURE:
<221> NAME/KEY: misc_feature
<223> OTHER INFORMATION: SC91.172 Heavy Chain Variable Region

<400> SEQUENCE: 82
caggtccaac tgcagcagcc tggggctgac cttgtgaagc ctggggcttc agtgaagctg      60
tcctgcaagg cttctggcta caccttcacc agttattgga tgcagtgggt aaaacagagg    120
cctggacagg gccttgagtg gatcggagag attgatccct ctgataccta ctactatgtac  180 aatcaaaagt tcaagggcaa ggccacattg actgttgaca catcctccag cacagcctac    240
```

```
atgcagctca gcagcctgac atctgaggac tctgcggtct attactgtgc aagatttggt    300
tactatgttg actactgggg ccaaggcacc actctcacag tctcttca                 348
```

<210> SEQ ID NO 83
<211> LENGTH: 116
<212> TYPE: PRT
<213> ORGANISM: Mus musculus
<220> FEATURE:
<221> NAME/KEY: MISC_FEATURE
<223> OTHER INFORMATION: SC91.172 Heavy Chain Variable Region

<400> SEQUENCE: 83

Gln Val Gln Leu Gln Gln Pro Gly Ala Asp Leu Val Lys Pro Gly Thr
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Glu Ile Asp Pro Ser Asp Thr Tyr Thr Met Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Phe Gly Tyr Tyr Val Asp Tyr Trp Gly Gln Gly Thr Thr Leu
            100                 105                 110

Thr Val Ser Ser
        115

<210> SEQ ID NO 84
<211> LENGTH: 336
<212> TYPE: DNA
<213> ORGANISM: Mus musculus
<220> FEATURE:
<221> NAME/KEY: misc_feature
<223> OTHER INFORMATION: SC91.187 Light Chain Variable Region

<400> SEQUENCE: 84

```
gatgttgtga tgacccaaac tccactctcc ctgcctgtca gtcttggaga gcaagcctcc    60
atctcttgca gatctagtca gagccttgta cacagtactg aaacaccta tttacattgg    120 tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttcca    300
ttcacgttcg gctcggggac aaagttggaa ataaaa                             336
```

<210> SEQ ID NO 85
<211> LENGTH: 112
<212> TYPE: PRT
<213> ORGANISM: Mus musculus
<220> FEATURE:
<221> NAME/KEY: MISC_FEATURE
<223> OTHER INFORMATION: SC91.187 Light Chain Variable Region

<400> SEQUENCE: 85

Asp Val Val Met Thr Gln Thr Pro Leu Ser Leu Pro Val Ser Leu Gly
1               5                   10                  15

Glu Gln Ala Ser Ile Ser Cys Arg Ser Ser Gln Ser Leu Val His Ser
            20                  25                  30

Thr Gly Asn Thr Tyr Leu His Trp Tyr Leu Gln Lys Pro Gly Gln Ser
                35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
                100                 105                 110

<210> SEQ ID NO 86
<211> LENGTH: 348
<212> TYPE: DNA
<213> ORGANISM: Mus musculus
<220> FEATURE:
<221> NAME/KEY: misc_feature
<223> OTHER INFORMATION: SC91.187 Heavy Chain Variable Region

<400> SEQUENCE: 86
caggtccaac tgcagcagcc tgggcctgag tttgtgaagc ctggggcttc agtgaagctg     60
tcctgcaagg cttctggcta caccttcacc agctactggg tgcagtgggt aaaacagagg    120
cctggacagg gccttgagtg gatcggagag attgatcctt ctgataacta tactctctac    180
aatcaaaatt tcaagggcaa ggccacattg actgtggaca catcctccag cacagcctac    240
atgcagctca gcagcctgac atctgaggac tctgcggtct attactgtgc aagatttggt    300
ttctatgttg actactgggg ccaaggcacc actctcacag tctcctca                 348

<210> SEQ ID NO 87
<211> LENGTH: 116
<212> TYPE: PRT
<213> ORGANISM: Mus musculus
<220> FEATURE:
<221> NAME/KEY: MISC_FEATURE
<223> OTHER INFORMATION: SC91.187 Heavy Chain Variable Region

<400> SEQUENCE: 87

Gln Val Gln Leu Gln Gln Pro Gly Pro Glu Phe Val Lys Pro Gly Ala
1               5                   10                  15

Ser Val Lys Leu Ser Cys Lys Ala Ser Gly Tyr Thr Phe Thr Ser Tyr
                20                  25                  30

Trp Val Gln Trp Val Lys Gln Arg Pro Gly Gln Gly Leu Glu Trp Ile
            35                  40                  45

Gly Glu Ile Asp Pro Ser Asp Asn Tyr Thr Leu Tyr Asn Gln Asn Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Phe Gly Phe Tyr Val Asp Tyr Trp Gly Gln Gly Thr Thr Leu
                100                 105                 110

Thr Val Ser Ser
        115

<210> SEQ ID NO 88
<211> LENGTH: 336
<212> TYPE: DNA
<213> ORGANISM: Mus musculus
<220> FEATURE:

<221> NAME/KEY: misc_feature
<223> OTHER INFORMATION: SC91.20 and SC91.27 Light Chain Variable Region

<400> SEQUENCE: 88

```
gatgttgtga tgacccaaac tccactctcc ctgcctgtca gtcttggaga tcaagcctcc      60
atctcttgca gatctagtca gagccttgta cacagtactg gaaacaccta tttacattgg     120
tacctgcaga agccaggcca gtctccaaac ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttcca     300
ttcacgttcg gctcggggac aaagttggaa ataaaa                               336
```

<210> SEQ ID NO 89
<211> LENGTH: 112
<212> TYPE: PRT
<213> ORGANISM: Mus musculus
<220> FEATURE:
<221> NAME/KEY: MISC_FEATURE
<223> OTHER INFORMATION: SC91.20 and SC91.27 Light Chain Variable Region

<400> SEQUENCE: 89

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Thr Gly Asn Thr Tyr Leu His Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110
```

<210> SEQ ID NO 90
<211> LENGTH: 348
<212> TYPE: DNA
<213> ORGANISM: Mus musculus
<220> FEATURE:
<221> NAME/KEY: misc_feature
<223> OTHER INFORMATION: SC91.20 Heavy Chain Variable Region

<400> SEQUENCE: 90

```
caggtccaac tgcagcagcc tggggctgag gttgtgaggc ctggggcttc tttgaagctg      60
tcctgcaagg cttctggcta caccttcacc agctactgga tgcagtggat aaaacagagg     120
cctggacagg gccttgaatg gatcggagaa attgatcctt ctgataacta tactatgtac     180
aatcagaagt tcaagggcaa ggccacattg actgtagaca catcctccag cacagcctac     240
atgcagctca gcagcctgac atctgaggac tctgcggtct atttctgtgc aagatttggt     300
ttctatgttg actactgggg ccaaggcacc actctcacag tctcctca                  348
```

<210> SEQ ID NO 91
<211> LENGTH: 116
<212> TYPE: PRT
<213> ORGANISM: Mus musculus
<220> FEATURE:
<221> NAME/KEY: MISC_FEATURE
<223> OTHER INFORMATION: SC91.20 Heavy Chain Variable Region

<400> SEQUENCE: 91

Gln Val Gln Leu Gln Gln Pro Gly Ala Glu Val Val Arg Pro Gly Ala
1               5                   10                  15

Ser Leu Lys Leu Ser Cys Lys Ala Ser Gly Tyr Thr Phe Thr Ser Tyr
            20                  25                  30

Trp Met Gln Trp Ile Lys Gln Arg Pro Gly Gln Gly Leu Glu Trp Ile
        35                  40                  45

Gly Glu Ile Asp Pro Ser Asp Asn Tyr Thr Met Tyr Asn Gln Lys Phe
    50                  55                  60

Lys Gly Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Phe Cys
            85                  90                  95

Ala Arg Phe Gly Phe Tyr Val Asp Tyr Trp Gly Gln Gly Thr Thr Leu
            100                 105                 110

Thr Val Ser Ser
        115

<210> SEQ ID NO 92
<211> LENGTH: 348
<212> TYPE: DNA
<213> ORGANISM: Mus musculus
<220> FEATURE:
<221> NAME/KEY: misc_feature
<223> OTHER INFORMATION: SC91.27 Heavy Chain Variable Region

<400> SEQUENCE: 92
caggtccaac tgcagcagcc tggggctgag gttgtgaagc ctggggcttc agtgaagctg       60
tcctgcaagg cttctggcta caccttcacc aactactgga tgcagtgggt aaaacagagg      120
cctggacagg ccttgaatg gatcggagaa attgatcctt ctgataggta tactatgtac       180
aatcagaagt tcaagggcaa ggccacattg attgtagaca catcctccag cacagcctac      240
atgcagctca gcagcctgac atctgaggac tctgcggtct atttctgtgc aagatttggt      300
tactatgttg actactgggg ccaaggcacc actctcacag tctcctca                   348

<210> SEQ ID NO 93
<211> LENGTH: 116
<212> TYPE: PRT
<213> ORGANISM: Mus musculus
<220> FEATURE:
<221> NAME/KEY: MISC_FEATURE
<223> OTHER INFORMATION: SC91.27 Heavy Chain Variable Region

<400> SEQUENCE: 93

Gln Val Gln Leu Gln Gln Pro Gly Ala Glu Val Val Lys Pro Gly Ala
1               5                   10                  15

Ser Val Lys Leu Ser Cys Lys Ala Ser Gly Tyr Thr Phe Thr Asn Tyr
            20                  25                  30

Trp Met Gln Trp Val Lys Gln Arg Pro Gly Gln Gly Leu Glu Trp Ile
        35                  40                  45

Gly Glu Ile Asp Pro Ser Asp Arg Tyr Thr Met Tyr Asn Gln Lys Phe
    50                  55                  60

Lys Gly Lys Ala Thr Leu Ile Val Asp Thr Ser Ser Thr Ala Tyr
65                  70                  75                  80

Met Gln Leu Ser Ser Leu Thr Ser Glu Asp Ser Ala Val Tyr Phe Cys
            85                  90                  95

```
Ala Arg Phe Gly Tyr Tyr Val Asp Tyr Trp Gly Gln Gly Thr Thr Leu
            100                 105                 110

Thr Val Ser Ser
        115

<210> SEQ ID NO 94
<211> LENGTH: 348
<212> TYPE: DNA
<213> ORGANISM: Mus musculus
<220> FEATURE:
<221> NAME/KEY: misc_feature
<223> OTHER INFORMATION: SC91.186 Heavy Chain Variable Region

<400> SEQUENCE: 94
caagttactc tgaaagagtc tggccctggg atattgcagc cctcccagac cctcagtcta      60
acttgttctt tctctggggtt ttcactgcgc acatctggta tgaatatagg ctggattcgt    120
cagccttcag ggaagggtct ggagtggctg acacacattt ggtggaatga tgataagtcc    180
tacaacccag ccctgaaaag ccggctcaca atctccaagg atacctccaa caaccaggta    240
ttcctcaaga tcgccagtgt ggtcactgca gataccgcca catactactg tgttcgaggt    300
gaccggtttg cttactgggg ccaagggact ctggtcactg tctctgca                 348

<210> SEQ ID NO 95
<211> LENGTH: 116
<212> TYPE: PRT
<213> ORGANISM: Mus musculus
<220> FEATURE:
<221> NAME/KEY: MISC_FEATURE
<223> OTHER INFORMATION: SC91.186 Heavy Chain Variable Region

<400> SEQUENCE: 95

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Ser
            20                  25                  30

Gly Met Asn Ile Gly Trp Ile Arg Gln Pro Ser Gly Lys Gly Leu Glu
        35                  40                  45

Trp Leu Thr His Ile Trp Trp Asn Asp Asp Lys Ser Tyr Asn Pro Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Val Thr Ala Asp Thr Ala Thr Tyr Tyr
                85                  90                  95

Cys Val Arg Gly Asp Arg Phe Ala Tyr Trp Gly Gln Gly Thr Leu Val
            100                 105                 110

Thr Val Ser Ala
        115

<210> SEQ ID NO 96

<400> SEQUENCE: 96

000

<210> SEQ ID NO 97

<400> SEQUENCE: 97

000
```

<210> SEQ ID NO 98

<400> SEQUENCE: 98

000

<210> SEQ ID NO 99

<400> SEQUENCE: 99

000

<210> SEQ ID NO 100
<211> LENGTH: 336
<212> TYPE: DNA
<213> ORGANISM: Homo sapiens
<220> FEATURE:
<221> NAME/KEY: misc_feature
<223> OTHER INFORMATION: hSC91.1 Light Chain Variable Region

<400> SEQUENCE: 100

```
gatatagtga tgactcaatc ccccgattct cttgccgtct ctctgggtga gagagcaact    60
ataaattgta gatcctcaca atctttggtc cactcaacag gcaacactta tttgcattgg   120
tatcagcaaa aacccggaca accaccaaaa ctcctcatat acaaagtgtc taatcgcttt   180
tctggagttc ccgaccgttt ttccgggtcc ggtagcggaa ctgactttac cctgaccata   240
tcttcactgc aagcagagga cgtggctgtg tattactgtt cacagagcac acacgtaccc   300
tttacattcg ggcaaggcac taaactcgag atcaag                              336
```

<210> SEQ ID NO 101
<211> LENGTH: 112
<212> TYPE: PRT
<213> ORGANISM: Homo sapiens
<220> FEATURE:
<221> NAME/KEY: MISC_FEATURE
<223> OTHER INFORMATION: hSC91.1 Light Chain Variable Region

<400> SEQUENCE: 101

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Val His Ser
            20                  25                  30

Thr Gly Asn Thr Tyr Leu His Trp Tyr Gln Gln Lys Pro Gly Gln Pro
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Ser Gln Ser
                85                  90                  95

Thr His Val Pro Phe Thr Phe Gly Gln Gly Thr Lys Leu Glu Ile Lys
            100                 105                 110
```

<210> SEQ ID NO 102
<211> LENGTH: 348
<212> TYPE: DNA
<213> ORGANISM: Homo sapiens
<220> FEATURE:
<221> NAME/KEY: misc_feature
<223> OTHER INFORMATION: hSC91.1 Heavy Chain Variable Region

<400> SEQUENCE: 102

-continued

```
gaggtccagt tggttcagtc aggagcagaa gtaaaaaagc ctggggaatc tcttaaaatt      60
tcatgtaagg gtagtggata cagtttcacc agttattgga tgcagtgggt gaggcagatg     120
cccggtaaag gattggaatg gatgggcgaa atagacccca gcgacaacta tacactttac    180
aatcagaagt ttaagggaca ggtgacaatc agcgcagata aaagcatctc caccgcttac    240
ttgcaatgga gctccctcaa ggcatcagat acagctatgt actactgtgc tcgtttcggc    300
tactatgtgg attactgggg gcagggcacc accgtaaccg taagctct                 348
```

<210> SEQ ID NO 103
<211> LENGTH: 116
<212> TYPE: PRT
<213> ORGANISM: Homo sapiens
<220> FEATURE:
<221> NAME/KEY: MISC_FEATURE
<223> OTHER INFORMATION: hSC91.1 Heavy Chain Variable Region

<400> SEQUENCE: 103

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Met Gln Trp Val Arg Gln Met Pro Gly Lys Gly Leu Glu Trp Met
        35                  40                  45

Gly Glu Ile Asp Pro Ser Asp Asn Tyr Thr Leu Tyr Asn Gln Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Phe Gly Tyr Tyr Val Asp Tyr Trp Gly Gln Gly Thr Thr Val
            100                 105                 110

Thr Val Ser Ser
        115
```

<210> SEQ ID NO 104
<211> LENGTH: 348
<212> TYPE: DNA
<213> ORGANISM: Homo sapiens
<220> FEATURE:
<221> NAME/KEY: misc_feature
<223> OTHER INFORMATION: hSC91.1 N55Q Heavy Chain Variable Region

<400> SEQUENCE: 104

```
gaggtgcaat tggtccaaag tggagccgaa gtcaaaaaac caggcgaaag tctgaaaata      60
tcttgcaagg gcagcggata ttcctttact tcatactgga tgcaatgggt tcgtcagatg    120
ccaggcaagg ggttggagtg gatggggaa atagatccca gcgatcaata tactctgtac    180
aatcagaaat tcaaaggaca ggtcaccatt tccgcagata gtcaatctc aacagcttac    240 ctccaatggt catcactcaa agcctcagat acagcaatgt actattgtgc ccgttttgga    300
tattacgtgg attactgggg tcaagggaca accgtcaccg ttagctct                 348
```

<210> SEQ ID NO 105
<211> LENGTH: 116
<212> TYPE: PRT
<213> ORGANISM: Homo sapiens
<220> FEATURE:
<221> NAME/KEY: MISC_FEATURE
<223> OTHER INFORMATION: hSC91.1 N55Q Heavy Chain Variable Region

<400> SEQUENCE: 105

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Met Gln Trp Val Arg Gln Met Pro Gly Lys Gly Leu Glu Trp Met
        35                  40                  45

Gly Glu Ile Asp Pro Ser Asp Gln Tyr Thr Leu Tyr Asn Gln Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Phe Gly Tyr Tyr Val Asp Tyr Trp Gly Gln Gly Thr Thr Val
            100                 105                 110

Thr Val Ser Ser
            115

<210> SEQ ID NO 106
<211> LENGTH: 321
<212> TYPE: DNA
<213> ORGANISM: Homo sapiens
<220> FEATURE:
<221> NAME/KEY: misc_feature
<223> OTHER INFORMATION: hSC91.9 Light Chain Variable Region

<400> SEQUENCE: 106
gatattcaaa tgactcaaag tcctagcagt ctgagtgcca gtgtgggtga tcgcgtgacc        60
atcacttgtc gtgcctcaca ggatattagt aacttcctca actggtatca acaaaaaccc       120
ggaaaggctc ccaagttgct tatctattat acttcccggt tgcattctgg tgtaccaagt       180
agattttcag gttccggtag cggtactgac tttactttga ccataagttc cctgcaacct       240
gaggacttcg caacttacta ctgtcaacaa ggtaatactc tgccatacac ctttggtggg       300
ggcaccaagg tcgaaataaa g                                                 321

<210> SEQ ID NO 107
<211> LENGTH: 107
<212> TYPE: PRT
<213> ORGANISM: Homo sapiens
<220> FEATURE:
<221> NAME/KEY: MISC_FEATURE
<223> OTHER INFORMATION: hSC91.9 Light Chain Variable Region

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

```
Thr Phe Gly Gly Gly Thr Lys Val Glu Ile Lys
            100                 105
```

<210> SEQ ID NO 108
<211> LENGTH: 372
<212> TYPE: DNA
<213> ORGANISM: Homo sapiens
<220> FEATURE:
<221> NAME/KEY: misc_feature
<223> OTHER INFORMATION: hSC91.9 Heavy Chain Variable Region

<400> SEQUENCE: 108

```
caggttcagc tcgtccagtc cggtgctgag gttaagaaac ccggagctag tgtgaaggtt      60
tcctgcaaag ccagcggata ccttcatt agctactgga tgcactgggt acgtcaggcc      120
cctggccagg gtttggaatg gatgggcat atacacccaa attccggtag taccaattac      180
aatgagaatt tcaaatctcg tgtgaccatg acacgagata cttcaacctc cactgtttat      240
atggagctgt caagtctgcg aagtgaggac acagcagtgt actactgcgc tcgtgacctc      300
cttatcgcca ctgttgtggt cactccatac tttgcatatt ggggtcaagg cacttggta      360 acagtgagta gt                                                        372
```

<210> SEQ ID NO 109
<211> LENGTH: 124
<212> TYPE: PRT
<213> ORGANISM: Homo sapiens
<220> FEATURE:
<221> NAME/KEY: MISC_FEATURE
<223> OTHER INFORMATION: hSC91.9 Heavy Chain Variable Region

<400> SEQUENCE: 109

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Trp Met His Trp Val Arg Gln Ala Pro Gly Gln Gly Leu Glu Trp Met
        35                  40                  45

Gly Met Ile His Pro Asn Ser Gly Ser Thr Asn Tyr Asn Glu Asn Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Leu Leu Ile Ala Thr Val Val Val Thr Pro Tyr Phe Ala
            100                 105                 110

Tyr Trp Gly Gln Gly Thr Leu Val Thr Val Ser Ser
        115                 120
```

<210> SEQ ID NO 110
<211> LENGTH: 219
<212> TYPE: PRT
<213> ORGANISM: Homo sapiens
<220> FEATURE:
<221> NAME/KEY: MISC_FEATURE
<223> OTHER INFORMATION: hSC91.1 Full length Light Chain

<400> SEQUENCE: 110

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Val His Ser
            20                  25                  30
```

```
Thr Gly Asn Thr Tyr Leu His Trp Tyr Gln Gln Lys Pro Gly Gln Pro
        35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Thr Ile
 65                  70                  75                  80

Ser Ser Leu Gln Ala Glu Asp Val Ala Val Tyr Tyr Cys Ser Gln Ser
                85                  90                  95

Thr His Val Pro Phe Thr Phe Gly Gln Gly Thr Lys Leu Glu Ile Lys
               100                 105                 110

Arg Thr Val Ala Ala Pro Ser Val Phe Ile Phe Pro Pro Ser Asp Glu
               115                 120                 125

Gln Leu Lys Ser Gly Thr Ala Ser Val Val Cys Leu Leu Asn Asn Phe
       130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
               165                 170                 175

Thr Tyr Ser Leu Ser Ser Thr Leu Thr Leu Ser Lys Ala Asp Tyr Glu
       180                 185                 190

Lys His Lys Val Tyr Ala Cys Glu Val Thr His Gln Gly Leu Ser Ser
       195                 200                 205

Pro Val Thr Lys Ser Phe Asn Arg Gly Glu Cys
       210                 215

<210> SEQ ID NO 111
<211> LENGTH: 445
<212> TYPE: PRT
<213> ORGANISM: Homo sapiens
<220> FEATURE:
<221> NAME/KEY: MISC_FEATURE
<223> OTHER INFORMATION: hSC91.1 Full length Heavy Chain

<400> SEQUENCE: 111

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Met Gln Trp Val Arg Gln Met Pro Gly Lys Gly Leu Glu Trp Met
        35                  40                  45

Gly Glu Ile Asp Pro Ser Asp Asn Tyr Thr Leu Tyr Asn Gln Lys Phe
 50                  55                  60

Lys Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Phe Gly Tyr Tyr Val Asp Tyr Trp Gly Gln Gly Thr Thr Val
               100                 105                 110

Thr Val Ser Ser Ala Ser Thr Lys Gly Pro Ser Val Phe Pro Leu Ala
       115                 120                 125

Pro Ser Ser Lys Ser Thr Ser Gly Gly Thr Ala Ala Leu Gly Cys Leu
       130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
```

```
                    165                 170                 175
Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 112

<400> SEQUENCE: 112

000

<210> SEQ ID NO 113
<211> LENGTH: 445
<212> TYPE: PRT
<213> ORGANISM: Homo sapiens
<220> FEATURE:
<221> NAME/KEY: MISC_FEATURE
<223> OTHER INFORMATION: hSC91.1MJ (N55Q) Full length Heavy Chain

<400> SEQUENCE: 113

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Met Gln Trp Val Arg Gln Met Pro Gly Lys Gly Leu Glu Trp Met
        35                  40                  45
```

```
Gly Glu Ile Asp Pro Ser Asp Gln Tyr Thr Leu Tyr Asn Gln Lys Phe
 50                  55                  60
Lys Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Phe Gly Tyr Tyr Val Asp Tyr Trp Gly Gln Gly Thr Thr Val
                100                 105                 110
Thr Val Ser Ser Ala Ser Thr Lys Gly Pro Ser Val Phe Pro Leu Ala
            115                 120                 125
Pro Ser Ser Lys Ser Thr Ser Gly Gly Thr Ala Ala Leu Gly Cys Leu
        130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Pro Lys Ser Cys Asp Lys Thr His Thr
210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Ala Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly
        435                 440                 445

<210> SEQ ID NO 114
```

```
<400> SEQUENCE: 114

000

<210> SEQ ID NO 115
<211> LENGTH: 445
<212> TYPE: PRT
<213> ORGANISM: Homo sapiens
<220> FEATURE:
<221> NAME/KEY: MISC_FEATURE
<223> OTHER INFORMATION: hSC91.1ss1 (N55Q) Full length Heavy Chain

<400> SEQUENCE: 115
```

| | | | | | | | | | | | | | | | |
|---|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Glu |
| 1 | | | | 5 | | | | | 10 | | | | | 15 | |
| Ser | Leu | Lys | Ile | Ser | Cys | Lys | Gly | Ser | Gly | Tyr | Ser | Phe | Thr | Ser | Tyr |
| | | | 20 | | | | | 25 | | | | | 30 | | |
| Trp | Met | Gln | Trp | Val | Arg | Gln | Met | Pro | Gly | Lys | Gly | Leu | Glu | Trp | Met |
| | | 35 | | | | | 40 | | | | | 45 | | | |
| Gly | Glu | Ile | Asp | Pro | Ser | Asp | Gln | Tyr | Thr | Leu | Tyr | Asn | Gln | Lys | Phe |
| | 50 | | | | | 55 | | | | | 60 | | | | |
| Lys | Gly | Gln | Val | Thr | Ile | Ser | Ala | Asp | Lys | Ser | Ile | Ser | Thr | Ala | Tyr |
| 65 | | | | | 70 | | | | | 75 | | | | | 80 |
| Leu | Gln | Trp | Ser | Ser | Leu | Lys | Ala | Ser | Asp | Thr | Ala | Met | Tyr | Tyr | Cys |
| | | | | 85 | | | | | 90 | | | | | 95 | |
| Ala | Arg | Phe | Gly | Tyr | Tyr | Val | Asp | Tyr | Trp | Gly | Gln | Gly | Thr | Thr | Val |
| | | | 100 | | | | | 105 | | | | | 110 | | |
| Thr | Val | Ser | Ser | Ala | Ser | Thr | Lys | Gly | Pro | Ser | Val | Phe | Pro | Leu | Ala |
| | | | 115 | | | | | 120 | | | | | 125 | | |
| Pro | Ser | Ser | Lys | Ser | Thr | Ser | Gly | Gly | Thr | Ala | Ala | Leu | Gly | Cys | Leu |
| | 130 | | | | | 135 | | | | | 140 | | | | |
| Val | Lys | Asp | Tyr | Phe | Pro | Glu | Pro | Val | Thr | Val | Ser | Trp | Asn | Ser | Gly |
| 145 | | | | | 150 | | | | | 155 | | | | | 160 |
| Ala | Leu | Thr | Ser | Gly | Val | His | Thr | Phe | Pro | Ala | Val | Leu | Gln | Ser | Ser |
| | | | | 165 | | | | | 170 | | | | | 175 | |
| Gly | Leu | Tyr | Ser | Leu | Ser | Ser | Val | Val | Thr | Val | Pro | Ser | Ser | Ser | Leu |
| | | | 180 | | | | | 185 | | | | | 190 | | |
| Gly | Thr | Gln | Thr | Tyr | Ile | Cys | Asn | Val | Asn | His | Lys | Pro | Ser | Asn | Thr |
| | | | 195 | | | | | 200 | | | | | 205 | | |
| Lys | Val | Asp | Lys | Lys | Val | Glu | Pro | Lys | Ser | Ser | Asp | Lys | Thr | His | Thr |
| | 210 | | | | | 215 | | | | | 220 | | | | |
| Cys | Pro | Pro | Cys | Pro | Ala | Pro | Glu | Leu | Leu | Gly | Gly | Pro | Ser | Val | Phe |
| 225 | | | | | 230 | | | | | 235 | | | | | 240 |
| Leu | Phe | Pro | Pro | Lys | Pro | Lys | Asp | Thr | Leu | Met | Ile | Ser | Arg | Thr | Pro |
| | | | | 245 | | | | | 250 | | | | | 255 | |
| Glu | Val | Thr | Cys | Val | Val | Val | Asp | Val | Ser | His | Glu | Asp | Pro | Glu | Val |
| | | | 260 | | | | | 265 | | | | | 270 | | |
| Lys | Phe | Asn | Trp | Tyr | Val | Asp | Gly | Val | Glu | Val | His | Asn | Ala | Lys | Thr |
| | | | 275 | | | | | 280 | | | | | 285 | | |
| Lys | Pro | Arg | Glu | Glu | Gln | Tyr | Asn | Ser | Thr | Tyr | Arg | Val | Val | Ser | Val |
| | 290 | | | | | 295 | | | | | 300 | | | | |
| Leu | Thr | Val | Leu | His | Gln | Asp | Trp | Leu | Asn | Gly | Lys | Glu | Tyr | Lys | Cys |
| 305 | | | | | 310 | | | | | 315 | | | | | 320 |
| Lys | Val | Ser | Asn | Lys | Ala | Leu | Pro | Ala | Pro | Ile | Glu | Lys | Thr | Ile | Ser |
| | | | | 325 | | | | | 330 | | | | | 335 | |
| Lys | Ala | Lys | Gly | Gln | Pro | Arg | Glu | Pro | Gln | Val | Tyr | Thr | Leu | Pro | Pro |

```
                340                 345                 350
Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 116

<400> SEQUENCE: 116

000

<210> SEQ ID NO 117
<211> LENGTH: 445
<212> TYPE: PRT
<213> ORGANISM: Homo sapiens
<220> FEATURE:
<221> NAME/KEY: MISC_FEATURE
<223> OTHER INFORMATION: hSC91.1ss1MJ (N55Q) Full length Heavy Chain

<400> SEQUENCE: 117

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Met Gln Trp Val Arg Gln Met Pro Gly Lys Gly Leu Glu Trp Met
        35                  40                  45

Gly Glu Ile Asp Pro Ser Asp Gln Tyr Thr Leu Tyr Asn Gln Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Phe Gly Tyr Tyr Val Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Ser Asp Lys Thr His Thr
    210                 215                 220
```

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Ala Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly
    435                 440                 445

<210> SEQ ID NO 118

<400> SEQUENCE: 118

000

<210> SEQ ID NO 119

<400> SEQUENCE: 119

000

<210> SEQ ID NO 120
<211> LENGTH: 214
<212> TYPE: PRT
<213> ORGANISM: Homo sapiens
<220> FEATURE:
<221> NAME/KEY: MISC_FEATURE
<223> OTHER INFORMATION: hSC91.9; hSC91.9MJ; and hSC91.9ss1MJ Full
      length Light Chain

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 121
<211> LENGTH: 453
<212> TYPE: PRT
<213> ORGANISM: Homo sapiens
<220> FEATURE:
<221> NAME/KEY: MISC_FEATURE
<223> OTHER INFORMATION: hSC91.9 Full length Heavy Chain

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Trp Met His Trp Val Arg Gln Ala Pro Gly Gln Gly Leu Glu Trp Met
        35                  40                  45

Gly Met Ile His Pro Asn Ser Gly Ser Thr Asn Tyr Asn Glu Asn Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Leu Leu Ile Ala Thr Val Val Thr Pro Tyr Phe Ala
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
            195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 122

<400> SEQUENCE: 122

000

<210> SEQ ID NO 123
<211> LENGTH: 453
<212> TYPE: PRT
<213> ORGANISM: Homo sapiens
<220> FEATURE:
<221> NAME/KEY: MISC_FEATURE
<223> OTHER INFORMATION: hSC91.9MJ Full length Heavy Chain

<400> SEQUENCE: 123

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
                20                  25                  30

Trp Met His Trp Val Arg Gln Ala Pro Gly Gln Gly Leu Glu Trp Met
            35                  40                  45

Gly Met Ile His Pro Asn Ser Gly Ser Thr Asn Tyr Asn Glu Asn Phe

```
            50                  55                  60
Lys Ser Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                     85                  90                  95

Ala Arg Asp Leu Leu Ile Ala Thr Val Val Thr Pro Tyr Phe Ala
                100                 105                 110

Tyr Trp Gly Gln Gly Thr Leu Val Thr Val Ser Ser Ala Ser Thr Lys
                115                 120                 125

Gly Pro Ser Val Phe Pro Leu Ala Pro Ser Ser Lys Ser Thr Ser Gly
                130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr Ala
                290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
                355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly
        450

<210> SEQ ID NO 124
```

<400> SEQUENCE: 124

000

<210> SEQ ID NO 125
<211> LENGTH: 453
<212> TYPE: PRT
<213> ORGANISM: Homo sapiens
<220> FEATURE:
<221> NAME/KEY: MISC_FEATURE
<223> OTHER INFORMATION: hSC91.9ss1MJ Full length Heavy Chain

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Trp Met His Trp Val Arg Gln Ala Pro Gly Gln Gly Leu Glu Trp Met
        35                  40                  45

Gly Met Ile His Pro Asn Ser Gly Ser Thr Asn Tyr Asn Glu Asn Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Leu Leu Ile Ala Thr Val Val Thr Pro Tyr Phe Ala
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Ser Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ala
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 126
<211> LENGTH: 348
<212> TYPE: DNA
<213> ORGANISM: Homo sapiens
<220> FEATURE:
<221> NAME/KEY: misc_feature
<223> OTHER INFORMATION: hSC91.1v2 (N55Q) Heavy Chain Variable Region

<400> SEQUENCE: 126
caggttcaac tccagcaacc tggagcagaa ttggtgaaac caggagcatc tgtcaagttg      60
agttgcaaag ccagcggata ccttcaca agttactgga tgcagtgggt aaaacagaga     120
cccggacaag gtctggaatg gataggagaa atagaccct ctgatcagta cactctttat     180
aatcagaagt tcaaaggcaa ggcaacactc actgttgaca ccagttcctc aactgcctat     240
atgcagctta gcagtctcac cagcgaggac agtgccgttt actattgtgc caggtttggt     300
tactacgttg attattgggg cctgggaaca accctcactg tgagttcc                 348

<210> SEQ ID NO 127
<211> LENGTH: 116
<212> TYPE: PRT
<213> ORGANISM: Homo sapiens
<220> FEATURE:
<221> NAME/KEY: MISC_FEATURE
<223> OTHER INFORMATION: hSC91.1v2 (N55Q) Heavy Chain Variable Region

<400> SEQUENCE: 127

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Glu Ile Asp Pro Ser Asp Gln Tyr Thr Leu Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

```
Ala Arg Phe Gly Tyr Tyr Val Asp Tyr Trp Gly Leu Gly Thr Thr Leu
            100                 105                 110
Thr Val Ser Ser
        115
```

ANTI-BMPR1B ANTIBODIES AND METHODS OF USE

CROSS REFERENCED APPLICATIONS

This application claims the benefit of U.S. Provisional Application No. 62/325,981 filed on Apr. 21, 2016, U.S. Provisional Application No. 62/443,404 filed on Jan. 6, 2017, and U.S. Provisional Application No. 62/486,140 filed on Apr. 17, 2017, each of which is incorporated herein by reference in its entirety.

SEQUENCE LISTING

This application contains a sequence listing which has been submitted in ASCII format via EFS-Web and is hereby incorporated by reference in its entirety. Said ASCII copy, created on Apr. 19, 2017, is named sc9101WOO1_ST25.txt and is 125 KB (129,021 bytes) in size.

FIELD OF THE INVENTION

This application generally relates to novel anti-BMPR1B antibodies or immunoreactive fragments thereof and compositions, including antibody drug conjugates (ADCs), comprising the same for the treatment, diagnosis or prophylaxis of cancer and any recurrence or metastasis thereof. Selected embodiments of the invention provide for the use of such anti-BMPR1B antibodies or antibody drug conjugates for the treatment of cancer comprising a reduction in tumorigenic cell frequency.

BACKGROUND OF THE INVENTION

Differentiation and proliferation of stem cells and progenitor cells are normal ongoing processes that act in concert to support tissue growth during organogenesis, cell repair and cell replacement. The system is tightly regulated to ensure that only appropriate signals are generated based on the needs of the organism. Cell proliferation and differentiation normally occur only as necessary for the replacement of damaged or dying cells or for growth. However, disruption of these processes can be triggered by many factors including the under- or overabundance of various signaling chemicals, the presence of altered microenvironments, genetic mutations or a combination thereof. Disruption of normal cellular proliferation and/or differentiation can lead to various disorders including proliferative diseases such as cancer.

Conventional therapeutic treatments for cancer include chemotherapy, radiotherapy and immunotherapy. Often these treatments are ineffective and surgical resection may not provide a viable clinical alternative. Limitations in the current standard of care are particularly evident in those cases where patients undergo first line treatments and subsequently relapse. In such cases refractory tumors, often aggressive and incurable, frequently arise. The overall survival rates for many tumors have remained largely unchanged over the years due, at least in part, to the failure of existing therapies to prevent relapse, tumor recurrence and metastasis. There remains therefore a great need to develop more targeted and potent therapies for proliferative disorders. The current invention addresses this need.

SUMMARY OF THE INVENTION

In a broad aspect the present invention provides isolated antibodies, and corresponding antibody drug or diagnostic conjugates (ADCs), or compositions thereof, which specifically bind to human BMPR1B determinants. In certain embodiments the BMPR1B determinant is a BMPR1B protein expressed on tumor cells while in other embodiments the BMPR1B determinant is expressed on tumor initiating cells. In other embodiments the antibodies of the invention bind to a BMPR1B protein and compete for binding with an antibody that binds to an epitope on human BMPR1B protein (hBMPR1B).

In selected embodiments the invention comprises an antibody that comprises or competes for binding with an isolated antibody that binds to human BMPR1B (SEQ ID NO: 1), wherein the isolated antibody comprises: (1) a light chain variable region (VL) of SEQ ID NO: 21 and a heavy chain variable region (VH) of SEQ ID NO: 23; or (2) a VL of SEQ ID NO: 25 and a VH of SEQ ID NO: 27; or (3) a VL of SEQ ID NO: 29 and a VH of SEQ ID NO: 31; or (4) a VL of SEQ ID NO: 33 and a VH of SEQ ID NO: 35; or (5) a VL of SEQ ID NO: 37 and a VH of SEQ ID NO: 39; or (6) a VL of SEQ ID NO: 41 and a VH of SEQ ID NO: 43; or (7) a VL of SEQ ID NO: 45 and a VH of SEQ ID NO: 47; or (8) a VL of SEQ ID NO: 49 and a VH of SEQ ID NO: 51; or (9) a VL of SEQ ID NO: 53 and a VH of SEQ ID NO: 55; or (10) a VL of SEQ ID NO: 57 and a VH of SEQ ID NO: 59; or (11) a VL of SEQ ID NO: 61 and a VH of SEQ ID NO: 63; or (12) a VL of SEQ ID NO: 65 and a VH of SEQ ID NO: 67; or (13) a VL of SEQ ID NO: 69 and a VH of SEQ ID NO: 71; or (14) a VL of SEQ ID NO: 73 and a VH of SEQ ID NO: 75; or (15) a VL of SEQ ID NO: 77 and a VH of SEQ ID NO: 79; or (16) a VL of SEQ ID NO: 81 and a VH of SEQ ID NO: 83; or (17) a VL of SEQ ID NO: 85 and a VH of SEQ ID NO: 87; or (18) a VL of SEQ ID NO: 89 and a VH of SEQ ID NO: 91; or (19) a VL of SEQ ID NO: 89 and a VH of SEQ ID NO: 93; or (20) a VL of SEQ ID NO: 37 and a VH of SEQ ID NO: 95. Note that SC91.20 (clone 18) and SC91.27 (clone 19) have the same light chain variable region (i.e., SEQ ID NO: 89) paired with two unique heavy chain variable regions (SEQ ID NOS: 93 and 95). Similarly, SC91.14 (clone 5) has the same VL (SEQ ID NO: 37) as SC91.186 (clone 20) though the antibodies comprise unique VH regions (SEQ ID NO: 39 and SEQ ID NO: 95 respectively).

In a further aspect, the invention comprises an antibody that binds to BMPR1B comprising a light chain variable region and a heavy chain variable region, wherein the light chain variable region has three CDRs of a light chain variable region set forth as SEQ ID NO: 21, SEQ ID NO: 25, SEQ ID NO: 29, SEQ ID NO: 33, SEQ ID NO: 37, SEQ ID NO: 41, SEQ ID NO: 45 or SEQ ID NO: 49; SEQ ID NO: 53, SEQ ID NO: 57, SEQ ID NO: 61, SEQ ID NO: 65, SEQ ID NO: 69, SEQ ID NO: 73, SEQ ID NO: 77, SEQ ID NO: 81, SEQ ID NO: 85 or SEQ ID NO: 89 and the heavy chain variable region has three CDRs of a heavy chain variable region set forth as SEQ ID NO: 23, SEQ ID NO: 27, SEQ ID NO: 31, SEQ ID NO: 35, SEQ ID NO: 39, SEQ ID NO: 43, SEQ ID NO: 47, SEQ ID NO: 51, SEQ ID NO: 55, SEQ ID NO: 59, SEQ ID NO: 63, SEQ ID NO: 67; SEQ ID NO: 71, SEQ ID NO: 75, SEQ ID NO: 79, SEQ ID NO: 83, SEQ ID NO: 87, SEQ ID NO: 91, SEQ ID NO: 93 or SEQ ID NO: 95.

In other aspects the invention comprises a humanized antibody having a VL comprising SEQ ID NO: 101 and a VH comprising SEQ ID NO: 103 or having a VL comprising SEQ ID NO: 101 and a VH comprising SEQ ID NO: 105 or having a VL comprising SEQ ID NO: 101 and a VH comprising SEQ ID NO: 127 or having a VL comprising SEQ ID NO: 107 and a VH comprising SEQ ID NO: 109.

In certain embodiments these humanized antibodies will comprise site-specific antibodies. In other embodiments such antibodies will comprise an N297A mutation (MJ mutation). In still other embodiments the antibodies of the invention may comprise site-specific antibodies having the MJ mutation. In yet other embodiments the disclosed SC91.1 derived antibodies may comprise a stabilizing N55Q mutation.

In other selected embodiments the invention will comprise a humanized antibody selected from the group consisting of hSC91.1 (comprising light and heavy chains set forth in SEQ ID NOS: 110 and 111), hSC91.1MJ (comprising light and heavy chains set forth in SEQ ID NOS: 110 and 113), hSC91.1ss1 (comprising light and heavy chains set forth in SEQ ID NOS: 110 and 115), hSC91.1ss1MJ (comprising light and heavy chains set forth in SEQ ID NOS: 110 and 117), hSC91.9 (comprising light and heavy chains set forth in SEQ ID NOS: 120 and 121), hSC91.9MJ (comprising light and heavy chains set forth in SEQ ID NOS: 120 and 123) and hSC91.9ss1MJ (comprising light and heavy chains set forth in SEQ ID NOS: 120 and 125).

In some aspects of the invention the antibody comprises a chimeric, CDR grafted, humanized or human antibody or an immunoreactive fragment thereof. In other aspects of the invention the antibody, preferably comprising all or part of the aforementioned sequences, is an internalizing antibody. In yet other embodiments the antibodies will comprise site-specific antibodies. In certain embodiments the anti-BMPR1B antibodies will inhibit the binding of BMPR1B ligands BMP4 and/or BMP2 to BMPR1B. In other selected embodiments the invention comprises antibody drug conjugates incorporating any of the aforementioned antibodies.

In certain aspects the invention comprises a nucleic acid encoding an anti-BMPR1B antibody of the invention or a fragment thereof. In other embodiments the invention comprises a vector comprising one or more of the above described nucleic acids or a host cell comprising said nucleic acids or vectors.

As alluded to above the present invention further provides anti-BMPR1B antibody drug conjugates where antibodies as disclosed herein are conjugated to a payload. In certain aspects the present invention comprises ADCs that immunopreferentially associate or bind to hBMPR1B. Compatible anti-BMPR1B antibody drug conjugates (ADCs) of the invention may generally comprise the formula:

Ab-[L-D]n or a pharmaceutically acceptable salt thereof wherein a) Ab comprises an anti-BMPR1B antibody;
b) L comprises an optional linker;
c) D comprises a drug; and
d) n is an integer from about 1 to about 20.

In certain aspects the ADCs of the invention comprise an anti-BMPR1B antibody such as those described above or an immunoreactive fragment thereof. In other embodiments the ADCs of the invention comprise a cytotoxic compound selected from radioisotopes, calicheamicins, pyrrolobenzodiazepines (PBDs), benzodiazepine derivatives, auristatins, dolastatins, duocarmycins, maytansinoids or an additional therapeutic moiety described herein. In certain preferred embodiments the disclosed ADCs will comprise a PBD.

Further provided are pharmaceutical compositions comprising an anti-BMPR1B ADC as disclosed herein. In certain embodiments the compositions will comprise a selected drug-antibody ratio (DAR) where the predominant ADC species comprises greater than about 50%, greater than about 60%, greater than about 70%, greater than about 80%, greater than about 90% or even greater than about 95% of the species present. In some embodiments the selected DAR will be two, while in other embodiments the selected DAR will be four and in other embodiments the selected DAR will be six and in yet other embodiments the selected DAR will be eight.

Another aspect of the invention is a method of treating cancer comprising administering a pharmaceutical composition such as those described herein to a subject in need thereof. In certain aspects the cancer comprises a hematologic malignancy such as, for example, acute myeloid leukemia or diffuse large B-cell lymphoma. In other aspects the subject will be suffering from a solid tumor. With regard to such embodiments the cancer is preferably selected from the group consisting of adrenal cancer, liver cancer, melanoma, kidney cancer, bladder cancer, breast cancer, gastric cancer, ovarian cancer, cervical cancer, uterine cancer, esophageal cancer, colorectal cancer, prostate cancer, pancreatic cancer, lung cancer (both small cell and non-small cell), thyroid cancer and glioblastoma. In certain embodiments the subject will be suffering from breast cancer and, in selected embodiments, luminal B breast cancer. Further, in selected embodiments the method of treating cancer described above comprises administering to the subject at least one additional therapeutic moiety besides the anti-BMPR1B ADCs of the invention.

In still another embodiment the invention comprises a method of reducing tumor initiating cells in a tumor cell population, wherein the method comprises contacting (e.g. in vitro or in vivo) a tumor initiating cell population with an ADCs as described herein whereby the frequency of the tumor initiating cells is reduced.

In one aspect, the invention comprises a method of delivering a cytotoxin to a cell comprising contacting the cell with any of the above described ADCs.

In another aspect, the invention comprises a method of detecting, diagnosing, or monitoring cancer (e.g. breast cancer or hematologic malignancies) in a subject, the method comprising the steps of contacting (e.g. in vitro or in vivo) tumor cells with an BMPR1B detection agent and detecting the BMPR1B agent associated with the tumor cells. In selected embodiments the detection agent shall comprise an anti-BMPR1B antibody or a nucleic acid probe that associates with a BMPR1B genotypic determinant. In related embodiments the diagnostic method will comprise immunohistochemistry (IHC) or in situ hybridization (ISH). In other embodiments the method will comprise contacting a circulating tumor cell with an anti-BMPR1B antibody. Those of skill in the art will further appreciate that such BMPR1B detection agents may be labeled or associated with effectors, markers or reporters as disclosed below and detected using any one of a number of standard in vivo imaging techniques (e.g., MRI, CAT scan, PET scan, etc.).

In a similar vein the present invention also provides kits or devices and associated methods that are useful in the diagnosis, monitoring or treatment of BMPR1B associated disorders such as cancer. To this end the present invention preferably provides an article of manufacture useful for detecting, diagnosing or treating BMPR1B associated disorders comprising a receptacle containing a BMPR1B ADC and instructional materials for using said BMPR1B ADC to treat, monitor or diagnose the BMPR1B associated disorder or provide a dosing regimen for the same. In selected embodiments the devices and associated methods will comprise the step of contacting at least one circulating tumor cell. In other embodiments the disclosed kits will comprise instructions, labels, inserts, readers or the like indicating that the kit or device is used for the diagnosis, monitoring or treatment of a BMPR1B associated cancer or provide a dosing regimen for the same.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description.

BRIEF DESCRIPTION OF THE FIGURES

FIGS. 1A and 1B provide, respectively, an annotated amino acid sequence of BMPR1B (FIG. 1A) along with a schematic representation of the same (FIG. 1B) with individual molecular components delineated for the purposes of explanation;

FIGS. 7A-7D provide, in a tabular form and graphical representations, data directed to antibody binding, cell killing, cross-reactivity and binning characteristics of exemplary anti-BMPR1B antibodies derived from two different hybridoma screenings (screen 1, FIG. 7A and screen 2, FIG. 7B) and the cell killing activity of the antibodies plotted as a function of their bin for each screening episode (screen 1, FIG. 7C and screen 2, FIG. 7D);

FIGS. 8A and 8B provide, in a tabular form, the measured cross reactivity of anti-BMPR1B antibodies from screen 1 (FIG. 8A) and screen 2 (FIG. 8B) with the BMPR1A homolog;

FIGS. 9A-9G provide annotated amino acid and nucleic acid sequences wherein FIGS. 9A and 9B show contiguous amino acid sequences of the light chain (FIG. 9A) and heavy chain (FIG. 9B) variable regions (SEQ ID NOS: 21-95, odd numbers) of exemplary murine anti-BMPR1B antibodies, FIG. 9C shows nucleic acid sequences encoding the aforementioned light and heavy chain variable regions (SEQ ID NOS: 20-94, even numbers), FIG. 9D depicts amino acid sequences and nucleic acid sequences of humanized VL and VH domains, FIG. 9E shows amino acid sequences of full length heavy and light chains of selected antibody constructs and FIGS. 9F and 9G depict the CDRs of light and heavy chain variable regions of the SC91.1 and SC91.9 murine antibodies as determined using Kabat, Chothia, ABM and Contact methodology;

FIGS. 11A-11G show, in tabular and graphical form, BMPR1B protein expression on a number of exemplary BR-LumB PDX tumor cell lines (FIG. 11A); on BR-LumB tumor microarray samples (FIGS. 11B and 11C); on primary BR-LumB tumor samples (FIGS. 11D and 11E) and on human prostate adenocarcinoma samples (FIGS. 11F and 11G) each as determined by immunohistochemistry;

FIGS. 19A-19E evidence the ability of exemplary BMPR1B-specific antibodies to inhibit the binding of BMP2 or BMP4 to its receptor BMPR1B wherein the data is presented in a tabular form (FIG. 19A), as a function of antibody concentration (FIGS. 19B and 19D) and as a function of of the antibody bin (FIGS. 19C and 19E).

DETAILED DESCRIPTION OF THE INVENTION

Figure 1B:
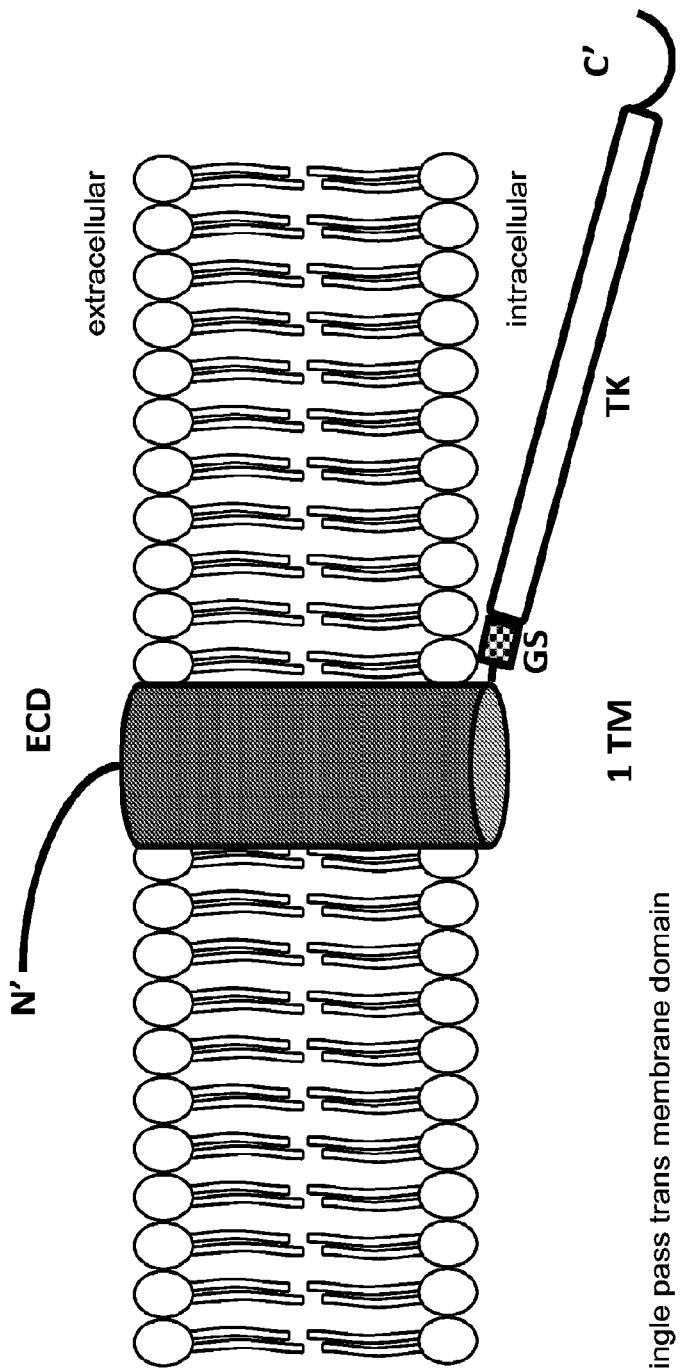

The invention may be embodied in many different forms. Disclosed herein are non-limiting, illustrative embodiments of the invention that exemplify the principles thereof. Any section headings used herein are for organizational purposes only and are not to be construed as limiting the subject matter described. For the purposes of the instant disclosure all identifying sequence accession numbers may be found in the NCBI Reference Sequence (RefSeq) database and/or the NCBI GenBank® archival sequence database unless otherwise noted.

It has surprisingly been found that BMPR1B phenotypic determinants are clinically associated with various proliferative disorders, including neoplasia, and that BMPR1B protein and variants or isoforms thereof provide useful tumor markers which may be exploited in the treatment of related diseases. In this regard the present invention provides novel anti-BMPR1B antibodies and antibody drug conjugates comprising an anti-BMPR1B antibody targeting agent and cytotoxic payload. As discussed in more detail below and set forth in the appended Examples, the disclosed anti-BMPR1B ADCs are particularly effective at eliminating tumorigenic cells and therefore useful for the treatment and prophylaxis of certain proliferative disorders or the progression or recurrence thereof. In addition, the disclosed ADC compositions may be engineered to exhibit a relatively high DAR=2 percentage and unexpected stability that can provide for an improved therapeutic index when compared with conventional ADC compositions comprising the same components.

Moreover, it has been found that BMPR1B markers or determinants such as cell surface BMPR1B protein are therapeutically associated with cancer stem cells (also known as tumor perpetuating cells) and may be effectively exploited to eliminate or silence the same. The ability to selectively reduce or eliminate cancer stem cells through the use of anti-BMPR1B conjugates as disclosed herein is surprising in that such cells are known to generally be resistant to many conventional treatments. That is, the effectiveness of traditional, as well as more recent targeted treatment methods, is often limited by the existence and/or emergence of resistant cancer stem cells that are capable of perpetuating tumor growth even in face of these diverse treatment methods. Further, determinants associated with cancer stem cells often make poor therapeutic targets due to low or inconsistent expression, failure to remain associated with the tumorigenic cell or failure to present at the cell surface. In sharp contrast to the teachings of the prior art, the instantly disclosed ADCs and methods effectively overcome this inherent resistance and to specifically eliminate, deplete, silence or promote the differentiation of such cancer stem cells thereby negating their ability to sustain or re-induce the underlying tumor growth.

Thus, it is particularly remarkable that BMPR1B conjugates such as those disclosed herein may advantageously be used in the treatment and/or prevention of selected proliferative (e.g., neoplastic) disorders or progression or recurrence thereof. It will be appreciated that, while preferred embodiments of the invention will be discussed extensively below, particularly in terms of particular domains, regions or epitopes or in the context of cancer stem cells and their interactions with the disclosed antibody drug conjugates, those skilled in the art will appreciate that the scope of the instant invention is not limited by such exemplary embodiments. Rather, the most expansive embodiments of the present invention and the appended claims are broadly and expressly directed to the disclosed anti-BMPR1B antibodies and conjugates and their use in the treatment and/or prevention of a variety of BMPR1B associated or mediated disorders, including neoplastic or cell proliferative disorders, regardless of any particular mechanism of action or specifically targeted tumor, cellular or molecular component.

I. BMPR1B PHYSIOLOGY

Bone morphogenetic protein receptor type-1B (BMPR1B, also known as ALK6, AMDD, BDA2, BDA1D or CDw293) is a 50-55 kDa single pass, type I transmembrane serine/threonine kinase from the BMP receptor family, and whose ligands are members of the transforming growth factor beta (TGF-β) superfamily. The BMP ligands transduce their signals through heteromeric complexes composed of two type I receptor proteins (of which BMPR1B is a representative) and two type 11 receptor proteins (e.g., BMPR2). Type 11 receptor proteins can bind the ligand but cannot signal in the absence of type 1 receptor proteins. Ligand binding to the complex typically permits the type 11 receptor to phosphorylate and activate the type 1 receptor, leading to its autophosphorylation, which permits it to bind and activate receptor-mediated Smad transcriptional regulators.

Representative BMPR1B protein orthologs include, but are not limited to, human (NP_001194; annotated sequence shown in FIG. 1A), rhesus monkey (NP_001253192), rat (NP_001019430) and mouse (NP_031586). In humans, the BMPR1B gene consists of 13 exons spanning approximately 400 kBp at chromosome 4q22-q24. Transcription of the human BMPR1B locus yields at least four RNA transcripts: a 5397 nucleotide transcript (NM_001256793) that encodes a 532 amino acid protein (NP_001243722); and three other longer transcripts (NM_001203, NM_001256794, NM_001256792) that use differing exons to give rise to unique 5'UTRs, although each of the three transcripts encode the same 502 amino acid protein (represented by NP_001194).

With regard to hBMPR1B FIG. 1A shows an annotated sequence wherein the leader sequence is underlined, the extracellular domain is bolded, the transmembrane domain is boxed, the glycine and serine rich sequence is underlined and the conserved protein tyrosine kinase domain is in bold italic. FIG. 1B provides a schematic diagram of the hBMPR1B protein associated with the cell membrane showing the major components of the molecule corresponding to the annotated sequence in FIG. 1A. In this respect the extracellular domain, transmembrane domain glycine serine rich domain and tyrosine kinase domain are shown in context with each other.

Various BMP ligands may signal through heteromeric receptor complexes containing BMPR1B. Mutations in the BMPR1B gene have been linked to bone disorders such as brachydactyly and acromesomelic dysplasia (OMIM, http://omim.org/entry/603248), the latter of which may be linked to perturbation of the binding of the TGF-β superfamily member GDF5 to the receptor (PMID: 16014698). BMPR1B is also a receptor for BMP2 (PMID: 14576167), BMP4 (PMID: 17425602) and BMP7 (PMID: 17624341). BMPs are also known to play an important role in various stem cell/niche interactions. For instance, in the hematopoietic system, thymocytes express BMPR1B, and T-cell differentiation may depend in part on response of BMPR1B-expressing thymocytes to thymic epithelium-derived BMP2 and BMP4 (PMID: 17425602). Similarly, leukemic myeloid progenitor expansion in CML has been linked to overexpression of BMPR1B sensitizing the cells to autocrine BMP4 and to paracrine BMP signals from the niche (PMID: 24100446). Chronic BMP2 production by the tumor microenvironment, mediated by BMPR1B, has also been reported to drive transformation of immature human mammary epithelial cells towards a luminal phenotype (PMID: 25601208).

II. CANCER STEM CELLS

According to current models, a tumor comprises non-tumorigenic cells and tumorigenic cells. Non-tumorigenic cells do not have the capacity to self-renew and are incapable of reproducibly forming tumors, even when transplanted into immunocompromised mice in excess cell numbers. Tumorigenic cells, also referred to herein as "tumor initiating cells" (TICs), which typically make up a fraction of the tumor's cell population of 0.01-10%, have the ability to form tumors. For hematopoietic malignancies TICs can be very rare ranging from $1:10^4$ to $1:10^7$ in particular in Acute Myeloid Malignancies (AML) or very abundant for example in lymphoma of the B cell lineage. Tumorigenic cells encompass both tumor perpetuating cells (TPCs), referred to interchangeably as cancer stem cells (CSCs), and tumor progenitor cells (TProgs).

CSCs, like normal stem cells that support cellular hierarchies in normal tissue, are able to self-replicate indefinitely while maintaining the capacity for multilineage differentiation. In this regard CSCs are able to generate both tumorigenic progeny and non-tumorigenic progeny and are able to completely recapitulate the heterogeneous cellular composition of the parental tumor as demonstrated by serial isolation and transplantation of low numbers of isolated CSCs into immunocompromised mice. Evidence indicates that unless these "seed cells" are eliminated tumors are much more likely to metastasize or reoccur leading to relapse and ultimate progression of the disease.

TProgs, like CSCs have the ability to fuel tumor growth in a primary transplant. However, unlike CSCs, they are not able to recapitulate the cellular heterogeneity of the parental tumor and are less efficient at reinitiating tumorigenesis in subsequent transplants because TProgs are typically only capable of a finite number of cell divisions as demonstrated by serial transplantation of low numbers of highly purified TProg into immunocompromised mice. TProgs may further be divided into early TProgs and late TProgs, which may be distinguished by phenotype (e.g., cell surface markers) and their different capacities to recapitulate tumor cell architecture. While neither can recapitulate a tumor to the same extent as CSCs, early TProgs have a greater capacity to recapitulate the parental tumor's characteristics than late TProgs. Notwithstanding the foregoing distinctions, it has been shown that some TProg populations can, on rare occasion, gain self-renewal capabilities normally attributed to CSCs and can themselves become CSCs.

CSCs exhibit higher tumorigenicity and are often relatively more quiescent than: (i) TProgs (both early and late TProgs); and (ii) non-tumorigenic cells such as terminally differentiated tumor cells and tumor-infiltrating cells, for example, fibroblasts/stroma, endothelial and hematopoietic cells that may be derived from CSCs and typically comprise the bulk of a tumor. Given that conventional therapies and regimens have, in large part, been designed to debulk tumors and attack rapidly proliferating cells, CSCs are therefore more resistant to conventional therapies and regimens than the faster proliferating TProgs and other bulk tumor cell populations such as non-tumorigenic cells. Other characteristics that may make CSCs relatively chemoresistant to conventional therapies are increased expression of multi-drug resistance transporters, enhanced DNA repair mechanisms and anti-apoptotic gene expression. Such CSC properties have been implicated in the failure of standard treatment regimens to provide a lasting response in patients with advanced stage neoplasia as standard chemotherapy does not effectively target the CSCs that actually fuel continued tumor growth and recurrence.

It has surprisingly been discovered that BMPR1B expression is associated with various tumorigenic cell subpopulations in a manner which renders them susceptible to treatment as set forth herein. The invention provides anti-BMPR1B antibodies that may be particularly useful for targeting tumorigenic cells and may be used to silence, sensitize, neutralize, reduce the frequency, block, abrogate, interfere with, decrease, hinder, restrain, control, deplete, moderate, mediate, diminish, reprogram, eliminate, kill or otherwise inhibit (collectively, "inhibit") tumorigenic cells, thereby facilitating the treatment, management and/or prevention of proliferative disorders (e.g. cancer). Advantageously, the anti-BMPR1B antibodies of the invention may be selected so they preferably reduce the frequency or tumorigenicity of tumorigenic cells upon administration to a subject regardless of the form of the BMPR1B determinant (e.g., phenotypic or genotypic). The reduction in tumorigenic cell frequency may occur as a result of (i) inhibition or eradication of tumorigenic cells; (ii) controlling the growth, expansion or recurrence of tumorigenic cells; (iii) interrupting the initiation, propagation, maintenance, or proliferation of tumorigenic cells; or (iv) by otherwise hindering the survival, regeneration and/or metastasis of the tumorigenic cells. In some embodiments, the inhibition of tumorigenic cells may occur as a result of a change in one or more physiological pathways. The change in the pathway, whether by inhibition or elimination of the tumorigenic cells, modification of their potential (for example, by induced differentiation or niche disruption) or otherwise interfering with the ability of tumorigenic cells to influence the tumor environment or other cells, allows for the more effective treatment of BMPR1B associated disorders by inhibiting tumorigenesis, tumor maintenance and/or metastasis and recurrence. It will further be appreciated that the same characteristics of the disclosed antibodies make them particularly effective at treating recurrent tumors which have proved resistant or refractory to standard treatment regimens.

Methods that can be used to assess the reduction in the frequency of tumorigenic cells, include but are not limited to, cytometric or immunohistochemical analysis, preferably by in vitro or in vivo limiting dilution analysis (Dylla et al. 2008, PMID: PMC2413402 and Hoey et al. 2009, PMID: 19664991).

In vitro limiting dilution analysis may be performed by culturing fractionated or unfractionated tumor cells (e.g. from treated and untreated tumors, respectively) on solid medium that fosters colony formation and counting and characterizing the colonies that grow. Alternatively, the tumor cells can be serially diluted onto plates with wells containing liquid medium and each well can be scored as either positive or negative for colony formation at any time after inoculation but preferably more than 10 days after inoculation.

In vivo limiting dilution is performed by transplanting tumor cells, from either untreated controls or from tumors exposed to selected therapeutic agents, into immunocompromised mice in serial dilutions and subsequently scoring each mouse as either positive or negative for tumor formation. The scoring may occur at any time after the implanted tumors are detectable but is preferably done 60 or more days after the transplant. The analysis of the results of limiting dilution experiments to determine the frequency of tumorigenic cells is preferably done using Poisson distribution statistics or assessing the frequency of predefined definitive events such as the ability to generate tumors in vivo or not (Fazekas et al., 1982, PMID: 7040548).

Flow cytometry and immunohistochemistry may also be used to determine tumorigenic cell frequency. Both techniques employ one or more antibodies or reagents that bind art recognized cell surface proteins or markers known to enrich for tumorigenic cells (see WO 2012/031280). As known in the art, flow cytometry (e.g. florescence activated cell sorting (FACS)) can also be used to characterize, isolate, purify, enrich or sort for various cell populations including tumorigenic cells. Flow cytometry measures tumorigenic cell levels by passing a stream of fluid, in which a mixed population of cells is suspended, through an electronic detection apparatus which is able to measure the physical and/or chemical characteristics of up to thousands of particles per second. Immunohistochemistry provides additional information in that it enables visualization of tumorigenic cells in situ (e.g., in a tissue section) by staining the tissue sample with labeled antibodies or reagents which bind to tumorigenic cell markers.

As such, the antibodies of the invention may be useful for identifying, characterizing, monitoring, isolating, sectioning or enriching populations or subpopulations of tumorigenic cells through methods such as, for example, flow cytometry, magnetic activated cell sorting (MACS), laser mediated sectioning or FACS. FACS is a reliable method used to isolate cell subpopulations at more than 99.5% purity based on specific cell surface markers. Other compatible techniques for the characterization and manipulation of tumorigenic cells including CSCs can be seen, for example, in U.S. patent Ser. Nos. 12/686,359, 12/669,136 and 12/757,649.

Listed below are markers that have been associated with CSC populations and have been used to isolate or characterize CSCs: ABCA1, ABCA3, ABCB5, ABCG2, ADAM9, ADCY9, ADORA2A, ALDH, AFP, AXIN1, B7H3, BCL9, Bmi-1, BMP-4, C20orf52, C4.4A, carboxypeptidase M, CAV1, CAV2, CD105, CD117, CD123, CD133, CD14, CD16, CD166, CD16a, CD16b, CD2, CD20, CD24, CD29, CD3, CD31, CD324, CD325, CD33, CD34, CD38, CD44, CD45, CD46, CD49b, CD49f, CD56, CD64, CD74, CD9, CD90, CD96, CEACAM6, CELSR1, CLEC12A, CPD, CRIM1, CX3CL1, CXCR4, DAF, decorin, easyh1, easyh2, EDG3, EGFR, ENPP1, EPCAM, EPHA1, EPHA2, FLJ10052, FLVCR, FZD1, FZD10, FZD2, FZD3, FZD4, FZD6, FZD7, FZD8, FZD9, GD2, GJA1, GLI1, GLI2, GPNMB, GPR54, GPRC5B, HAVCR2, IL1R1, IL1RAP, JAM3, Lgr5, Lgr6, LRP3, LY6E, MCP, mf2, mllt3, MPZL1, MUC1, MUC16, MYC, N33, NANOG, NB84, NES, NID2, NMA, NPC1, OSM, OCT4, OPN3, PCDH7, PCDHA10, PCDHB2, PPAP2C, PTPN3, PTS, RARRES1, SEMA4B, SLC19A2, SLC1A1, SLC39A1, SLC4A11, SLC6A14, SLC7A8, SMARCA3, SMARCD3, SMARCE1, SMARCA5, SOX1, STAT3, STEAP, TCF4, TEM8, TGFBR3, TMEPAI, TMPRSS4, TFRC, TRKA, WNT10B, WNT16, WNT2, WNT2B, WNT3, WNT5A, YY1 and CTNNB1. See, for example, Schulenburg et al., 2010, PMID: 20185329, U.S. Pat. No. 7,632,678 and U.S.P.N.s. 2007/0292414, 2008/0175870, 2010/0275280, 2010/0162416 and 2011/0020221.

Similarly, non-limiting examples of cell surface phenotypes associated with CSCs of certain tumor types include $CD44^{hi}CD24^{low}$, $ALDH^+$, $CD133^+$, $CD123^+$, $CD34^+CD38^-$, $CD44^+CD24^-$, $CD46^{hi}CD324^+CD66c^-$, $CD133^+CD34^+CD10^-CD19^-$, $CD138^-CD34^-CD19^+$, $CD133^+RC2^+$, $CD44^+\alpha_2\beta_1^{hi}CD133^+$, $CD44^+CD24^+ESA^+$, $CD271^+$, $ABCB5^+$ as well as other CSC surface phenotypes that are known in the art. See, for example, Schulenburg et al., 2010, supra, Visvader et al., 2008, PMID: 18784658 and U.S.P.N. 2008/0138313. Of particular interest with respect to the instant invention are CSC preparations comprising $CD46^{hi}CD324^+$ phenotypes in solid tumors and $CD34^+CD38^-$ in leukemias.

"Positive," "low" and "negative" expression levels as they apply to markers or marker phenotypes are defined as follows. Cells with negative expression (i.e. "−") are herein defined as those cells expressing less than, or equal to, the 95th percentile of expression observed with an isotype control antibody in the channel of fluorescence in the presence of the complete antibody staining cocktail labeling for other proteins of interest in additional channels of fluorescence emission. Those skilled in the art will appreciate that this procedure for defining negative events is referred to as "fluorescence minus one", or "FMO", staining. Cells with expression greater than the 95th percentile of expression observed with an isotype control antibody using the FMO staining procedure described above are herein defined as "positive" (i.e. "+"). As defined herein there are various populations of cells broadly defined as "positive." A cell is defined as positive if the mean observed expression of the antigen is above the 95th percentile determined using FMO staining with an isotype control antibody as described above. The positive cells may be termed cells with low expression (i.e. "lo") if the mean observed expression is above the $95^{th}$ percentile determined by FMO staining and is within one standard deviation of the $95^{th}$ percentile. Alternatively, the positive cells may be termed cells with high expression (i.e. "hi") if the mean observed expression is above the $95^{th}$ percentile determined by FMO staining and greater than one standard deviation above the $95^{th}$ percentile. In other embodiments the 99th percentile may preferably be used as a demarcation point between negative and positive FMO staining and in some embodiments the percentile may be greater than 99%.

The $CD46^{hi}CD324^+$ or $CD34^+CD38^-$ marker phenotype and those exemplified immediately above may be used in conjunction with standard flow cytometric analysis and cell sorting techniques to characterize, isolate, purify or enrich TIC and/or TPC cells or cell populations for further analysis.

The ability of the antibodies of the current invention to reduce the frequency of tumorigenic cells can therefore be determined using the techniques and markers described above. In some instances, the anti-BMPR1B antibodies may reduce the frequency of tumorigenic cells by 10%, 15%, 20%, 25%, 30% or even by 35%. In other embodiments, the reduction in frequency of tumorigenic cells may be in the order of 40%, 45%, 50%, 55%, 60% or 65%. In certain embodiments, the disclosed compounds may reduce the frequency of tumorigenic cells by 70%, 75%, 80%, 85%, 90% or even 95%. It will be appreciated that any reduction of the frequency of tumorigenic cells is likely to result in a corresponding reduction in the tumorigenicity, persistence, recurrence and aggressiveness of the neoplasia.

III. ANTIBODIES

A. Antibody Structure

Antibodies and variants and derivatives thereof, including accepted nomenclature and numbering systems, have been extensively described, for example, in Abbas et al. (2010), *Cellular and Molecular Immunology* ($6^{th}$ Ed.), W.B. Saunders Company; or Murphey et al. (2011), *Janeway's Immunobiology* (8*th* Ed.), Garland Science.

An "antibody" or "intact antibody" typically refers to a Y-shaped tetrameric protein comprising two heavy (H) and two light (L) polypeptide chains held together by covalent disulfide bonds and non-covalent interactions. Each light chain is composed of one variable domain (VL) and one constant domain (CL). Each heavy chain comprises one variable domain (VH) and a constant region, which in the case of IgG, IgA, and IgD antibodies, comprises three domains termed CH1, CH2, and CH3 (IgM and IgE have a fourth domain, CH4). In IgG, IgA, and IgD classes the CH1 and CH2 domains are separated by a flexible hinge region, which is a proline and cysteine rich segment of variable length (from about 10 to about 60 amino acids in various IgG subclasses). The variable domains in both the light and heavy chains are joined to the constant domains by a "J" region of about 12 or more amino acids and the heavy chain also has a "D" region of about 10 additional amino acids. Each class of antibody further comprises inter-chain and intra-chain disulfide bonds formed by paired cysteine residues.

As used herein the term "antibody" includes polyclonal antibodies, multiclonal antibodies, monoclonal antibodies, chimeric antibodies, humanized and primatized antibodies, CDR grafted antibodies, human antibodies (including recombinantly produced human antibodies), recombinantly produced antibodies, intrabodies, multispecific antibodies, bispecific antibodies, monovalent antibodies, multivalent antibodies, anti-idiotypic antibodies, synthetic antibodies, including muteins and variants thereof, immunospecific antibody fragments such as Fd, Fab, F(ab')$_2$, F(ab') fragments, single-chain fragments (e.g. ScFv and ScFvFc); and derivatives thereof including Fc fusions and other modifications, and any other immunoreactive molecule so long as it exhibits preferential association or binding with a determinant. Moreover, unless dictated otherwise by contextual constraints the term further comprises all classes of antibodies (i.e. IgA, IgD, IgE, IgG, and IgM) and all subclasses (i.e., IgG1, IgG2, IgG3, IgG4, IgA1, and IgA2). Heavy-chain constant domains that correspond to the different classes of antibodies are typically denoted by the corresponding lower case Greek letter α, δ, ε, γ, and μ, respectively. Light chains of the antibodies from any vertebrate species can be assigned to one of two clearly distinct types, called kappa (κ) and lambda (λ), based on the amino acid sequences of their constant domains.

The variable domains of antibodies show considerable variation in amino acid composition from one antibody to another and are primarily responsible for antigen recognition and binding. Variable regions of each light/heavy chain pair form the antibody binding site such that an intact IgG antibody has two binding sites (i.e. it is bivalent). VH and VL domains comprise three regions of extreme variability, which are termed hypervariable regions, or more commonly, complementarity-determining regions (CDRs), framed and separated by four less variable regions known as framework regions (FRs). Non-covalent association between the VH and the VL region forms the Fv fragment (for "fragment variable") which contains one of the two antigen-binding sites of the antibody.

As used herein, the assignment of amino acids to each domain, framework region and CDR may be in accordance with one of the schemes provided by Kabat et al. (1991) *Sequences of Proteins of Immunological Interest* (5*th* Ed.), US Dept. of Health and Human Services, PHS, NIH, NIH Publication no. 91-3242; Chothia et al., 1987, PMID: 3681981; Chothia et al., 1989, PMID: 2687698; MacCallum et al., 1996, PMID: 8876650; or Dubel, Ed. (2007) *Handbook of Therapeutic Antibodies*, 3*rd* Ed., Wily-VCH Verlag GmbH and Co or AbM (Oxford Molecular/MSI Pharmacopia) unless otherwise noted. As is well known in the art variable region residue numbering is typically as set forth in Chothia or Kabat. Amino acid residues which comprise CDRs as defined by Kabat, Chothia, MacCallum (also known as Contact) and AbM as obtained from the Abysis website database (infra.) are set out below in Table 1. Note that MacCallum uses the Chothia numbering system.

TABLE 1

|  | Kabat | Chothia | MacCallum | AbM |
| --- | --- | --- | --- | --- |
| VH CDR1 | 31-35 | 26-32 | 30-35 | 26-35 |
| VH CDR2 | 50-65 | 52-56 | 47-58 | 50-58 |
| VH CDR3 | 95-102 | 95-102 | 93-101 | 95-102 |
| VL CDR1 | 24-34 | 24-34 | 30-36 | 24-34 |
| VL CDR2 | 50-56 | 50-56 | 46-55 | 50-56 |
| VL CDR3 | 89-97 | 89-97 | 89-96 | 89-97 |

Variable regions and CDRs in an antibody sequence can be identified according to general rules that have been developed in the art (as set out above, such as, for example, the Kabat numbering system) or by aligning the sequences against a database of known variable regions. Methods for identifying these regions are described in Kontermann and Dubel, eds., Antibody Engineering, Springer, New York, N.Y., 2001 and Dinarello et al., Current Protocols in Immunology, John Wiley and Sons Inc., Hoboken, N.J., 2000. Exemplary databases of antibody sequences are described in, and can be accessed through, the "Abysis" website at www.bioinf.org.uk/abs (maintained by A. C. Martin in the Department of Biochemistry & Molecular Biology University College London, London, England) and the VBASE2 website at www.vbase2.org, as described in Retter et al., Nucl. Acids Res., 33 (Database issue): D671-D674 (2005).

Preferably the sequences are analyzed using the Abysis database, which integrates sequence data from Kabat, IMGT and the Protein Data Bank (PDB) with structural data from the PDB. See Dr. Andrew C. R. Martin's book chapter *Protein Sequence and Structure Analysis of Antibody Variable Domains.* In: *Antibody Engineering Lab Manual* (Ed.: Duebel, S. and Kontermann, R., Springer-Verlag, Heidelberg, ISBN-13: 978-3540413547, also available on the website bioinforg.uk/abs). The Abysis database website further includes general rules that have been developed for identifying CDRs which can be used in accordance with the teachings herein. FIGS. 9F and 9G appended hereto show the results of such analysis in the annotation of exemplary heavy and light chain variable regions (VH and VL) for the SC91.1 and SC91.9 antibodies. Unless otherwise indicated, all CDRs set forth herein are derived according to the Abysis database website as per Kabat et al.

For heavy chain constant region amino acid positions discussed in the invention, numbering is according to the Eu index first described in Edelman et al., 1969, Proc. Natl. Acad. Sci. USA 63(1): 78-85 describing the amino acid sequence of the myeloma protein Eu, which reportedly was the first human IgG1 sequenced. The Eu index of Edelman is also set forth in Kabat et al., 1991 (supra.). Thus, the terms "Eu index as set forth in Kabat" or "Eu index of Kabat" or "Eu index" or "Eu numbering" in the context of the heavy chain refers to the residue numbering system based on the human IgG1 Eu antibody of Edelman et al. as set forth in Kabat et al., 1991 (supra.) The numbering system used for the light chain constant region amino acid sequence is similarly set forth in Kabat et al., (supra.) Exemplary kappa (SEQ ID NO: 5) and lambda (SEQ ID NO: 8) light chain constant region amino acid sequences compatible with the present invention is set forth immediately below:

```
                                               (SEQ ID NO: 5)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.

(SEQ ID NO: 8)
QPKANPTVTLFPPSSEELQANKATLVCLISDFYPGAVTVAWKADGSPVKA

GVETTKPSKQSNNKYAASSYLSLTPEQWKSHRSYSCQVTHEGSTVEKTVA

PTECS.
```

Similarly, an exemplary IgG1 heavy chain constant region amino acid sequence compatible with the present invention is set forth immediately below:

```
                                               (SEQ ID NO: 2)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPG.
```

Those of skill in the art will appreciate that such heavy and light chain constant region sequences, either wild-type (e.g., see SEQ ID NOS: 2, 5 or 8) or engineered as disclosed herein to provide unpaired cysteines (e.g., see SEQ ID NOS: 3, 4, 6, 7, 9 or 10) may be operably associated with the disclosed heavy and light chain variable regions using standard molecular biology techniques to provide full-length antibodies that may be incorporated in the BMPR1B antibody drug conjugates of the instant invention. Sequences of full-length heavy and light chains comprising selected antibodies of the instant invention (hSC91.1, hSC91.1MJ, hSC91.1ss1, hSC91.1ss1MJ, hSC91.9, hSC91.9MJ, hSC91.9ss1MJ) are set forth in FIG. 9E appended hereto.

There are two types of disulfide bridges or bonds in immunoglobulin molecules: interchain and intrachain disulfide bonds. As is well known in the art the location and number of interchain disulfide bonds vary according to the immunoglobulin class and species. While the invention is not limited to any particular class or subclass of antibody, the IgG1 immunoglobulin shall be used throughout the instant disclosure for illustrative purposes. In wild-type IgG1 molecules there are twelve intrachain disulfide bonds (four on each heavy chain and two on each light chain) and four interchain disulfide bonds. Intrachain disulfide bonds are generally somewhat protected and relatively less susceptible to reduction than interchain bonds. Conversely, interchain disulfide bonds are located on the surface of the immunoglobulin, are accessible to solvent and are usually relatively easy to reduce. Two interchain disulfide bonds exist between the heavy chains and one from each heavy chain to its respective light chain. It has been demonstrated that interchain disulfide bonds are not essential for chain association. The IgG1 hinge region contain the cysteines in the heavy chain that form the interchain disulfide bonds, which provide structural support along with the flexibility that facilitates Fab movement. The heavy/heavy IgG1 interchain disulfide bonds are located at residues C226 and C229 (Eu numbering) while the IgG1 interchain disulfide bond between the light and heavy chain of IgG1 (heavy/light) are formed between C214 of the kappa or lambda light chain and C220 in the upper hinge region of the heavy chain.

B. Antibody Generation and Production

Antibodies of the invention can be produced using a variety of methods known in the art.

1. Generation of Polyclonal Antibodies in Host Animals

The production of polyclonal antibodies in various host animals is well known in the art (see for example, Harlow and Lane (Eds.) (1988) Antibodies: A Laboratory Manual, CSH Press; and Harlow et al. (1989) Antibodies, NY, Cold Spring Harbor Press). In order to generate polyclonal antibodies, an immunocompetent animal (e.g., mouse, rat, rabbit, goat, non-human primate, etc.) is immunized with an antigenic protein or cells or preparations comprising an antigenic protein. After a period of time, polyclonal antibody-containing serum is obtained by bleeding or sacrificing the animal. The serum may be used in the form obtained from the animal or the antibodies may be partially or fully purified to provide immunoglobulin fractions or isolated antibody preparations.

In this regard antibodies of the invention may be generated from any BMPR1B determinant that induces an immune response in an immunocompetent animal. As used herein "determinant" or "target" means any detectable trait, property, marker or factor that is identifiably associated with, or specifically found in or on a particular cell, cell population or tissue. Determinants or targets may be morphological, functional or biochemical in nature and are preferably phenotypic. In preferred embodiments a determinant is a protein that is differentially expressed (over- or under-expressed) by specific cell types or by cells under certain conditions (e.g., during specific points of the cell cycle or cells in a particular niche). For the purposes of the instant invention a determinant preferably is differentially expressed on aberrant cancer cells and may comprise a BMPR1B protein, or any of its splice variants, isoforms, homologs or family members, or specific domains, regions or epitopes thereof. An "antigen", "immunogenic determinant", "antigenic determinant" or "immunogen" means any BMPR1B protein or any fragment, region or domain thereof that can stimulate an immune response when introduced into an immunocompetent animal and is recognized by the antibodies produced by the immune response. The presence or absence of the BMPR1B determinants contemplated herein may be used to identify a cell, cell subpopulation or tissue (e.g., tumors, tumorigenic cells or CSCs).

Any form of antigen, or cells or preparations containing the antigen, can be used to generate an antibody that is specific for the BMPR1B determinant. As set forth herein the term "antigen" is used in a broad sense and may comprise any immunogenic fragment or determinant of the selected target including a single epitope, multiple epitopes, single or multiple domains or the entire extracellular domain (ECD) or protein. The antigen may be an isolated full-length protein, a cell surface protein (e.g., immunizing with cells expressing at least a portion of the antigen on their surface), or a soluble protein (e.g., immunizing with only the ECD portion of the protein) or protein construct (e.g., Fc-antigen). The antigen may be produced in a genetically modified cell. Any of the aforementioned antigens may be used alone or in combination with one or more immunogenicity enhancing adjuvants known in the art. DNA encoding the antigen may be genomic or non-genomic (e.g., cDNA) and may encode at least a portion of the ECD, sufficient to elicit an immunogenic response. Any vectors may be employed to transform the cells in which the antigen is expressed, including but not limited to adenoviral vectors, lentiviral vectors, plasmids, and non-viral vectors, such as cationic lipids.

2. Monoclonal Antibodies

In selected embodiments, the invention contemplates use of monoclonal antibodies. As known in the art, the term "monoclonal antibody" or "mAb" refers to an antibody obtained from a population of substantially homogeneous antibodies, i.e., the individual antibodies comprising the population are identical except for possible mutations (e.g., naturally occurring mutations), that may be present in minor amounts.

Monoclonal antibodies can be prepared using a wide variety of techniques known in the art including hybridoma techniques, recombinant techniques, phage display technologies, transgenic animals (e.g., a XenoMouse®) or some combination thereof. For example, monoclonal antibodies can be produced using hybridoma and biochemical and genetic engineering techniques such as described in more detail in An, Zhigiang (ed.) *Therapeutic Monoclonal Antibodies: From Bench to Clinic*, John Wiley and Sons, 1$^{st}$ ed. 2009; Shire et. al. (eds.) *Current Trends in Monoclonal Antibody Development and Manufacturing*, Springer Science+Business Media LLC, 1$^{st}$ ed. 2010; Dimitrov. Antony (ed.) *Therapeutic Antibodies: Methods and Protocols*, Humana Press; 2009; Harlow et al., *Antibodies: A Laboratory Manual*, Cold Spring Harbor Laboratory Press, 2nd ed. 1988; Hammerling, et al., in: *Monoclonal Antibodies and T-Cell Hybridomas* 563-681 (Elsevier, N.Y., 1981). Following production of multiple monoclonal antibodies that bind specifically to a determinant, particularly effective antibodies may be selected through various screening processes, based on, for example, its affinity for the determinant or rate of internalization. Antibodies produced as described herein may be used as "source" antibodies and further modified to, for example, improve affinity for the target, improve its production in cell culture, reduce immunogenicity in vivo, create multispecific constructs, etc. A more detailed description of monoclonal antibody production and screening is set out below and in the appended Examples.

3. Human Antibodies

In another embodiment, the antibodies may comprise fully human antibodies. The term "human antibody" refers to an antibody which possesses an amino acid sequence that corresponds to that of an antibody produced by a human and/or has been made using any of the techniques for making human antibodies described below.

Human antibodies can be produced using various techniques known in the art. One technique is phage display in which a library of (preferably human) antibodies is synthesized on phages, the library is screened with the antigen of interest or an antibody-binding portion thereof, and the phage that binds the antigen is isolated, from which one may obtain the immunoreactive fragments. Methods for preparing and screening such libraries are well known in the art and kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; and Barbas et al., *Proc. Natl. Acad. Sci. USA* 88:7978-7982 (1991)).

In one embodiment, recombinant human antibodies may be isolated by screening a recombinant combinatorial antibody library prepared as above. In one embodiment, the library is a scFv phage display library, generated using human VL and VH cDNAs prepared from mRNA isolated from B-cells.

The antibodies produced by naive libraries (either natural or synthetic) can be of moderate affinity ($K_a$ of about $10^6$ to $10^7$ M$^{-1}$), but affinity maturation can also be mimicked in vitro by constructing and reselecting from secondary libraries as described in the art. For example, mutation can be introduced at random in vitro by using error-prone polymerase (reported in Leung et al., *Technique*, 1: 11-15 (1989)). Additionally, affinity maturation can be performed by randomly mutating one or more CDRs, e.g. using PCR with primers carrying random sequence spanning the CDR of interest, in selected individual Fv clones and screening for higher-affinity clones. WO 9607754 described a method for inducing mutagenesis in a CDR of an immunoglobulin light chain to create a library of light chain genes. Another effective approach is to recombine the VH or VL domains selected by phage display with repertoires of naturally occurring V domain variants obtained from unimmunized donors and to screen for higher affinity in several rounds of chain reshuffling as described in Marks et al., *Biotechnol.*, 10: 779-783 (1992). This technique allows the production of antibodies and antibody fragments with a dissociation constant $K_D$ ($k_{off}/k_{on}$) of about $10^{-9}$ M or less.

In other embodiments, similar procedures may be employed using libraries comprising eukaryotic cells (e.g., yeast) that express binding pairs on their surface. See, for example, U.S. Pat. No. 7,700,302 and U.S. Ser. No. 12/404, 059. In one embodiment, the human antibody is selected from a phage library, where that phage library expresses human antibodies (Vaughan et al. Nature *Biotechnology* 14:309-314 (1996): Sheets et al. *Proc. Natl. Acad. Sci. USA* 95:6157-6162 (1998). In other embodiments, human binding pairs may be isolated from combinatorial antibody libraries generated in eukaryotic cells such as yeast. See e.g., U.S. Pat. No. 7,700,302. Such techniques advantageously allow for the screening of large numbers of candidate modulators and provide for relatively easy manipulation of candidate sequences (e.g., by affinity maturation or recombinant shuffling).

Human antibodies can also be made by introducing human immunoglobulin loci into transgenic animals, e.g., mice in which the endogenous immunoglobulin genes have been partially or completely inactivated and human immunoglobulin genes have been introduced. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661, 016, and 6,075,181 and 6,150,584 regarding XenoMouse® technology; and Lonberg and Huszar, *Intern. Rev. Immunol.* 13:65-93 (1995). Alternatively, the human antibody may be prepared via immortalization of human B lymphocytes producing an antibody directed against a target antigen (such B lymphocytes may be recovered from an individual suffering from a neoplastic disorder or may have been immunized in vitro). See, e.g., Cole et al., *Monoclonal Antibodies* and *Cancer Therapy*, Alan R. Liss, p. 77 (1985); Boerner et al., *J. Immunol,* 147 (I):86-95 (1991); and U.S. Pat. No. 5,750,373.

Whatever the source it will be appreciated that the human antibody sequence may be fabricated using art-known molecular engineering techniques and introduced into expression systems and host cells as described herein. Such non-natural recombinantly produced human antibodies (and subject compositions) are entirely compatible with the teachings of this disclosure and are expressly held to be within the scope of the instant invention. In certain select aspects the BMPR1B ADCs of the invention will comprise a recombinantly produced human antibody acting as a cell binding agent.

4. Derived Antibodies:

Once source antibodies have been generated, selected and isolated as described above they may be further altered to provide anti-BMPR1B antibodies having improved pharmaceutical characteristics. Preferably the source antibodies are modified or altered using known molecular engineering techniques to provide derived antibodies having the desired therapeutic properties.

4.1. Chimeric and Humanized Antibodies

Selected embodiments of the invention comprise murine monoclonal antibodies that immunospecifically bind to BMPR1B and which can be considered "source" antibodies. In selected embodiments, antibodies of the invention can be derived from such "source" antibodies through optional modification of the constant region and/or the epitope-binding amino acid sequences of the source antibody. In certain embodiments an antibody is "derived" from a source antibody if selected amino acids in the source antibody are altered through deletion, mutation, substitution, integration or combination. In another embodiment, a "derived" antibody is one in which fragments of the source antibody (e.g., one or more CDRs or domains or the entire heavy and light chain variable regions) are combined with or incorporated into an acceptor antibody sequence to provide the derivative antibody (e.g. chimeric, CDR grafted or humanized antibodies). These "derived" antibodies can be generated using genetic material from the antibody producing cell and standard molecular biological techniques as described below, such as, for example, to improve affinity for the determinant; to improve antibody stability; to improve production and yield in cell culture; to reduce immunogenicity in vivo; to reduce toxicity; to facilitate conjugation of an active moiety; or to create a multispecific antibody. Such antibodies may also be derived from source antibodies through modification of the mature molecule (e.g., glycosylation patterns or pegylation) by chemical means or post-translational modification.

In one embodiment, the antibodies of the invention comprise chimeric antibodies that are derived from protein segments from at least two different species or class of antibodies that have been covalently joined. The term "chimeric" antibody is directed to constructs in which a portion of the heavy and/or light chain is identical or homologous to corresponding sequences in antibodies from a particular species or belonging to a particular antibody class or subclass, while the remainder of the chain(s) is identical or homologous to corresponding sequences in antibodies from another species or belonging to another antibody class or subclass, as well as fragments of such antibodies (U.S. Pat. No. 4,816,567). In some embodiments chimeric antibodies of the instant invention may comprise all or most of the selected murine heavy and light chain variable regions operably linked to human light and heavy chain constant regions. In other selected embodiments, anti-BMPR1B antibodies may be "derived" from the mouse antibodies disclosed herein and comprise less than the entire heavy and light chain variable regions.

In other embodiments, chimeric antibodies of the invention are "CDR-grafted" antibodies, where the CDRs (as defined using Kabat, Chothia, McCallum, etc.) are derived from a particular species or belonging to a particular antibody class or subclass, while the remainder of the antibody is largely derived from an antibody from another species or belonging to another antibody class or subclass. For use in humans, one or more selected rodent CDRs (e.g., mouse CDRs) may be grafted into a human acceptor antibody, replacing one or more of the naturally occurring CDRs of the human antibody. These constructs generally have the advantages of providing full strength human antibody functions, e.g., complement dependent cytotoxicity (CDC) and antibody-dependent cell-mediated cytotoxicity (ADCC) while reducing unwanted immune responses to the antibody by the subject. In one embodiment the CDR grafted antibodies will comprise one or more CDRs obtained from a mouse incorporated in a human framework sequence.

Similar to the CDR-grafted antibody is a "humanized" antibody. As used herein, a "humanized" antibody is a human antibody (acceptor antibody) comprising one or more amino acid sequences (e.g. CDR sequences) derived from one or more non-human antibodies (donor or source antibody). In certain embodiments, "back mutations" can be introduced into the humanized antibody, in which residues in one or more FRs of the variable region of the recipient human antibody are replaced by corresponding residues from the non-human species donor antibody. Such back mutations may to help maintain the appropriate three-dimensional configuration of the grafted CDR(s) and thereby improve affinity and antibody stability. Antibodies from various donor species may be used including, without limitation, mouse, rat, rabbit, or non-human primate. Furthermore, humanized antibodies may comprise new residues that are not found in the recipient antibody or in the donor antibody to, for example, further refine antibody performance. CDR grafted and humanized antibodies compatible with the instant invention comprising murine components from source antibodies and human components from acceptor antibodies may be provided as set forth in the Examples below.

Various art-recognized techniques can be used to determine which human sequences to use as acceptor antibodies to provide humanized constructs in accordance with the instant invention. Compilations of compatible human germline sequences and methods of determining their suitability as acceptor sequences are disclosed, for example, in Dubel and Reichert (Eds.) (2014) *Handbook of Therapeutic Antibodies,* $2^{nd}$ Edition, Wiley-Blackwell GmbH; Tomlinson, I. A. et al. (1992) *J. Mol. Biol.* 227:776-798; Cook, G. P. et al. (1995) *Immunol. Today* 16: 237-242; Chothia, D. et al. (1992) *J. Mol. Biol.* 227:799-817; and Tomlinson et al. (1995) *EMBO J* 14:4628-4638). The V-BASE directory (VBASE2—Retter et al., Nucleic Acid Res. 33; 671-674, 2005) which provides a comprehensive directory of human immunoglobulin variable region sequences (compiled by Tomlinson, I. A. et al. MRC Centre for Protein Engineering, Cambridge, UK) may also be used to identify compatible acceptor sequences. Additionally, consensus human framework sequences described, for example, in U.S. Pat. No. 6,300,064 may also prove to be compatible acceptor sequences are can be used in accordance with the instant teachings. In general, human framework acceptor sequences are selected based on homology with the murine source framework sequences along with an analysis of the CDR canonical structures of the source and acceptor antibodies. The derived sequences of the heavy and light chain variable regions of the derived antibody may then be synthesized using art recognized techniques.

By way of example CDR grafted and humanized antibodies, and associated methods, are described in U.S. Pat. Nos. 6,180,370 and 5,693,762. For further details, see, e.g., Jones et al., 1986, (PMID: 3713831); and U.S. Pat. Nos. 6,982,321 and 7,087,409.

The sequence identity or homology of the CDR grafted or humanized antibody variable region to the human acceptor variable region may be determined as discussed herein and, when measured as such, will preferably share at least 60% or 65% sequence identity, more preferably at least 70%, 75%, 80%, 85%, or 90% sequence identity, even more preferably at least 93%, 95%, 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution.

It will be appreciated that the annotated CDRs and framework sequences as provided in the appended FIGS. 9A and 9B are defined as per Kabat et al. using a proprietary Abysis database. However, as discussed herein and shown in FIGS. 9F and 9G, one skilled in the art could readily identify CDRs in accordance with definitions provided by Chothia et al., ABM or MacCallum et al. as well as Kabat et al. As such, anti-BMPR1B humanized antibodies comprising one or more CDRs derived according to any of the aforementioned systems are explicitly held to be within the scope of the instant invention.

4.2. Site-Specific Antibodies

The antibodies of the instant invention may be engineered to facilitate conjugation to a cytotoxin or other anti-cancer agent (as discussed in more detail below). It is advantageous for the antibody drug conjugate (ADC) preparation to comprise a homogenous population of ADC molecules in terms of the position of the cytotoxin on the antibody and the drug to antibody ratio (DAR). Based on the instant disclosure one skilled in the art could readily fabricate site-specific engineered constructs as described herein. As used herein a "site-specific antibody" or "site-specific construct" means an antibody, or immunoreactive fragment thereof, wherein at least one amino acid in either the heavy or light chain is deleted, altered or substituted (preferably with another amino acid) to provide at least one free cysteine. Similarly, a "site-specific conjugate" shall be held to mean an ADC comprising a site-specific antibody and at least one cytotoxin or other compound (e.g., a reporter molecule) conjugated to the unpaired or free cysteine(s). In certain embodiments the unpaired cysteine residue will comprise an unpaired intrachain cysteine residue. In other embodiments the free cysteine residue will comprise an unpaired interchain cysteine residue. In still other embodiments the free cysteine may be engineered into the amino acid sequence of the antibody (e.g., in the CH3 domain). In any event the site-specific antibody can be of various isotypes, for example, IgG, IgE, IgA or IgD; and within those classes the antibody can be of various subclasses, for example, IgG1, IgG2, IgG3 or IgG4. For IgG constructs the light chain of the antibody can comprise either a kappa or lambda isotype each incorporating a C214 that, in selected embodiments, may be unpaired due to a lack of a C220 residue in the IgG1 heavy chain.

Thus, as used herein, the terms "free cysteine" or "unpaired cysteine" may be used interchangeably unless otherwise dictated by context and shall mean any cysteine (or thiol containing) constituent (e.g., a cysteine residue) of an antibody, whether naturally present or specifically incorporated in a selected residue position using molecular engineering techniques, that is not part of a naturally occurring (or "native") disulfide bond under physiological conditions. In certain selected embodiments the free cysteine may comprise a naturally occurring cysteine whose native interchain or intrachain disulfide bridge partner has been substituted, eliminated or otherwise altered to disrupt the naturally occurring disulfide bridge under physiological conditions thereby rendering the unpaired cysteine suitable for site-specific conjugation. In other preferred embodiments the free or unpaired cysteine will comprise a cysteine residue that is selectively placed at a predetermined site within the antibody heavy or light chain amino acid sequences. It will be appreciated that, prior to conjugation, free or unpaired cysteines may be present as a thiol (reduced cysteine), as a capped cysteine (oxidized) or as part of a non-native intra- or intermolecular disulfide bond (oxidized) with another cysteine or thiol group on the same or different molecule depending on the oxidation state of the system. As discussed in more detail below, mild reduction of the appropriately engineered antibody construct will provide thiols available for site-specific conjugation. Accordingly, in particularly preferred embodiments the free or unpaired cysteines (whether naturally occurring or incorporated) will be subject to selective reduction and subsequent conjugation to provide homogenous DAR compositions.

It will be appreciated that the favorable properties exhibited by the disclosed engineered conjugate preparations is predicated, at least in part, on the ability to specifically direct the conjugation and largely limit the fabricated conjugates in terms of conjugation position and the absolute DAR value of the composition. Unlike most conventional ADC preparations the present invention need not rely entirely on partial or total reduction of the antibody to provide random conjugation sites and relatively uncontrolled generation of DAR species. Rather, in certain aspects the present invention preferably provides one or more predetermined unpaired (or free) cysteine sites by engineering the targeting antibody to disrupt one or more of the naturally occurring (i.e., "native") interchain or intrachain disulfide bridges or to introduce a cysteine residue at any position. To this end it will be appreciated that, in selected embodiments, a cysteine residue may be incorporated anywhere along the antibody (or immunoreactive fragment thereof) heavy or light chain or appended thereto using standard molecular engineering techniques. In other preferred embodiments disruption of native disulfide bonds may be effected in combination with the introduction of a non-native cysteine (which will then comprise the free cysteine) that may then be used as a conjugation site.

In certain embodiments the engineered antibody comprises at least one amino acid deletion or substitution of an intrachain or interchain cysteine residue. As used herein "interchain cysteine residue" means a cysteine residue that is involved in a native disulfide bond either between the light and heavy chain of an antibody or between the two heavy chains of an antibody while an "intrachain cysteine residue" is one naturally paired with another cysteine in the same heavy or light chain. In one embodiment the deleted or substituted interchain cysteine residue is involved in the formation of a disulfide bond between the light and heavy chain. In another embodiment the deleted or substituted cysteine residue is involved in a disulfide bond between the two heavy chains. In a typical embodiment, due to the complementary structure of an antibody, in which the light chain is paired with the VH and CH1 domains of the heavy chain and wherein the CH2 and CH3 domains of one heavy chain are paired with the CH2 and CH3 domains of the complementary heavy chain, a mutation or deletion of a single cysteine in either the light chain or in the heavy chain would result in two unpaired cysteine residues in the engineered antibody.

In some embodiments an interchain cysteine residue is deleted. In other embodiments an interchain cysteine is substituted for another amino acid (e.g., a naturally occurring amino acid). For example, the amino acid substitution can result in the replacement of an interchain cysteine with a neutral (e.g. serine, threonine or glycine) or hydrophilic (e.g. methionine, alanine, valine, leucine or isoleucine) residue. In selected embodiments an interchain cysteine is replaced with a serine.

In some embodiments contemplated by the invention the deleted or substituted cysteine residue is on the light chain (either kappa or lambda) thereby leaving a free cysteine on the heavy chain. In other embodiments the deleted or substituted cysteine residue is on the heavy chain leaving the free cysteine on the light chain constant region. Upon assembly it will be appreciated that deletion or substitution of a single cysteine in either the light or heavy chain of an intact antibody results in a site-specific antibody having two unpaired cysteine residues.

In one embodiment the cysteine at position 214 (C214) of the IgG light chain (kappa or lambda) is deleted or substituted. In another embodiment the cysteine at position 220 (C220) on the IgG heavy chain is deleted or substituted. In further embodiments the cysteine at position 226 or position 229 on the heavy chain is deleted or substituted. In one embodiment C220 on the heavy chain is substituted with serine (C220S) to provide the desired free cysteine in the light chain. In another embodiment C214 in the light chain is substituted with serine (C214S) to provide the desired free cysteine in the heavy chain. Such site-specific constructs are described in more detail in the Examples below. A summary of compatible site-specific constructs is shown in Table 2 immediately below where numbering is generally according to the Eu index as set forth in Kabat, WT stands for "wild-type" or native constant region sequences without alterations and delta (Δ) designates the deletion of an amino acid residue (e.g., C214Δ indicates that the cysteine residue at position 214 has been deleted).

TABLE 2

| Designation | Antibody Component | Alteration | SEQ ID NOS: |
|---|---|---|---|
| ss1 | Heavy Chain | C220S | SEQ ID NO: 3 |
|  | Light Chain | WT | SEQ ID NOS: 5, 8 |
| ss2 | Heavy Chain | C220Δ | SEQ ID NO: 4 |
|  | Light Chain | WT | SEQ ID NOS: 5, 8 |
| ss3 | Heavy Chain | WT | SEQ ID NO: 2 |
|  | Light Chain | C214Δ | SEQ ID NOS: 7, 10 |
| ss4 | Heavy Chain | WT | SEQ ID NO: 2 |
|  | Light Chain | C214S | SE ID NOS: 6, 9 |

Exemplary engineered light and heavy chain constant regions compatible with site-specific constructs of the instant invention are set forth immediately below where SEQ ID NOS: 3 and 4 comprise, respectively, C220S IgG1 and C220Δ IgG1 heavy chain constant regions, SEQ ID NOS: 6 and 7 comprise, respectively, C214S and C214Δ kappa light chain constant regions and SEQ ID NOS: 9 and 10 comprise, respectively, exemplary C214S and C214Δ lambda light chain constant regions. In each case the site of the altered or deleted amino acid (along with the flanking residues) is underlined.

(SEQ ID NO: 3)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KS<u>S</u>DKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPG (SEQ ID NO: 4)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KS<u>D</u>KTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQ

QGNVFSCSVMHEALHNHYTQKSLSLSPG (SEQ ID NO: 6)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGE<u>S</u>

(SEQ ID NO: 7)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRG<u>E</u>

(SEQ ID NO: 9)
QPKANPTVTLFPPSSEELQANKATLVCLISDFYPGAVTVAWKADGSPVKA

GVETTKPSKQSNNKYAASSYLSLTPEQWKSHRSYSCQVTHEGSTVEKTVA

PTE<u>SS</u>

(SEQ ID NO: 10)
QPKANPTVTLFPPSSEELQANKATLVCLISDFYPGAVTVAWKADGSPVKA

GVETTKPSKQSNNKYAASSYLSLTPEQWKSHRSYSCQVTHEGSTVEKTVA

PTE<u>S</u>

As discussed above each of the heavy and light chain variants may be operably associated with the disclosed heavy and light chain variable regions (or derivatives thereof such as humanized or CDR grafted constructs) to provide site-specific anti-BMPR1B antibodies as disclosed herein. Such engineered antibodies are particularly compatible for use in the disclosed ADCs.

With regard to the introduction or addition of a cysteine residue or residues to provide a free cysteine (as opposed to disrupting a native disulfide bond) compatible position(s) on the antibody or antibody fragment may readily be discerned by one skilled in the art. Accordingly, in selected embodiments the cysteine(s) may be introduced in the CH1 domain, the CH2 domain or the CH3 domain or any combination thereof depending on the desired DAR, the antibody construct, the selected payload and the antibody target. In other preferred embodiments the cysteines may be introduced into a kappa or lambda CL domain and, in particularly preferred embodiments, in the c-terminal region of the CL domain. In each case other amino acid residues proximal to the site of cysteine insertion may be altered, removed or substituted to facilitate molecular stability, conjugation efficiency or provide a protective environment for the payload once it is attached. In particular embodiments, the substituted residues occur at any accessible sites of the antibody. By substituting such surface residues with cysteine, reactive thiol groups are thereby positioned at readily accessible sites on the antibody and may be selectively reduced as described further herein. In particular embodiments, the substituted residues occur at accessible sites of the antibody. By substituting those residues with cysteine, reactive thiol groups are thereby positioned at accessible sites of the antibody and may be used to selectively conjugate the antibody. In certain embodiments, any one or more of the following residues may be substituted with cysteine: V205 (Kabat numbering) of the light chain; A118 (Eu numbering) of the heavy chain; and S400 (Eu numbering) of the heavy chain Fc region. Additional substitution positions and methods of fabricating compatible site-specific antibodies are set forth in U.S. Pat. No. 7,521,541 which is incorporated herein in its entirety.

The strategy for generating antibody drug conjugates with defined sites and stoichiometries of drug loading, as disclosed herein, is broadly applicable to all anti-BMPR1B antibodies as it primarily involves engineering of the conserved constant domains of the antibody. As the amino acid sequences and native disulfide bridges of each class and subclass of antibody are well documented, one skilled in the art could readily fabricate engineered constructs of various antibodies without undue experimentation and, accordingly, such constructs are expressly contemplated as being within the scope of the instant invention.

4.3. Constant Region Modifications and Altered Glycosylation

Selected embodiments of the present invention may also comprise substitutions or modifications of the constant region (i.e. the Fc region), including without limitation, amino acid residue substitutions, mutations and/or modifications, which result in a compound with characteristics including, but not limited to: altered pharmacokinetics, increased serum half-life, increase binding affinity, reduced immunogenicity, increased production, altered Fc ligand binding to an Fc receptor (FcR), enhanced or reduced ADCC or CDC, altered glycosylation and/or disulfide bonds and modified binding specificity.

Compounds with improved Fc effector functions can be generated, for example, through changes in amino acid residues involved in the interaction between the Fc domain and an Fc receptor (e.g., FcγRI, FcγRIIA and B, FcγRIII and FcRn), which may lead to increased cytotoxicity and/or altered pharmacokinetics, such as increased serum half-life (see, for example, Ravetch and Kinet, Annu. Rev. Immunol 9:457-92 (1991); Capel et al., Immunomethods 4:25-34 (1994); and de Haas et al., J. Lab. Clin. Med. 126:330-41 (1995).

In embodiments of the present invention may also comprise substitutions or modifications of the constant region (i.e. the Fc region), including without limitation, amino acid residue substitutions, mutations and/or modifications, which result in a compound with characteristics including, but not limited to: altered pharmacokinetics, increased serum half-life, increase binding affinity, reduced immunogenicity, increased production, altered Fc ligand binding to an Fc receptor (FcR), enhanced or reduced ADCC or CDC, altered glycosylation and/or disulfide bonds and modified binding specificity.

Compounds with improved Fc effector functions can be generated, for example, through changes in amino acid residues involved in the interaction between the Fc domain and an Fc receptor (e.g., FcγRI, FcγRIIA and B, FcγRIII and FcRn), which may lead to increased cytotoxicity and/or altered pharmacokinetics, such as increased serum half-life (see, for example, Ravetch and Kinet, Annu. Rev. Immunol 9:457-92 (1991); Capel et al., Immunomethods 4:25-34 (1994); and de Haas et al., J. Lab. Clin. Med. 126:330-41 (1995).

In selected embodiments, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S.P.N. 2003/0190311). With regard to such embodiments, Fc variants may provide half-lives in a mammal, preferably a human, of greater than 5 days, greater than 10 days, greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-life results in a higher serum titer which thus reduces the frequency of the administration of the antibodies and/or reduces the concentration of the antibodies to be administered. Binding to human FcRn in vivo and serum half-life of human FcRn high affinity binding polypeptides can be assayed, e.g., in transgenic mice or transfected human cell lines expressing human FcRn, or in primates to which the polypeptides with a variant Fc region are administered. WO 2000/42072 describes antibody variants with improved or diminished binding to FcRns. See also, e.g., Shields et al. J. Biol. Chem. 9(2):6591-6604 (2001).

In other embodiments, Fc alterations may lead to enhanced or reduced ADCC or CDC activity. As in known in the art, CDC refers to the lysing of a target cell in the presence of complement, and ADCC refers to a form of cytotoxicity in which secreted Ig bound onto FcRs present on certain cytotoxic cells (e.g., Natural Killer cells, neutrophils, and macrophages) enables these cytotoxic effector cells to bind specifically to an antigen-bearing target cell and subsequently kill the target cell with cytotoxins. In the context of the instant invention antibody variants are provided with "altered" FcR binding affinity, which is either enhanced or diminished binding as compared to a parent or unmodified antibody or to an antibody comprising a native sequence FcR. Such variants which display decreased binding may possess little or no appreciable binding, e.g., 0-20% binding to the FcR compared to a native sequence, e.g. as determined by techniques well known in the art. In other embodiments the variant will exhibit enhanced binding as compared to the native immunoglobulin Fc domain. It will be appreciated that these types of Fc variants may advantageously be used to enhance the effective anti-neoplastic properties of the disclosed antibodies. In yet other embodiments, such alterations lead to increased binding affinity, reduced immunogenicity, increased production, altered glycosylation and/or disulfide bonds (e.g., for conjugation sites), modified binding specificity, increased phagocytosis; and/or down regulation of cell surface receptors (e.g. B cell receptor; BCR), etc.

Still other embodiments comprise one or more engineered glycoforms, e.g., a site-specific antibody comprising an altered glycosylation pattern or altered carbohydrate composition that is covalently attached to the protein (e.g., in the Fc domain). See, for example, Shields, R. L. et al. (2002) *J. Biol. Chem.* 277:26733-26740. Engineered glycoforms may be useful for a variety of purposes, including but not limited to enhancing or reducing effector function, increasing the affinity of the antibody for a target or facilitating production of the antibody. In certain embodiments where reduced effector function is desired, the molecule may be engineered to express an aglycosylated form. Substitutions that may result in elimination of one or more variable region framework glycosylation sites to thereby eliminate glycosylation at that site are well known (see e.g. U.S. Pat. Nos. 5,714,350 and 6,350,861). Conversely, enhanced effector functions or improved binding may be imparted to the Fc containing molecule by engineering in one or more additional glycosylation sites.

Other embodiments include an Fc variant that has an altered glycosylation composition, such as a hypofucosylated antibody having reduced amounts of fucosyl residues or an antibody having increased bisecting GlcNAc structures. Such altered glycosylation patterns have been demonstrated to increase the ADCC ability of antibodies. Engineered glycoforms may be generated by any method known to one skilled in the art, for example by using engineered or variant expression strains, by co-expression with one or more enzymes (for example N-acetylglucosaminyltransferase III (GnTIII)), by expressing a molecule comprising an Fc region in various organisms or cell lines from various organisms or by modifying carbohydrate(s) after the molecule comprising Fc region has been expressed (see, for example, WO 2012/117002).

4.4. Fragments

Regardless of which form of antibody (e.g. chimeric, humanized, etc.) is selected to practice the invention it will be appreciated that immunoreactive fragments, either by themselves or as part of an antibody drug conjugate, of the same may be used in accordance with the teachings herein. An "antibody fragment" comprises at least a portion of an intact antibody. As used herein, the term "fragment" of an antibody molecule includes antigen-binding fragments of antibodies, and the term "antigen-binding fragment" refers to a polypeptide fragment of an immunoglobulin or antibody that immunospecifically binds or reacts with a selected antigen or immunogenic determinant thereof or competes with the intact antibody from which the fragments were derived for specific antigen binding.

Exemplary immunoreactive fragments include: variable light chain fragments (VL), variable heavy chain fragments (VH), scFvs, F(ab')2 fragment, Fab fragment, Fd fragment, Fv fragment, single domain antibody fragments, diabodies, linear antibodies, single-chain antibody molecules and multispecific antibodies formed from antibody fragments. In addition, an active site-specific fragment comprises a portion of the antibody that retains its ability to interact with the antigen/substrates or receptors and modify them in a manner similar to that of an intact antibody (though maybe with somewhat less efficiency). Such antibody fragments may further be engineered to comprise one or more free cysteines as described herein.

In particularly preferred embodiments the BMPR1B binding domain will comprise a scFv construct. As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain and light chain fragments are linked via a spacer sequence. Various methods for preparing a scFv are known, and include methods described in U.S. Pat. No. 4,694,778.

In other embodiments, an antibody fragment is one that comprises the Fc region and that retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence comprising at least one free cysteine capable of conferring in vivo stability to the fragment.

As would be well recognized by those skilled in the art, fragments can be obtained by molecular engineering or via chemical or enzymatic treatment (such as papain or pepsin) of an intact or complete antibody or antibody chain or by recombinant means. See, e.g., Fundamental Immunology, W. E. Paul, ed., Raven Press, N.Y. (1999), for a more detailed description of antibody fragment.

In selected embodiments antibody fragments of the invention will comprise ScFv constructs which may be used in various configurations. For example such anti-BMPR1B ScFv constructs may be used in adoptive immunity gene therapy to treat tumors. In certain embodiments the antibodies of the invention (e.g. ScFv fragments) may be used to generate a chimeric antigen receptors (CAR) that immunoselectively react with BMPR1B. In accordance with the instant disclosure an anti-BMPR1B CAR is a fused protein comprising the anti-BMPR1B antibodies of the invention or immunoreactive fragments thereof (e.g. ScFv fragments), a transmembrane domain, and at least one intracellular domain. In certain embodiments, T-cells, natural killer cells or dendritic cells that have been genetically engineered to express an anti-BMPR1B CAR can be introduced into a subject suffering from cancer in order to stimulate the immune system of the subject to specifically target tumor cells expressing BMPR1B. In some embodiments the CARs of the invention will comprise an intracellular domain that initiates a primary cytoplasmic signaling sequence, that is, a sequence for initiating antigen-dependent primary activation via a T-cell receptor complex, for example, intracellular domains derived from CD3ζ, FcRγ, FcRβ, CD3γ, CD3δ, CD3ε, CD5, CD22, CD79a, CD79b, and CD66d. In other embodiments, the CARs of the invention will comprise an intracellular domain that initiates a secondary or co-stimulating signal, for example, intracellular domains derived from CD2, CD4, CD5, CD8α, CD8β, CD28, CD134, CD137, ICOS, CD154, 4-1BB and glucocorticoid-induced tumor necrosis factor receptor (see U.S.P.N. US/2014/0242701).

4.5. Multivalent Constructs

In other embodiments, the antibodies and conjugates of the invention may be monovalent or multivalent (e.g., bivalent, trivalent, etc.). As used herein, the term "valency" refers to the number of potential target binding sites associated with an antibody. Each target binding site specifically binds one target molecule or specific position or locus on a target molecule. When an antibody is monovalent, each binding site of the molecule will specifically bind to a single antigen position or epitope. When an antibody comprises more than one target binding site (multivalent), each target binding site may specifically bind the same or different molecules (e.g., may bind to different ligands or different antigens, or different epitopes or positions on the same antigen). See, for example, U.S.P.N. 2009/0130105.

In one embodiment, the antibodies are bispecific antibodies in which the two chains have different specificities, as described in Millstein et al., 1983, *Nature,* 305:537-539. Other embodiments include antibodies with additional specificities such as trispecific antibodies. Other more sophisticated compatible multispecific constructs and methods of their fabrication are set forth in U.S.P.N. 2009/0155255, as well as WO 94/04690; Suresh et al., 1986, *Methods in Enzymology,* 121:210; and WO96/27011.

Multivalent antibodies may immunospecifically bind to different epitopes of the desired target molecule or may immunospecifically bind to both the target molecule as well as a heterologous epitope, such as a heterologous polypeptide or solid support material. While selected embodiments may only bind two antigens (i.e. bispecific antibodies), antibodies with additional specificities such as trispecific antibodies are also encompassed by the instant invention. Bispecific antibodies also include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

5. Recombinant Production of Antibodies

Antibodies and fragments thereof may be produced or modified using genetic material obtained from antibody producing cells and recombinant technology (see, for example; Dubel and Reichert (Eds.) (2014) *Handbook of Therapeutic Antibodies,* $2^{nd}$ Edition, Wiley-Blackwell GmbH; Sambrook and Russell (Eds.) (2000) *Molecular Cloning: A Laboratory Manual* ($3^{rd}$ Ed.), NY, Cold Spring Harbor Laboratory Press; Ausubel et al. (2002) *Short Protocols in Molecular Biology: A Compendium of Methods from Current Protocols in Molecular Biology*, Wiley, John & Sons, Inc.; and U.S. Pat. No. 7,709,611).

Another aspect of the invention pertains to nucleic acid molecules that encode the antibodies of the invention. The nucleic acids may be present in whole cells, in a cell lysate, or in a partially purified or substantially pure form. A nucleic acid is "isolated" or rendered substantially pure when separated from other cellular components or other contaminants, e.g., other cellular nucleic acids or proteins, by standard techniques, including alkaline/SDS treatment, CsCl banding, column chromatography, agarose gel electrophoresis and others well known in the art. A nucleic acid of the invention can be, for example, DNA (e.g. genomic DNA, cDNA), RNA and artificial variants thereof (e.g., peptide nucleic acids), whether single-stranded or double-stranded or RNA, RNA and may or may not contain introns. In selected embodiments the nucleic acid is a cDNA molecule.

Nucleic acids of the invention can be obtained using standard molecular biology techniques. For antibodies expressed by hybridomas (e.g., hybridomas prepared as described in the Examples below), cDNAs encoding the light and heavy chains of the antibody can be obtained by standard PCR amplification or cDNA cloning techniques. For antibodies obtained from an immunoglobulin gene library (e.g., using phage display techniques), nucleic acid molecules encoding the antibody can be recovered from the library.

DNA fragments encoding VH and VL segments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, means that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3 in the case of IgG1). The sequences of human heavy chain constant region genes are known in the art (see e.g., Kabat, et al. (1991) (supra)) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. An exemplary IgG1 constant region is set forth in SEQ ID NO: 2. For a Fab fragment heavy chain gene, the VH-encoding DNA can be operatively linked to another DNA molecule encoding only the heavy chain CH1 constant region.

Isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, et al. (1991) (supra)) and DNA fragments encompassing these regions can be obtained by standard PCR amplification. The light chain constant region can be a kappa or lambda constant region, but most preferably is a kappa constant region. An exemplary compatible kappa light chain constant region is set forth in SEQ ID NO: 5 while an exemplary compatible lambda light chain constant region is set forth in SEQ ID NO: 8.

In each case the VH or VL domains may be operatively linked to their respective constant regions (CH or CL) where the constant regions are site-specific constant regions and provide site-specific antibodies. In selected embodiments the resulting site-specific antibodies will comprise two unpaired cysteines on the heavy chains while in other embodiments the site-specific antibodies will comprise two unpaired cysteines in the CL domain.

Contemplated herein are certain polypeptides (e.g. antigens or antibodies) that exhibit "sequence identity", sequence similarity" or "sequence homology" to the polypeptides of the invention. For example, a derived humanized antibody VH or VL domain may exhibit a sequence similarity with the source (e.g., murine) or acceptor (e.g., human) VH or VL domain. A "homologous" polypeptide may exhibit 65%, 70%, 75%, 80%, 85%, or 90% sequence identity. In other embodiments a "homologous" polypeptides may exhibit 93%, 95% or 98% sequence identity. As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting Examples below.

The percent identity between two amino acid sequences can be determined using the algorithm of E. Meyers and W. Miller (*Comput. Appl. Biosci.,* 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When using BLAST and Gapped BLAST programs, the default parameters of the respective programs (e.g., XBLAST and NBLAST) can be used.

Residue positions which are not identical may differ by conservative amino acid substitutions or by non-conservative amino acid substitutions. A "conservative amino acid substitution" is one in which an amino acid residue is substituted by another amino acid residue having a side chain with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. In cases where there is a substitution with a non-conservative amino acid, in embodiments the polypeptide exhibiting sequence identity will retain the desired function or activity of the polypeptide of the invention (e.g., antibody.)

Also contemplated herein are nucleic acids that that exhibit "sequence identity", sequence similarity" or "sequence homology" to the nucleic acids of the invention. A "homologous sequence" means a sequence of nucleic acid molecules exhibiting at least about 65%, 70%, 75%, 80%, 85%, or 90% sequence identity. In other embodiments, a "homologous sequence" of nucleic acids may exhibit 93%, 95% or 98% sequence identity to the reference nucleic acid.

The instant invention also provides vectors comprising such nucleic acids described above, which may be operably linked to a promoter (see, e.g., WO 86/05807; WO 89/01036; and U.S. Pat. No. 5,122,464); and other transcriptional regulatory and processing control elements of the eukaryotic secretory pathway. The invention also provides host cells harboring those vectors and host-expression systems.

As used herein, the term "host-expression system" includes any kind of cellular system that can be engineered to generate either the nucleic acids or the polypeptides and antibodies of the invention. Such host-expression systems include, but are not limited to microorganisms (e.g., *E. coli* or *B. subtilis*) transformed or transfected with recombinant bacteriophage DNA or plasmid DNA; yeast (e.g., *Saccharomyces*) transfected with recombinant yeast expression vectors; or mammalian cells (e.g., COS, CHO-S, HEK293T, 3T3 cells) harboring recombinant expression constructs containing promoters derived from the genome of mammalian cells or viruses (e.g., the adenovirus late promoter). The host cell may be co-transfected with two expression vectors, for example, the first vector encoding a heavy chain derived polypeptide and the second vector encoding a light chain derived polypeptide.

Methods of transforming mammalian cells are well known in the art. See, for example, U.S. Pat. Nos. 4,399,216, 4,912,040, 4,740,461, and 4,959,455. The host cell may also be engineered to allow the production of an antigen binding molecule with various characteristics (e.g. modified glycoforms or proteins having GnTIII activity).

For long-term, high-yield production of recombinant proteins stable expression is preferred. Accordingly, cell lines that stably express the selected antibody may be engineered using standard art recognized techniques and form part of the invention. Rather than using expression vectors that contain viral origins of replication, host cells can be transformed with DNA controlled by appropriate expression control elements (e.g., promoter or enhancer sequences, transcription terminators, polyadenylation sites, etc.), and a selectable marker. Any of the selection systems well known in the art may be used, including the glutamine synthetase gene expression system (the GS system) which provides an efficient approach for enhancing expression under selected conditions. The GS system is discussed in whole or part in connection with EP 0 216 846, EP 0 256 055, EP 0 323 997 and EP 0 338 841 and U.S. Pat. Nos. 5,591,639 and 5,879,936. Another compatible expression system for the development of stable cell lines is the Freedom™ CHO-S Kit (Life Technologies).

Once an antibody of the invention has been produced by recombinant expression or any other of the disclosed techniques, it may be purified or isolated by methods known in the art in that it is identified and separated and/or recovered from its natural environment and separated from contaminants that would interfere with diagnostic or therapeutic uses for the antibody or related ADC. Isolated antibodies include antibodies in situ within recombinant cells.

These isolated preparations may be purified using various art-recognized techniques, such as, for example, ion exchange and size exclusion chromatography, dialysis, diafiltration, and affinity chromatography, particularly Protein A or Protein G affinity chromatography. Compatible methods are discussed more fully in the Examples below.

6. Post-Production Selection

No matter how obtained, antibody producing cells (e.g., hybridomas, yeast colonies, etc.) may be selected, cloned and further screened for desirable characteristics including, for example, robust growth, high antibody production and desirable antibody characteristics such as high affinity for the antigen of interest. Hybridomas can be expanded in vitro in cell culture or in vivo in syngeneic immunocompromised animals. Methods of selecting, cloning and expanding hybridomas and/or colonies are well known to those of ordinary skill in the art. Once the desired antibodies are identified the relevant genetic material may be isolated, manipulated and expressed using common, art-recognized molecular biology and biochemical techniques.

The antibodies produced by naïve libraries (either natural or synthetic) may be of moderate affinity ($K_a$ of about $10^6$ to $10^7$ $M^{-1}$). To enhance affinity, affinity maturation may be mimicked in vitro by constructing antibody libraries (e.g., by introducing random mutations in vitro by using error-prone polymerase) and reselecting antibodies with high affinity for the antigen from those secondary libraries (e.g. by using phage or yeast display). WO 9607754 describes a method for inducing mutagenesis in a CDR of an immunoglobulin light chain to create a library of light chain genes.

Various techniques can be used to select antibodies, including but not limited to, phage or yeast display in which a library of human combinatorial antibodies or scFv fragments is synthesized on phages or yeast, the library is screened with the antigen of interest or an antibody-binding portion thereof, and the phage or yeast that binds the antigen is isolated, from which one may obtain the antibodies or immunoreactive fragments (Vaughan et al., 1996, PMID: 9630891; Sheets et al., 1998, PMID: 9600934; Boder et al., 1997, PMID: 9181578; Pepper et al., 2008, PMID: 18336206). Kits for generating phage or yeast display libraries are commercially available. There also are other methods and reagents that can be used in generating and screening antibody display libraries (see U.S. Pat. No. 5,223,409; WO 92/18619, WO 91/17271, WO 92/20791, WO 92/15679, WO 93/01288, WO 92/01047, WO 92/09690; and Barbas et al., 1991, PMID: 1896445). Such techniques advantageously allow for the screening of large numbers of candidate antibodies and provide for relatively easy manipulation of sequences (e.g., by recombinant shuffling).

IV. CHARACTERISTICS OF ANTIBODIES

In certain embodiments, antibody-producing cells (e.g., hybridomas or yeast colonies) may be selected, cloned and further screened for favorable properties including, for example, robust growth, high antibody production and, as discussed in more detail below, desirable site-specific antibody characteristics. In other cases characteristics of the antibody may be imparted by selecting a particular antigen (e.g., a specific BMPR1B isoform) or immunoreactive fragment of the target antigen for inoculation of the animal. In still other embodiments the selected antibodies may be engineered as described above to enhance or refine immunochemical characteristics such as affinity or pharmacokinetics.

A. Neutralizing Antibodies

In selected embodiments the antibodies of the invention may be "antagonists" or "neutralizing" antibodies, meaning that the antibody may associate with a determinant and block or inhibit the activities of said determinant either directly or by preventing association of the determinant with a binding partner such as a ligand or a receptor, thereby interrupting the biological response that otherwise would result from the interaction of the molecules. A neutralizing or antagonist antibody will substantially inhibit binding of the determinant to its ligand or substrate when an excess of antibody reduces the quantity of binding partner bound to the determinant by at least about 20%, 30%, 40%, 50%, 60%, 70%, 80%, 85%, 90%, 95%, 97%, 99% or more as measured, for example, by target molecule activity or in an in vitro competitive binding assay. It will be appreciated that the modified activity may be measured directly using art recognized techniques or may be measured by the impact the altered activity has downstream (e.g., oncogenesis or cell survival). As set forth below in Example 21 and shown in FIGS. 19A-19E it may readily be determined if an antibody of the invention is capable of blocking or inhibiting the binding of BMP4 and/or BMP2 (naturally occurring ligands of BMPR1B). Thus, in some embodiments exemplarly antibodies of the invention will block the binding of BMP4 to BMPR1B by at least about 20%, 30%, 40%, 50%, 60%, 70%, 80%, 85%, 90%, 95%, 97%, 99% or more when measured as set forth below. In other embodiments certain antibodies of the invention will block the binding of BMP2 to BMPR1B by at least about 20%, 30%, 40%, 50%, 60%, 70%, 80%, 85%, 90%, 95%, 97%, 99% or more when measured as set forth below. As certain ADCs comprising such antagonistic antibodies (e.g., hSC91.1 and hSC91.9) have been shown to be particularly effective in killing tumor cells such neutralizing or blocking antibodies may be particularly compatible for use in the disclosed ADCs or in treating cancer as disclosed herein.

B. Internalizing Antibodies

In certain embodiments the antibodies may comprise internalizing antibodies such that the antibody will bind to a determinant and will be internalized (along with any conjugated pharmaceutically active moiety) into a selected target cell including tumorigenic cells. The number of antibody molecules internalized may be sufficient to kill an antigen-expressing cell, especially an antigen-expressing tumorigenic cell. Depending on the potency of the antibody or, in some instances, antibody drug conjugate, the uptake of a single antibody molecule into the cell may be sufficient to kill the target cell to which the antibody binds. With regard to the instant invention there is evidence that a substantial portion of expressed BMPR1B protein remains associated with the tumorigenic cell surface, thereby allowing for localization and internalization of the disclosed antibodies or ADCs. In selected embodiments such antibodies will be associated with, or conjugated to, one or more drugs that kill the cell upon internalization. In some embodiments the ADCs of the instant invention will comprise an internalizing site-specific ADC.

As used herein, an antibody that "internalizes" is one that is taken up (along with any conjugated cytotoxin) by a target cell upon binding to an associated determinant. The number of such ADCs internalized will preferably be sufficient to kill the determinant-expressing cell, especially a determinant expressing cancer stem cell. Depending on the potency of the cytotoxin or ADC as a whole, in some instances the uptake of a few antibody molecules into the cell is sufficient to kill the target cell to which the antibody binds. For example, certain drugs such as PBDs or calicheamicin are so potent that the internalization of a few molecules of the toxin conjugated to the antibody is sufficient to kill the target cell. Whether an antibody internalizes upon binding to a mammalian cell can be determined by various art-recognized assays (e.g., saporin assays such as Mab-Zap and Fab-Zap; Advanced Targeting Systems) including those described in the Examples below. Methods of detecting whether an antibody internalizes into a cell are also described in U.S. Pat. No. 7,619,068.

C. Depleting Antibodies

In other embodiments the antibodies of the invention are depleting antibodies. The term "depleting" antibody refers to an antibody that preferably binds to an antigen on or near the cell surface and induces, promotes or causes the death of the cell (e.g., by CDC, ADCC or introduction of a cytotoxic agent). In embodiments, the selected depleting antibodies will be conjugated to a cytotoxin.

Preferably a depleting antibody will be able to kill at least 20%, 30%, 40%, 50%, 60%, 70%, 80%, 85%, 90%, 95%, 97%, or 99% of BMPR1B-expressing cells in a defined cell population. The term "apparent IC50", as used herein, refers to the concentration at which a primary antibody linked to a toxin kills 50 percent of the cells expressing the antigen(s) recognized by the primary antibody. The toxin can be directly conjugated to the primary antibody, or can be associated with the primary antibody via a secondary antibody or antibody fragment that recognizes the primary antibody, and which secondary antibody or antibody fragment is directly conjugated to a toxin. Preferably a depleting antibody will have an IC50 of less than 5 µM, less than 1 µM, less than 100 nM, less than 50 nM, less than 30 nM, less than 20 nM, less than 10 nM, less than 5 nM, less than 2 nM or less than 1 nM. In some embodiments the cell population may comprise enriched, sectioned, purified or isolated tumorigenic cells, including cancer stem cells. In other embodiments the cell population may comprise whole tumor samples or heterogeneous tumor extracts that comprise cancer stem cells. Standard biochemical techniques may be used to monitor and quantify the depletion of tumorigenic cells in accordance with the teachings herein.

D. Binding Affinity

Disclosed herein are antibodies that have a high binding affinity for a specific determinant e.g. BMPR1B. The term "$K_D$" refers to the dissociation constant or apparent affinity of a particular antibody-antigen interaction. An antibody of the invention can immunospecifically bind its target antigen when the dissociation constant $K_D$ ($k_{off}/k_{on}$) is $\leq 10^{-7}$ M. The antibody specifically binds antigen with high affinity when the $K_D$ is $\leq 5 \times 10^{-9}$ M, and with very high affinity when the $K_D$ is $\leq 5 \times 10^{-10}$ M. In one embodiment of the invention, the antibody has a $K_D$ of $\leq 10^{-9}$ M and an off-rate of about $1 \times 10^{-4}$/sec. In one embodiment of the invention, the off-rate is $<1 \times 10^{-5}$/sec. In other embodiments of the invention, the antibodies will bind to a determinant with a $K_D$ of between about $10^{-7}$ M and $10^{-10}$ M, and in yet another embodiment it will bind with a $K_D \leq 2 \times 10^{-10}$ M. Still other selected embodiments of the invention comprise antibodies that have a $K_D$ ($k_{off}/k_{on}$) of less than $10^{-6}$ M, less than $5 \times 10^{-6}$ M, less than $10^{-7}$ M, less than $5 \times 10^{-7}$ M, less than $10^{-8}$ M, less than $5 \times 10^{-8}$ M, less than $10^{-9}$ M, less than $5 \times 10^{-9}$ M, less than $10^{-10}$ M, less than $5 \times 10^{-10}$ M, less than $10^{-11}$ M, less than $5 \times 10^{-11}$ M, less than $10^{-12}$ M, less than $5 \times 10^{-12}$ M, less than $10^{-13}$ M, less than $5 \times 10^{-13}$ M, less than $10^{-14}$ M, less than $5 \times 10^{-14}$ M, less than $10^{-15}$ M or less than $5 \times 10^{-15}$ M.

In certain embodiments, an antibody of the invention that immunospecifically binds to a determinant e.g. BMPR1B may have an association rate constant or $k_{on}$ (or $k_a$) rate (antibody+antigen (Ag)$^{k_{on}} \leftarrow$ antibody-Ag) of at least $10^5$ M$^{-1}$s$^{-1}$, at least $2 \times 10^5$ M$^{-1}$s$^{-1}$, at least $5 \times 10^5$ M$^{-1}$s$^{-1}$, at least $10^6$ M$^{-1}$s$^{-1}$, at least $5 \times 10^6$ M$^{-1}$s$^{-1}$, at least $10^7$ M$^{-1}$s$^{-1}$, at least $5 \times 10^7$ M$^{-1}$s$^{-1}$, or at least $10^8$ M$^{-1}$s$^{-1}$.

In another embodiment, an antibody of the invention that immunospecifically binds to a determinant e.g. BMPR1B may have a disassociation rate constant or $k_{off}$ (or $k_d$) rate (antibody+antigen (Ag)$^{k_{off}} \leftarrow$ antibody-Ag) of less than $10^{-1}$ s$^{-1}$, less than $5 \times 10^{-1}$ s$^{-1}$, less than $10^{-2}$ s$^{-1}$, less than $5 \times 10^{-2}$ s$^{-1}$, less than $10^{-3}$ s$^{-1}$, less than $5 \times 10^{-3}$ s$^{-1}$, less than $10^{-4}$ s$^{-1}$, less than $5 \times 10^{-4}$ s$^{-1}$, less than $10^{-5}$ s$^{-1}$, less than $5 \times 10^{-5}$ s$^{-1}$, less than $10^{-6}$ s$^{-1}$, less than $5 \times 10^{-6}$ s$^{-1}$ less than $10^{-7}$ s$^{-1}$, less than $5 \times 10^{-7}$ s$^{-1}$, less than $10^{-8}$ s$^{-1}$, less than $5 \times 10^{-8}$ s$^{-1}$, less than $10^{-9}$ s$^{-1}$, less than $5 \times 10^{-9}$ s$^{-1}$ or less than $10^{-10}$ s$^{-1}$.

Binding affinity may be determined using various techniques known in the art, for example, surface plasmon resonance, bio-layer interferometry, dual polarization interferometry, static light scattering, dynamic light scattering, isothermal titration calorimetry, ELISA, analytical ultracentrifugation, and flow cytometry.

E. Binning and Epitope Mapping

Antibodies disclosed herein may be characterized in terms of the discrete epitope with which they associate. An "epitope" is the portion(s) of a determinant to which the antibody or immunoreactive fragment specifically binds. Immunospecific binding can be confirmed and defined based on binding affinity, as described above, or by the preferential recognition by the antibody of its target antigen in a complex mixture of proteins and/or macromolecules (e.g. in competition assays). A "linear epitope", is formed by contiguous amino acids in the antigen that allow for immunospecific binding of the antibody. The ability to preferentially bind linear epitopes is typically maintained even when the antigen is denatured. Conversely, a "conformational epitope", usually comprises non-contiguous amino acids in the antigen's amino acid sequence but, in the context of the antigen's secondary, tertiary or quaternary structure, are sufficiently proximate to be bound concomitantly by a single antibody. When antigens with conformational epitopes are denatured, the antibody will typically no longer recognize the antigen. An epitope (contiguous or non-contiguous) typically includes at least 3, and more usually, at least 5 or 8-10 or 12-20 amino acids in a unique spatial conformation.

It is also possible to characterize the antibodies of the invention in terms of the group or "bin" to which they belong. "Binning" refers to the use of competitive antibody binding assays to identify pairs of antibodies that are incapable of binding an immunogenic determinant simultaneously, thereby identifying antibodies that "compete" for binding. Competing antibodies may be determined by an assay in which the antibody or immunologically functional fragment being tested prevents or inhibits specific binding of a reference antibody to a common antigen. Typically, such an assay involves the use of purified antigen (e.g., BMPR1B or a domain or fragment thereof) bound to a solid surface or cells, an unlabeled test antibody and a labeled reference antibody. Competitive inhibition is measured by determining the amount of label bound to the solid surface or cells in the presence of the test antibody. Additional details regarding methods for determining competitive binding are provided in the Examples herein. Usually, when a competing antibody is present in excess, it will inhibit specific binding of a reference antibody to a common antigen by at least 30%, 40%, 45%, 50%, 55%, 60%, 65%, 70% or 75%. In some instance, binding is inhibited by at least 80%, 85%, 90%, 95%, or 97% or more. Conversely, when the reference antibody is bound it will preferably inhibit binding of a subsequently added test antibody (i.e., a BMPR1B antibody) by at least 30%, 40%, 45%, 50%, 55%, 60%, 65%, 70% or 75%. In some instance, binding of the test antibody is inhibited by at least 80%, 85%, 90%, 95%, or 97% or more.

Generally binning or competitive binding may be determined using various art-recognized techniques, such as, for example, immunoassays such as western blots, radioimmunoassays, enzyme linked immunosorbent assay (ELISA), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays. Such immunoassays are routine and well known in the art (see, Ausubel et al, eds, (1994) *Current Protocols in Molecular Biology*, Vol. 1, John Wiley & Sons, Inc., New York). Additionally, cross-blocking assays may be used (see, for example, WO 2003/48731; and Harlow et al. (1988) *Antibodies, A Laboratory Manual*, Cold Spring Harbor Laboratory, Ed Harlow and David Lane).

Other technologies used to determine competitive inhibition (and hence "bins"), include: surface plasmon resonance using, for example, the BIAcore™ 2000 system (GE Healthcare); bio-layer interferometry using, for example, a ForteBio® Octet RED (ForteBio); or flow cytometry bead arrays using, for example, a FACSCanto II (BD Biosciences) or a multiplex LUMINEX™ detection assay (Luminex).

Luminex is a bead-based immunoassay platform that enables large scale multiplexed antibody pairing. The assay compares the simultaneous binding patterns of antibody pairs to the target antigen. One antibody of the pair (capture mAb) is bound to Luminex beads, wherein each capture mAb is bound to a bead of a different color. The other antibody (detector mAb) is bound to a fluorescent signal (e.g. phycoerythrin (PE)). The assay analyzes the simultaneous binding (pairing) of antibodies to an antigen and associates antibodies with similar pairing profiles. Similar profiles of a detector mAb and a capture mAb indicates that the two antibodies bind to the same or closely related epitopes. In one embodiment, pairing profiles can be determined using Pearson correlation coefficients to identify the antibodies which most closely correlate to any particular antibody on the panel of antibodies that are tested. In embodiments a test/detector mAb will be determined to be in the same bin as a reference/capture mAb if the Pearson's correlation coefficient of the antibody pair is at least 0.9. In other embodiments the Pearson's correlation coefficient is at least 0.8, 0.85, 0.87 or 0.89. In further embodiments, the Pearson's correlation coefficient is at least 0.91, 0.92, 0.93, 0.94, 0.95, 0.96, 0.97, 0.98, 0.99 or 1. Other methods of analyzing the data obtained from the Luminex assay are described in U.S. Pat. No. 8,568,992. The ability of Luminex to analyze 100 different types of beads (or more) simultaneously provides almost unlimited antigen and/or antibody surfaces, resulting in improved throughput and resolution in antibody epitope profiling over a biosensor assay (Miller, et al., 2011, PMID: 21223970).

Similarly binning techniques comprising surface plasmon resonance are compatible with the instant invention. As used herein "surface plasmon resonance," refers to an optical phenomenon that allows for the analysis of real-time specific interactions by detection of alterations in protein concentrations within a biosensor matrix. Using commercially available equipment such as the BIAcore™ 2000 system it may readily be determined if selected antibodies compete with each other for binding to a defined antigen.

In other embodiments, a technique that can be used to determine whether a test antibody "competes" for binding with a reference antibody is "bio-layer interferometry", an optical analytical technique that analyzes the interference pattern of white light reflected from two surfaces: a layer of immobilized protein on a biosensor tip, and an internal reference layer. Any change in the number of molecules bound to the biosensor tip causes a shift in the interference pattern that can be measured in real-time. Such biolayer interferometry assays may be conducted using a ForteBio® Octet RED machine as follows. A reference antibody (Ab1) is captured onto an anti-mouse capture chip, a high concentration of non-binding antibody is then used to block the chip and a baseline is collected. Monomeric, recombinant target protein is then captured by the specific antibody (Ab1) and the tip is dipped into a well with either the same antibody (Ab1) as a control or into a well with a different test antibody (Ab2). If no further binding occurs, as determined by comparing binding levels with the control Ab1, then Ab1 and Ab2 are determined to be "competing" antibodies. If additional binding is observed with Ab2, then Ab1 and Ab2 are determined not to compete with each other. This process can be expanded to screen large libraries of unique antibodies using a full row of antibodies in a 96-well plate representing unique bins. In embodiments a test antibody will compete with a reference antibody if the reference antibody inhibits specific binding of the test antibody to a common antigen by at least 40%, 45%, 50%, 55%, 60%, 65%, 70% or 75%. In other embodiments, binding is inhibited by at least 80%, 85%, 90%, 95%, or 97% or more.

Once a bin, encompassing a group of competing antibodies, has been defined further characterization can be carried out to determine the specific domain or epitope on the antigen to which that group of antibodies binds. Domain-level epitope mapping may be performed using a modification of the protocol described by Cochran et al., 2004, PMID: 15099763. Fine epitope mapping is the process of determining the specific amino acids on the antigen that comprise the epitope of a determinant to which the antibody binds.

In certain embodiments fine epitope mapping can be performed using phage or yeast display. Other compatible epitope mapping techniques include alanine scanning mutants, peptide blots (Reineke, 2004, PMID: 14970513), or peptide cleavage analysis. In addition, methods such as epitope excision, epitope extraction and chemical modification of antigens can be employed (Tomer, 2000, PMID: 10752610) using enzymes such as proteolytic enzymes (e.g., trypsin, endoproteinase Glu-C, endoproteinase Asp-N, chymotrypsin, etc.); chemical agents such as succinimidyl esters and their derivatives, primary amine-containing compounds, hydrazines and carbohydrazines, free amino acids, etc. In another embodiment Modification-Assisted Profiling, also known as Antigen Structure-based Antibody Profiling (ASAP) can be used to categorize large numbers of monoclonal antibodies directed against the same antigen according to the similarities of the binding profile of each antibody to chemically or enzymatically modified antigen surfaces (U.S.P.N. 2004/0101920).

Once a desired epitope on an antigen is determined, it is possible to generate additional antibodies to that epitope, e.g., by immunizing with a peptide comprising the selected epitope using techniques described herein.

V. ANTIBODY CONJUGATES

In some embodiments the antibodies of the invention may be conjugated with pharmaceutically active or diagnostic moieties to form an "antibody drug conjugate" (ADC) or "antibody conjugate". The term "conjugate" is used broadly and means the covalent or non-covalent association of any pharmaceutically active or diagnostic moiety with an antibody of the instant invention regardless of the method of association. In certain embodiments the association is effected through a lysine or cysteine residue of the antibody. In some embodiments the pharmaceutically active or diagnostic moieties may be conjugated to the antibody via one or more site-specific free cysteine(s). The disclosed ADCs may be used for therapeutic and diagnostic purposes.

It will be appreciated that the ADCs of the instant invention may be used to selectively deliver predetermined warheads to the target location (e.g., tumorigenic cells and/or cells expressing BMPR1B). As set forth herein the terms "drug" or "warhead" may be used interchangeably and will mean any biologically active (e.g., a pharmaceutically active compound or therapeutic moiety) or detectable molecule or compound that has a physiological effect or reporter function when introduced into a subject. For the avoidance of doubt such warheads include the anti-cancer agents or cytotoxins as described below. A "payload" may comprise a drug or warhead in combination with an optional linker compound (e.g., a therapeutic payload) that preferably provides a relatively stable pharmaceutical complex until the ADC reaches the target. By way of example the warhead or drug on the conjugate may comprise peptides, proteins or prodrugs which are metabolized to an active agent in vivo, polymers, nucleic acid molecules, small molecules, binding agents, mimetic agents, synthetic drugs, inorganic molecules, organic molecules and radioisotopes. In certain embodiments the drug or warhead will be covalently conjugated to the antibody through a linker. In other embodiments (e.g., a radioisotope) the drug or warhead will be directly conjugated to, or incorporated in, the antibody.

In preferred embodiments the disclosed ADCs will direct the bound payload (e.g., drug linker) to the target site in a relatively unreactive, non-toxic state before releasing and activating the warhead (e.g., PBDS 1-5 as disclosed herein). This targeted release of the warhead is preferably achieved through stable conjugation of the payloads (e.g., via one or more cysteines or lysines on the antibody) and relatively homogeneous composition of the ADC preparations which minimize over-conjugated toxic ADC species. Coupled with drug linkers that are designed to largely release the warhead upon delivery to the tumor site, the conjugates of the instant invention can substantially reduce undesirable non-specific toxicity. This advantageously provides for relatively high levels of the active cytotoxin at the tumor site while minimizing exposure of non-targeted cells and tissue thereby providing an enhanced therapeutic index.

It will be appreciated that, while some embodiments of the invention comprise payloads incorporating therapeutic moieties (e.g., cytotoxins), other payloads incorporating diagnostic agents and biocompatible modifiers may benefit from the targeted delivery provided by the disclosed conjugates. Accordingly, any disclosure directed to exemplary therapeutic payloads is also applicable to payloads comprising diagnostic agents or biocompatible modifiers as discussed herein unless otherwise dictated by context. The selected payload may be covalently or non-covalently linked to the antibody and exhibit various stoichiometric molar ratios depending, at least in part, on the method used to effect the conjugation.

Conjugates of the instant invention may be generally represented by the formula:

Ab-[L-D]n or a pharmaceutically acceptable salt thereof wherein:

a) Ab comprises an anti-BMPR1B antibody;
b) L comprises an optional linker;
c) D comprises a drug; and
d) n is an integer from about 1 to about 20.

Those of skill in the art will appreciate that conjugates according to the aforementioned formula may be fabricated using a number of different linkers and drugs and that conjugation methodology will vary depending on the selection of components. As such, any drug or drug linker compound that associates with a reactive residue (e.g., cysteine or lysine) of the disclosed antibodies are compatible with the teachings herein. Similarly, any reaction conditions that allow for conjugation (including site-specific conjugation) of the selected drug to an antibody are within the scope of the present invention. Notwithstanding the foregoing, some preferred embodiments of the instant invention comprise selective conjugation of the drug or drug linker to free cysteines using stabilization agents in combination with mild reducing agents as described herein. Such reaction conditions tend to provide more homogeneous preparations with less non-specific conjugation and contaminants and correspondingly less toxicity.

A. Payloads and Warheads

1. Therapeutic Agents

As discussed the antibodies of the invention may be conjugated, linked or fused to or otherwise associated with any pharmaceutically active compound comprising a therapeutic moiety or a drug such as an anti-cancer agent including, but not limited to, cytotoxic agents (or cytotoxins), cytostatic agents, anti-angiogenic agents, debulking agents, chemotherapeutic agents, radiotherapeutic agents, targeted anti-cancer agents, biological response modifiers, cancer vaccines, cytokines, hormone therapies, anti-metastatic agents and immunotherapeutic agents.

Exemplary anti-cancer agents or cytotoxins (including homologs and derivatives thereof) comprise 1-dehydrotestosterone, anthramycins, actinomycin D, bleomycin, calicheamicins (including n-acetyl calicheamicin), colchicin, cyclophosphamide, cytochalasin B, dactinomycin (formerly actinomycin), dihydroxy anthracin, dione, duocarmycin, emetine, epirubicin, ethidium bromide, etoposide, glucocorticoids, gramicidin D, lidocaine, maytansinoids such as DM-1 and DM-4 (Immunogen), benzodiazepine derivatives (Immunogen), mithramycin, mitomycin, mitoxantrone, paclitaxel, procaine, propranolol, puromycin, tenoposide, tetracaine and pharmaceutically acceptable salts or solvates, acids or derivatives of any of the above.

Additional compatible cytotoxins comprise dolastatins and auristatins, including monomethyl auristatin E (MMAE) and monomethyl auristatin F (MMAF) (Seattle Genetics), amanitins such as alpha-amanitin, beta-amanitin, gamma-amanitin or epsilon-amanitin (Heidelberg Pharma), DNA minor groove binding agents such as duocarmycin derivatives (Syntarga), alkylating agents such as modified or dimeric pyrrolobenzodiazepines (PBD), mechlorethamine, thioepa, chlorambucil, melphalan, carmustine (BCNU), lomustine (CCNU), cyclothosphamide, busulfan, dibromomannitol, streptozotocin, mitomycin C and cisdichlorodiamine platinum (II) (DDP) cisplatin, splicing inhibitors such as meayamycin analogs or derivatives (e.g., FR901464 as set forth in U.S. Pat. No. 7,825,267), tubular binding agents such as epothilone analogs and tubulysins, paclitaxel and DNA damaging agents such as calicheamicins and esperamicins, antimetabolites such as methotrexate, 6-mercaptopurine, 6-thioguanine, cytarabine, and 5-fluorouracil decarbazine, anti-mitotic agents such as vinblastine and vincristine and anthracyclines such as daunorubicin (formerly daunomycin) and doxorubicin and pharmaceutically acceptable salts or solvates, acids or derivatives of any of the above.

In selected embodiments the antibodies of the instant invention may be associated with anti-CD3 binding molecules to recruit cytotoxic T-cells and have them target tumorigenic cells (BiTE technology; see e.g., Fuhrmann et. al. (2010) Annual Meeting of AACR Abstract No. 5625).

In further embodiments ADCs of the invention may comprise cytotoxins comprising therapeutic radioisotopes conjugated using appropriate linkers. Exemplary radioisotopes that may be compatible with such embodiments include, but are not limited to, iodine ($^{131}$I, $^{125}$I, $^{123}$I, $^{121}$I), carbon ($^{14}$C), copper ($^{62}$Cu, $^{64}$Cu, $^{67}$Cu), sulfur ($^{35}$S), radium ($^{223}$R), tritium ($^{3}$H), indium ($^{115}$In, $^{113}$In, $^{112}$In, $^{111}$In,), bismuth ($^{212}$Bi, $^{213}$Bi), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, $^{117}$Sn, $^{76}$Br, $^{211}$At and $^{225}$Ac. Other radionuclides are also available as diagnostic and therapeutic agents, especially those in the energy range of 60 to 4,000 keV.

In other selected embodiments the ADCs of the instant invention will be conjugated to a cytotoxic benzodiazepine derivative warhead. Compatible benzodiazepine derivatives (and optional linkers) that may be conjugated to the disclosed antibodies are described, for example, in U.S. Pat. No. 8,426,402 and PCT filings WO2012/128868 and WO2014/031566. As with PBDs, compatible benzodiazepine derivatives are believed to bind in the minor grove of DNA and inhibit nucleic acid synthesis. Such compounds reportedly have potent antitumor properties and, as such, are particularly suitable for use in the ADCs of the instant invention.

In some embodiments, the ADCs of the invention may comprise PBDs, and pharmaceutically acceptable salts or solvates, acids or derivatives thereof, as warheads. PBDs are alkylating agents that exert antitumor activity by covalently binding to DNA in the minor groove and inhibiting nucleic acid synthesis. PBDs have been shown to have potent antitumor properties while exhibiting minimal bone marrow depression. PBDs compatible with the invention may be linked to an antibody using several types of linkers (e.g., a peptidyl linker comprising a maleimido moiety with a free sulfhydryl), and in certain embodiments are dimeric in form (i.e., PBD dimers). Compatible PBDs (and optional linkers) that may be conjugated to the disclosed antibodies are described, for example, in U.S. Pat. Nos. 6,362,331, 7,049, 311, 7,189,710, 7,429,658, 7,407,951, 7,741,319, 7,557,099, 8,034,808, 8,163,736, 2011/0256157 and PCT filings WO2011/130613, WO2011/128650, WO2011/130616, WO2014/057073 and WO2014/057074. Examples of PBD compounds compatible with the instant invention are discussed in more detail immediately below.

With regard to the instant invention PBDs have been shown to have potent antitumor properties while exhibiting minimal bone marrow depression. PBDs compatible with the present invention may be linked to the BMPR1B targeting agent using any one of several types of linker (e.g., a peptidyl linker comprising a maleimido moiety with a free sulfhydryl) and, in certain embodiments are dimeric in form (i.e., PBD dimers). PBDs are of the general structure:

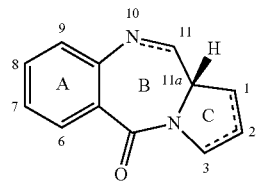

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position which is the electrophilic center responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). Their ability to form an adduct in the minor groove enables them to interfere with DNA processing and act as cytotoxic agents. As alluded to above, in order to increase their potency PBDs are often used in a dimeric form which may be conjugated to anti-BMPR1B antibodies as described herein.

In certain embodiments of the instant invention compatible PBDs that may be conjugated to the disclosed modulators are described in U.S.P.N. 2011/0256157. This disclosure provides PBD dimers, (i.e. those comprising two PBD moieties) that are shown to have certain advantageous properties. In this regard selected ADCs of the present invention comprise PBD toxins having the formula (AB) or (AC):

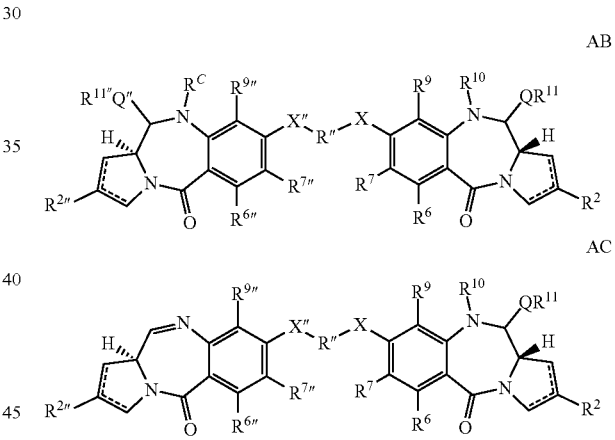

wherein:
the dotted lines indicate the optional presence of a double bond between C1 and C2 or C2 and C3;
$R^2$ is independently selected from H, OH, =O, =CH$_2$, CN, R, OR, =CH—R$^D$, =C(R$^D$)$_2$, O—SO$_2$—R, CO$_2$R and COR, and optionally further selected from halo or dihalo;
where R$^D$ is independently selected from R, CO$_2$R, COR, CHO, CO$_2$H, and halo;
$R^6$ and $R^9$ are independently selected from H, R, OH, OR, SH, SR, NH$_2$, NHR, NRR', NO$_2$, Me$_3$Sn and halo;
$R^7$ is independently selected from H, R, OH, OR, SH, SR, NH$_2$, NHR, NRR', NO$_2$, Me$_3$Sn and halo;
$R^{10}$ is a linker connected to a BMPR1B antibody or fragment or derivative thereof, as described herein;
Q is independently selected from O, S and NH;
$R^{11}$ is either H, or R or, where Q is O, $R^{11}$ may be SO$_3$M, where M is a metal cation;
X is selected from O, S, or N(H) and in selected embodiments comprises O;

R" is a $C_{3-12}$ alkylene group, which chain may be interrupted by one or more heteroatoms (e.g., O, S, N(H), NMe and/or aromatic rings, e.g. benzene or pyridine, which rings are optionally substituted);

R and R' are each independently selected from optionally substituted $C_{1-12}$ alkyl, $C_{3-20}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring; and wherein $R^{2"}$, $R^{6"}$, $R^{7"}$, $R^{9"}$, $X"$, $Q"$ and $R^{11"}$ (where present) are as defined according to $R^2$, $R^6$, $R^7$, $R^9$, X, Q and $R^{11}$ respectively, and $R^C$ is a capping group.

Selected embodiments comprising the aforementioned structures are described in more detail immediately below.

Double Bond

In one embodiment, there is no double bond present between C1 and C2, and C2 and C3.

In one embodiment, the dotted lines indicate the optional presence of a double bond between C2 and C3, as shown below:

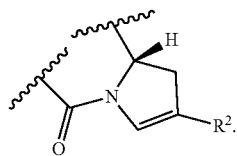

In one embodiment, a double bond is present between C2 and C3 when $R^2$ is $C_{5-20}$ aryl or $C_{1-12}$ alkyl. In a preferred embodiment $R^2$ comprises a methyl group.

In one embodiment, the dotted lines indicate the optional presence of a double bond between C1 and C2, as shown below:

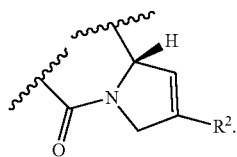

In one embodiment, a double bond is present between C1 and C2 when $R^2$ is $C_{5-20}$ aryl or $C_{1-12}$ alkyl. In a preferred embodiment $R^2$ comprises a methyl group.

$R^2$

In one embodiment, $R^2$ is independently selected from H, OH, =O, =CH$_2$, CN, R, OR, =CH—$R^D$, =C($R^D$)$_2$, O—SO$_2$—R, CO$_2$R and COR, and optionally further selected from halo or dihalo.

In one embodiment, $R^2$ is independently selected from H, OH, =O, =CH$_2$, CN, R, OR, =CH—$R^D$, =C($R^D$)$_2$, O—SO$_2$—R, CO$_2$R and COR.

In one embodiment, $R^2$ is independently selected from H, =O, =CH$_2$, R, =CH—$R^D$, and =C($R^D$)$_2$.

In one embodiment, $R^2$ is independently H.

In one embodiment $R^2$ is independently R wherein R comprises $CH_3$.

In one embodiment, $R^2$ is independently =O.

In one embodiment, $R^2$ is independently =CH$_2$.

In one embodiment, $R^2$ is independently =CH—$R^D$.

Within the PBD compound, the group =CH—$R^D$ may have either configuration shown below:

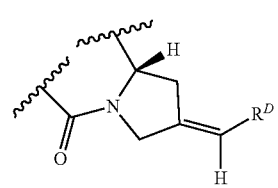

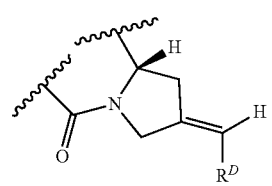

In one embodiment, the configuration is configuration (I).

In one embodiment, $R^2$ is independently =C($R^D$)$_2$.
In one embodiment, $R^2$ is independently =CF$_2$.
In one embodiment, $R^2$ is independently R.
In one embodiment, $R^2$ is independently optionally substituted $C_{5-20}$ aryl.
In one embodiment, $R^2$ is independently optionally substituted $C_{1-12}$ alkyl.
In one embodiment, $R^2$ is independently optionally substituted $C_{5-20}$ aryl.
In one embodiment, $R^2$ is independently optionally substituted $C_{5-7}$ aryl.
In one embodiment, $R^2$ is independently optionally substituted $C_{8-10}$ aryl.
In one embodiment, $R^2$ is independently optionally substituted phenyl.
In one embodiment, $R^2$ is independently optionally substituted napthyl.
In one embodiment, $R^2$ is independently optionally substituted pyridyl.
In one embodiment, $R^2$ is independently optionally substituted quinolinyl or isoquinolinyl.

In one embodiment, $R^2$ bears one to three substituent groups, with 1 and 2 being more preferred, and singly substituted groups being most preferred. The substituents may be any position.

Where $R^2$ is a $C_{5-7}$ aryl group, a single substituent is preferably on a ring atom that is not adjacent the bond to the remainder of the compound, i.e. it is preferably β or γ to the bond to the remainder of the compound. Therefore, where the $C_{5-7}$ aryl group is phenyl, the substituent is preferably in the meta- or para-positions, and more preferably is in the para-position.

In one embodiment, $R^2$ is selected from:

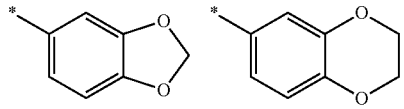

where the asterisk indicates the point of attachment.

Where $R^2$ is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

In one embodiment, where $R^2$ is optionally substituted, the substituents are selected from those substituents given in the substituent section below.

Where R is optionally substituted, the substituents are preferably selected from:

Halo, Hydroxyl, Ether, Formyl, Acyl, Carboxy, Ester, Acyloxy, Amino, Amido, Acylamido, Aminocarbonyloxy, Ureido, Nitro, Cyano and Thioether.

In one embodiment, where R or $R^2$ is optionally substituted, the substituents are selected from the group consisting of R, OR, SR, NRR', $NO_2$, halo, $CO_2R$, COR, $CONH_2$, CONHR, and CONRR'.

Where $R^2$ is $C_{1-12}$ alkyl, the optional substituent may additionally include $C_{3-20}$ heterocyclyl and $C_{6-20}$ aryl groups.

Where $R^2$ is $C_{3-20}$ heterocyclyl, the optional substituent may additionally include $C_{1-12}$ alkyl and $C_{6-20}$ aryl groups.

Where $R^2$ is $C_{6-20}$ aryl groups, the optional substituent may additionally include $C_{3-20}$ heterocyclyl and $C_{1-12}$ alkyl groups.

It is understood that the term "alkyl" encompasses the sub-classes alkenyl and alkynyl as well as cycloalkyl. Thus, where $R^2$ is optionally substituted $C_{1-12}$ alkyl, it is understood that the alkyl group optionally contains one or more carbon-carbon double or triple bonds, which may form part of a conjugated system. In one embodiment, the optionally substituted $C_{1-12}$ alkyl group contains at least one carbon-carbon double or triple bond, and this bond is conjugated with a double bond present between C1 and C2, or C2 and C3. In one embodiment, the $C_{1-12}$ alkyl group is a group selected from saturated $C_{1-12}$ alkyl, $C_{2-12}$ alkenyl, $C_{2-12}$ alkynyl and $C_{3-12}$ cycloalkyl.

If a substituent on $R^2$ is halo, it is preferably F or Cl, more preferably Cl.

If a substituent on $R^2$ is ether, it may in some embodiments be an alkoxy group, for example, a $C_{1-7}$ alkoxy group (e.g. methoxy, ethoxy) or it may in some embodiments be a $C_{6-7}$ aryloxy group (e.g phenoxy, pyridyloxy, furanyloxy).

If a substituent on $R^2$ is $C_{1-7}$ alkyl, it may preferably be a $C_{1-4}$ alkyl group (e.g. methyl, ethyl, propyl, butyl).

If a substituent on $R^2$ is $C_{3-7}$ heterocyclyl, it may in some embodiments be $C_6$ nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups.

If a substituent on $R^2$ is bis-oxy-$C_{1-3}$ alkylene, this is preferably bis-oxy-methylene or bis-oxy-ethylene.

Particularly preferred substituents for $R^2$ include methoxy, ethoxy, fluoro, chloro, cyano, bis-oxy-methylene, methyl-piperazinyl, morpholino and methyl-thienyl.

Particularly preferred substituted $R^2$ groups include, but are not limited to, 4-methoxy-phenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthienyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl.

In one embodiment, $R^2$ is halo or dihalo. In one embodiment, $R^2$ is —F or —$F_2$, which substituents are illustrated below as (III) and (IV) respectively:

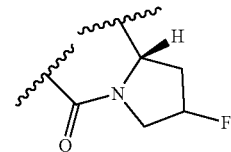

(III)

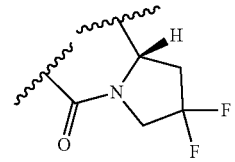

(IV)

$R^D$

In one embodiment, $R^D$ is independently selected from R, $CO_2R$, COR, CHO, $CO_2H$, and halo.

In one embodiment, $R^D$ is independently R.

In one embodiment, $R^D$ is independently halo.

$R^6$

In one embodiment, $R^6$ is independently selected from H, R, OH, OR, SH, SR, $NH_2$, NHR, NRR', $NO_2$, $Me_3Sn$— and Halo.

In one embodiment, $R^6$ is independently selected from H, OH, OR, SH, $NH_2$, $NO_2$ and Halo.

In one embodiment, $R^6$ is independently selected from H and Halo.

In one embodiment, $R^6$ is independently H.

In one embodiment, $R^6$ and $R^7$ together form a group —O—$(CH_2)_p$—O—, where p is 1 or 2.

$R^7$ $R^7$ is independently selected from H, R, OH, OR, SH, SR, $NH_2$, NHR, NRR', $NO_2$, $Me_3Sn$ and halo.

In one embodiment, $R^7$ is independently OR.

In one embodiment, $R^7$ is independently $OR^{7A}$, where $R^{7A}$ is independently optionally substituted $C_{1-6}$ alkyl.

In one embodiment, $R^{7A}$ is independently optionally substituted saturated $C_{1-6}$ alkyl.

In one embodiment, $R^{7A}$ is independently optionally substituted $C_{2-4}$ alkenyl.

In one embodiment, $R^{7A}$ is independently Me.

In one embodiment, $R^{7A}$ is independently $CH_2Ph$.

In one embodiment, $R^{7A}$ is independently allyl.

In one embodiment, the compound is a dimer where the $R^7$ groups of each monomer form together a dimer bridge having the formula X—R"—X linking the monomers.

$R^9$

In one embodiment, $R^9$ is independently selected from H, R, OH, OR, SH, SR, $NH_2$, NHR, NRR', $NO_2$, $Me_3Sn$— and Halo.

In one embodiment, $R^9$ is independently H.

In one embodiment, $R^9$ is independently R or OR.

$R^{10}$

Preferably compatible linkers such as those described herein attach the BMPR1B antibody to the PBD drug moiety through covalent bond(s) at the $R^{10}$ position (i.e., N10).

Q

In certain embodiments Q is independently selected from O, S and NH.

In one embodiment, Q is independently O.

In one embodiment, Q is independently S.

In one embodiment, Q is independently NH.

$R^{11}$

In selected embodiments $R^{11}$ is either H, or R or, where Q is O, may be $SO_3M$ where M is a metal cation. The cation may be $Na^+$.

In certain embodiments $R^{11}$ is H.

In certain embodiments $R^{11}$ is R.

In certain embodiments, where Q is O, $R^{11}$ is $SO_3M$ where M is a metal cation. The cation may be $Na^+$.

In certain embodiments where Q is O, $R^{11}$ is H.

In certain embodiments where Q is O, $R^{11}$ is R.

X

In one embodiment, X is selected from O, S, or N(H).

Preferably, X is O.

R"

R" is a $C_{3-12}$ alkylene group, which chain may be interrupted by one or more heteroatoms, e.g. O, S, N(H), NMe and/or aromatic rings, e.g. benzene or pyridine, which rings are optionally substituted.

In one embodiment, R" is a $C_{3-12}$ alkylene group, which chain may be interrupted by one or more heteroatoms and/or aromatic rings, e.g. benzene or pyridine.

In one embodiment, the alkylene group is optionally interrupted by one or more heteroatoms selected from O, S, and NMe and/or aromatic rings, which rings are optionally substituted.

In one embodiment, the aromatic ring is a $C_{5-20}$ arylene group, where arylene pertains to a divalent moiety obtained by removing two hydrogen atoms from two aromatic ring atoms of an aromatic compound, which moiety has from 5 to 20 ring atoms.

In one embodiment, R" is a $C_{3-12}$ alkylene group, which chain may be interrupted by one or more heteroatoms, e.g. O, S, N(H), NMe and/or aromatic rings, e.g. benzene or pyridine, which rings are optionally substituted by $NH_2$.

In one embodiment, R" is a $C_{3-12}$ alkylene group.

In one embodiment, R" is selected from a $C_3$, $C_5$, $C_7$, $C_9$ and a $C_{11}$ alkylene group.

In one embodiment, R" is selected from a $C_3$, $C_5$ and a $C_7$ alkylene group.

In one embodiment, R" is selected from a $C_3$ and a $C_5$ alkylene group.

In one embodiment, R" is a $C_3$ alkylene group.

In one embodiment, R" is a $C_5$ alkylene group.

The alkylene groups listed above may be optionally interrupted by one or more heteroatoms and/or aromatic rings, e.g. benzene or pyridine, which rings are optionally substituted.

The alkylene groups listed above may be optionally interrupted by one or more heteroatoms and/or aromatic rings, e.g. benzene or pyridine.

The alkylene groups listed above may be unsubstituted linear aliphatic alkylene groups.

R and R'

In one embodiment, R is independently selected from optionally substituted $C_{1-12}$ alkyl, $C_{3-20}$ heterocyclyl and $C_{5-20}$ aryl groups.

In one embodiment, R is independently optionally substituted $C_{1-12}$ alkyl.

In one embodiment, R is independently optionally substituted $C_{3-20}$ heterocyclyl.

In one embodiment, R is independently optionally substituted $C_{5-20}$ aryl.

Described above in relation to $R^2$ are various embodiments relating to preferred alkyl and aryl groups and the identity and number of optional substituents. The preferences set out for $R^2$ as it applies to R are applicable, where appropriate, to all other groups R, for examples where $R^6$, $R^7$, $R^8$ or $R^9$ is R.

The preferences for R apply also to R'.

In some embodiments of the invention there is provided a compound having a substituent group —NRR'. In one embodiment, R and R' together with the nitrogen atom to which they are attached form an optionally substituted 4-, 5-, 6- or 7-membered heterocyclic ring. The ring may contain a further heteroatom, for example N, O or S.

In one embodiment, the heterocyclic ring is itself substituted with a group R. Where a further N heteroatom is present, the substituent may be on the N heteroatom.

In addition to the aforementioned PBDs certain dimeric PBDs have been shown to be particularly active and may be used in conjunction with the instant invention. To this end antibody drug conjugates (i.e., ADCs 1-6 as disclosed herein) of the instant invention may comprise a PBD compound set forth immediately below as PBD 1-5. Note that PBDs 1-5 below comprise the cytotoxic warhead released following separation of a linker such as those described in more detail herein. The synthesis of each of PBD 1-5 as a component of drug linker compounds is presented in great detail in WO 2014/130879 which is hereby incorporated by reference as to such synthesis. In view of WO 2014/130879 cytotoxic compounds that may comprise selected warheads of the ADCs of the present invention could readily be generated and employed as set forth herein. Accordingly, selected PBD compounds that may be released from the disclosed ADCs upon separation from a linker are set forth immediately below:

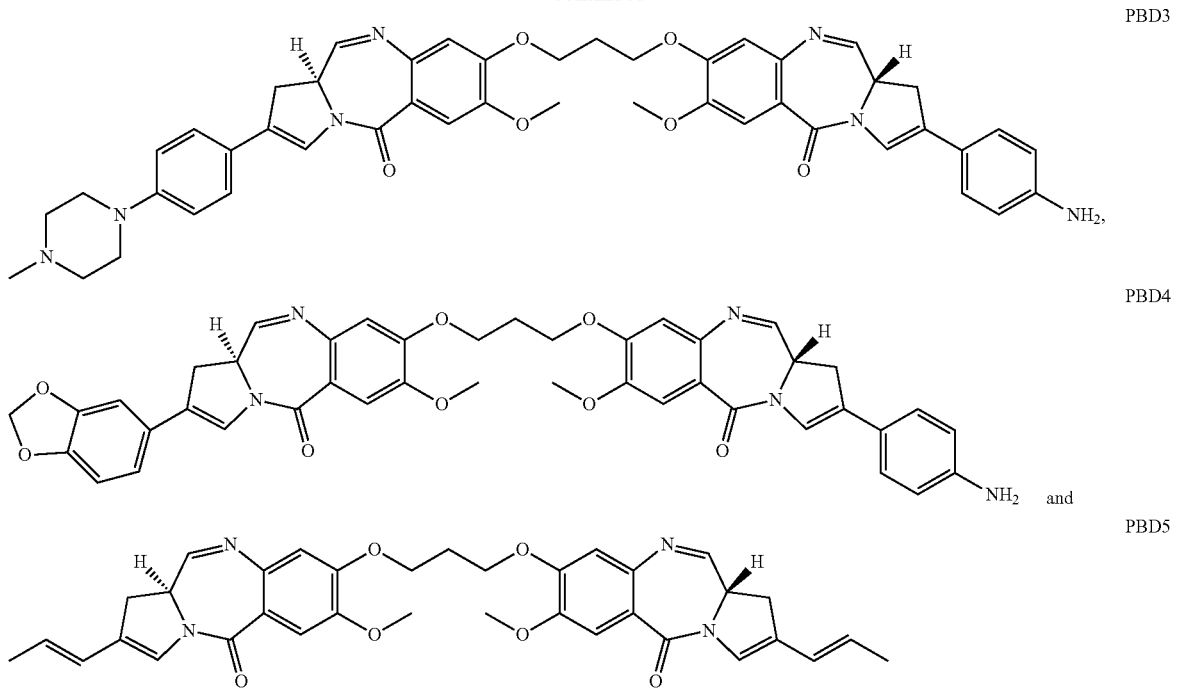

It will be appreciated that each of the aforementioned dimeric PBD warheads will preferably be released upon internalization by the target cell and destruction of the linker. As described in more detail below, certain linkers will comprise cleavable linkers which may incorporate a self-immolation moiety that allows release of the active PBD warhead without retention of any part of the linker. Upon release the PBD warhead will then bind and cross-link with the target cell's DNA. Such binding reportedly blocks division of the target cancer cell without distorting its DNA helix, thus potentially avoiding the common phenomenon of emergent drug resistance. In other preferred embodiments the warhead may be attached to the BMPR1B targeting moiety through a cleavable linker that does not comprise a self-immolating moiety.

Delivery and release of such compounds at the tumor site(s) may prove clinically effective in treating or managing proliferative disorders in accordance with the instant disclosure. With regard to the compounds it will be appreciated that each of the disclosed PBDs have two $sp^2$ centers in each C-ring, which may allow for stronger binding in the minor groove of DNA (and hence greater toxicity), than for compounds with only one $sp^2$ center in each C-ring. Thus, when used in BMPR1B ADCs as set forth herein the disclosed PBDs may prove to be particularly effective for the treatment of proliferative disorders.

The foregoing provides exemplary PBD compounds that are compatible with the instant invention and is in no way meant to be limiting as to other PBDs that may be successfully incorporated in anti-BMPR1B conjugates according to the teachings herein. Rather, any PBD that may be conjugated to an antibody as described herein and set forth in the Examples below is compatible with the disclosed conjugates and expressly within the metes and bounds of the invention.

In addition to the aforementioned agents the antibodies of the present invention may also be conjugated to biological response modifiers. In certain embodiments the biological response modifier will comprise interleukin 2, interferons, or various types of colony-stimulating factors (e.g., CSF, GM-CSF, G-CSF).

More generally, the associated drug moiety can be a polypeptide possessing a desired biological activity. Such proteins may include, for example, a toxin such as abrin, ricin A, Onconase (or another cytotoxic RNase), pseudomonas exotoxin, cholera toxin, diphtheria toxin; an apoptotic agent such as tumor necrosis factor e.g. TNF-α or TNF-β, α-interferon, β-interferon, nerve growth factor, platelet derived growth factor, tissue plasminogen activator, AIM I (WO 97/33899), AIM II (WO 97/34911), Fas Ligand (Takahashi et al., 1994, PMID: 7826947), and VEGI (WO 99/23105), a thrombotic agent, an anti-angiogenic agent, e.g., angiostatin or endostatin, a lymphokine, for example, interleukin-1 (IL-1), interleukin-2 (IL-2), interleukin-6 (IL-6), granulocyte macrophage colony stimulating factor (GM-CSF), and granulocyte colony stimulating factor (G-CSF), or a growth factor e.g., growth hormone (GH).

2. Diagnostic or Detection Agents

In other embodiments, the antibodies of the invention, or fragments or derivatives thereof, are conjugated to a diagnostic or detectable agent, marker or reporter which may be, for example, a biological molecule (e.g., a peptide or nucleotide), a small molecule, fluorophore, or radioisotope. Labeled antibodies can be useful for monitoring the development or progression of a hyperproliferative disorder or as part of a clinical testing procedure to determine the efficacy of a particular therapy including the disclosed antibodies (i.e. theragnostics) or to determine a future course of treatment. Such markers or reporters may also be useful in purifying the selected antibody, for use in antibody analytics (e.g., epitope binding or antibody binning), separating or isolating tumorigenic cells or in preclinical procedures or toxicology studies.

Such diagnosis, analysis and/or detection can be accomplished by coupling the antibody to detectable substances including, but not limited to, various enzymes comprising for example horseradish peroxidase, alkaline phosphatase, beta-galactosidase, or acetylcholinesterase; prosthetic groups, such as but not limited to streptavidinlbiotin or avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I,), carbon ($^{14}$C), sulfur ($^{35}$S), tritium ($^{3}$H), indium ($^{115}$In, $^{113}$In, $^{112}$In, $^{111}$In,), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{89}$Zr, $^{153}$Gd, $^{169}$Yb, $^{51}$Cr, $^{54}$Mn, $^{75}$Se, $^{113}$Sn, and $^{117}$Tin; positron emitting metals using various positron emission tomographies, non-radioactive paramagnetic metal ions, and molecules that are radiolabeled or conjugated to specific radioisotopes. In such embodiments appropriate detection methodology is well known in the art and readily available from numerous commercial sources.

In other embodiments the antibodies or fragments thereof can be fused or conjugated to marker sequences or compounds, such as a peptide or fluorophore to facilitate purification or diagnostic or analytic procedures such as immunohistochemistry, bio-layer interferometry, surface plasmon resonance, flow cytometry, competitive ELISA, FACs, etc. In some embodiments, the marker comprises a histidine tag such as that provided by the pQE vector (Qiagen), among others, many of which are commercially available. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag (U.S. Pat. No. 4,703,004).

3. Biocompatible Modifiers

In selected embodiments the antibodies of the invention may be conjugated with biocompatible modifiers that may be used to adjust, alter, improve or moderate antibody characteristics as desired. For example, antibodies or fusion constructs with increased in vivo half-lives can be generated by attaching relatively high molecular weight polymer molecules such as commercially available polyethylene glycol (PEG) or similar biocompatible polymers. Those skilled in the art will appreciate that PEG may be obtained in many different molecular weights and molecular configurations that can be selected to impart specific properties to the antibody (e.g. the half-life may be tailored). PEG can be attached to antibodies or antibody fragments or derivatives with or without a multifunctional linker either through conjugation of the PEG to the N- or C-terminus of said antibodies or antibody fragments or via epsilon-amino groups present on lysine residues. Linear or branched polymer derivatization that results in minimal loss of biological activity may be used. The degree of conjugation can be closely monitored by SDS-PAGE and mass spectrometry to ensure optimal conjugation of PEG molecules to antibody molecules. Unreacted PEG can be separated from antibody-PEG conjugates by, e.g., size exclusion or ion-exchange chromatography. In a similar manner, the disclosed antibodies can be conjugated to albumin in order to make the antibody or antibody fragment more stable in vivo or have a longer half-life in vivo. The techniques are well known in the art, see e.g., WO 93/15199, WO 93/15200, and WO 01/77137; and EP 0 413, 622. Other biocompatible conjugates are evident to those of ordinary skill and may readily be identified in accordance with the teachings herein.

B. Linker Compounds

As indicated above payloads compatible with the instant invention comprise one or more warheads and, optionally, a linker associating the warheads with the antibody targeting agent. Numerous linker compounds can be used to conjugate the antibodies of the invention to the relevant warhead. The linkers merely need to covalently bind with the reactive residue on the antibody (preferably a cysteine or lysine) and the selected drug compound. Accordingly, any linker that reacts with the selected antibody residue and may be used to provide the relatively stable conjugates (site-specific or otherwise) of the instant invention is compatible with the teachings herein.

Compatible linkers can advantageously bind to reduced cysteines and lysines, which are nucleophilic. Conjugation reactions involving reduced cysteines and lysines include, but are not limited to, thiol-maleimide, thiol-halogeno (acyl halide), thiol-ene, thiol-yne, thiol-vinylsulfone, thiol-bisulfone, thiol-thiosulfonate, thiol-pyridyl disulfide and thiol-parafluoro reactions. As further discussed herein, thiol-maleimide bioconjugation is one of the most widely used approaches due to its fast reaction rates and mild conjugation conditions. One issue with this approach is the possibility of the retro-Michael reaction and loss or transfer of the maleimido-linked payload from the antibody to other proteins in the plasma, such as, for example, human serum albumin. However, in some embodiments the use of selective reduction and site-specific antibodies as set forth herein in the Examples below may be used to stabilize the conjugate and reduce this undesired transfer. Thiol-acyl halide reactions provide bioconjugates that cannot undergo retro-Michael reaction and therefore are more stable. However, the thiol-halide reactions in general have slower reaction rates compared to maleimide-based conjugations and are thus not as efficient in providing undesired drug to antibody ratios. Thiol-pyridyl disulfide reaction is another popular bioconjugation route. The pyridyl disulfide undergoes fast exchange with free thiol resulting in the mixed disulfide and release of pyridine-2-thione. Mixed disulfides can be cleaved in the reductive cell environment releasing the payload. Other approaches gaining more attention in bioconjugation are thiol-vinylsulfone and thiol-bisulfone reactions, each of which are compatible with the teachings herein and expressly included within the scope of the invention.

In selected embodiments compatible linkers will confer stability on the ADCs in the extracellular environment, prevent aggregation of the ADC molecules and keep the ADC freely soluble in aqueous media and in a monomeric state. Before transport or delivery into a cell, the ADC is preferably stable and remains intact, i.e. the antibody remains linked to the drug moiety. While the linkers are stable outside the target cell they may be designed to be cleaved or degraded at some efficacious rate inside the cell. Accordingly an effective linker will: (i) maintain the specific binding properties of the antibody; (ii) allow intracellular delivery of the conjugate or drug moiety; (iii) remain stable and intact, i.e. not cleaved or degraded, until the conjugate has been delivered or transported to its targeted site; and (iv) maintain a cytotoxic, cell-killing effect or a cytostatic effect of the drug moiety (including, in some cases, any bystander effects). The stability of the ADC may be measured by standard analytical techniques such as HPLC/UPLC, mass spectroscopy, HPLC, and the separation/analysis techniques LC/MS and LC/MS/MS. As set forth above covalent attachment of the antibody and the drug moiety requires the linker to have two reactive functional groups, i.e. bivalency in a reactive sense. Bivalent linker reagents that are useful to attach two or more functional or biologically active moieties, such as MMAE and antibodies are known, and methods have been described to provide resulting conjugates compatible with the teachings herein.

Linkers compatible with the present invention may broadly be classified as cleavable and non-cleavable linkers. Cleavable linkers, which may include acid-labile linkers (e.g., oximes and hydrozones), protease cleavable linkers and disulfide linkers, are internalized into the target cell and are cleaved in the endosomal-lysosomal pathway inside the cell. Release and activation of the cytotoxin relies on endosome/lysosome acidic compartments that facilitate cleavage of acid-labile chemical linkages such as hydrazone or oxime. If a lysosomal-specific protease cleavage site is engineered into the linker the cytotoxins will be released in proximity to their intracellular targets. Alternatively, linkers containing mixed disulfides provide an approach by which cytotoxic payloads are released intracellularly as they are selectively cleaved in the reducing environment of the cell, but not in the oxygen-rich environment in the bloodstream. By way of contrast, compatible non-cleavable linkers containing amide linked polyethylene glycol or alkyl spacers liberate toxic payloads during lysosomal degradation of the ADC within the target cell. In some respects the selection of linker will depend on the particular drug used in the conjugate, the particular indication and the antibody target.

Accordingly, certain embodiments of the invention comprise a linker that is cleavable by a cleaving agent that is present in the intracellular environment (e.g., within a lysosome or endosome or caveolae). The linker can be, for example, a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, each of which is known to hydrolyze dipeptide drug derivatives resulting in the release of active drug inside target cells. Exemplary peptidyl linkers that are cleavable by the thiol-dependent protease cathepsin-B are peptides comprising Phe-Leu since cathepsin-B has been found to be highly expressed in cancerous tissue. Other examples of such linkers are described, for example, in U.S. Pat. No. 6,214,345. In specific embodiments, the peptidyl linker cleavable by an intracellular protease is a Val-Cit linker, a Val-Ala linker or a Phe-Lys linker. One advantage of using intracellular proteolytic release of the therapeutic agent is that the agent is typically attenuated when conjugated and the serum stabilities of the conjugates are relatively high.

In other embodiments, the cleavable linker is pH-sensitive. Typically, the pH-sensitive linker will be hydrolyzable under acidic conditions. For example, an acid-labile linker that is hydrolyzable in the lysosome (e.g., a hydrazone, oxime, semicarbazone, thiosemicarbazone, cis-aconitic amide, orthoester, acetal, ketal, or the like) can be used (See, e.g., U.S. Pat. Nos. 5,122,368; 5,824,805; 5,622,929). Such linkers are relatively stable under neutral pH conditions, such as those in the blood, but are unstable (e.g., cleavable) at below pH 5.5 or 5.0 which is the approximate pH of the lysosome.

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio) butyrate) and SMPT (N-succinimidyl-oxycarbonyl-alpha-methyl-alpha-(2-pyridyl-dithio) toluene). In yet other specific embodiments, the linker is a malonate linker (Johnson et al., 1995, *Anticancer Res.* 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10):1305-12).

In certain aspects of the invention the selected linker will comprise a compound of the formula:

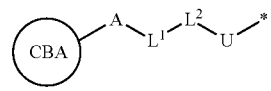

wherein the asterisk indicates the point of attachment to the drug, CBA (i.e. cell binding agent) comprises the anti-BMPR1B antibody, $L^1$ comprises a linker unit and optionally a cleavable linker unit, A is a connecting group (optionally comprising a spacer) connecting $L^1$ to a reactive residue on the antibody, $L^2$ is preferably a covalent bond and U, which may or may not be present, can comprise all or part of a self-immolative unit that facilitates a clean separation of the linker from the warhead at the tumor site.

In some embodiments (such as those set forth in U.S.P.N. 2011/0256157) compatible linkers may comprise:

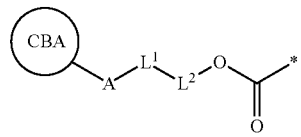

where the asterisk indicates the point of attachment to the drug, CBA (i.e. cell binding agent) comprises the anti-BMPR1B antibody, $L^1$ comprises a linker and optionally a cleavable linker, A is a connecting group (optionally comprising a spacer) connecting $L^1$ to a reactive residue on the antibody and $L^2$ is a covalent bond or together with —OC (=O)— forms a self-immolative moiety.

It will be appreciated that the nature of $L^1$ and $L^2$, where present, can vary widely. These groups are chosen on the basis of their cleavage characteristics, which may be dictated by the conditions at the site to which the conjugate is delivered. Those linkers that are cleaved by the action of enzymes are preferred, although linkers that are cleavable by changes in pH (e.g. acid or base labile), temperature or upon irradiation (e.g. photolabile) may also be used. Linkers that are cleavable under reducing or oxidizing conditions may also find use in the present invention.

In certain embodiments $L^1$ may comprise a contiguous sequence of amino acids. The amino acid sequence may be the target substrate for enzymatic cleavage, thereby allowing release of the drug.

In one embodiment, $L^1$ is cleavable by the action of an enzyme. In one embodiment, the enzyme is an esterase or a peptidase.

In another embodiment $L^1$ is as a cathepsin labile linker.

In one embodiment, $L^1$ comprises a dipeptide. The dipeptide may be represented as —NH—$X_1$—$X_2$—CO—, where —NH— and —CO— represent the N- and C-terminals of the amino acid groups $X_1$ and $X_2$ respectively. The amino acids in the dipeptide may be any combination of natural amino acids. Where the linker is a cathepsin labile linker, the dipeptide may be the site of action for cathepsin-mediated cleavage.

Additionally, for those amino acids groups having carboxyl or amino side chain functionality, for example Glu and Lys respectively, CO and NH may represent that side chain functionality.

In one embodiment, the group —$X_1$—$X_2$— in dipeptide, —NH—$X_1$—$X_2$—CO—, is selected from: -Phe-Lys-, -Val-Ala-, -Val-Lys-, -Ala-Lys-, -Val-Cit-, -Phe-Cit-, -Leu-Cit-, -Ile-Cit-, -Phe-Arg- and -Trp-Cit- where Cit is citrulline.

Preferably, the group —$X_1$—$X_2$— in dipeptide, —NH—$X_1$—$X_2$—CO—, is selected from: -Phe-Lys-, -Val-Ala-, -Val-Lys-, -Ala-Lys-, and -Val-Cit-.

Most preferably, the group —$X_1$—$X_2$— in dipeptide, —NH—$X_1$—$X_2$—CO—, is -Phe-Lys- or -Val-Ala- or Val-Cit. In certain selected embodiments the dipeptide will comprise -Val-Ala-.

In one embodiment, $L^2$ is present in the form of a covalent bond.

In one embodiment, $L^2$ is present and together with —C(=O)O— forms a self-immolative linker.

In one embodiment, $L^2$ is a substrate for enzymatic activity, thereby allowing release of the warhead.

In one embodiment, where $L^1$ is cleavable by the action of an enzyme and $L^2$ is present, the enzyme cleaves the bond between $L^1$ and $L^2$.

$L^1$ and $L^2$, where present, may be connected by a bond selected from: —C(=O)NH—, —C(=O)O—, —NHC(=O)—, —OC(=O)—, —OC(=O)O—, —NHC(=O)O—, —OC(=O)NH—, and —NHC(=O)NH—.

An amino group of $L^1$ that connects to $L^2$ may be the N-terminus of an amino acid or may be derived from an amino group of an amino acid side chain, for example a lysine amino acid side chain.

A carboxyl group of $L^1$ that connects to $L^2$ may be the C-terminus of an amino acid or may be derived from a carboxyl group of an amino acid side chain, for example a glutamic acid amino acid side chain.

A hydroxyl group of $L^1$ that connects to $L^2$ may be derived from a hydroxyl group of an amino acid side chain, for example a serine amino acid side chain.

The term "amino acid side chain" includes those groups found in: (i) naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; (ii) minor amino acids such as ornithine and citrulline; (iii) unnatural amino acids, beta-amino acids, synthetic analogs and derivatives of naturally occurring amino acids; and (iv) all enantiomers, diastereomers, isomerically enriched, isotopically labelled (e.g. $^2$H, $^3$H, $^{14}$C, $^{15}$N), protected forms, and racemic mixtures thereof.

In one embodiment, —C(=O)O— and $L^2$ together form the group:

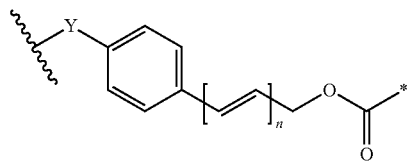

where the asterisk indicates the point of attachment to the drug or cytotoxic agent position, the wavy line indicates the point of attachment to the linker $L^1$, Y is —N(H)—, —O—, —C(=O)N(H)— or —C(=O)O—, and n is 0 to 3. The phenylene ring is optionally substituted with one, two or three substituents. In one embodiment, the phenylene group is optionally substituted with halo, $NO_2$, alkyl or hydroxyalkyl.

In one embodiment, Y is NH.

In one embodiment, n is 0 or 1. Preferably, n is 0.

Where Y is NH and n is 0, the self-immolative linker may be referred to as a p-aminobenzylcarbonyl linker (PABC).

In other embodiments the linker may include a self-immolative linker and the dipeptide together form the group —NH-Val-Cit-CO—NH-PABC-. In other selected embodiments the linker may comprise the group —NH-Val-Ala-CO—NH-PABC-, which is illustrated below:

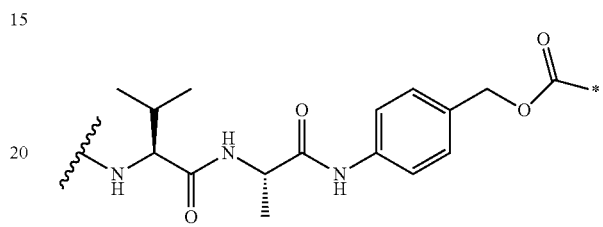

where the asterisk indicates the point of attachment to the selected cytotoxic moiety, and the wavy line indicates the point of attachment to the remaining portion of the linker (e.g., the spacer-antibody binding segments) which may be conjugated to the antibody. Upon enzymatic cleavage of the dipeptide, the self-immolative linker will allow for clean release of the protected compound (i.e., the cytotoxin) when a remote site is activated, proceeding along the lines shown below:

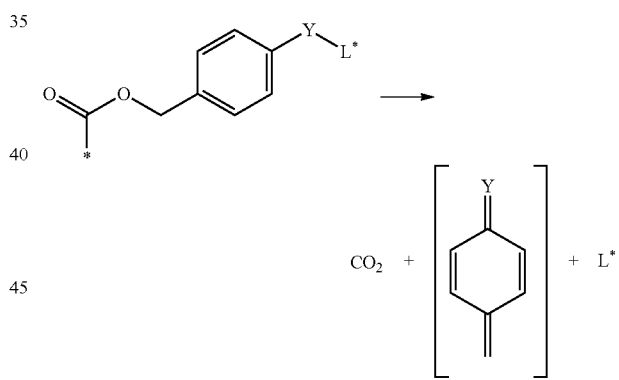

where the asterisk indicates the point of attachment to the selected cytotoxic moiety and where L* is the activated form of the remaining portion of the linker comprising the now cleaved peptidyl unit. The clean release of the warhead ensures it will maintain the desired toxic activity.

In one embodiment, A is a covalent bond. Thus, $L^1$ and the antibody are directly connected. For example, where $L^1$ comprises a contiguous amino acid sequence, the N-terminus of the sequence may connect directly to the antibody residue.

In another embodiment, A is a spacer group. Thus, $L^1$ and the antibody are indirectly connected.

In certain embodiments $L^1$ and A may be connected by a bond selected from: —C(=O)NH—, —C(=O)O—, —NHC(=O)—, —OC(=O)—, —OC(=O)O—, —NHC(=O)O—, —OC(=O)NH—, and —NHC(=O)NH—.

As will be discussed in more detail below the drug linkers of the instant invention will preferably be linked to reactive thiol nucleophiles on cysteines, including free cysteines. To this end the cysteines of the antibodies may be made reactive for conjugation with linker reagents by treatment with various reducing agent such as DTT or TCEP or mild reducing agents as set forth herein. In other embodiments the drug linkers of the instant invention will preferably be linked to a lysine.

Preferably, the linker contains an electrophilic functional group for reaction with a nucleophilic functional group on the antibody. Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) maleimide groups (ii) activated disulfides, (iii) active esters such as NHS (N-hydroxysuccinimide) esters, HOBt (N-hydroxybenzotriazole) esters, haloformates, and acid halides; (iv) alkyl and benzyl halides such as haloacetamides; and (v) aldehydes, ketones and carboxyl groups.

Exemplary functional groups compatible with the invention are illustrated immediately below:

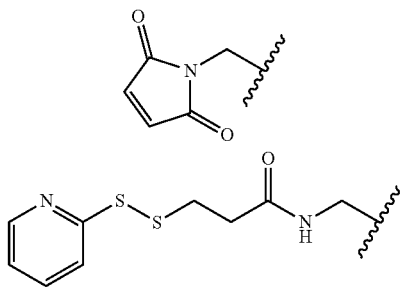

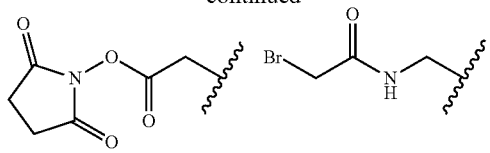

In some embodiments the connection between a cysteine (including a free cysteine of a site-specific antibody) and the drug linker moiety is through a thiol residue and a terminal maleimide group of present on the linker. In such embodiments, the connection between the antibody and the drug linker may be:

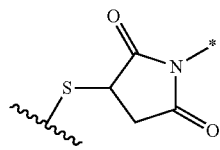 [SMILES: *SC1CC(=O)N(*)C1=O]

where the asterisk indicates the point of attachment to the remaining portion of drug linker and the wavy line indicates the point of attachment to the remaining portion of the antibody. In such embodiments, the S atom may preferably be derived from a site-specific free cysteine.

With regard to other compatible linkers the binding moiety may comprise a terminal bromo or iodoacetamide that may be reacted with activated residues on the antibody to provide the desired conjugate. In any event one skilled in the art could readily conjugate each of the disclosed drug linker compounds with a compatible anti-BMPR1B antibody (including site-specific antibodies) in view of the instant disclosure.

In accordance with the instant disclosure the invention provides methods of making compatible antibody drug conjugates comprising conjugating an anti-BMPR1B antibody with a drug linker compound selected from the group consisting of:

DL1

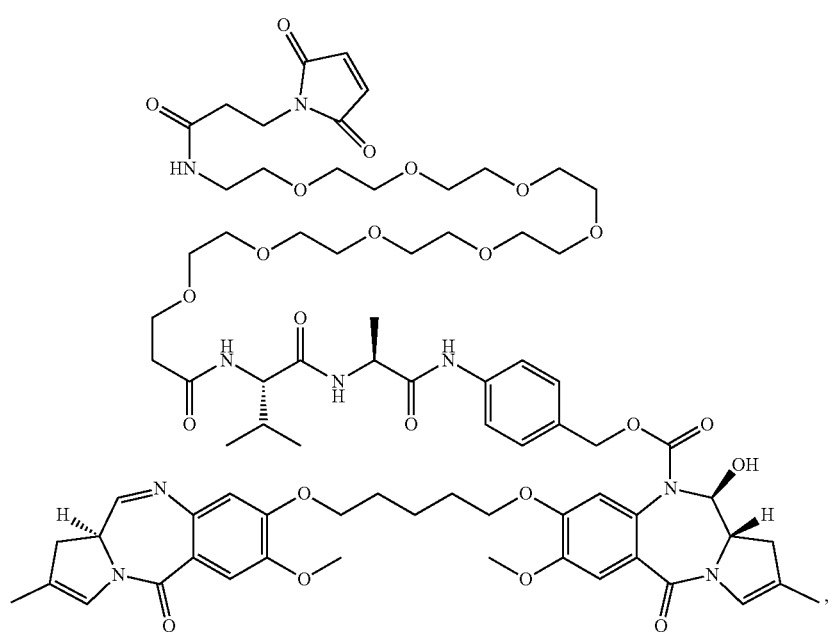

-continued
DL2
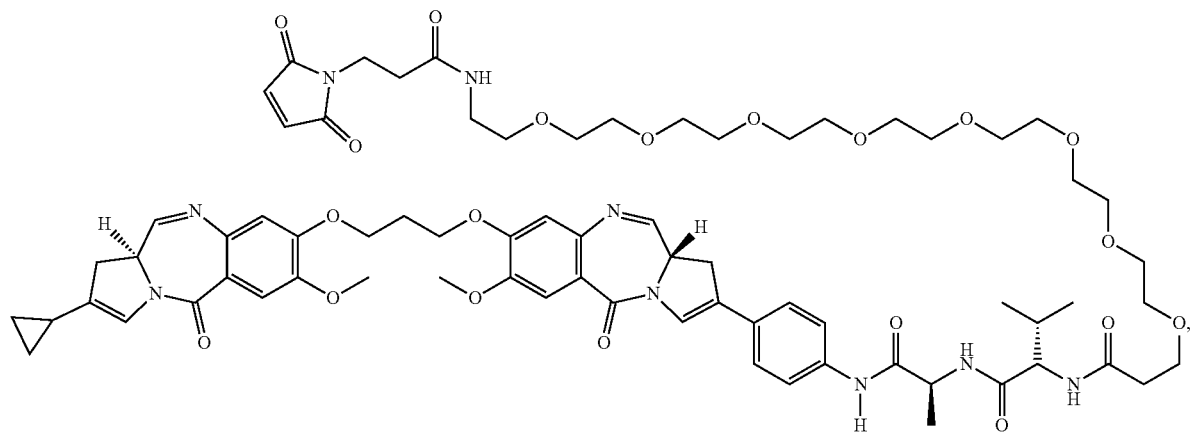
DL3
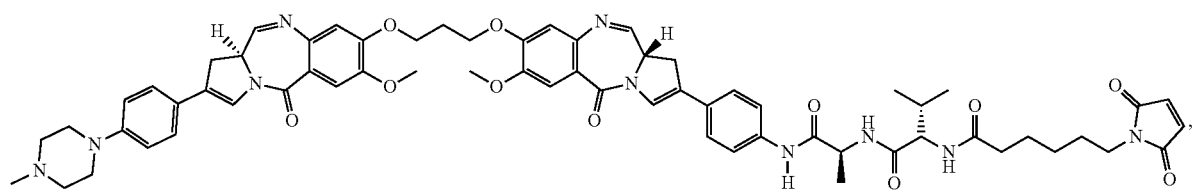
DL4
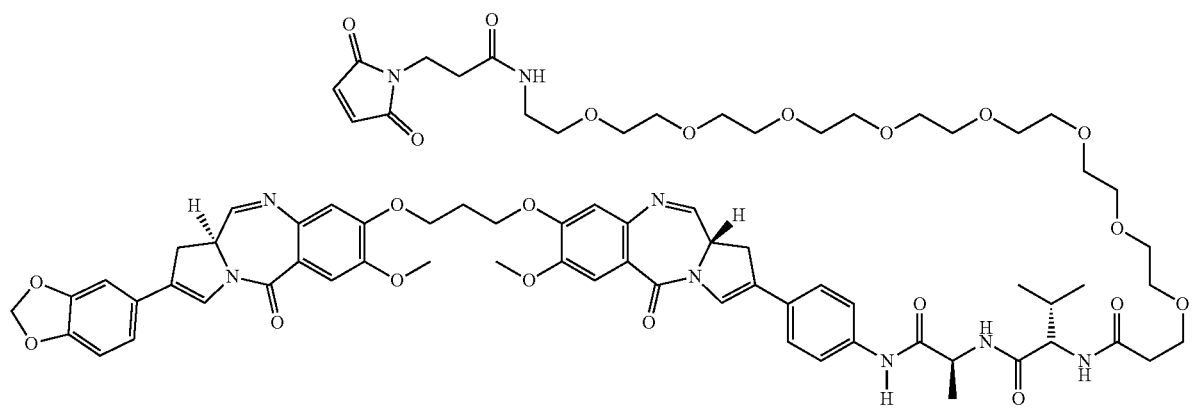
DL5
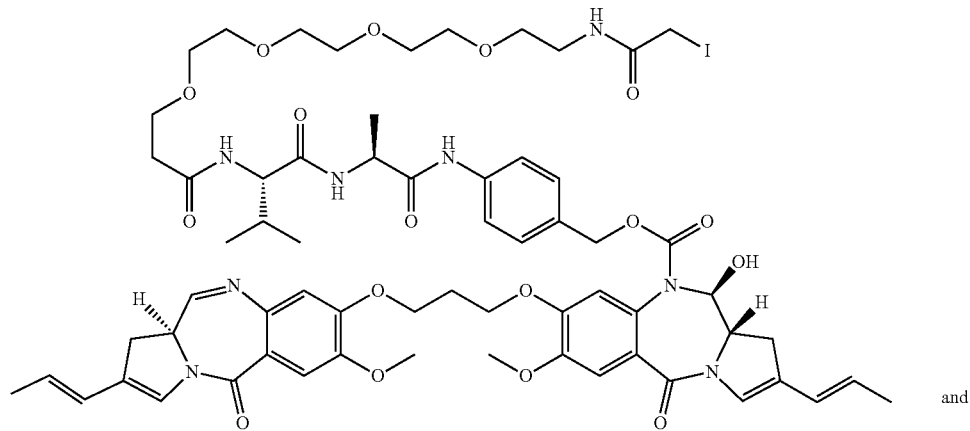
and

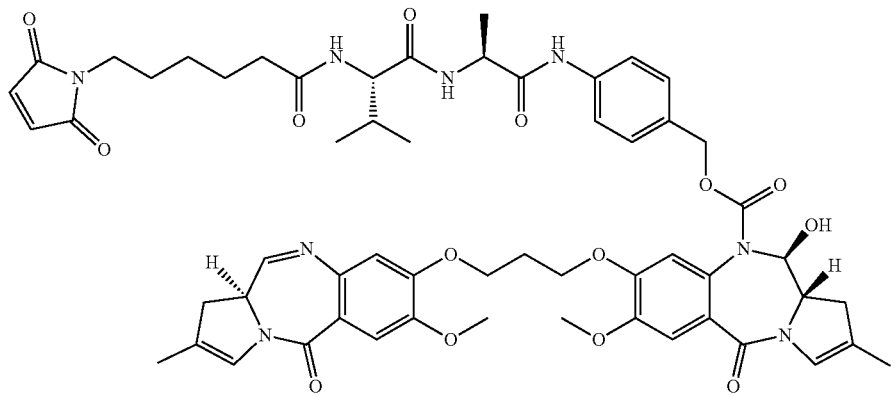

DL6

For the purposes of then instant application DL will be used as an abbreviation for "drug linker" (or linker-drug "L-D" in the formula Ab-[L-D]n) and will comprise drug linkers 1-6 (i.e., DL1, DL2, DL3, DL4 DL5, and DL6) as set forth above. Note that DL1 and DL6 comprise the same warhead and same dipeptide subunit but differ in the connecting group spacer. Accordingly, upon cleavage of the linker both DL1 and DL6 will release PBD1.

It will be appreciated that the linker appended terminal maleimido moiety (DL1-DL4 and DL6) or iodoacetamide moiety (DL5) may be conjugated to free sulfhydryl(s) on the selected BMPR1B antibody using art-recognized techniques as disclosed herein. Synthetic routes for the aforementioned compounds are set forth in WO2014/130879 which is incorporated herein by reference explicitly for the synthesis of the aforementioned DL compounds while specific methods of conjugating such PBDs linker combinations are set forth in the Examples below.

Thus, in selected aspects the present invention relates to BMPR1B antibodies conjugated to the disclosed DL moieties to provide BMPR1B immunoconjugates substantially set forth in ADCs 1-6 immediately below. Accordingly, in certain aspects the invention is directed to an ADC of the formula Ab-[L-D]n comprising a structure selected from the group consisting of:

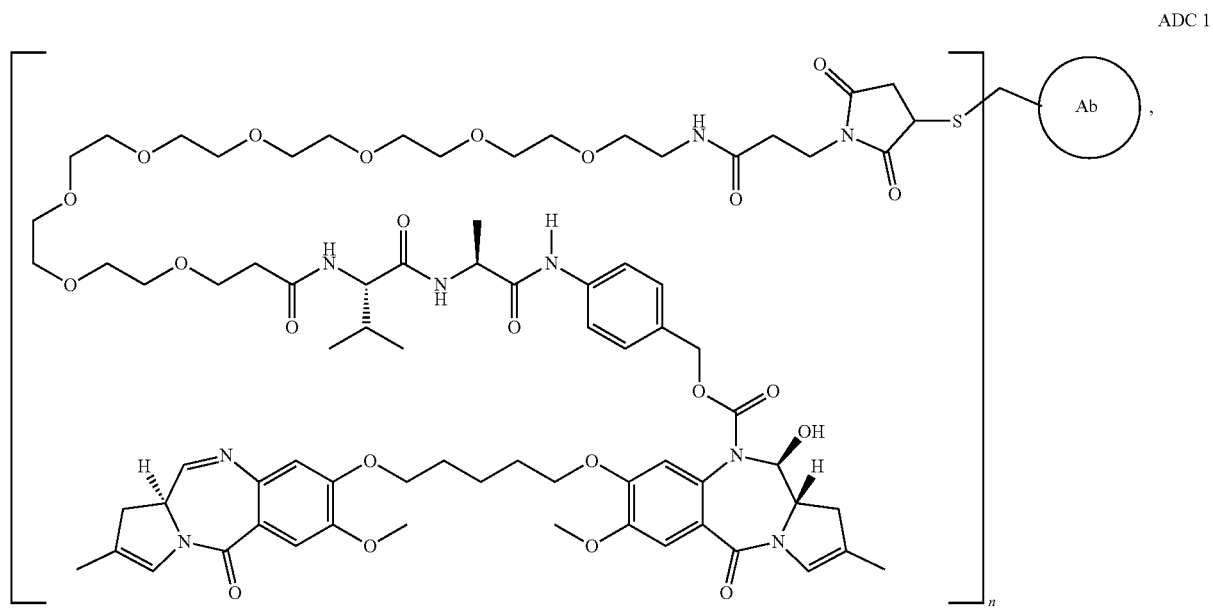

ADC 1

-continued
ADC 2
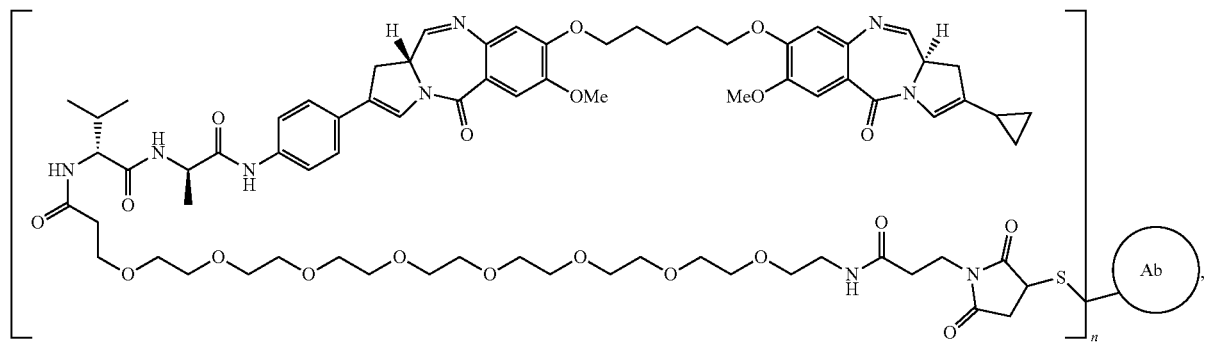
ADC 3
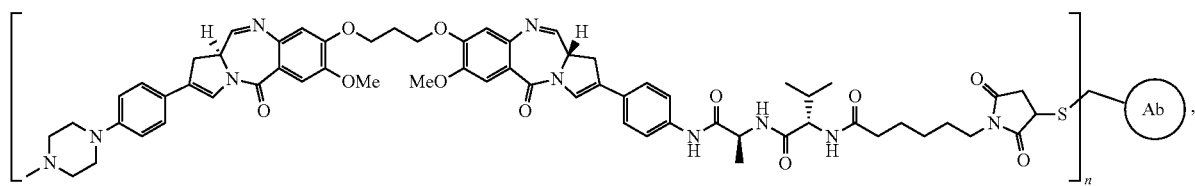
ADC 4
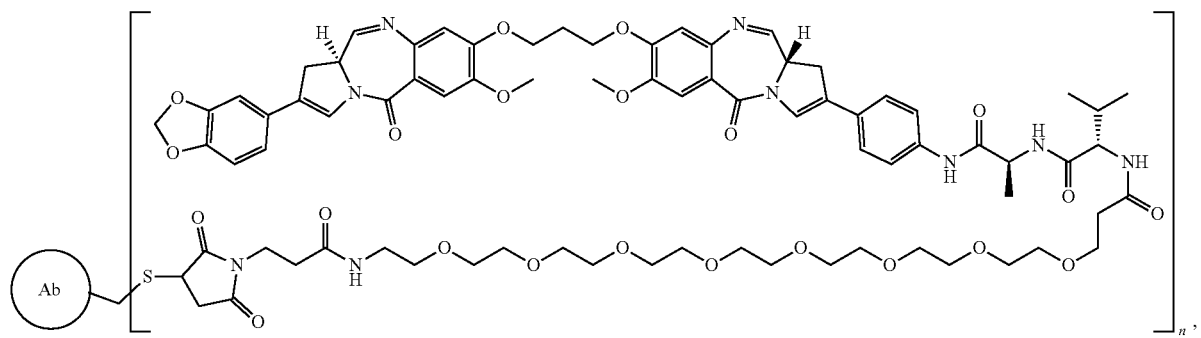
ADC 5
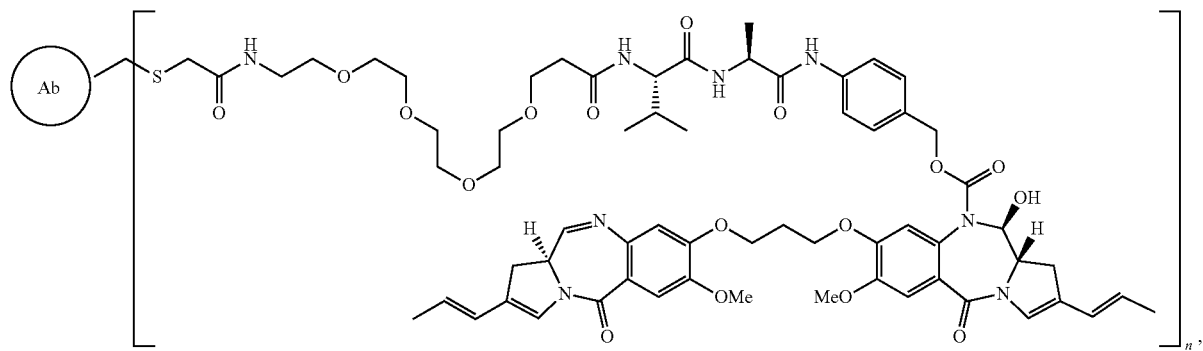

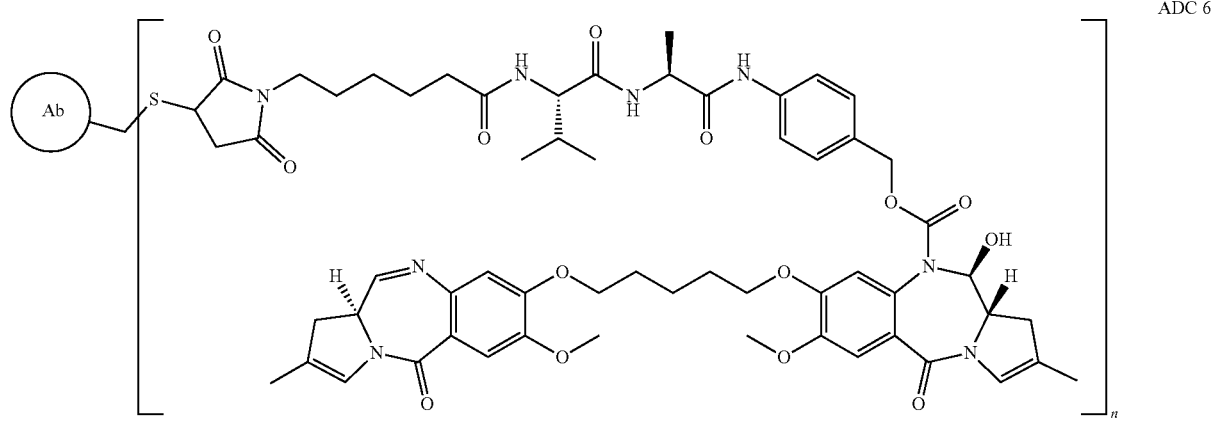

wherein Ab comprises an anti-BMPR1B antibody or immunoreactive fragment thereof and n is an integer from 1 to 20. In certain embodiments n will comprise an integer from 1 to 8 and in selected embodiments n will comprise 2 or 4.

Those of skill in the art will appreciate that the aforementioned ADC structures are defined by the formula Ab-[L-D]n and more than one drug linker molecule as depicted therein may be covalently conjugated to the BMPR1B antibody (e.g., n may be an integer from about 1 to about 20). More particularly, as discussed in more detail below it will be appreciated that more than one payload may be conjugated to each antibody and that the schematic representations above must be construed as such. By way of example ADC3 as set forth above may comprise a BMPR1B antibody conjugated to 1, 2, 3, 4, 5, 6, 7 or 8 or more payloads and that compositions of such ADCs will generally comprise a mixture of drug loaded species.

In certain aspects the BMPR1B PBD ADCs of the invention will comprise an anti-BMPR1B antibody as set forth in the appended Examples or an immunoreactive fragment thereof. In a particular embodiment ADC3 will comprise hSC91.1ss1MJ (e.g., hSC91.1ss1MJ PBD3). In other aspects the BMPR1B PBD ADCs of the invention will comprise hSC91.9ss1MJ (e.g., hSC91.9ss1MJ PBD3). In such embodiments the ADCs will preferably comprise 2 payloads. In other preferred embodiments the BMPR1B ADC will comprise ADC3 wherein n is 2.

C. Conjugation

It will be appreciated that a number of well-known reactions may be used to attach the drug moiety and/or linker to the selected antibody. For example, various reactions exploiting sulfhydryl groups of cysteines may be employed to conjugate the desired moiety. Some embodiments will comprise conjugation of antibodies comprising one or more free cysteines as discussed in detail below. In other embodiments ADCs of the instant invention may be generated through conjugation of drugs to solvent-exposed amino groups of lysine residues present in the selected antibody. Still other embodiments comprise activation of N-terminal threonine and serine residues which may then be used to attach the disclosed payloads to the antibody. The selected conjugation methodology will preferably be tailored to optimize the number of drugs attached to the antibody and provide a relatively high therapeutic index.

Various methods are known in the art for conjugating a therapeutic compound to a cysteine residue and will be apparent to the skilled artisan. Under basic conditions the cysteine residues will be deprotonated to generate a thiolate nucleophile which may be reacted with soft electrophiles such as maleimides and iodoacetamides. Generally reagents for such conjugations may react directly with a cysteine thiol to form the conjugated protein or with a linker-drug to form a linker-drug intermediate. In the case of a linker, several routes, employing organic chemistry reactions, conditions, and reagents are known to those skilled in the art, including: (1) reaction of a cysteine group of the protein of the invention with a linker reagent, to form a protein-linker intermediate, via a covalent bond, followed by reaction with an activated compound; and (2) reaction of a nucleophilic group of a compound with a linker reagent, to form a drug linker intermediate, via a covalent bond, followed by reaction with a cysteine group of a protein of the invention. As will be apparent to the skilled artisan from the foregoing, bifunctional (or bivalent) linkers are useful in the present invention. For example, the bifunctional linker may comprise a thiol modification group for covalent linkage to the cysteine residue(s) and at least one attachment moiety (e.g., a second thiol modification moiety) for covalent or non-covalent linkage to the compound.

Prior to conjugation, antibodies may be made reactive for conjugation with linker reagents by treatment with a reducing agent such as dithiothreitol (DTT) or (tris(2-carboxyethyl)phosphine (TCEP). In other embodiments additional nucleophilic groups can be introduced into antibodies through the reaction of lysines with reagents, including but not limited to, 2-iminothiolane (Traut's reagent), SATA, SATP or SAT(PEG)4, resulting in conversion of an amine into a thiol.

With regard to such conjugations cysteine thiol or lysine amino groups are nucleophilic and capable of reacting to form covalent bonds with electrophilic groups on linker reagents or compound-linker intermediates or drugs including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a compound or linker include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Conjugation reagents commonly include maleimide, haloacetyl, iodoacetamide succinimidyl ester, isothiocyanate, sulfonyl chloride, 2,6-dichlorotriazinyl, pentafluorophenyl ester, and phosphoramidite, although other functional groups can also be used. In certain embodiments methods include, for example, the use of maleimides, iodoacetimides or haloacetyl/alkyl halides, aziridne, acryloyl derivatives to react with the thiol of a cysteine to produce a thioether that is reactive with a compound. Disulphide exchange of a free thiol with an activated piridyldisulphide is also useful for producing a conjugate (e.g., use of 5-thio-2-nitrobenzoic (TNB) acid). Preferably, a maleimide is used.

As indicated above, lysine may also be used as a reactive residue to effect conjugation as set forth herein. The nucleophilic lysine residue is commonly targeted through amine-reactive succinimidylesters. To obtain an optimal number of deprotonated lysine residues, the pH of the aqueous solution must be below the pKa of the lysine ammonium group, which is around 10.5, so the typical pH of the reaction is about 8 and 9. The common reagent for the coupling reaction is NHS-ester which reacts with nucleophilic lysine through a lysine acylation mechanism. Other compatible reagents that undergo similar reactions comprise isocyanates and isothiocyanates which also may be used in conjunction with the teachings herein to provide ADCs. Once the lysines have been activated, many of the aforementioned linking groups may be used to covalently bind the warhead to the antibody.

Methods are also known in the art for conjugating a compound to a threonine or serine residue (preferably a N-terminal residue). For example methods have been described in which carbonyl precursors are derived from the 1,2-aminoalcohols of serine or threonine, which can be selectively and rapidly converted to aldehyde form by periodate oxidation. Reaction of the aldehyde with a 1,2-aminothiol of cysteine in a compound to be attached to a protein of the invention forms a stable thiazolidine product. This method is particularly useful for labeling proteins at N-terminal serine or threonine residues.

In some embodiments reactive thiol groups may be introduced into the selected antibody (or fragment thereof) by introducing one, two, three, four, or more free cysteine residues (e.g., preparing antibodies comprising one or more free non-native cysteine amino acid residues). Such site-specific antibodies or engineered antibodies allow for conjugate preparations that exhibit enhanced stability and substantial homogeneity due, at least in part, to the provision of engineered free cysteine site(s) and/or the novel conjugation procedures set forth herein. Unlike conventional conjugation methodology that fully or partially reduces each of the intrachain or interchain antibody disulfide bonds to provide conjugation sites (and is fully compatible with the instant invention), the present invention additionally provides for the selective reduction of certain prepared free cysteine sites and attachment of the drug linker to the same.

In this regard it will be appreciated that the conjugation specificity promoted by the engineered sites and the selective reduction allows for a high percentage of site directed conjugation at the desired positions. Significantly some of these conjugation sites, such as those present in the terminal region of the light chain constant region, are typically difficult to conjugate effectively as they tend to cross-react with other free cysteines. However, through molecular engineering and selective reduction of the resulting free cysteines, efficient conjugation rates may be obtained which considerably reduces unwanted high-DAR contaminants and non-specific toxicity. More generally the engineered constructs and disclosed novel conjugation methods comprising selective reduction provide ADC preparations having improved pharmacokinetics and/or pharmacodynamics and, potentially, an improved therapeutic index.

In certain embodiments site-specific constructs present free cysteine(s) which, when reduced, comprise thiol groups that are nucleophilic and capable of reacting to form covalent bonds with electrophilic groups on linker moieties such as those disclosed above. As discussed above antibodies of the instant invention may have reducible unpaired interchain or intrachain cysteines or introduced non-native cysteines, i.e. cysteines providing such nucleophilic groups. Thus, in certain embodiments the reaction of free sulfhydryl groups of the reduced free cysteines and the terminal maleimido or haloacetamide groups of the disclosed drug linkers will provide the desired conjugation. In such cases free cysteines of the antibodies may be made reactive for conjugation with linker reagents by treatment with a reducing agent such as dithiothreitol (DTT) or (tris (2-carboxyethyl)phosphine (TCEP). Each free cysteine will thus present, theoretically, a reactive thiol nucleophile. While such reagents are particularly compatible with the instant invention it will be appreciated that conjugation of site-specific antibodies may be effected using various reactions, conditions and reagents generally known to those skilled in the art.

In addition it has been found that the free cysteines of engineered antibodies may be selectively reduced to provide enhanced site-directed conjugation and a reduction in unwanted, potentially toxic contaminants. More specifically "stabilizing agents" such as arginine have been found to modulate intra- and inter-molecular interactions in proteins and may be used, in conjunction with selected reducing agents (preferably relatively mild), to selectively reduce the free cysteines and to facilitate site-specific conjugation as set forth herein. As used herein the terms "selective reduction" or "selectively reducing" may be used interchangeably and shall mean the reduction of free cysteine(s) without substantially disrupting native disulfide bonds present in the engineered antibody. In selected embodiments this selective reduction may be effected by the use of certain reducing agents or certain reducing agent concentrations. In other embodiments selective reduction of an engineered construct will comprise the use of stabilization agents in combination with reducing agents (including mild reducing agents). It will be appreciated that the term "selective conjugation" shall mean the conjugation of an engineered antibody that has been selectively reduced in the presence of a cytotoxin as described herein. In this respect the use of such stabilizing agents (e.g., arginine) in combination with selected reducing agents can markedly improve the efficiency of site-specific conjugation as determined by extent of conjugation on the heavy and light antibody chains and DAR distribution of the preparation. Compatible antibody constructs and selective conjugation techniques and reagents are extensively disclosed in WO2015/031698 which is incorporated herein specifically as to such methodology and constructs.

While not wishing to be bound by any particular theory, such stabilizing agents may act to modulate the electrostatic microenvironment and/or modulate conformational changes at the desired conjugation site, thereby allowing relatively mild reducing agents (which do not materially reduce intact native disulfide bonds) to facilitate conjugation at the desired free cysteine site(s). Such agents (e.g., certain amino acids) are known to form salt bridges (via hydrogen bonding and electrostatic interactions) and can modulate protein-protein interactions in such a way as to impart a stabilizing effect that may cause favorable conformational changes and/or reduce unfavorable protein-protein interactions.

Moreover, such agents may act to inhibit the formation of undesired intramolecular (and intermolecular) cysteine-cysteine bonds after reduction thus facilitating the desired conjugation reaction wherein the engineered site-specific cysteine is bound to the drug (preferably via a linker). Since selective reduction conditions do not provide for the significant reduction of intact native disulfide bonds, the subsequent conjugation reaction is naturally driven to the relatively few reactive thiols on the free cysteines (e.g., preferably 2 free thiols per antibody). As previously alluded to, such techniques may be used to considerably reduce levels of non-specific conjugation and corresponding unwanted DAR species in conjugate preparations fabricated in accordance with the instant disclosure.

In selected embodiments stabilizing agents compatible with the present invention will generally comprise compounds with at least one moiety having a basic pKa. In certain embodiments the moiety will comprise a primary amine while in other embodiments the amine moiety will comprise a secondary amine. In still other embodiments the amine moiety will comprise a tertiary amine or a guanidinium group. In other selected embodiments the amine moiety will comprise an amino acid while in other compatible embodiments the amine moiety will comprise an amino acid side chain. In yet other embodiments the amine moiety will comprise a proteinogenic amino acid. In still other embodiments the amine moiety comprises a non-proteinogenic amino acid. In some embodiments, compatible stabilizing agents may comprise arginine, lysine, proline and cysteine. In certain preferred embodiments the stabilizing agent will comprise arginine. In addition compatible stabilizing agents may include guanidine and nitrogen containing heterocycles with basic pKa.

In certain embodiments compatible stabilizing agents comprise compounds with at least one amine moiety having a pKa of greater than about 7.5, in other embodiments the subject amine moiety will have a pKa of greater than about 8.0, in yet other embodiments the amine moiety will have a pKa greater than about 8.5 and in still other embodiments the stabilizing agent will comprise an amine moiety having a pKa of greater than about 9.0. Other embodiments will comprise stabilizing agents where the amine moiety will have a pKa of greater than about 9.5 while certain other embodiments will comprise stabilizing agents exhibiting at least one amine moiety having a pKa of greater than about 10.0. In still other embodiments the stabilizing agent will comprise a compound having the amine moiety with a pKa of greater than about 10.5, in other embodiments the stabilizing agent will comprise a compound having a amine moiety with a pKa greater than about 11.0, while in still other embodiments the stabilizing agent will comprise a amine moiety with a pKa greater than about 11.5. In yet other embodiments the stabilizing agent will comprise a compound having an amine moiety with a pKa greater than about 12.0, while in still other embodiments the stabilizing agent will comprise an amine moiety with a pKa greater than about 12.5. Those of skill in the art will understand that relevant pKa's may readily be calculated or determined using standard techniques and used to determine the applicability of using a selected compound as a stabilizing agent.

The disclosed stabilizing agents are shown to be particularly effective at targeting conjugation to free site-specific cysteines when combined with certain reducing agents. For the purposes of the instant invention, compatible reducing agents may include any compound that produces a reduced free site-specific cysteine for conjugation without significantly disrupting the native disulfide bonds of the engineered antibody. Under such conditions, preferably provided by the combination of selected stabilizing and reducing agents, the activated drug linker is largely limited to binding to the desired free site-specific cysteine site(s). Relatively mild reducing agents or reducing agents used at relatively low concentrations to provide mild conditions are particularly preferred. As used herein the terms "mild reducing agent" or "mild reducing conditions" shall be held to mean any agent or state brought about by a reducing agent (optionally in the presence of stabilizing agents) that provides thiols at the free cysteine site(s) without substantially disrupting native disulfide bonds present in the engineered antibody. That is, mild reducing agents or conditions (preferably in combination with a stabilizing agent) are able to effectively reduce free cysteine(s) (provide a thiol) without significantly disrupting the protein's native disulfide bonds. The desired reducing conditions may be provided by a number of sulfhydryl-based compounds that establish the appropriate environment for selective conjugation. In embodiments mild reducing agents may comprise compounds having one or more free thiols while in some embodiments mild reducing agents will comprise compounds having a single free thiol. Non-limiting examples of reducing agents compatible with the selective reduction techniques of the instant invention comprise glutathione, n-acetyl cysteine, cysteine, 2-aminoethane-1-thiol and 2-hydroxyethane-1-thiol.

It will be appreciated that selective reduction process set forth above is particularly effective at targeted conjugation to the free cysteine. In this respect the extent of conjugation to the desired target site (defined here as "conjugation efficiency") in site-specific antibodies may be determined by various art-accepted techniques. The efficiency of the site-specific conjugation of a drug to an antibody may be determined by assessing the percentage of conjugation on the target conjugation site(s) (e.g. free cysteines on the c-terminus of each light chain) relative to all other conjugated sites. In certain embodiments, the method herein provides for efficiently conjugating a drug to an antibody comprising free cysteines. In some embodiments, the conjugation efficiency is at least 5%, at least 10%, at least 15%, at least 20%, at least 25%, at least 30%, at least 35%, at least 40%, at least 45%, at least 50%, at least 55%, at least 60%, at least 70%, at least 75%, at least 80%, at least 85%, at least 90%, at least 95%, at least 98% or more as measured by the percentage of target conjugation relative to all other conjugation sites.

It will further be appreciated that engineered antibodies capable of conjugation may contain free cysteine residues that comprise sulfhydryl groups that are blocked or capped as the antibody is produced or stored. Such caps include small molecules, proteins, peptides, ions and other materials that interact with the sulfhydryl group and prevent or inhibit conjugate formation. In some cases the unconjugated engineered antibody may comprise free cysteines that bind other free cysteines on the same or different antibodies. As discussed herein such cross-reactivity may lead to various contaminants during the fabrication procedure. In some embodiments, the engineered antibodies may require uncapping prior to a conjugation reaction. In specific embodiments, antibodies herein are uncapped and display a free sulfhydryl group capable of conjugation. In specific embodiments, antibodies herein are subjected to an uncapping reaction that does not disturb or rearrange the naturally occurring disulfide bonds. It will be appreciated that in most cases the uncapping reactions will occur during the normal reduction reactions (reduction or selective reduction).

D. DAR Distribution and Purification

In selected embodiments conjugation and purification methodology compatible with the present invention advantageously provides the ability to generate relatively homogeneous ADC preparations comprising a narrow DAR distribution. In this regard the disclosed constructs (e.g., site-specific constructs) and/or selective conjugation provides for homogeneity of the ADC species within a sample in terms of the stoichiometric ratio between the drug and the engineered antibody and with respect to the toxin location. As briefly discussed above the term "drug to antibody ratio" or "DAR" refers to the molar ratio of drug to antibody in an ADC preparation. In certain embodiments a conjugate preparation may be substantially homogeneous with respect to its DAR distribution, meaning that within the ADC preparation is a predominant species of site-specific ADC with a particular drug loading (e.g., a drug loading of 2 or 4) that is also uniform with respect to the site of loading (i.e., on the free cysteines). In other certain embodiments of the invention it is possible to achieve the desired homogeneity through the use of site-specific antibodies and/or selective reduction and conjugation. In other embodiments the desired homogeneity may be achieved through the use of site-specific constructs in combination with selective reduction. In yet other embodiments compatible preparations may be purified using analytical or preparative chromatography techniques to provide the desired homogeneity. In each of these embodiments the homogeneity of the ADC sample can be analyzed using various techniques known in the art including but not limited to mass spectrometry, HPLC (e.g. size exclusion HPLC, RP-HPLC, HIC-HPLC etc.) or capillary electrophoresis.

With regard to the purification of ADC preparations it will be appreciated that standard pharmaceutical preparative methods may be employed to obtain the desired purity. As discussed herein liquid chromatography methods such as reverse phase (RP) and hydrophobic interaction chromatography (HIC) may separate compounds in the mixture by drug loading value. In some cases, ion-exchange (IEC) or mixed-mode chromatography (MMC) may also be used to isolate species with a specific drug load.

In any event the disclosed ADCs and preparations thereof may comprise drug and antibody moieties in various stoichiometric molar ratios depending on the configuration of the antibody and, at least in part, on the method used to effect conjugation. In certain embodiments the drug loading per ADC may comprise from 1-20 warheads (i.e., n is 1-20). Other selected embodiments may comprise ADCs with a drug loading of from 1 to 15 warheads. In still other embodiments the ADCs may comprise from 1-12 warheads or, more preferably, from 1-10 warheads. In some embodiments the ADCs will comprise from 1 to 8 warheads.

While theoretical drug loading may be relatively high, practical limitations such as free cysteine cross reactivity and warhead hydrophobicity tend to limit the generation of homogeneous preparations comprising such DAR due to aggregates and other contaminants. That is, higher drug loading, e.g. >8 or 10, may cause aggregation, insolubility, toxicity, or loss of cellular permeability of certain antibody-drug conjugates depending on the payload. In view of such concerns drug loading provided by the instant invention preferably ranges from 1 to 8 drugs per conjugate, i.e. where 1, 2, 3, 4, 5, 6, 7, or 8 drugs are covalently attached to each antibody (e.g., for IgG1, other antibodies may have different loading capacity depending the number of disulfide bonds). Preferably the DAR of compositions of the instant invention will be approximately 2, 4 or 6 and in some embodiments the DAR will comprise approximately 2.

Despite the relatively high level of homogeneity provided by the instant invention the disclosed compositions actually comprise a mixture of conjugates with a range of drug compounds (potentially from 1 to 8 in the case of an IgG1). As such, the disclosed ADC compositions include mixtures of conjugates where most of the constituent antibodies are covalently linked to one or more drug moieties and (despite the relative conjugate specificity provided by engineered constructs and selective reduction) where the drug moieties may be attached to the antibody by various thiol groups. That is, following conjugation, compositions of the invention will comprise a mixture of ADCs with different drug loads (e.g., from 1 to 8 drugs per IgG1 antibody) at various concentrations (along with certain reaction contaminants primarily caused by free cysteine cross reactivity). However using selective reduction and post-fabrication purification the conjugate compositions may be driven to the point where they largely contain a single predominant desired ADC species (e.g., with a drug loading of 2) with relatively low levels of other ADC species (e.g., with a drug loading of 1, 4, 6, etc.). The average DAR value represents the weighted average of drug loading for the composition as a whole (i.e., all the ADC species taken together). Due to inherent uncertainty in the quantification methodology employed and the difficulty in completely removing the non-predominant ADC species in a commercial setting, acceptable DAR values or specifications are often presented as an average, a range or distribution (i.e., an average DAR of 2+/−0.5). Preferably compositions comprising a measured average DAR within the range (i.e., 1.5 to 2.5) would be used in a pharmaceutical setting.

Thus, in some embodiments the present invention will comprise compositions having an average DAR of 1, 2, 3, 4, 5, 6, 7 or 8 each +/−0.5. In other embodiments the present invention will comprise an average DAR of 2, 4, 6 or 8+/−0.5. Finally, in selected embodiments the present invention will comprise an average DAR of 2+/−0.5 or 4+/−0.5. It will be appreciated that the range or deviation may be less than 0.4 in some embodiments. Thus, in other embodiments the compositions will comprise an average DAR of 1, 2, 3, 4, 5, 6, 7 or 8 each +/−0.3, an average DAR of 2, 4, 6 or 8+/−0.3, even more preferably an average DAR of 2 or 4+/−0.3 or even an average DAR of 2+/−0.3. In other embodiments IgG1 conjugate compositions will preferably comprise a composition with an average DAR of 1, 2, 3, 4, 5, 6, 7 or 8 each +/−0.4 and relatively low levels (i.e., less than 30%) of non-predominant ADC species. In other embodiments the ADC composition will comprise an average DAR of 2, 4, 6 or 8 each +/−0.4 with relatively low levels (<30%) of non-predominant ADC species. In some embodiments the ADC composition will comprise an average DAR of 2+/−0.4 with relatively low levels (<30%) of non-predominant ADC species. In yet other embodiments the predominant ADC species (e.g., with a drug loading of 2 or drug loading of 4) will be present at a concentration of greater than 50%, at a concentration of greater than 55%, at a concentration of greater than 60%, at a concentration of greater than 65%, at a concentration of greater than 70%, at a concentration of greater than 75%, at a concentration of greater that 80%, at a concentration of greater than 85%, at a concentration of greater than 90%, at a concentration of greater than 93%, at a concentration of greater than 95% or even at a concentration of greater than 97% when measured against all other DAR species present in the composition.

As detailed in the Examples below the distribution of drugs per antibody in preparations of ADC from conjugation reactions may be characterized by conventional means such as UV-Vis spectrophotometry, reverse phase HPLC, HIC, mass spectroscopy, ELISA, and electrophoresis. The quantitative distribution of ADC in terms of drugs per antibody may also be determined. By ELISA, the averaged value of the drugs per antibody in a particular preparation of ADC may be determined. However, the distribution of drug per antibody values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues.

VI. DIAGNOSTICS AND SCREENING

A. Diagnostics

The invention provides in vitro and in vivo methods for detecting, diagnosing or monitoring proliferative disorders and methods of screening cells from a patient to identify tumor cells including tumorigenic cells. Such methods include identifying an individual having cancer for treatment or monitoring progression of a cancer, comprising contacting the patient or a sample obtained from a patient (either in vivo or in vitro) with a detection agent (e.g., an antibody or nucleic acid probe) capable of specifically recognizing and associating with a BMPR1B determinant and detecting the presence or absence, or level of association of the detection agent in the sample. In selected embodiments the detection agent will comprise an antibody associated with a detectable label or reporter molecule as described herein. In certain other embodiments the BMPR1B antibody will be administered and detected using a secondary labelled antibody (e.g., an anti-murine antibody). In yet other embodiments (e.g., In situ hybridization or ISH) a nucleic acid probe that reacts with a genomic BMPR1B determinant will be used in the detection, diagnosis or monitoring of the proliferative disorder.

More generally the presence and/or levels of BMPR1B determinants may be measured using any of a number of techniques available to the person of ordinary skill in the art for protein or nucleic acid analysis, e.g., direct physical measurements (e.g., mass spectrometry), binding assays (e.g., immunoassays, agglutination assays, and immunochromatographic assays), Polymerase Chain Reaction (PCR, RT-PCR; RT-qPCR) technology, branched oligonucleotide technology, Northern blot technology, oligonucleotide hybridization technology and in situ hybridization technology. The method may also comprise measuring a signal that results from a chemical reaction, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

In some embodiments, the association of the detection agent with particular cells or cellular components in the sample indicates that the sample may contain tumorigenic cells, thereby denoting that the individual having cancer may be effectively treated with an antibody or ADC as described herein.

In certain preferred embodiments the assays may comprise immunohistochemistry (IHC) assays or variants thereof (e.g., fluorescent, chromogenic, standard ABC, standard LSAB, etc.), immunocytochemistry or variants thereof (e.g., direct, indirect, fluorescent, chromogenic, etc.) or In situ hybridization (ISH) or variants thereof (e.g., chromogenic in situ hybridization (CISH) or fluorescence in situ hybridization (DNA-FISH or RNA-FISH]))

In this regard certain aspects of the instant invention comprise the use of labeled BMPR1B for immunohistochemistry (IHC). More particularly BMPR1B IHC may be used as a diagnostic tool to aid in the diagnosis of various proliferative disorders and to monitor the potential response to treatments including BMPR1B antibody therapy. In certain embodiments the BMPR1B antibody will be conjugated to one or more reporter molecules. In other embodiments the BMPR1B antibody will be unlabeled and will be detected with a separate agent (e.g., an anti-murine antibody) associated with one or more reporter molecules. As discussed herein and shown in the Examples below compatible diagnostic assays may be performed on tissues that have been chemically fixed (including but not limited to: formaldehyde, gluteraldehyde, osmium tetroxide, potassium dichromate, acetic acid, alcohols, zinc salts, mercuric chloride, chromium tetroxide and picric acid) and embedded (including but not limited to: glycol methacrylate, paraffin and resins) or preserved via freezing. Such assays can be used to guide treatment decisions and determine dosing regimens and timing.

Other particularly compatible aspects of the invention involve the use of in situ hybridization to detect or monitor BMPR1B determinants. In situ hybridization technology or ISH is well known to those of skill in the art. Briefly, cells are fixed and detectable probes which contain a specific nucleotide sequence are added to the fixed cells. If the cells contain complementary nucleotide sequences, the probes, which can be detected, will hybridize to them. Using the sequence information set forth herein, probes can be designed to identify cells that express genotypic BMPR1B determinants. Probes preferably hybridize to a nucleotide sequence that corresponds to such determinants. Hybridization conditions can be routinely optimized to minimize background signal by non-fully complementary hybridization though preferably the probes are preferably fully complementary to the selected BMPR1B determinant. In selected embodiments the probes are labeled with fluorescent dye attached to the probes that is readily detectable by standard fluorescent methodology.

Compatible in vivo theragnostics or diagnostic assays may comprise art-recognized imaging or monitoring techniques such as magnetic resonance imaging, computerized tomography (e.g. CAT scan), positron tomography (e.g., PET scan) radiography, ultrasound, etc., as would be known by those skilled in the art.

In certain embodiments the antibodies of the instant invention may be used to detect and quantify levels of a particular determinant (e.g., BMPR1B protein) in a patient sample (e.g., plasma or blood) which may, in turn, be used to detect, diagnose or monitor proliferative disorders that are associated with the relevant determinant. For example, blood and bone marrow samples may be used in conjunction with flow cytometry to detect and measure BMPR1B expression (or another co-expressed marker) and monitor the progression of the disease and/or response to treatment. In related embodiments the antibodies of the instant invention may be used to detect, monitor and/or quantify circulating tumor cells either in vivo or in vitro (WO 2012/0128801). In still other embodiments the circulating tumor cells may comprise tumorigenic cells.

In certain embodiments of the invention, the tumorigenic cells in a subject or a sample from a subject may be assessed or characterized using the disclosed antibodies prior to therapy or regimen to establish a baseline. In other examples, the tumorigenic cells can be assessed from a sample that is derived from a subject that was treated.

In another embodiment, the invention provides a method of analyzing cancer progression and/or pathogenesis in vivo. In another embodiment, analysis of cancer progression and/or pathogenesis in vivo comprises determining the extent of tumor progression. In another embodiment, analysis comprises the identification of the tumor. In another embodiment, analysis of tumor progression is performed on the primary tumor. In another embodiment, analysis is performed over time depending on the type of cancer as known to one skilled in the art. In another embodiment, further analysis of secondary tumors originating from metastasizing cells of the primary tumor is conducted in vivo. In another embodiment, the size and shape of secondary tumors are analyzed. In some embodiments, further ex vivo analysis is performed.

In another embodiment, the invention provides a method of analyzing cancer progression and/or pathogenesis in vivo including determining cell metastasis or detecting and quantifying the level of circulating tumor cells. In yet another embodiment, analysis of cell metastasis comprises determination of progressive growth of cells at a site that is discontinuous from the primary tumor. In some embodiments, procedures may be undertaken to monitor tumor cells that disperse via blood vasculature, lymphatics, within body cavities or combinations thereof. In another embodiment, cell metastasis analysis is performed in view of cell migration, dissemination, extravasation, proliferation or combinations thereof.

In certain examples, the tumorigenic cells in a subject or a sample from a subject may be assessed or characterized using the disclosed antibodies prior to therapy to establish a baseline. In other examples the sample is derived from a subject that was treated. In some examples the sample is taken from the subject at least about 1, 2, 4, 6, 7, 8, 10, 12, 14, 15, 16, 18, 20, 30, 60, 90 days, 6 months, 9 months, 12 months, or >12 months after the subject begins or terminates treatment. In certain examples, the tumorigenic cells are assessed or characterized after a certain number of doses (e.g., after 2, 5, 10, 20, 30 or more doses of a therapy). In other examples, the tumorigenic cells are characterized or assessed after 1 week, 2 weeks, 1 month, 2 months, 1 year, 2 years, 3 years, 4 years or more after receiving one or more therapies.

B. Screening

In certain embodiments, antibodies of the instant invention can be used to screen samples in order to identify compounds or agents (e.g., antibodies or ADCs) that alter a function or activity of tumor cells by interacting with a determinant. In one embodiment, tumor cells are put in contact with an antibody or ADC and the antibody or ADC can be used to screen the tumor for cells expressing a certain target (e.g. BMPR1B) in order to identify such cells for purposes, including but not limited to, diagnostic purposes, to monitor such cells to determine treatment efficacy or to enrich a cell population for such target-expressing cells.

In yet another embodiment, a method includes contacting, directly or indirectly, tumor cells with a test agent or compound and determining if the test agent or compound modulates an activity or function of the determinant-associated tumor cells for example, changes in cell morphology or viability, expression of a marker, differentiation or de-differentiation, cell respiration, mitochondrial activity, membrane integrity, maturation, proliferation, viability, apoptosis or cell death. One example of a direct interaction is physical interaction, while an indirect interaction includes, for example, the action of a composition upon an intermediary molecule that, in turn, acts upon the referenced entity (e.g., cell or cell culture).

Screening methods include high throughput screening, which can include arrays of cells (e.g., microarrays) positioned or placed, optionally at pre-determined locations, for example, on a culture dish, tube, flask, roller bottle or plate. High-throughput robotic or manual handling methods can probe chemical interactions and determine levels of expression of many genes in a short period of time. Techniques have been developed that utilize molecular signals, for example via fluorophores or microarrays (Mocellin and Rossi, 2007, PMID: 17265713) and automated analyses that process information at a very rapid rate (see, e.g., Pinhasov et al., 2004, PMID: 15032660). Libraries that can be screened include, for example, small molecule libraries, phage display libraries, fully human antibody yeast display libraries (Adimab), siRNA libraries, and adenoviral transfection vectors.

VII. PHARMACEUTICAL PREPARATIONS AND THERAPEUTIC USES

A. Formulations and Routes of Administration

The antibodies or ADCs of the invention can be formulated in various ways using art recognized techniques. In some embodiments, the therapeutic compositions of the invention can be administered neat or with a minimum of additional components while others may optionally be formulated to contain suitable pharmaceutically acceptable carriers. As used herein, "pharmaceutically acceptable carriers" comprise excipients, vehicles, adjuvants and diluents that are well known in the art and can be available from commercial sources for use in pharmaceutical preparation (see, e.g., Gennaro (2003) *Remington: The Science and Practice of Pharmacy with Facts and Comparisons: Drugfacts Plus,* 20th ed., Mack Publishing; Ansel et al. (2004) *Pharmaceutical Dosage Forms and Drug Delivery Systems,* 7$^{th}$ ed., Lippencott Williams and Wilkins; Kibbe et al. (2000) *Handbook of Pharmaceutical Excipients,* 3$^{rd}$ ed., Pharmaceutical Press.)

Suitable pharmaceutically acceptable carriers comprise substances that are relatively inert and can facilitate administration of the antibody or ADC or can aid processing of the active compounds into preparations that are pharmaceutically optimized for delivery to the site of action.

Such pharmaceutically acceptable carriers include agents that can alter the form, consistency, viscosity, pH, tonicity, stability, osmolarity, pharmacokinetics, protein aggregation or solubility of the formulation and include buffering agents, wetting agents, emulsifying agents, diluents, encapsulating agents and skin penetration enhancers. Certain non-limiting examples of carriers include saline, buffered saline, dextrose, arginine, sucrose, water, glycerol, ethanol, sorbitol, dextran, sodium carboxymethyl cellulose and combinations thereof. Antibodies for systemic administration may be formulated for enteral, parenteral or topical administration. Indeed, all three types of formulation may be used simultaneously to achieve systemic administration of the active ingredient. Excipients as well as formulations for parenteral and nonparenteral drug delivery are set forth in *Remington: The Science and Practice of Pharmacy* (2000) 20th Ed. Mack Publishing.

Suitable formulations for enteral administration include hard or soft gelatin capsules, pills, tablets, including coated tablets, elixirs, suspensions, syrups or inhalations and controlled release forms thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additionally contain other pharmaceutically acceptable carriers, such as anti-oxidants, buffers, preservatives, stabilizers, bacteriostats, suspending agents, thickening agents, and solutes that render the formulation isotonic with the blood (or other relevant bodily fluid) of the intended recipient. Examples of excipients include, for example, water, alcohols, polyols, glycerol, vegetable oils, and the like. Examples of suitable isotonic pharmaceutically acceptable carriers for use in such formulations include Sodium Chloride Injection, Ringer's Solution, or Lactated Ringer's Injection.

In particularly preferred embodiments formulated compositions of the present invention may be lyophilized to provide a powdered form of the antibody or ADC which may then be reconstituted prior to administration. Sterile powders for the preparation of injectable solutions may be generated by lyophilizing a solution comprising the disclosed antibodies or ADCs to yield a powder comprising the active ingredient along with any optional co-solubilized biocompatible ingredients. Generally, dispersions or solutions are prepared by incorporating the active compound into a sterile vehicle that contains a basic dispersion medium or solvent (e.g., a diluent) and, optionally, other biocompatible ingredients. A compatible diluent is one which is pharmaceutically acceptable (safe and non-toxic for administration to a human) and is useful for the preparation of a liquid formulation, such as a formulation reconstituted after lyophilization. Exemplary diluents include sterile water, bacteriostatic water for injection (BWFI), a pH buffered solution (e.g. phosphate-buffered saline), sterile saline solution, Ringer's solution or dextrose solution. In an alternative embodiment, diluents can include aqueous solutions of salts and/or buffers.

In certain preferred embodiments the anti-BMPR1B antibodies or ADCs will be lyophilized in combination with a pharmaceutically acceptable sugar. A "pharmaceutically acceptable sugar" is a molecule which, when combined with a protein of interest, significantly prevents or reduces chemical and/or physical instability of the protein upon storage. When the formulation is intended to be lyophilized and then reconstituted. As used herein pharmaceutically acceptable sugars may also be referred to as a "lyoprotectant". Exemplary sugars and their corresponding sugar alcohols include: an amino acid such as monosodium glutamate or histidine; a methylamine such as betaine; a lyotropic salt such as magnesium sulfate; a polyol such as trihydric or higher molecular weight sugar alcohols, e.g. glycerin, dextran, erythritol, glycerol, arabitol, xylitol, sorbitol, and mannitol; propylene glycol; polyethylene glycol; PLURONICS®; and combinations thereof. Additional exemplary lyoprotectants include glycerin and gelatin, and the sugars mellibiose, melezitose, raffinose, mannotriose and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Preferred sugar alcohols are monoglycosides, especially those compounds obtained by reduction of disaccharides such as lactose, maltose, lactulose and maltulose. The glycosidic side group can be either glucosidic or galactosidic. Additional examples of sugar alcohols are glucitol, maltitol, lactitol and iso-maltulose. The preferred pharmaceutically-acceptable sugars are the non-reducing sugars trehalose or sucrose. Pharmaceutically acceptable sugars are added to the formulation in a "protecting amount" (e.g. pre-lyophilization) which means that the protein essentially retains its physical and chemical stability and integrity during storage (e.g., after reconstitution and storage).

Those skilled in the art will appreciate that compatible lyprotecatants may be added to the liquid or lyophilized formulation at concentrations ranging from about 1 mM to about 1000 mM, from about 25 mM to about 750 mM, from about 50 mM to about 500 mM, from about 100 mM to about 300 mM, from about 125 mM to about 250 mM, from about 150 mM to about 200 mM or from about 165 mM to about 185 mM. In certain embodiments the lyoprotectant(s) may be added to provide a concentration of about 10 mM, about 25 mM, about 50 mM, about 75 mM, about 100 mM, about 125 mM, about 130 mM, about 140 mM, about 150 mM, about 160 mM, about 165 mM, about 170 mM, about 175 mM, about 180 mM, about 185 mM about 190 mM, about 200 mM, about 225 mM, about 250 mM, about 300 mM, about 400 mM, about 500 mM, about 600 mM, about 700 mM, about 800 mM about 900 mM, or about 1000 mM. In certain preferred embodiments the lyoprotectant(s) may comprise pharmaceutically acceptable sugars. In particularly preferred aspects the pharmaceutically acceptable sugars will comprise trehalose or sucrose.

In other selected embodiments liquid and lyophilized formulations of the instant invention may comprise certain compounds, including amino acids or pharmaceutically acceptable salts thereof, to act as stabilizing or buffering agents. Such compounds may be added at concentrations ranging from about 1 mM to about 100 mM, from about 5 mM to about 75 mM, from about 5 mM to about 50 mM, from about 10 mM to about 30 mM or from about 15 mM to about 25 mM. In certain embodiments the buffering agent(s) may be added to provide a concentration of about 1 mM, about 5 mM, about 10 mM, about 15 mM, about 20 mM, about 25 mM, about 30 mM, about 35 mM, about 40 mM, about 50 mM, about 60 mM, about 70 mM, about 80 mM, about 90 mM or about 100 mM. In other selected embodiments the buffering agent may be added to provide a concentration of about 5 mM, about 10 mM, about 15 mM, about 20 mM, about 25 mM, about 30 mM, about 35 mM, about 40 mM, about 50 mM, about 80 mM, about 70 mM, about 80 mM, about 90 mM or about 100 mM. In certain preferred embodiments the buffering agent will comprise histidine hydrochloride.

In yet other selected embodiments liquid and lyophilized formulations of the instant invention may comprise nonionic surfactants such as polysorbate 20, polysorbate 40, polysorbate 60 or polysorbate 80 as stabilizing agents. Such compounds may be added at concentrations ranging from about 0.1 mg/ml to about 2.0 mg/ml, from about 0.1 mg/ml to about 1.0 mg/ml, from about 0.2 mg/ml to about 0.8 mg/ml, from about 0.2 mg/ml to about 0.6 mg/ml or from about 0.3 mg/ml to about 0.5 mg/ml. In certain embodiments the surfactant may be added to provide a concentration of about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml or about 1.0 mg/ml. In other selected embodiments the surfactant may be added to provide a concentration of about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml or about 2.0 mg/ml. In certain preferred embodiments the surfactant will comprise polysorbate 20 or polysorbate 40.

Compatible formulations of the disclosed antibodies or ADCs for parenteral administration (e.g., intravenous injection) may comprise ADC or antibody concentrations of from about 10 µg/mL to about 100 mg/mL. In certain selected embodiments antibody or ADC concentrations will comprise 20 µg/mL, 40 µg/mL, 60 µg/mL, 80 µg/mL, 100 µg/mL, 200 µg/mL, 300, µg/mL, 400 µg/mL, 500 µg/mL, 600 µg/mL, 700 µg/mL, 800 µg/mL, 900 µg/mL or 1 mg/mL. In other embodiments ADC concentrations will comprise 2 mg/mL, 3 mg/mL, 4 mg/mL, 5 mg/mL, 6 mg/mL, 8 mg/mL, 10 mg/mL, 12 mg/mL, 14 mg/mL, 16 mg/mL, 18 mg/mL, 20 mg/mL, 25 mg/mL, 30 mg/mL, 35 mg/mL, 40 mg/mL, 45 mg/mL, 50 mg/mL, 60 mg/mL, 70 mg/mL, 80 mg/mL, 90 mg/mL or 100 mg/mL.

Whether reconstituted from lyophilized powder or not, the liquid BMPR1B ADC formulations (e.g., as set forth immediately above) may be further diluted (preferably in an aqueous carrier) prior to administration. For example the aforementioned liquid formulations may further be diluted into an infusion bag containing 0.9% Sodium Chloride Injection, USP, or equivalent (mutatis mutandis), to achieve the desired dose level for administration. In certain aspects the fully diluted BMPR1B ADC solution will be administered via intravenous infusion using an IV apparatus. Preferably the administered BMPR1B ADC drug solution (whether by intravenous (IV) infusion or injection) is clear, colorless and free from visible particulates.

The compounds and compositions of the invention may be administered in vivo, to a subject in need thereof, by various routes, including, but not limited to, oral, intravenous, intra-arterial, subcutaneous, parenteral, intranasal, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

B. Dosages and Dosing Regimens

The particular dosage regimen, i.e., dose, timing and repetition, will depend on the particular individual, as well as empirical considerations such as pharmacokinetics (e.g., half-life, clearance rate, etc.). Determination of the frequency of administration may be made by persons skilled in the art, such as an attending physician based on considerations of the condition and severity of the condition being treated, age and general state of health of the subject being treated and the like. Frequency of administration may be adjusted over the course of therapy based on assessment of the efficacy of the selected composition and the dosing regimen. Such assessment can be made on the basis of markers of the specific disease, disorder or condition. In embodiments where the individual has cancer, these include direct measurements of tumor size via palpation or visual observation; indirect measurement of tumor size by x-ray or other imaging techniques; an improvement as assessed by direct tumor biopsy and microscopic examination of a tumor sample; the measurement of an indirect tumor marker (e.g., PSA for prostate cancer) or an antigen identified according to the methods described herein; reduction in the number of proliferative or tumorigenic cells, maintenance of the reduction of such neoplastic cells; reduction of the proliferation of neoplastic cells; or delay in the development of metastasis.

The BMPR1B antibodies or ADCs of the invention may be administered in various ranges. These include about 5 µg/kg body weight to about 100 mg/kg body weight per dose; about 50 µg/kg body weight to about 5 mg/kg body weight per dose; about 100 µg/kg body weight to about 10 mg/kg body weight per dose. Other ranges include about 100 µg/kg body weight to about 20 mg/kg body weight per dose and about 0.5 mg/kg body weight to about 20 mg/kg body weight per dose. In certain embodiments, the dosage is at least about 100 µg/kg body weight, at least about 250 µg/kg body weight, at least about 750 µg/kg body weight, at least about 3 mg/kg body weight, at least about 5 mg/kg body weight, at least about 10 mg/kg body weight.

In selected embodiments the BMPR1B antibodies or ADCs will be administered (preferably intravenously) at approximately 10, 20, 30, 40, 50, 60, 70, 80, 90 or 100 µg/kg body weight per dose. Other embodiments may comprise the administration of antibodies or ADCs at about 200, 300, 400, 500, 600, 700, 800, 900, 1000, 1100, 1200, 1300, 1400, 1500, 1600, 1700, 1800, 1900 or 2000 µg/kg body weight per dose. In other embodiments the disclosed conjugates will be administered at 2.5, 3, 3.5, 4, 4.5, 5, 5.5, 6, 6.5, 7, 7.5, 8, 9 or 10 mg/kg. In still other embodiments the conjugates may be administered at 12, 14, 16, 18 or 20 mg/kg body weight per dose. In yet other embodiments the conjugates may be administered at 25, 30, 35, 40, 45, 50, 55, 60, 65, 70, 75, 80, 90 or 100 mg/kg body weight per dose. With the teachings herein one of skill in the art could readily determine appropriate dosages for various BMPR1B antibodies or ADCs based on preclinical animal studies, clinical observations and standard medical and biochemical techniques and measurements.

Other dosing regimens may be predicated on Body Surface Area (BSA) calculations as disclosed in U.S. Pat. No. 7,744,877. As is well known, the BSA is calculated using the patient's height and weight and provides a measure of a subject's size as represented by the surface area of his or her body. In certain embodiments, the conjugates may be administered in dosages from 1 $mg/m^2$ to 800 $mg/m^2$, from 50 $mg/m^2$ to 500 $mg/m^2$ and at dosages of 100 $mg/m^2$, 150 $mg/m^2$, 200 $mg/m^2$, 250 $mg/m^2$, 300 $mg/m^2$, 350 $mg/m^2$, 400 $mg/m^2$ or 450 $mg/m^2$. It will also be appreciated that art recognized and empirical techniques may be used to determine appropriate dosage.

Anti-BMPR1B antibodies or ADCs may be administered on a specific schedule. Generally, an effective dose of the BMPR1B conjugate is administered to a subject one or more times. More particularly, an effective dose of the ADC is administered to the subject once a month, more than once a month, or less than once a month. In certain embodiments, the effective dose of the BMPR1B antibody or ADC may be administered multiple times, including for periods of at least a month, at least six months, at least a year, at least two years or a period of several years. In yet other embodiments, several days (2, 3, 4, 5, 6 or 7), several weeks (1, 2, 3, 4, 5, 6, 7 or 8) or several months (1, 2, 3, 4, 5, 6, 7 or 8) or even a year or several years may lapse between administration of the disclosed antibodies or ADCs.

In some embodiments the course of treatment involving conjugated antibodies will comprise multiple doses of the selected drug product over a period of weeks or months. More specifically, antibodies or ADCs of the instant invention may administered once every day, every two days, every four days, every week, every ten days, every two weeks, every three weeks, every month, every six weeks, every two months, every ten weeks or every three months. In this regard it will be appreciated that the dosages may be altered or the interval may be adjusted based on patient response and clinical practices. The invention also contemplates discontinuous administration or daily doses divided into several partial administrations. The compositions of the instant invention and anti-cancer agent may be administered interchangeably, on alternate days or weeks; or a sequence of antibody treatments may be given, followed by one or more treatments of anti-cancer agent therapy. In any event, as will be understood by those of ordinary skill in the art, the appropriate doses of chemotherapeutic agents will be generally around those already employed in clinical therapies wherein the chemotherapeutics are administered alone or in combination with other chemotherapeutics.

In another embodiment the BMPR1B antibodies or ADCs of the instant invention may be used in maintenance therapy to reduce or eliminate the chance of tumor recurrence following the initial presentation of the disease. Preferably the disorder will have been treated and the initial tumor mass eliminated, reduced or otherwise ameliorated so the patient is asymptomatic or in remission. At such time the subject may be administered pharmaceutically effective amounts of the disclosed antibodies one or more times even though there is little or no indication of disease using standard diagnostic procedures.

In another preferred embodiment the modulators of the present invention may be used to prophylactically or as an adjuvant therapy to prevent or reduce the possibility of tumor metastasis following a debulking procedure. As used in the instant disclosure a "debulking procedure" means any procedure, technique or method that reduces the tumor mass or ameliorates the tumor burden or tumor proliferation. Exemplary debulking procedures include, but are not limited to, surgery, radiation treatments (i.e., beam radiation), chemotherapy, immunotherapy or ablation. At appropriate times readily determined by one skilled in the art in view of the instant disclosure the disclosed ADCs may be administered as suggested by clinical, diagnostic or theragnostic procedures to reduce tumor metastasis.

Yet other embodiments of the invention comprise administering the disclosed antibodies or ADCs to subjects that are asymptomatic but at risk of developing cancer. That is, the antibodies or ADCs of the instant invention may be used in a truly preventative sense and given to patients that have been examined or tested and have one or more noted risk factors (e.g., genomic indications, family history, in vivo or in vitro test results, etc.) but have not developed neoplasia.

Dosages and regimens may also be determined empirically for the disclosed therapeutic compositions in individuals who have been given one or more administration(s). For example, individuals may be given incremental dosages of a therapeutic composition produced as described herein. In selected embodiments the dosage may be gradually increased or reduced or attenuated based respectively on empirically determined or observed side effects or toxicity. To assess efficacy of the selected composition, a marker of the specific disease, disorder or condition can be followed as described previously. For cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or a tumorigenic antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

C. Anti-Cancer Agents

The term "anti-cancer agent" as used herein is one subset of "therapeutic moieties", which in turn is a subset of the agents described as "pharmaceutically active compounds or moieties". More particularly "anti-cancer agent" means any agent (or a pharmaceutically acceptable salt thereof) that can be used to treat a cell proliferative disorder such as cancer, and includes, but is not limited to, cytotoxic agents, cytostatic agents, anti-angiogenic agents, debulking agents, chemotherapeutic agents, radiotherapeutic agents, targeted anti-cancer agents, biological response modifiers, therapeutic antibodies, cancer vaccines, cytokines, hormone therapy, anti-metastatic agents and immunotherapeutic agents. Note that the foregoing classifications of anti-cancer agents are not exclusive of each other and that selected agents may fall into one or more categories. For example, a compatible anti-cancer agent may be classified as a cytotoxic agent and a chemotherapeutic agent. As such, each of the foregoing terms should be construed in view of the instant disclosure and then in accordance with their use in the medical arts.

In preferred embodiments an anti-cancer agent can include any chemical agent (e.g., a chemotherapeutic agent) that inhibits or eliminates, or is designed to inhibit or eliminate, a cancerous cell or a cell likely to become cancerous or generate tumorigenic progeny (e.g., tumorigenic cells). In this regard selected chemical agents (cell-cycle dependent agents) are often directed to intracellular processes necessary for cell growth or division, and are thus particularly effective against cancerous cells, which generally grow and divide rapidly. For example, vincristine depolymerizes microtubules and thus inhibits rapidly dividing tumor cells from entering mitosis. In other cases the selected chemical agents are cell-cycle independent agents that interfere with cell survival at any point of its lifecycle and may be effective in directed therapeutics (e.g., ADCs). By way of example certain pyrrolobenzodiazepines bind to the minor groove of cellular DNA and inhibit transcription upon delivery to the nucleus. With regard to combination therapy or selection of an ADC component it will be appreciated that one skilled in the art could readily identify compatible cell-cycle dependent agents and cell-cycle independent agents in view of the instant disclosure.

In any event, and as alluded to above, it will be appreciated that the selected anti-cancer agents may be administered in combination with each other (e.g., CHOP therapy) in addition to the disclosed anti-BMPR1B antibodies and ADCs disclosed herein. Moreover, it will further be appreciated that in selected embodiments such anti-cancer agents may comprise conjugates and may be associated with antibodies prior to administration. In certain embodiments the disclosed anti-cancer agent will be linked to an anti-BMPR1B antibody to provide an ADC as disclosed herein.

As used herein the term "cytotoxic agent" (or cytotoxin) generally means a substance that is toxic to cells in that it decreases or inhibits cellular function and/or causes the destruction of tumor cells. In certain embodiments the substance is a naturally occurring molecule derived from a living organism or an analog thereof (purified from natural sources or synthetically prepared). Examples of cytotoxic agents include, but are not limited to, small molecule toxins or enzymatically active toxins of bacteria (e.g., calicheamicin, Diptheria toxin, *Pseudomonas* endotoxin and exotoxin, Staphylococcal enterotoxin A), fungal (e.g., α-sarcin, restrictocin), plants (e.g., abrin, ricin, modeccin, viscumin, pokeweed anti-viral protein, saporin, gelonin, momoridin, trichosanthin, barley toxin, *Aleurites fordii* proteins, dianthin proteins, *Phytolacca mericana* proteins [PAPI, PAPII, and PAP-S], *Momordica charantia* inhibitor, curcin, crotin, *Saponaria officinalis* inhibitor, mitegellin, restrictocin, phenomycin, neomycin, and the tricothecenes) or animals, (e.g., cytotoxic RNases, such as extracellular pancreatic RNases; DNase I, including fragments and/or variants thereof). Additional compatible cytotoxic agents including certain radioisotopes, maytansinoids, auristatins, dolastatins, duocarmycins, amanitins and pyrrolobenzodiazepines are set forth herein.

More generally examples of cytotoxic agents or anti-cancer agents that may be used in combination with (or conjugated to) the antibodies of the invention include, but are not limited to, alkylating agents, alkyl sulfonates, anastrozole, amanitins, aziridines, ethylenimines and methylamelamines, acetogenins, a camptothecin, BEZ-235, bortezomib, bryostatin, callystatin, CC-1065, ceritinib, crizotinib, cryptophycins, dolastatin, duocarmycin, eleutherobin, erlotinib, pancratistatin, a sarcodictyin, spongistatin, nitrogen mustards, antibiotics, enediyne dynemicin, bisphosphonates, esperamicin, chromoprotein enediyne antiobiotic chromophores, aclacinomysins, actinomycin, authramycin, azaserine, bleomycins, cactinomycin, canfosfamide, carabicin, carminomycin, carzinophilin, chromomycinis, cyclosphosphamide, dactinomycin, daunorubicin, detorubicin, 6-diazo-5-oxo-L-norleucine, doxorubicin, epirubicin, esorubicin, exemestane, fluorouracil, fulvestrant, gefitinib, idarubicin, lapatinib, letrozole, lonafarnib, marcellomycin, megestrol acetate, mitomycins, mycophenolic acid, nogalamycin, olivomycins, pazopanib, peplomycin, potfiromycin, puromycin, quelamycin, rapamycin, rodorubicin, sorafenib, streptonigrin, streptozocin, tamoxifen, tamoxifen citrate, temozolomide, tepodina, tipifarnib, tubercidin, ubenimex, vandetanib, vorozole, XL-147, zinostatin, zorubicin; antimetabolites, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, polysaccharide complex, razoxane; rhizoxin; SF-1126, sizofiran; spirogermanium; tenuazonic acid; triaziquone; 2,2',2"-trichlorotriethylamine; trichothecenes (T-2 toxin, verracurin A, roridin A and anguidine); urethan; vindesine; dacarbazine; mannomustine; mitobronitol; mitolactol; pipobroman; gacytosine; arabinoside; cyclophosphamide; thiotepa; taxoids, chloranbucil; gemcitabine; 6-thioguanine; mercaptopurine; methotrexate; platinum analogs, vinblastine; platinum; etoposide; ifosfamide; mitoxantrone; vincristine; vinorelbine; novantrone; teniposide; edatrexate; daunomycin; aminopterin; xeloda; ibandronate; irinotecan, topoisomerase inhibitor RFS 2000; difluorometlhylornithine; retinoids; capecitabine; combretastatin; leucovorin; oxaliplatin; XL518, inhibitors of PKC-alpha, Raf, H-Ras, EGFR and VEGF-A that reduce cell proliferation and pharmaceutically acceptable salts or solvates, acids or derivatives of any of the above. Also included in this definition are anti-hormonal agents that act to regulate or inhibit hormone action on tumors such as anti-estrogens and selective estrogen receptor antibodies, aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides, ribozymes such as a VEGF expression inhibitor and a HER2 expression inhibitor; vaccines, PROLEUKIN® rIL-2; LURTOTECAN® topoisomerase 1 inhibitor; ABARELIX® rmRH; Vinorelbine and Esperamicins and pharmaceutically acceptable salts or solvates, acids or derivatives of any of the above.

Compatible cytotoxic agents or anti-cancer agents may also comprise commercially or clinically available compounds such as erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®). Additional commercially or clinically available anti-cancer agents comprise oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclophosphamide (CYTOXAN®, NEOSAR®); vinorelbine (NAVELBINE®); capecitabine (XELODA®, Roche), tamoxifen (including NOLVADEX®; tamoxifen citrate, FARESTON® (toremifine citrate) MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca).

The term "pharmaceutically acceptable salt" or "salt" means organic or inorganic salts of a molecule or macromolecule. Acid addition salts can be formed with amino groups. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1' methylene bis-(2-hydroxy 3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Where multiple charged atoms are part of the pharmaceutically acceptable salt, the salt can have multiple counter ions. Hence, a pharmaceutically acceptable salt can have one or more charged atoms and/or one or more counterion.

Similarly a "Pharmaceutically acceptable solvate" or "solvate" refers to an association of one or more solvent molecules and a molecule or macromolecule. Examples of solvents that form pharmaceutically acceptable solvates include, but are not limited to, water, isopropanol, ethanol, methanol, DMSO, ethyl acetate, acetic acid, and ethanolamine.

In other embodiments the antibodies or ADCs of the instant invention may be used in combination with any one of a number of antibodies (or immunotherapeutic agents) presently in clinical trials or commercially available. The disclosed antibodies may be used in combination with an antibody selected from the group consisting of abagovomab, adecatumumab, afutuzumab, alemtuzumab, altumomab, amatuximab, anatumomab, arcitumomab, atezolizumab, avelumab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, dacetuzumab, dalotuzumab, daratumumab, detumomab, drozitumab, duligotumab, durvalumab, dusigitumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lambrolizumab, lexatumumab, lintuzumab, lorvotuzumab, lucatumumab, mapatumumab, matuzumab, milatuzumab, minretumumab, mitumomab, moxetumomab, narnatumab, naptumomab, necitumumab, nimotuzumab, nivolumab, nofetumomabn, obinutuzumab, ocaratuzumab, ofatumumab, olaratumab, olaparib, onartuzumab, oportuzumab, oregovomab, panitumumab, parsatuzumab, patritumab, pembrolizumab pemtumomab, pertuzumab, pidilizumab, pintumomab, pritumumab, racotumomab, radretumab, ramucirumab, rilotumumab, rituximab, robatumumab, satumomab, selumetinib, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49, 3F8, MED10680, MDX-1105 and combinations thereof.

Other embodiments comprise the use of antibodies approved for cancer therapy including, but not limited to, rituximab, gemtuzumab ozogamcin, alemtuzumab, ibritumomab tiuxetan, tositumomab, bevacizumab, cetuximab, patitumumab, ofatumumab, ipilimumab and brentuximab vedotin. Those skilled in the art will be able to readily identify additional anti-cancer agents that are compatible with the teachings herein.

D. Radiotherapy

The present invention also provides for the combination of antibodies or ADCs with radiotherapy (i.e., any mechanism for inducing DNA damage locally within tumor cells such as gamma-irradiation, X-rays, UV-irradiation, microwaves, electronic emissions and the like). Combination therapy using the directed delivery of radioisotopes to tumor cells is also contemplated, and the disclosed antibodies or ADCs may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

VIII. INDICATIONS

The invention provides for the use of antibodies and ADCs of the invention for the diagnosis, theragnosis, treatment and/or prophylaxis of various disorders including neoplastic, inflammatory, angiogenic and immunologic disorders and disorders caused by pathogens. In certain embodiments the diseases to be treated comprise neoplastic conditions comprising solid tumors. In other embodiments the diseases to be treated comprise hematologic malignancies. In certain embodiments the antibodies or ADCs of the invention will be used to treat tumors or tumorigenic cells expressing a BMPR1B determinant. Preferably the "subject" or "patient" to be treated will be human although, as used herein, the terms are expressly held to comprise any mammalian species.

It will be appreciated that the compounds and compositions of the instant invention may be used to treat subjects at various stages of disease and at different points in their treatment cycle. Accordingly, in certain embodiments the antibodies and ADCs of the instant invention will be used as a front line therapy and administered to subjects who have not previously been treated for the cancerous condition. In other embodiments the antibodies and ADCs of the invention will be used to treat second and third line patients (i.e., those subjects that have previously been treated for the same condition one or two times respectively). Still other embodiments will comprise the treatment of fourth line or higher patients (e.g., SCLC or BR patients) that have been treated for the same or related condition three or more times with the disclosed BMPR1B ADCs or with different therapeutic agents. In other embodiments the compounds and compositions of the present invention will be used to treat subjects that have previously been treated (with antibodies or ADCs of the present invention or with other anti-cancer agents) and have relapsed or are determined to be refractory to the previous treatment. In selected embodiments the compounds and compositions of the instant invention may be used to treat subjects that have recurrent tumors.

In certain aspects the proliferative disorder will comprise a solid tumor including, but not limited to, adrenal, liver, kidney, bladder, melanoma, breast, gastric, ovarian, cervical, uterine, esophageal, colorectal, prostate, pancreatic, lung (both small cell and non-small cell), thyroid, carcinomas, sarcomas, glioblastomas and various head and neck tumors. In other preferred embodiments, and as shown in the Examples below, the disclosed ADCs are particularly effective at treating breast cancer and, in selected aspects, luminal B (BR-LumB) breast cancer. In certain embodiments the lung cancer is refractory, relapsed or resistant to an anthracyclines and/or a taxane (e.g., docetaxel, paclitaxel, larotaxel or cabazitaxel). In still other aspects of the invention the disclosed antibodies and ADCs may be used for the treatment of medullary thyroid cancer, large cell neuroendocrine carcinoma (LCNEC), glioblastoma, neuroendocrine prostate cancer (NEPC), high-grade gastroenteropancreatic cancer (GEP) and malignant melanoma.

It will be appreciated that breast cancer is a heterogeneous disease with several biologic subtypes identified. In this regard breast cancer is now recognized as comprising at least four distinct neoplastic subtypes based on the expression of estrogen receptor (ER), progesterone receptor (PR), and erbB2/Her2. These subtypes include: basal-like/triple negative breast cancer, Her2-positive breast cancer, luminal A breast cancer and luminal B breast cancer. Luminal A is the most common breast cancer subtype (40% of all invasive breast cancer) and is characterized by ER+ and/or PR+/Her2− status, low-grade tumors and good prognosis. Luminal B subtype accounts for roughly 25% of all invasive breast cancer and is distinguished by ER+ and/or PR+/Her2+ status with poor outcomes. Breast cancer subtypes (20% of all invasive breast cancer) with negative ER, PR and Her2 status are typically called triple negative breast cancer or basal-like breast cancer. The Her2-enriched subtype (Her2+/ER−/PR−) is least common, with 15% of all invasive breast cancer. While the antibodies and ADCs of the instant invention may be used to treat all different types of BMPR1B positive breast cancers, it may be particularly effective treating basal-like breast cancer and luminal-B breast cancer, where therapeutic resistance is common and, as shown in the Examples below, where molecular profiling has identified BMPR1B as a promising new therapeutic target.

Multiple gene expression studies have reproduced luminal-A and luminal-B subtypes. Both subtypes have expression patterns reminiscent of the luminal epithelial component of the breast, including expression of luminal cytokeratins 8/18, ER and genes associated with ER activation such as CCND1 (cyclin D1). The major molecular distinction between the two luminal subtypes is that, in general, luminal B has lower expression of ER-related genes and higher expression of proliferative genes. A review of several gene expression studies noted that approximately 20% of luminal-B breast cancers were HER2-positive by immunohistochemistry. Approximately 30% of HER2-positive tumors defined by immunohistochemistry are assigned to the luminal-B subtype. In many subsequent studies, luminal-B breast cancer has been defined as ER-positive breast cancer with increased proliferation. In gene expression studies, proliferation genes such as CCNB1, MKI67 and MYBL2 are more highly expressed in luminal-B compared with luminal-A subtypes, correlating with a higher proportion of histological grade III also observed in luminal-B cancers. Proliferation has been consistently identified as the most important feature of several prognostic multigene signatures, including the intrinsic molecular classification. In ER-positive/HER2-negative tumors, proliferation is the strongest predictor of early relapse risk that differentiates high-risk luminal-B tumors from low-risk luminal-A tumors.

Overall survival in untreated luminal-B breast cancer is similar to the basal-like and HER2-positive subgroups, which are widely recognized as high risk. In a study using a 50-gene classifier to assign intrinsic subtypes to 761 untreated breast cancer patients, with correlation of subtype with outcome; a multivariate analysis of untreated early breast cancer, using the luminal-A subtype as a reference, luminal-B breast cancers were demonstrated to have a hazard ratio of 2.43 (P<0.0001) for relapse-free survival (RFS), similar to hazard ratios for erbB2/HER2 amplified (2.53, P=0.00012) tumors. Triple negative/basal-like breast cancer had intermediate survival times, with deaths occurring earlier than luminal A breast cancer. Survival declined precipitously during the first 3 to 4 years of follow-up for both Her2-enriched and luminal B subtypes, followed by a slowing in the decline over subsequent years of follow-up. The triple negative subtype showed a similar early decline over the first 2 to 2.5 years with a more gradual decline to about 13 years of follow up. Moreover, luminal breast cancers appear to have a predilection for metastasis to lung, bone and pleura. Several studies suggest luminal-B breast cancer is relatively insensitive to endocrine therapy compared with luminal-A breast cancer, and to chemotherapy compared with HER2-enriched and basal-like breast cancers.

In contrast to the current clinical situation, the ADCs and antibodies of the instant invention have been shown to exhibit anti-tumor activity as shown in the Examples below. More specifically the disclosed anti-BMPR1B ADCs are shown to effectively and specifically associate with tumorigenic cells in luminal-B breast cancer. This targeting of the selected tumor cells is indicative of agents with substantial therapeutic potential.

More generally exemplary neoplastic conditions subject to treatment in accordance with the instant invention may be benign or malignant; solid tumors or hematologic malignancies; and may be selected from the group including, but not limited to: adrenal gland tumors, AIDS-associated cancers, alveolar soft part sarcoma, astrocytic tumors, autonomic ganglia tumors, bladder cancer (squamous cell carcinoma and transitional cell carcinoma), blastocoelic disorders, bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, epithelial disorders, Ewing's tumors, extraskeletal myxoid chondrosarcoma, fibrogenesis imperfecta ossium, fibrous dysplasia of the bone, gallbladder and bile duct cancers, gastric cancer, gastrointestinal, gestational trophoblastic disease, germ cell tumors, glandular disorders, head and neck cancers, hypothalamic, intestinal cancer, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), macrophagal disorders, medulloblastoma, melanoma, meningiomas, medullary thyroid cancer, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, stromal disorders, synovial sarcoma, testicular cancer, thymic carcinoma, thymoma, thyroid metastatic cancer, and uterine cancers (carcinoma of the cervix, endometrial carcinoma, and leiomyoma). In certain embodiments the compounds and compositions of the instant invention will be used as a front line therapy and administered to subjects who have not previously been treated for the cancerous condition. In other embodiments the compounds and compositions of the present invention will be used to treat subjects that have previously been treated (with antibodies or ADCs of the present invention or with other anti-cancer agents) and have relapsed or determined to be refractory to the previous treatment. In selected embodiments the compounds and compositions of the instant invention may be used to treat subjects that have recurrent tumors.

With regard to hematologic malignancies it will be further be appreciated that the compounds and methods of the present invention may be particularly effective in treating a variety of leukemias including acute myeloid leukemia (AML, cognizant of its various subtypes based on the FAB nomenclature (M0-M7), WHO classification, molecular marker/mutations, karyotype, morphology, and other characteristics), lineage acute lymphoblastic leukemia (ALL), chronic myeloid leukemia (CML), chronic lymphocytic leukemia (CLL), hairy cell leukemia (HCL), chronic myelomonocytic leukemia (CMML), juvenile myelomonocytic leukemia (JMML) and large granular lymphocytic leukemia (LGL) as well as B-cell lymphomas, including Hodgkin's lymphoma (classic Hodgkin's lymphoma and nodular lymphocyte-predominant Hodgkin lymphoma), Non-Hodgkin's lymphoma including diffuse large B-cell lymphoma (DLBCL), follicular lymphoma (FL), low grade/NHL follicular cell lymphoma (FCC), small lymphocytic lymphoma (SLL), mucosa-associated lymphatic tissue (MALT) lymphoma, mantle cell lymphoma (MCL), and Burkitt lymphoma (BL); intermediate grade/follicular NHL, intermediate grade diffuse NHL, high grade immunoblastic NHL, high grade lymphoblastic NHL, high grade small non-cleaved cell NHL, bulky disease NHL, Waldenstrom's Macroglobulinemia, lymphoplasmacytoid lymphoma (LPL), AIDS-related lymphomas, monocytic B cell lymphoma, angioimmunoblastic lymphoadenopathy, diffuse small cleaved cell, large cell immunoblastic lymphoblastoma, small, non-cleaved, Burkitt's and non-Burkitt's, follicular, predominantly large cell; follicular, predominantly small cleaved cell; and follicular, mixed small cleaved and large cell lymphomas. See, Gaidono et al., "Lymphomas", IN CANCER: PRINCIPLES & PRACTICE OF ONCOLOGY, Vol. 2: 2131-2145 (DeVita et al., eds., 5.sup.th ed. 1997). It should be clear to those of skill in the art that these lymphomas will often have different names due to changing systems of classification, and that patients having lymphomas classified under different names may also benefit from the combined therapeutic regimens of the present invention.

IX. ARTICLES OF MANUFACTURE

The invention includes pharmaceutical packs and kits comprising one or more containers or receptacles, wherein a container can comprise one or more doses of an antibody or ADC of the invention. Such kits or packs may be diagnostic or therapeutic in nature. In certain embodiments, the pack or kit contains a unit dosage, meaning a predetermined amount of a composition comprising, for example, an antibody or ADC of the invention, with or without one or more additional agents and optionally, one or more anti-cancer agents. In certain other embodiments, the pack or kit contains a detectable amount of an anti-BMPR1B antibody or ADC, with or without an associated reporter molecule and optionally one or more additional agents for the detection, quantitation and/or visualization of cancerous cells.

In any event kits of the invention will generally comprise an antibody or ADC of the invention in a suitable container or receptacle a pharmaceutically acceptable formulation and, optionally, one or more anti-cancer agents in the same or different containers. The kits may also contain other pharmaceutically acceptable formulations or devices, either for diagnosis or combination therapy. Examples of diagnostic devices or instruments include those that can be used to detect, monitor, quantify or profile cells or markers associated with proliferative disorders (for a full list of such markers, see above). In some embodiments the devices may be used to detect, monitor and/or quantify circulating tumor cells either in vivo or in vitro (see, for example, WO 2012/0128801). In still other embodiments the circulating tumor cells may comprise tumorigenic cells. The kits contemplated by the invention can also contain appropriate reagents to combine the antibody or ADC of the invention with an anti-cancer agent or diagnostic agent (e.g., see U.S. Pat. No. 7,422,739).

When the components of the kit are provided in one or more liquid solutions, the liquid solution can be non-aqueous, though typically an aqueous solution is preferred, with a sterile aqueous solution being particularly preferred. The formulation in the kit can also be provided as dried powder(s) or in lyophilized form that can be reconstituted upon addition of an appropriate liquid. The liquid used for reconstitution can be contained in a separate container. Such liquids can comprise sterile, pharmaceutically acceptable buffer(s) or other diluent(s) such as bacteriostatic water for injection, phosphate-buffered saline, Ringer's solution or dextrose solution. Where the kit comprises the antibody or ADC of the invention in combination with additional therapeutics or agents, the solution may be pre-mixed, either in a molar equivalent combination, or with one component in excess of the other. Alternatively, the antibody or ADC of the invention and any optional anti-cancer agent or other agent (e.g., steroids) can be maintained separately within distinct containers prior to administration to a patient.

In certain preferred embodiments the aforementioned kits comprising compositions of the invention will comprise a label, marker, package insert, bar code and/or reader indicating that the kit contents may be used for the treatment, prevention and/or diagnosis of cancer. In other preferred embodiments the kit may comprise a label, marker, package insert, bar code and/or reader indicating that the kit contents may be administered in accordance with a certain dosage or dosing regimen to treat a subject suffering from cancer. In a particularly preferred aspect the label, marker, package insert, bar code and/or reader indicates that the kit contents may be used for the treatment, prevention and/or diagnosis of a hematologic malignancy (e.g., AML) or provide dosages or a dosing regimen for treatment of the same. In other particularly preferred aspects the label, marker, package insert, bar code and/or reader indicates that the kit contents may be used for the treatment, prevention and/or diagnosis of lung cancer (e.g., adenocarcinoma) or a dosing regimen for treatment of the same.

Suitable containers or receptacles include, for example, bottles, vials, syringes, infusion bags (i.v. bags), etc. The containers can be formed from a variety of materials such as glass or pharmaceutically compatible plastics. In certain embodiments the receptacle(s) can comprise a sterile access port. For example, the container may be an intravenous solution bag or a vial having a stopper that can be pierced by a hypodermic injection needle.

In some embodiments the kit can contain a means by which to administer the antibody and any optional components to a patient, e.g., one or more needles or syringes (pre-filled or empty), an eye dropper, pipette, or other such like apparatus, from which the formulation may be injected or introduced into the subject or applied to a diseased area of the body. The kits of the invention will also typically include a means for containing the vials, or such like, and other components in close confinement for commercial sale, such as, e.g., blow-molded plastic containers into which the desired vials and other apparatus are placed and retained.

X. MISCELLANEOUS

Unless otherwise defined herein, scientific and technical terms used in connection with the invention shall have the meanings that are commonly understood by those of ordinary skill in the art. Further, unless otherwise required by context, singular terms shall include pluralities and plural terms shall include the singular. In addition, ranges provided in the specification and appended claims include both end points and all points between the end points. Therefore, a range of 2.0 to 3.0 includes 2.0, 3.0, and all points between 2.0 and 3.0.

Generally, techniques of cell and tissue culture, molecular biology, immunology, microbiology, genetics and chemistry described herein are those well-known and commonly used in the art. The nomenclature used herein, in association with such techniques, is also commonly used in the art. The methods and techniques of the invention are generally performed according to conventional methods well known in the art and as described in various references that are cited throughout the present specification unless otherwise indicated.

XI. REFERENCES

The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PBD, and translations from annotated coding regions in GenBank and RefSeq) cited herein are incorporated by reference, regardless of whether the phrase "incorporated by reference" is or is not used in relation to the particular reference. The foregoing detailed description and the examples that follow have been given for clarity of understanding only. No unnecessary limitations are to be understood therefrom. The invention is not limited to the exact details shown and described. Variations obvious to one skilled in the art are included in the invention defined by the claims. Any section headings used herein are for organizational purposes only and are not to be construed as limiting the subject matter described.

EXAMPLES

The invention, generally described above, will be understood more readily by reference to the following examples, which are provided by way of illustration and are not intended to be limiting of the instant invention. The examples are not intended to represent that the experiments below are all or the only experiments performed. Unless indicated otherwise, parts are parts by weight, molecular weight is weight average molecular weight, temperature is in degrees Centigrade, and pressure is at or near atmospheric.

Sequence Listing Summary

Table 3 provides a summary of amino acid and nucleic acid sequences included herein.

TABLE 3

| SEQ ID NO | Description |
| --- | --- |
| 1 | Amino acid sequence of BMPR1B |
| 2 | IgG1 heavy chain constant region protein |
| 3 | C220S IgG1 heavy chain constant region protein |
| 4 | C220Δ IgG1 heavy chain constant region protein |
| 5 | kappa light chain constant region protein |
| 6 | C214S kappa light chain constant region protein |
| 7 | C214Δ kappa light chain constant region protein |
| 8 | lambda light chain constant region protein |
| 9 | C214S lambda light chain constant region protein |
| 10 | C214Δ lambda light chain constant region protein |
| 11-19 | reserved |
| 20 | SC91.1 VL DNA |
| 21 | SC91.1 VL protein |
| 22 | SC91.1 VH DNA |
| 23 | SC91.1 VH protein |
| 24-91 | Additional murine clones in the same order as SEQ ID NOS 20-23 |
| 92 | SC91.27 VH DNA |
| 93 | SC91.27 VH protein |
| 94 | SC91.186 VH DNA |
| 95 | SC91.186 VH protein |
| 96-99 | reserved |
| 100 | hSC91.1 VL DNA |
| 101 | hSC91.1 VL protein |
| 102 | hSC91.1 VH DNA |
| 103 | hSC91.1 VH protein |
| 104 | hSC91.1 VH DNA (N55Q) |
| 105 | hSC91.1 VH protein (N55Q) |
| 106 | hSC91.9 VL DNA |
| 107 | hSC91.9 VL protein |
| 108 | hSC91.9 VH DNA |
| 109 | hSC91.9 VH protein |
| 110 | hSC91.1 full length light chain protein |
| 111 | hSC91.1 full length heavy chain protein |
| 112 | reserved |
| 113 | hSC91.1MJ (N55Q) full length heavy chain protein |
| 114 | reserved |
| 115 | hSC91.1ss1 (N55Q) full length heavy chain protein |
| 116 | reserved |
| 117 | hSC91.1ss1MJ (N55Q) full length heavy chain protein |
| 118-119 | reserved |
| 120 | hSC91.9 full length light chain protein |
| 121 | hSC91.9 full length heavy chain protein |
| 122 | reserved |
| 123 | hSC91.9MJ full length heavy chain protein |
| 124 | reserved |
| 125 | hSC91.9ss1MJ full length heavy chain protein |
| 126 | hSC91.1v2 VH DNA |
| 127 | hSC91.1v2 VH protein |

Tumor Cell Line Summary

PDX tumor cell types are denoted by an abbreviation followed by a number, which indicates the particular tumor cell line. The passage number of the tested sample is indicated by p0-p# appended to the sample designation where p0 is indicative of an unpassaged sample obtained directly from a patient tumor and p# is indicative of the number of times the tumor has been passaged through a mouse prior to testing. As used herein, the abbreviations of the tumor types and subtypes are shown in Table 4 as follows:

TABLE 4

| Tumor Type | Abbreviation | Tumor subtype | Abbreviation |
|---|---|---|---|
| Acute myelogenous leukemia | AML | | |
| Bladder | BL | | |
| Breast | BR | | |
| | | basal-like | BR-Basal-Like |
| | | estrogen receptor positive and/or progesterone receptor positive | BR-ERPR |
| | | ERBB2/Neu positive | BR-ERBB2/Neu |
| | | HER2 positive | BR-HER2 |
| | | triple-negative | TNBC |
| | | luminal A | BR-LumA |
| | | luminal B | BR-LumB |
| | | claudin subtype of triple-negative | TNBC-CL |
| | | claudin low | BR-CLDN-Low |
| | | normal-like | BR-NL |
| Cervical | CER | | |
| Colorectal | CR | | |
| | | rectum adenocarcinoma | RE-Ad |
| Endometrial | EM | | |
| Esophageal | ES | | |
| Gastric | GA | | |
| | | diffuse adenocarcinoma | GA-Ad-Dif/Muc |
| | | intestinal adenocarcinoma | GA-Ad-Int |
| | | stromal tumors | GA-GIST |
| Glioblastoma | GB | | |
| Head and neck | HN | | |
| Kidney | KDY | | |
| | | clear renal cell carcinoma | KDY-CC |
| | | papillary renal cell carcinoma | KDY-PAP |
| | | transitional cell or urothelial carcinoma | KDY-URO |
| | | unknown | KDY-UNK |
| Liver | LIV | | |
| | | hepatocellular carcinoma | LIV-HCC |
| | | cholangiocarcinoma | LIV-CHOL |
| Lymphoma | LYM | | |
| | DLBC | diffuse large B-cell | |
| Lung | LU | | |
| | | adenocarcinoma | LU-Ad |
| | | carcinoid | LU-CAR |
| | | large cell neuroendocrine | LU-LCC |
| | | non-small cell | NSCLC |
| | | squamous cell | LU-SCC |
| | | small cell | SCLC |
| | | spindle cell | LU-SPC |
| Multiple Myeloma | MM | | |
| Ovarian | OV | | |
| | | clear cell | OV-CC |
| | | endometroid | OV-END |
| | | mixed subtype | OV-MIX |
| | | malignant mixed mesodermal | OV-MMMT |
| | | mucinous | OV-MUC |
| | | neuroendocrine | OV-NET |
| | | papillary serous | OV-PS |
| | | serous | OV-S |
| | | small cell | OV-SC |
| | | transitional cell carcinoma | OV-TCC |
| Pancreatic | PA | | |
| | | acinar cell carcinoma | PA-ACC |
| | | duodenal carcinoma | PA-DC |
| | | mucinous adenocarcinoma | PA-MAD |
| | | neuroendocrine | PA-NET |
| | | adenocarcinoma | PA-PAC |
| | | adenocarcinoma exocrine type | PA-PACe |
| | | ductal adenocarcinoma | PA-PDAC |
| | | ampullary adenocarcinoma | PA-AAC |

TABLE 4-continued

| Tumor Type | Abbreviation | Tumor subtype | Abbreviation |
|---|---|---|---|
| Prostate | PR | | |
| Skin | SK | | |
| | | melanoma | MEL |
| | | squamous cell carcinomas | SK-SCC |
| | | uveal melanoma | UVM |
| Testicular | TES | | |
| Thyroid | THY | | |
| | | medullary thyroid carcinoma | MTC |

Example 1

Identification of BMPR1B Expression Using Whole Transcriptome Sequencing

To characterize the cellular heterogeneity of solid tumors as they exist in cancer patients and identify clinically relevant therapeutic targets, a large PDX tumor bank was developed and maintained using art recognized techniques. The PDX tumor bank, comprising a large number of discrete tumor cell lines, was propagated in immunocompromised mice through multiple passages of tumor cells originally obtained from cancer patients afflicted by a variety of solid tumor malignancies. Low passage PDX tumors are representative of tumors in their native environments, providing clinically relevant insight into underlying mechanisms driving tumor growth and resistance to current therapies.

As previously alluded to tumor cells may be divided broadly into two types of cell subpopulations: non-tumorigenic cells (NTG) and tumor initiating cells (TICs). TICs have the ability to form tumors when implanted into immunocompromised mice. Cancer stem cells (CSCs) are a subset of TICs that are able to self-replicate indefinitely while maintaining the capacity for multilineage differentiation. NTGs, while sometimes able to grow in vivo, will not form tumors that recapitulate the heterogeneity of the original tumor when implanted.

In order to perform whole transcriptome analysis, PDX tumors were resected from mice after they reached 800-2,000 mm$^3$ or for AML after the leukemia was established in the bone marrow (<5% of bone marrow cellularity of human origin). Resected PDX tumors were dissociated into single cell suspensions using art-recognized enzymatic digestion techniques (see, for example, U.S.P.N. 2007/0292414). Dissociated bulk tumor cells were incubated with 4',6-diamidino-2-phenylindole (DAPI) to detect dead cells, anti-mouse CD45 and H-2K$^d$ antibodies to identify mouse cells and anti-human EPCAM antibody to identify human cells. In addition the tumor cells were incubated with fluorescently conjugated anti-human CD46 and/or CD324 antibodies to identify CD324$^+$ CSCs or CD324$^-$ NTG cells and were then sorted using a FACS Aria cell sorter (BD Biosciences) (see U.S.P.Ns 2013/0260385, 2013/0061340 and 2013/0061342). Anti-human CD49f and EPCAM antibodies were also used to identify four different subpopulations as described by Lim et. al., 2009 (PMID: 19648928) within the normal human breast, including differentiated luminal, progenitor and mammary stem/basal epithelial cells, as well as stromal cells.

RNA was extracted from tumor cells by lysing the cells in RLTplus RNA lysis buffer (Qiagen) supplemented with 1% 2-mercaptoethanol, freezing the lysates at −80° C. and then thawing the lysates for RNA extraction using an RNeasy isolation kit (Qiagen). RNA was quantified using a Nanodrop spectrophotometer (Thermo Scientific) and/or a Bioanalyzer 2100 (Agilent Technologies). Normal tissue RNA was purchased from various sources (Life Technology, Agilent, ScienCell, BioChain, and Clontech). The resulting total RNA preparations were assessed by genetic sequencing and gene expression analyses.

More particularly whole transcriptome sequencing of high quality RNA was performed using Illumina HiSeq 2000 or 2500 next generation sequencing system (Illumina, Inc.).

Figure 2:
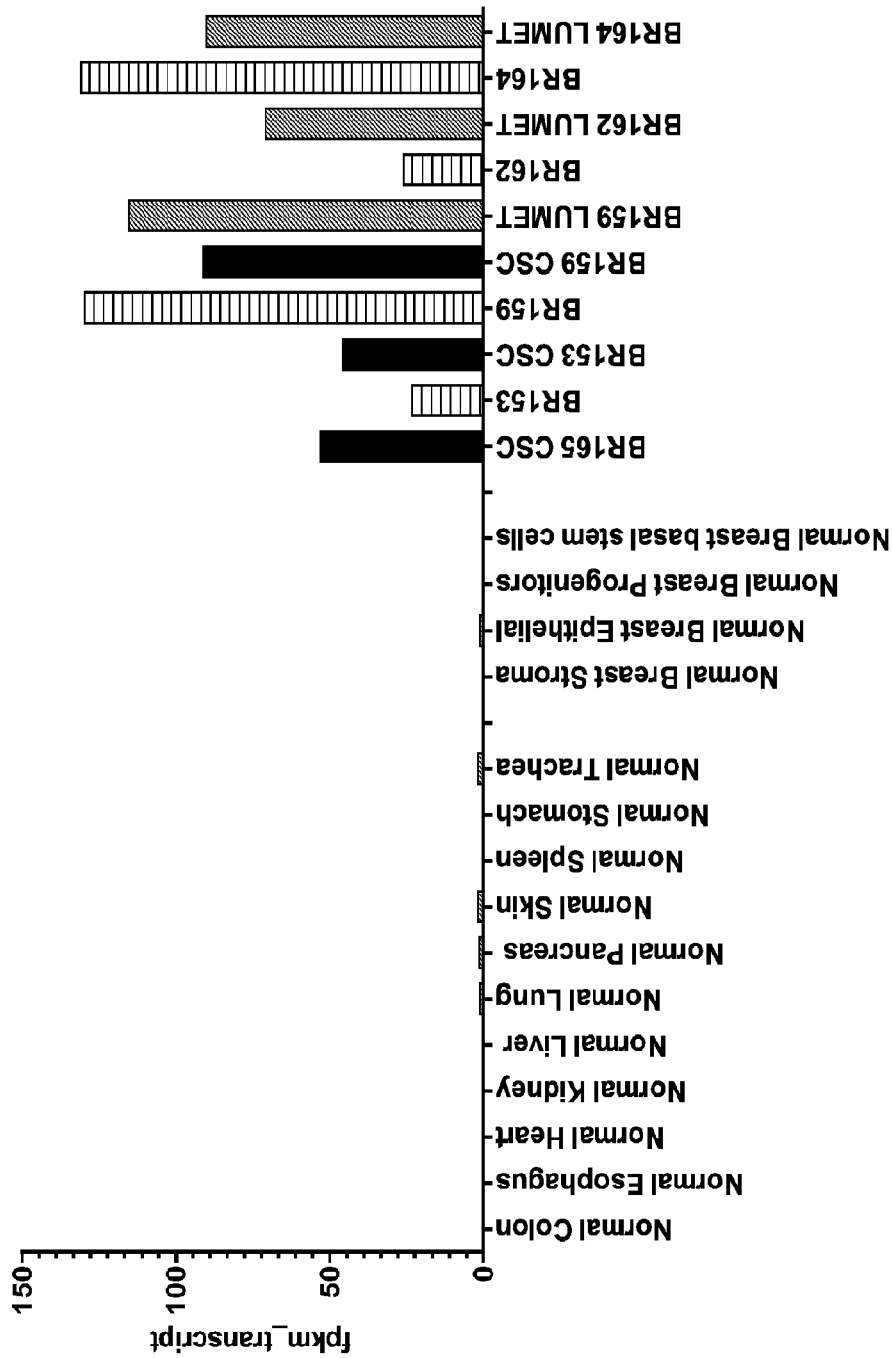
FIG. 2 shows expression levels of BMPR1B as measured through whole transcriptome sequencing using an Illumina platform where the samples comprise (BR-LumB) PDX tumors (patterned bars), lung metastases arising in BR-LumB PDX bearing mice (dark grey bars), sorted breast cancer stem cell subpopulations (black bars) and normal tissue controls.

Illumina whole transcriptome analysis was performed with cDNA that was generated using 5 ng total RNA extracted from either bulk, metastasized lung (LU MET) or CSC tumor subpopulations that were isolated as described above. The library was created using the TruSeq RNA Sample Preparation Kit v2 (Illumina, Inc.). The resulting cDNA library was fragmented and barcoded. Sequencing data from the Illumina platform is nominally represented as a fragment expression value using the metric FPKM (fragment per kilobase per million) mapped to exon regions of genes, enabling basic gene expression analysis to be normalized and enumerated as FPKM transcript. As shown in FIG. 2 BMPR1B mRNA expression is upregulated in luminal B (BR-LumB) PDX tumors (patterned bars), lung metastases arising in BR-LumB PDX bearing mice (dark grey bars) and sorted breast cancer stem cell subpopulations (black bars). BMPR1B expression was generally higher in BR-LumB tumors than BMPR1B expression in both normal tissues and various sorted normal breast populations.

The identification of elevated BMPR1B mRNA expression in BR-LumB tumor, lung metastases and CSC populations indicated that BMPR1B has potential as a diagnostic and immunotherapeutic target. Furthermore, increased expression of BMPR1B in sorted populations indicates that BMPR1B is a good marker of tumorigenic cells. This is particularly true of BR-LumB derived cells.

Example 2

Expression of BMPR1B mRNA in Tumors Using qRT-PCR

To confirm BMPR1B RNA expression in tumor cells, qRT-PCR was performed on various PDX cell lines using the Fluidigm BioMark™ HD System according to industry standard protocols. RNA was extracted from bulk PDX tumor cells or sorted CSC and NTG subpopulations as described in Example 1. Following extraction 1.0 ng of RNA was converted to cDNA using the High Capacity cDNA Archive kit (Life Technologies) according to the manufacturer's instructions. cDNA material, pre-amplified using an BMPR1B probe specific Taqman assay, was then used for subsequent qRT-PCR experiments BMPR1B expression in normal tissues (NormTox or Norm) was compared to expression in various molecular subtypes of breast (BR) tumors—unclassified BR, BR-Basal Like, BR-HER2 positive, BR-LumA, and BR-LumB, as well as NSCLC (LU-Ad and LU-SCC), OV-S/PS and pancreatic (PA-PAC/PDAC) PDX as well as primary prostate (PR) tumor samples (FIG. 3; each dot represents the average relative expression of each individual tissue or PDX cell line, with the small horizontal line representing the geometric mean). "NormTox" represents samples of various normal tissues as follows: adrenal, colon, dorsal root ganglion, endothelial cells (artery, vein), esophagus, heart, kidney, liver, lung, pancreas, skeletal muscle, skin (fibroblasts, keratinocytes), small intestine, spleen, stomach, and trachea. Another set of normal tissues designated "Norm" represents the following samples of normal tissue with a presumed lower risk for toxicity in relation to ADC-type drugs: peripheral blood mononuclear cells and various sorted subpopulations (B cells, monocytes, NK cells, neutrophils, T cells), adipose, bladder, brain, breast, cervix, fetal liver, melanocytes, normal bone marrow and various sorted subpopulations, ovary, prostate, testes, thymus, thyroid and uterus.

Figure 3:
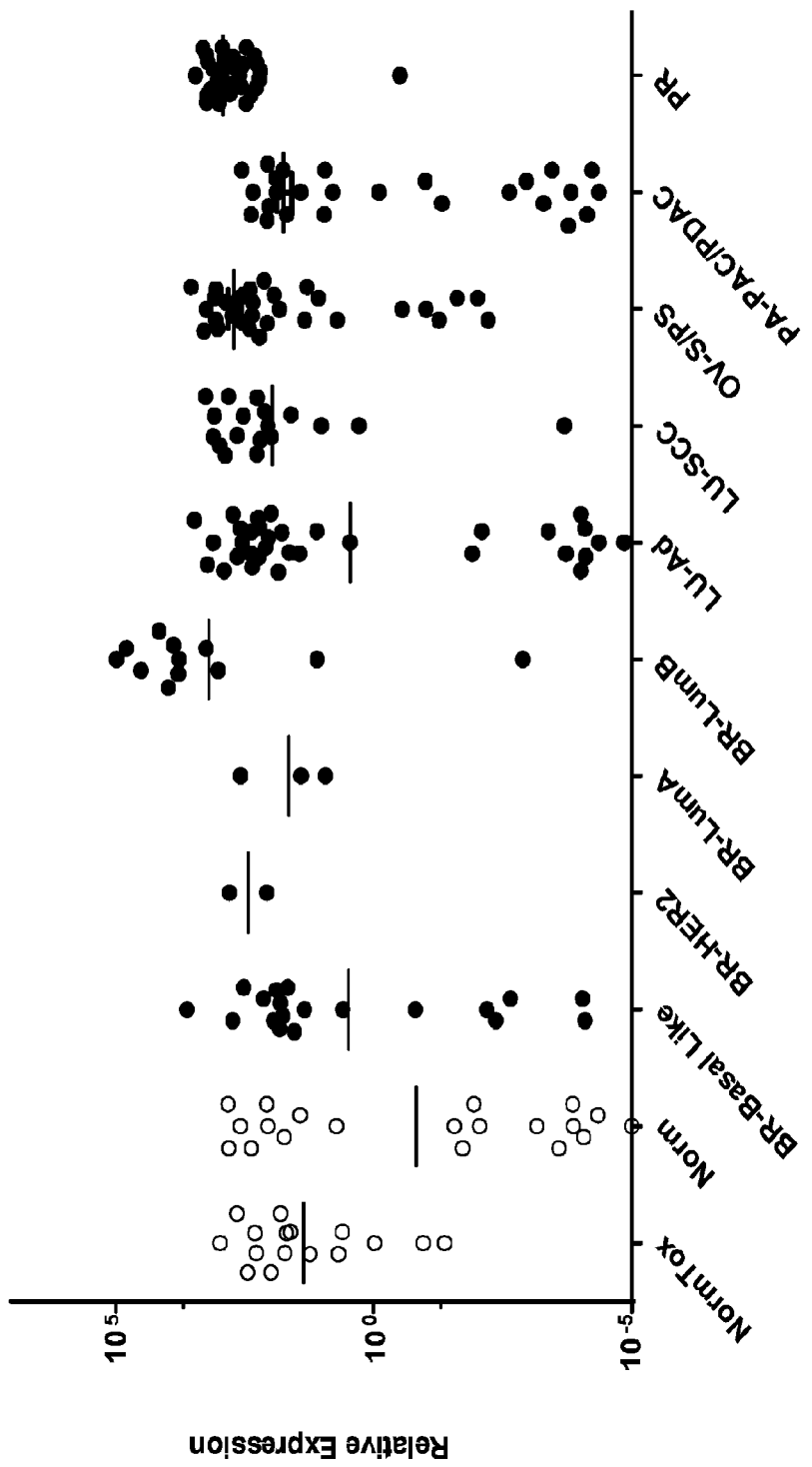
FIG. 3 depicts the relative expression levels of BMPR1B transcripts as measured by qRT-PCR in RNA samples isolated from normal tissue and from a variety of PDX tumors and normal tissue controls.

FIG. 3 shows that on average BMPR1B expression was elevated in BR-Lum PDX and primary PR tumors, with lower expression seen in other molecular subtypes of BR, LU-Ad, LU-SCC, PA-PAC/PDAC and OV, though the geometric mean was lower overall in these tumor specimens. This data supports the earlier finding of elevated expression of BMPR1B in Lum-B and in addition highlights overexpression in primary PR tumors compared to most normal tissues.

Example 3

Determination of Expression of BMPR1B mRNA in Tumors Using Microarray Analysis

Microarray experiments to determine the expression levels of BMPR1B in various tumor cell lines were conducted and data was analyzed as follows. 1-2 µg of whole tumor total RNA was extracted, substantially as described in Example 1, from various molecular subtypes of BR PDX (BR-Basal like, BR-CLDN-Low, BR-HER2, BR-LumA, BR-LumB, BR-NL) as well as primary BR tumor samples representing various molecular subtypes. Additionally, RNA was extracted from samples of normal tissues (e.g., breast, colon, heart, kidney, liver, lung, ovary, pancreas, skin, spleen, PBMC, and stomach). The RNA samples were analyzed using the Agilent SurePrint GE Human 8×60 v2 microarray platform, which contains 50,599 biological probes designed against 27,958 genes and 7,419 lncRNAs in the human genome. Standard industry practices were used to normalize and transform the intensity values to quantify gene expression for each sample. The normalized intensity of BMPR1B expression in each sample is plotted in FIG. 4 and the geometric mean derived for each tumor type is indicated by the horizontal bar.

Figure 4:
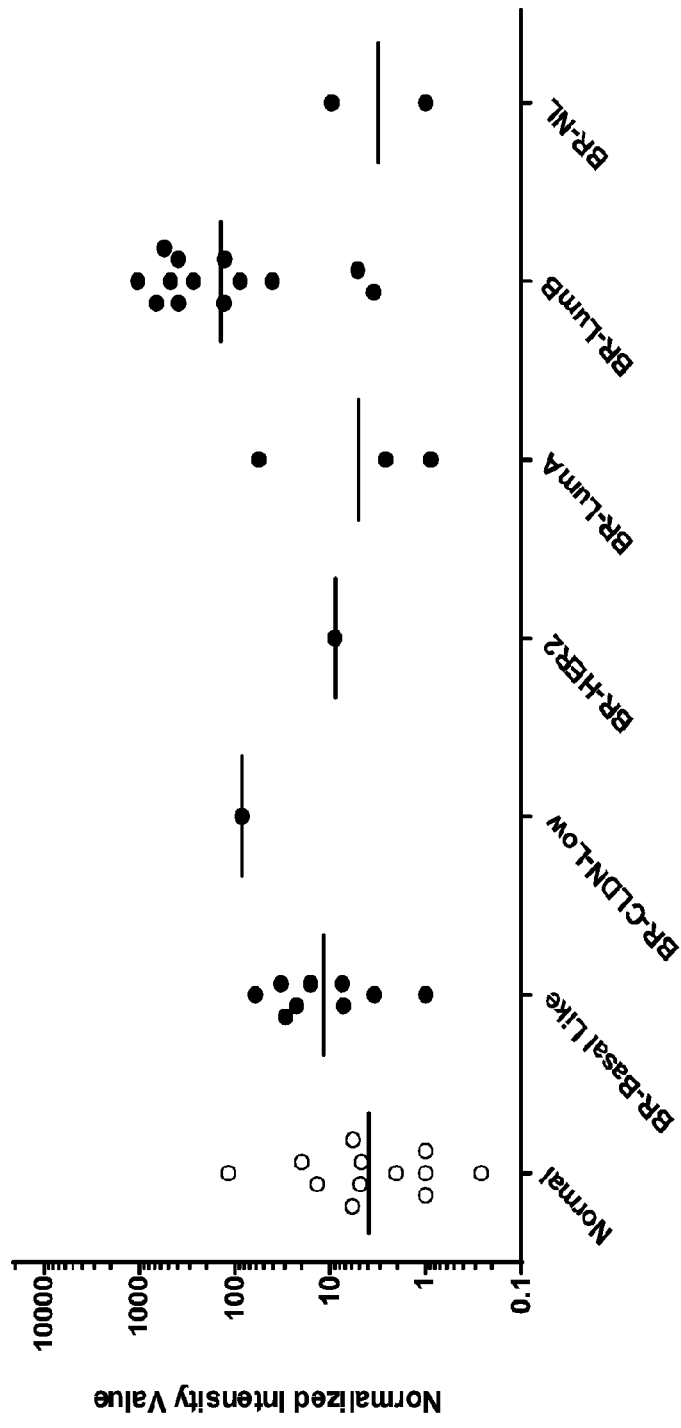
FIG. 4 shows the normalized intensity value of BMPR1B transcript expression measured by microarray hybridization on RNA derived from normal tissues and a variety of PDX cell lines.

A closer review of FIG. 4 shows that BMPR1B expression is upregulated in most BR-LumB and BR-basal like PDX lines compared to normal tissues and other molecular subtypes of breast cancer. The observation of elevated BMPR1B expression in the aforementioned tumor types confirms the results of the previous Examples.

Example 4

BMPR1B Expression in Tumors Using the Cancer Genome Atlas

Figure 5:
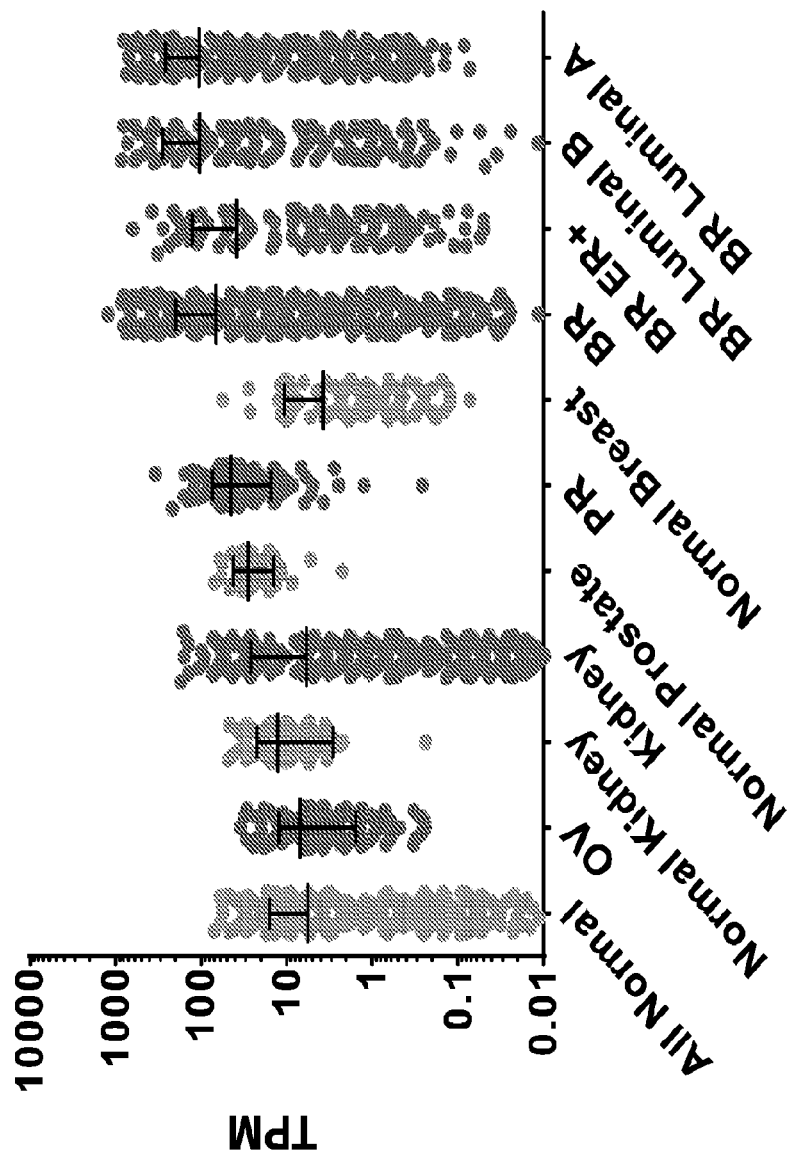
FIG. 5 shows expression levels of BMPR1B transcripts in normal tissues and primary tumors as mined from The Cancer Genome Atlas (TCGA), a publicly available dataset.

Overexpression of BMPR1B mRNA in various tumors was confirmed using a large, publically available dataset of primary tumors and normal samples known as The Cancer Genome Atlas (TCGA). BMPR1B expression data from the IlluminaHiSeq_RNASeqV2 platform was downloaded from the Genomic Data Commons (GDC) Legacy Archive (https://gdc-portal.nci.nih.gov/legacy-archive) and the scaled_estimate from RSEM was multiplied by 1,000,000 to yield transcripts per million (TPM) [Li and Dewey, BMC Bioinformatics 2011]. FIG. 5 shows that BMPR1B expression is elevated in breast, prostate adenocarcinoma, ovarian and chromophobe renal cell carcinoma (KICH) primary patient samples compared to normal tissue. These data further confirm that elevated levels of BMPR1B mRNA may be found in various tumor types, indicating that anti-BMPR1B antibodies and ADCs may be useful therapeutics for these tumors.

Figure 6A:
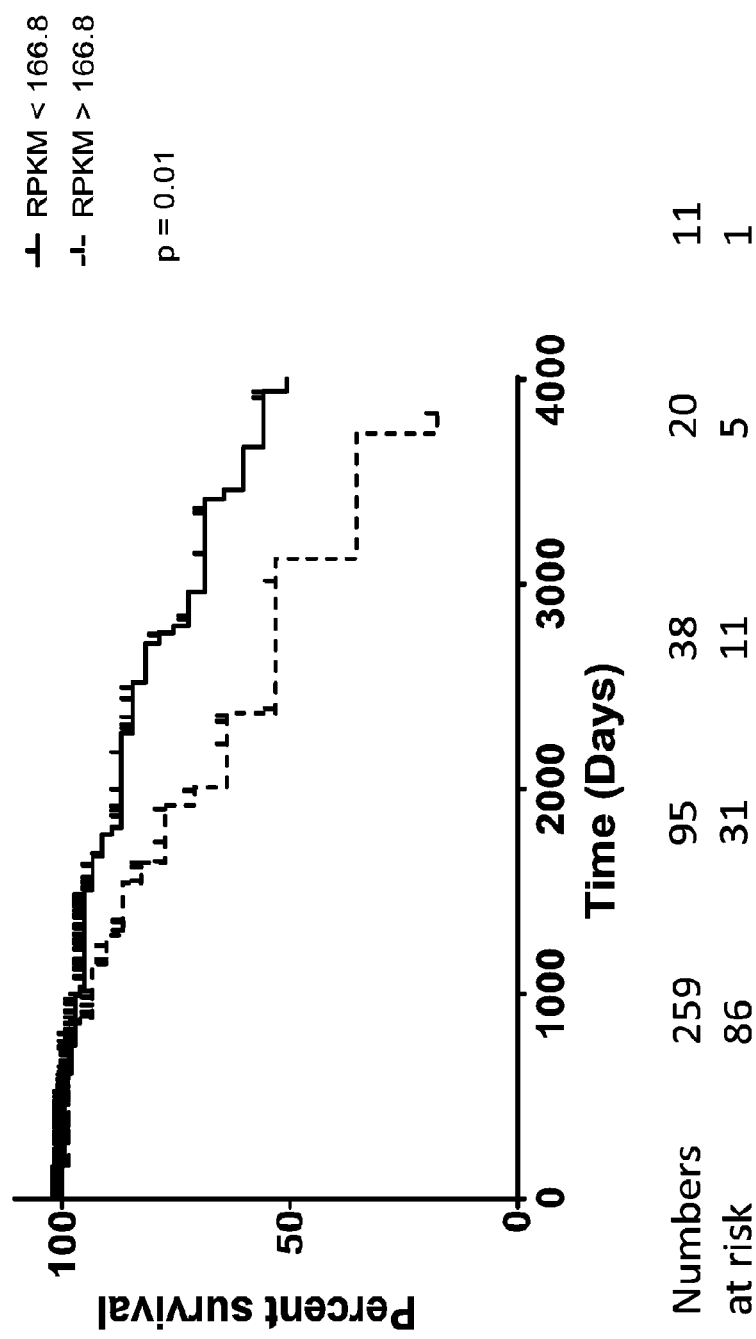
FIGS. 6A-6C depict Kaplan-Meier survival curves based on high and low expression of BMPR1B transcripts in; (a) primary Luminal A breast tumors from the TCGA dataset (FIG. 6A) wherein the threshold index value is determined using the arithmetic mean of the TPM values; (b) in primary chromophobe renal cell carcinoma (KICH) tumors from the TCGA dataset (FIG. 6B) wherein the threshold index value is determined using the arithmetic mean of the RPKM values; and (c) primary Luminal A breast tumors from the METABRIC dataset (FIG. 6C) wherein the threshold index value is derived from normalized Illumina HT-12 Expression Beadchip values.

FIG. 6A shows Kaplan Meier survival curves for a subset of BR-LumA TCGA tumors where patient survival data was available. Patients were stratified based on high expression of BMPR1B mRNA i.e. expression over the threshold index value or low expression of BMPR1B mRNA i.e. expression under the threshold index value in BR-LumA tumors. The threshold index value was calculated as 166.8 which is the 75% quartile of the TPM values. The "numbers at risk" listed below the plot shows the number of surviving patients remaining in the dataset every 1000 days after the day at which each patient was first diagnosed (day 0). The two survival curves are significantly different (p=0.01) by the Log-rank (Mantel-Cox) test or p=0.09 by the Gehan-Breslow-Wilcoxon test. These data show that patients with BR-LumA tumors exhibiting high expression of BMPR1B have a shorter survival time compared to patients with BR-LumA tumors exhibiting low expression of BMPR1B.

Overexpression of BMPR1B mRNA in various tumors was also confirmed using a large, publically available dataset of primary tumors and normal samples known as The Cancer Genome Atlas (TCGA). BMPR1B expression data from the IlluminaHiSeq_RNASeqV2 and Illumina-HiSeq_RNASeq platforms was downloaded from the TCGA Data Portal (https://tcga-data.nci.nih.gov/tcga/tcgaDownload.jsp) and parsed to aggregate the reads from the individual exons of each gene to generate a single value read per kilobase of exon per million mapped reads (RPKM).

Figure 6B:
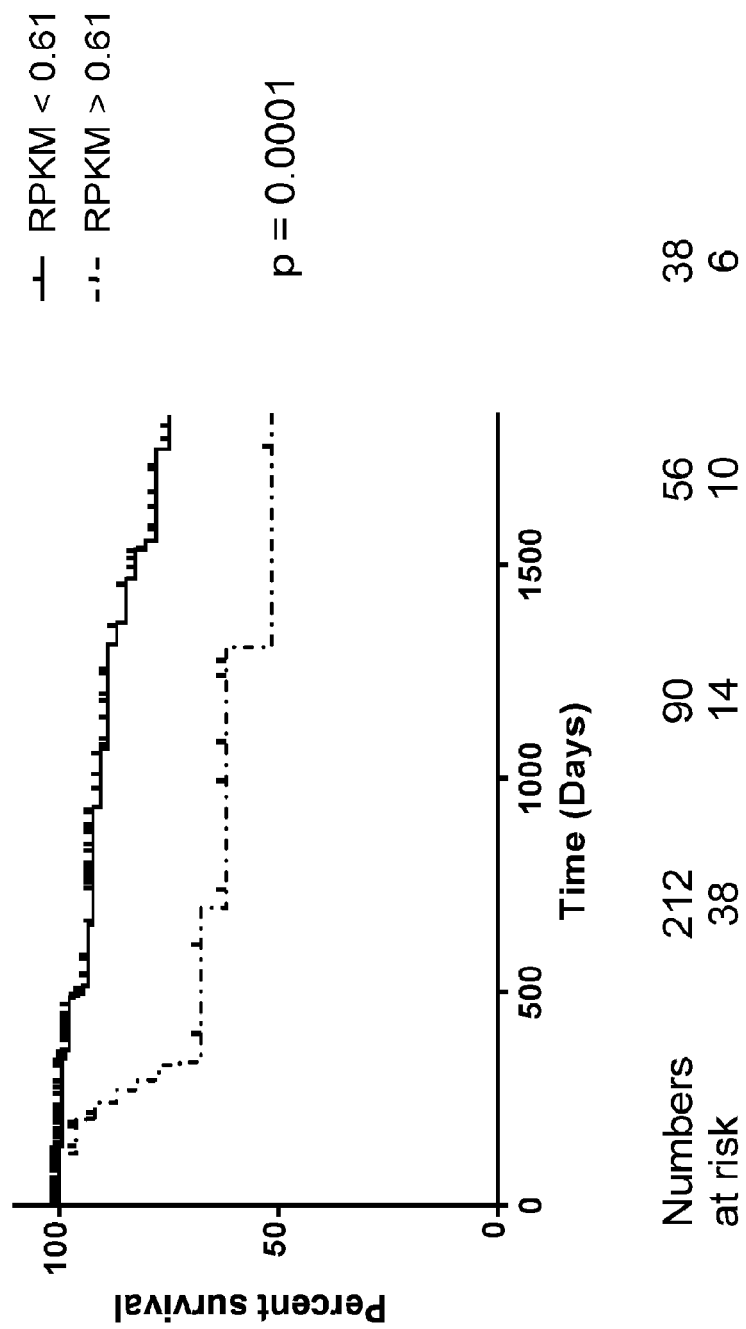

FIG. 6B shows Kaplan Meier survival curves for a subset of KICH TCGA tumors where patient survival data was available. Patients were stratified based on high expression of BMPR1B mRNA i.e. expression over the threshold index value or low expression of BMPR1B mRNA i.e. expression under the threshold index value in KICH tumors. The threshold index value was calculated as 0.61 which is the $85^{th}$ percentile of the RPKM values. The "numbers at risk" listed below the plot shows the number of surviving patients remaining in the dataset every 500 days after the day at which each patient was first diagnosed (day 0). The two survival curves are significantly different (p=0.0020) by the Log-rank (Mantel-Cox) test or p=0.0001 by the Gehan-Breslow-Wilcoxon test. These data show that patients with KICH tumors exhibiting high expression of BMPR1B have a shorter survival time compared to patients with KICH tumors exhibiting low expression of BMPR1B.

Based on the results derived from the TCGA database a decision was made to interrogate other data sources to confirm the findings set forth immediately above. In this regard data generated by the Molecular Taxonomy of Breast Cancer International Consortium, commonly termed the METABRIC dataset (Curtis et al., Nature 2012 Apr. 18; 486 (7403):346-52, PMID 22522925), was probed to determine survival rates for certain subsets of breast cancer patients. The resulting data is set forth in FIG. 6C appended hereto.

Figure 6C:
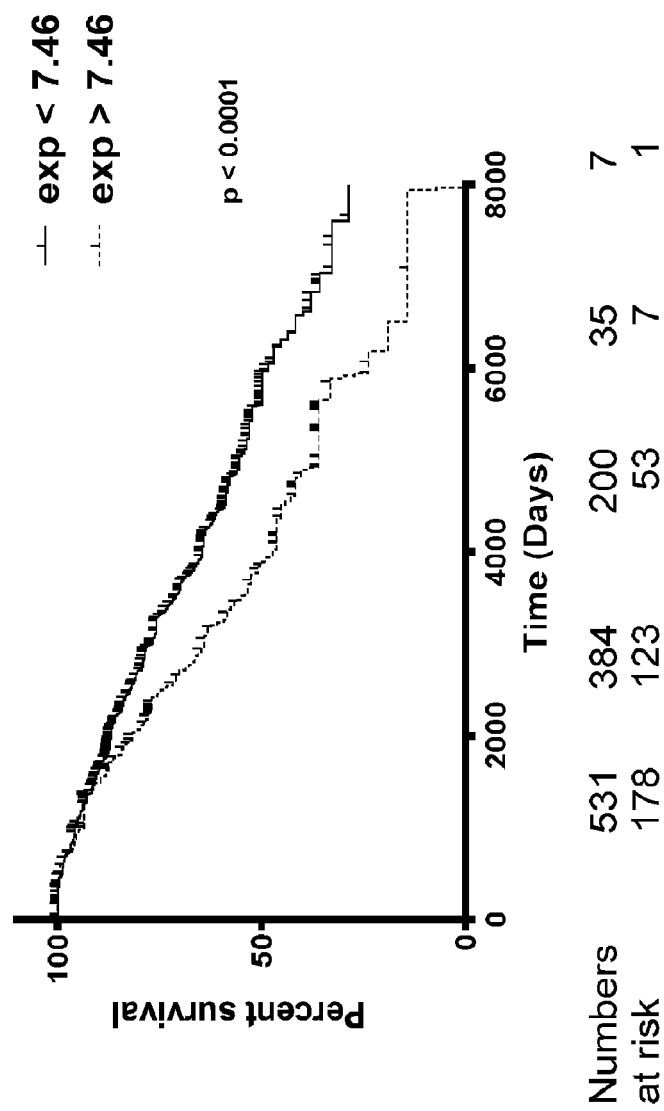

More specifically, FIG. 6C shows Kaplan Meier survival curves for a subset of BR-LumA METABRIC dataset tumors where patient survival data was available. Patients were stratified based on high expression of BMPR1B mRNA i.e. expression over the threshold index value or low expression of BMPR1B mRNA i.e. expression under the threshold index value in BR-LumA tumors. Expression values are normalized values (HT-12 Expression Beadchip Kit, Illumina) from the METABRIC study. The normalization procedure is described in detail in Curtis et al., supra. The threshold index value was calculated as the third quartile of the normalized expression values, which was calculated to be 7.46.

The "numbers at risk" listed below the plot in FIG. 6C shows the number of surviving patients remaining in the dataset every 2000 days after the day at which each patient was first diagnosed (day 0). The two survival curves are significantly different (p<0.0001) by the Log-rank (Mantel-Cox) test or p=0.0014 by the Gehan-Breslow-Wilcoxon test. As with the results from the TCGA dataset these data show that patients with BR-LumA tumors exhibiting high expression of BMPR1B have a shorter survival time compared to patients with BR-LumA tumors exhibiting low expression of BMPR1B.

Taken together these data suggest the usefulness of anti-BMPR1B therapies to treat KICH and BR-LumA, and the usefulness of BMPR1B expression as a prognostic biomarker on the basis of which treatment decisions can be made. In this regard, it may be clinically beneficial to treat patients exhibiting high levels of BMPR1B sooner rather than waiting until they finish one or more courses of standard of care chemotherapy.

Example 5

Cloning and Expression of Recombinant BMPR1B Proteins and Engineering of Cell Lines Overexpressing Cell Surface BMPR1B Proteins Human BMPR1B (hBMPR1B) Lentiviral DNA Constructs To generate cell lines overexpressing hBMPR1B protein, lentiviral vectors containing an open reading frame encoding the hBMPR1B protein were constructed as follows. First, standard molecular cloning techniques were used to introduce nucleotide sequences encoding an IgK signal peptide followed by an Asp-Lys epitope tag upstream of the multiple cloning site of pCDH-CMV-MCS-EF1-copGFP (System Biosciences), creating the vector pLMEGPA. This dual promoter construct employs a CMV promoter to drive expression of Asp-Lys-tagged cell-surface proteins independent of a downstream EF1 promoter that drives expression of the copGFP T2A Puro reporter and selectable marker. The T2A sequence in pLMEGPA promotes ribosomal skipping of a peptide bond condensation, resulting in expression of two independent proteins: high level expression of the reporter copGFP encoded upstream of the T2A peptide, with co-expression of the Puro selectable marker protein encoded downstream of the T2A peptide to allow selection of transduced cells in the presence of puromycin.

A synthetic DNA fragment encoding the hBMPR1B protein was ordered from GeneArt (ThermoFisher Scientific) using NCBI accession NM_001203 as reference for design. The synthetic gene was codon optimized for expression in mammalian lines, and was flanked with restriction endonuclease sites to enable in-frame subcloning downstream of the IgK signal peptide-Asp-Lys epitope tag in pLMEGPA. This yielded the pLMEGPA-hBMPR1B-NFlag lentiviral vector, which encodes a fusion protein with the Asp-Lys tag appended to the N-terminus of the hBMPR1B protein.

DNA Constructs Encoding hBMPR1B Extracellular Domain (ECD) Fusion Proteins.

To generate fusion proteins containing the ECD of the hBMPR1B protein, PCR was performed using the pLMEGPA-hBMPR1B-NFlag DNA as template and primers that would amplify a fragment of the hBMPR1B ORF between residues K14 and R126, inclusive. This PCR-amplified DNA was subcloned into a CMV-driven expression vector in-frame and downstream of an immunoglobulin kappa (IgK) signal peptide sequence and upstream and in-frame with DNA encoding either a 9×-Histidine tag (yielding pEMA-hBMPR1B-CHis) or a human IgG2 Fc protein (yielding pEMA-hBMPR1B-Fc), using standard molecular techniques. These CMV-driven expression vectors permit high level transient expression in HEK293T and/or CHO-S cells.

Cynomolgus BMPR1B (cBMPR1B) DNA Constructs

To generate cell lines overexpressing cBMPR1B protein, the lentiviral vector pLMEGPA-cBMPR1B-NFlag was constructed by subcloning a codon-optimized, synthetic DNA fragment (GeneArt) encoding the cBMPR1B protein (sequence derived from NCBI accession XP_005555526) into the multiple cloning site of the lentiviral vector pLMEGPA described above. The pLMEGPA dual promoter lentiviral vector permits co-expression of the N-terminal Asp-Lys-tagged cBMPR1B protein along with GFP and puromycin N-acetyl transferase selection markers.

To generate fusion proteins containing the ECD of the cBMPR1B protein, a synthetic DNA fragment (GeneArt) encoding the ECD of cBMPR1B (e.g., residues K14 to K126, inclusive) was subcloned into a CMV-driven expression vector in-frame and downstream of an immunoglobulin kappa (IgK) signal peptide sequence and upstream and in-frame with DNA encoding either a 9×-Histidine tag (yielding pEMA-cBMPR1B-CHis) or a human IgG2 Fc protein (yielding pEMA-cBMPR1B-Fc), using standard molecular techniques.

Rat BMPR1B (rBMPR1B) DNA Constructs

To generate cell lines overexpressing rBMPR1B protein, the lentiviral vector pLMEGPA-rBMPR1B-NFlag was constructed by subcloning a codon-optimized, synthetic DNA fragment (GeneArt) encoding the rBMPR1B protein (sequence derived from NCBI accession XM_006233398) into the multiple cloning site of the lentiviral vector pLMEGPA described above. The pLMEGPA dual promoter lentiviral vector permits co-expression of the N-terminal Asp-Lys-tagged rBMPR1B protein along with GFP and puromycin N-acetyl transferase selection markers.

To generate fusion proteins containing the ECD of the rBMPR1B protein, PCR was performed using the pLMEGPA-rBMPR1B-NFlag DNA as template and primers that would amplify a fragment of the rat BMPR1B ORF between residues K14 and K126, inclusive. This PCR-amplified DNA was subcloned into a CMV-driven expression vector in-frame and downstream of an immunoglobulin kappa (IgK) signal peptide sequence and upstream and in-frame with DNA encoding either a 9×-Histidine tag (yielding pEMA-rBMPR1B-CHis) or a human IgG2 Fc protein (yielding pEMA-rBMPR1B-Fc), using standard molecular techniques.

BMPR1B ECD Fusion Protein Production

Suspension or adherent cultures of HEK293T cells, or suspension CHO-S cells were transfected with an expression construct selected from one of the following: pEMA-hBMPR1B-CHis, pEMA-hBMPR1B-Fc, pEMA-cBMPR1B-CHis, pEMA-cBMPR1B-Fc, pEMA-rBMPR1B-CHis, or pEMA-rBMPR1B-Fc, using polyethylenimine polymer as the transfecting reagent. Three to five days after transfection, the His or Fc fusion proteins were purified from clarified cell-supernatants using either Nickel-EDTA (Qiagen) or MabSelect SuRe™ Protein A (GE Healthcare Life Sciences) columns as appropriate to the tag, per manufacturer's instructions.

Cell Line Engineering

Lentiviral vectors—pLMEGPA-hBMPR1B-NFlag, pLMEGPA-cBMPR1B-NFlag, or pLMEGPA-rBMPR1B-NFlag—were used to create stable HEK293T-based cell lines overexpressing hBMPR1B, cBMPR1B, or rBMPR1B proteins, respectively, using standard lentiviral transduction techniques well known to those skilled in the art. Transduced cells were selected using puromycin, followed by fluorescent activated cell sorting (FACS) of high-expressing HEK293T subclones (e.g., cells that were strongly positive for GFP and the Asp-Lys-tag).

Example 6

Generation of BMPR1B Antibodies

Anti-BMPR1B mouse antibodies were produced by inoculating three mice, one BALB/c, one CD-1 and one FVB, with 10 µg hBMPR1B protein, emulsified with an equal volume of TiterMax® Gold Adjuvant (Sigma Aldrich #H4 T2684-1ML). Following the initial inoculation, the mice were injected at weekly intervals, 9 times with 10 µg hBMPR1B protein emulsified with an equal volume of Imject® Alum (ThermoScientific #77161) plus "CpG" (InvivoGen ODN1826 #tlr1-1826-1). The final injection prior to the fusion was with 10 µg hBMPR1B in PBS.

Mice were sacrificed and draining lymph nodes (popliteal, inguinal, and medial iliac) were dissected and used as a source for antibody producing cells. A single-cell suspension of B cells was produced and ($210 \times 10^6$ cells) were fused with non-secreting SP2/0-Ag14 myeloma cells (ATCC #CRL-1581) at a ratio of 1:1 by electro cell fusion using a model BTX Hybrimmune System (BTX Harvard Apparatus). Cells were re-suspended in hybridoma selection medium consisting of DMEM medium supplemented with azaserine, 15% fetal clone I serum (Thermo #SH30080-03), 10% BM condimed (Roche #10663573001), 1 mM nonessential amino acids (Corning #25-025-CI) 1 mM HEPES Corning #25-060-CI), 100 IU penicillin-streptomycin (Corning #30-002-CI), 100 IU L-glutamine (Corning #25-005-CI) and were cultured in two T225 flasks containing 100 mL selection medium. The flasks were placed in a humidified 37° C. incubator containing 7% $CO_2$ and 95% air for 6 days.

On days 6 and 7 after the fusion, the Hybridoma cells were sorted from the flask and plated at one cell per well (using a BD FACSAria cell sorter) in 90 µL of supplemented hybridoma selection medium (as described above) into 12 Falcon 384-well plates. Remaining unused hybridoma library cells were frozen in liquid nitrogen for future library testing and screening.

Sorted clonal hybridomas were cultured for 8 days and the supernatants were collected, re-arrayed onto 384-well plates, and screened for antibodies specific to hBMPR1B (human) and rBMPR1B (rat) expressed on the surface of transduced HEK/293T cells using flow cytometry, as follows. A mixture of the 293T cells stably transduced with hBMPR1B and rBMPR1B in each well were incubated for 30 minutes with 25 µL hybridoma supernatant and then washed with PBS/2% FCS. Cells were incubated for 15 minutes with 25 µL per sample Alexa Fluor® 647 AffiniPure F(ab')2 Fragment Goat Anti-Mouse IgG, Fcγ Fragment Specific secondary antibody diluted in PBS/2% FCS, washed twice and re-suspended with PBS/2% FCS. The cells were then analyzed by flow cytometry (BD FACSCanto II).

From this initial screen (screen 1) a number of hBMPR1B/rBMPR1B immunospecific antibodies (termed SC91.1 to SC91.84, see FIG. 7A) were identified.

A similar screening process was subsequently conducted (screen 2) using the same hybridoma library to provide additional anti-BMPR1B antibodies of interest (termed SC91.101-SC91.195, see FIG. 7B). This time stably transduced 293T cells with cBMPR1B expression were also used. Sorted clonal hybridomas were cultured for 8 days and supernatants were collected, re-arrayed onto 384-well plates, and screened for antibodies specific to hBMPR1B, cBMPR1B and rBMPR1B expressed on the surface of transduced HEK/293T cells (ATCC CRL-11268) using flow cytometry, as follows. A mixture of the 293T cells stably transduced with hBMPR1B, cBMPR1B and rBMPR1B in each well were incubated for 30 minutes with 25 µL hybridoma supernatant and then washed with PBS/2% FCS. Cells were incubated for 15 minutes with 25 µL per sample Alexa Fluor® 647 AffiniPure F(ab')2 Fragment Goat Anti-Mouse IgG, Fcγ Fragment Specific secondary antibody diluted in PBS/2% FCS, washed twice and re-suspended with PBS/2% FCS. The cells were then analyzed by flow cytometry (BD FACSCanto II). This second screen identified a number of hBMPR1B/cBMPR1B/rBMPR1B immunospecific antibodies that may be used in conjunction with the teachings herein.

Example 7

Characteristics of BMPR1B Antibodies

Various methods were used to characterize the anti-BMPR1B murine antibodies generated in Example 6 in terms of binning, binding affinity, and the ability to recognize and kill cells expressing human BMPR1B. FIGS. 7A and 7B provide tabular summaries of the aforementioned characteristics for a number of exemplary murine antibodies.

Antibody Binding and Affinity:

For screen 1 affinities to human, cyno and rat BMPR1B were determined by measuring binding kinetics on Biacore 2000 and T200 instruments (GE Healthcare). Antibodies were immobilized onto anti-mouse capture (AMC) chips and human, cyno and rat BMPR1B were injected either at a single 200 nM concentration for qualitative assessment ("+++", "++", "+") or at three different concentrations, (i.e. 22, 66, 200 nM) for equilibrium constant ($K_D$) determination. Sensograms were reference-subtracted by using an irrelevant immunoglobulin and finally fit using a 1:1 binding model. Combined results of these studies are visible in the three columns of FIG. 7A labeled as "Biacore".

For screen 2 affinities to human, cyno and rat BMPR1B were determined by measuring binding kinetics on the BiacoreT200 instrument (GE Healthcare). Antibodies were immobilized onto anti-mouse capture (AMC) chips and human, cyno and rat BMPR1B-his were injected by single cycle kinetics at three different concentrations (22, 66, 200 nM) for equilibrium constant ($K_D$) determination. Sensograms were reference-subtracted by using an irrelevant immunoglobulin and fit using a 1:1 binding model. Combined results of these studies are visible in the three columns of FIG. 7B labeled as "Biacore".

The exemplary antibodies from screen 1 were also tested using flow cytometry for their ability to associate with hBMPR1B and rBMPR1B on the surface of cells. To this end engineered HEK293T cells overexpressing hBMPR1B (prepared as per Example 5) along with HEK293T cells overexpressing rBMPR1B (prepared as per Example 5) were incubated for 30 minutes with the denoted antibodies and analyzed for hBMPR1B expression by flow cytometry using a BD FACS Canto II flow cytometer according to the manufacturer's instructions. Antigen expression is quantified as the change in geometric mean fluorescence intensity ($\Delta$MFI) observed on the surface of the engineered cells which have been stained with an anti-BMPR1B antibody compared to the same cells that have been stained with an isotype control antibody. Results of the assay in terms of mean fluorescence intensity are set forth in FIG. 7A in the columns labelled "Flow cytometry". A review of the data shows that several of the disclosed antibodies bind hBMPR1B on the surface of cells.

With regard to screen 2 exemplary antibodies were tested using flow cytometry for their ability to associate with hBMPR1B, cBMPR1B and rBMPR1B on the surface of cells. To this end engineered HEK293T cells overexpressing hBMPR1B (prepared as per Example 6) along with HEK293T cells overexpressing cBMPR1B (prepared as per Example 6) and HEK293T cells overexpressing rBMPR1B (prepared as per Example 6) were incubated for 30 minutes with the denoted antibodies and analyzed for hBMPR1B expression by flow cytometry using a BD FACS Canto II flow cytometer according to the manufacturer's instructions. Antigen expression is quantified as the change in geometric mean fluorescence intensity ($\Delta$MFI) observed on the surface of the engineered cells which have been stained with an anti-BMPR1B antibody compared to the same cells that have been stained with an isotype control antibody. Results of the assay in terms of mean fluorescence intensity are set forth in FIG. 7B in the columns labelled "Flow cytometry". A review of the data shows that several of the disclosed antibodies bind hBMPR1B on the surface of cells.

Binning:

Antibodies were grouped into bins using a multiplexed competition immunoassay (Luminex®). 100 µl of each unique anti-BMPR1B antibody (capture mAb) at a concentration of 10 µg/mL was incubated for 1 hour with magnetic beads (Luminex®) that had been conjugated to an anti-mouse kappa antibody (Miller et al., 2011, PMID: 21223970). The capture mAb/conjugated bead complexes were washed with PBSTA buffer (1% BSA in PBS with 0.05% Tween20) and then pooled. Following removal of residual wash buffer the beads were incubated for 1 hour with 2 µg/mL hBMPR1B-His protein, washed and then resuspended in PBSTA. The pooled bead mixture was distributed into a 96 well plate, each well containing a unique anti-BMPR1B antibody (detector mAb) and incubated for 1 hour with shaking. Following a wash step, anti-mouse kappa antibody (the same as that used above), conjugated to PE, was added at a concentration of 5 µg/ml to the wells and incubated for 1 hour. Beads were washed again and resuspended in PBSTA. Mean fluorescence intensity (MFI) values were measured with a Luminex MAGPIX instrument. Antibody pairing was visualized as a dendrogram of a distance matrix computed from the Pearson correlation coefficients of the antibody pairs. Binning was determined on the basis of the dendrogram and analysis of the MFI values of antibody pairs. The data is presented in the column headed Luminex Binning in each of FIGS. 7A (screen 1) and 7B (screen 2) where the results show that the screened anti-BMPR1B antibodies can be grouped into at least six bins (A-F). Note that screen 2 indicated some potential overlap between bins B and D and that empty cells or cells labeled "x" indicates that the bin was not determined for that particular antibody.

In Vitro Killing:

To determine whether anti-BMPR1B antibodies of the invention were able to internalize in order to mediate the delivery of cytotoxic agents to live tumor cells, an in vitro cell killing assay was performed using exemplary anti-BMPR1B antibodies and a secondary anti-mouse antibody FAB fragment linked to saporin. Saporin is a plant toxin that deactivates ribosomes, thereby inhibiting protein synthesis and resulting in the death of the cell. Saporin is only cytotoxic inside the cell where it has access to ribosomes, but is unable to internalize independently. Therefore, saporin-mediated cellular cytotoxicity in these assays is indicative of the ability of the anti-mouse FAB-saporin construct to internalize upon binding and internalization of the associated anti-BMPR1B mouse antibodies into the target cells.

Single cell suspensions of HEK293T cells overexpressing human BMPR1B, rat BMPR1B or cyno BMPR1B (prepared as per Example 5) were plated at 500 cells per well into BD Tissue Culture plates (BD Biosciences). One day later, 100 pM of purified anti-BMPR1B antibodies characterized in screen 1 or screen 2 were added to the culture together with a fixed concentration of 2 nM anti-mouse IgG FAB-saporin constructs (Advanced Targeting Systems). After incubation for 96 hours viable cells were enumerated using CellTiter-Glo® (Promega) as per the manufacturer's instructions. Raw luminescence counts using cultures containing cells incubated only with the secondary FAB-saporin conjugate were set as 100% reference values and all other counts were calculated as a percentage of the reference value. The results, shown in FIGS. 7A and 7B in the columns labeled "in vitro killing" are presented as the percentage of surviving cells.

These data demonstrate that a subset of anti-BMPR1B antibody-saporin conjugates at a concentration of 100 pM effectively killed HEK293T cells overexpressing human BMPR1B with varying efficacy (FIGS. 7A and 7B).

Figure 7C:
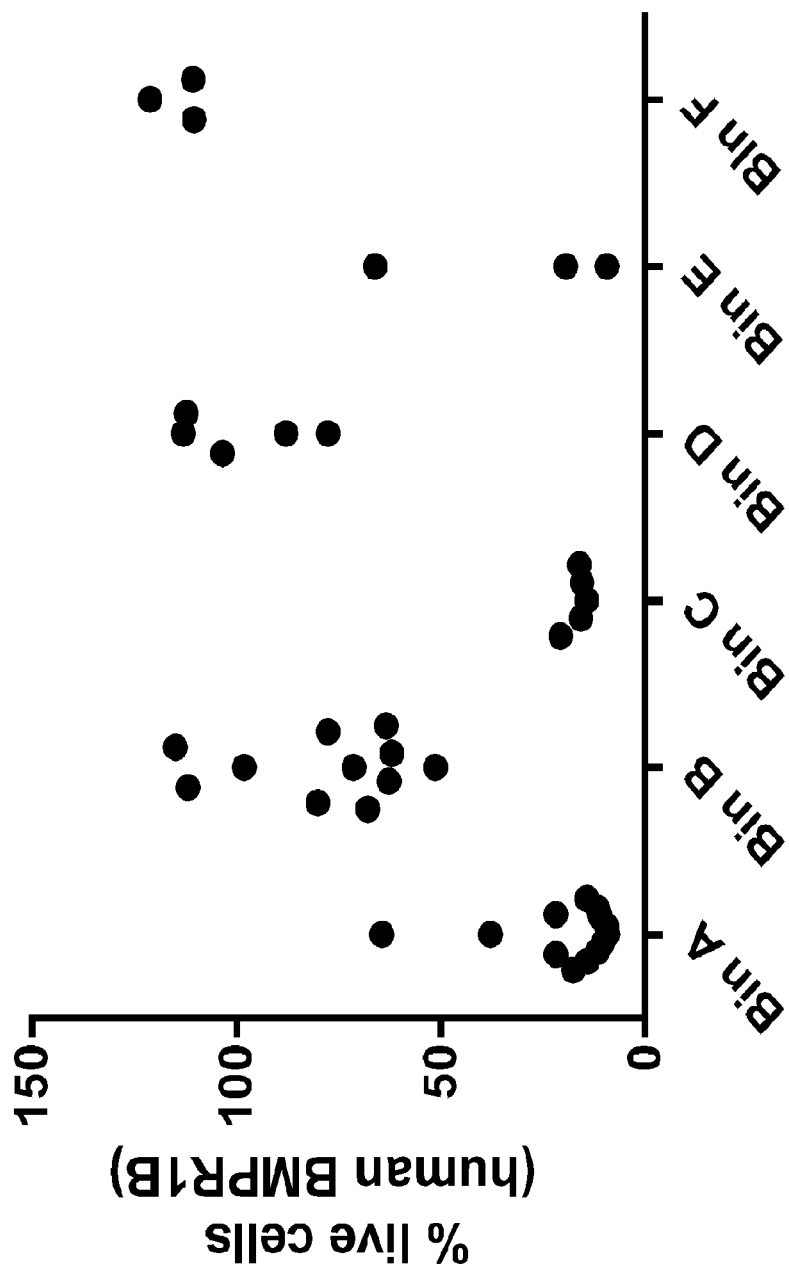
Figure 7D:
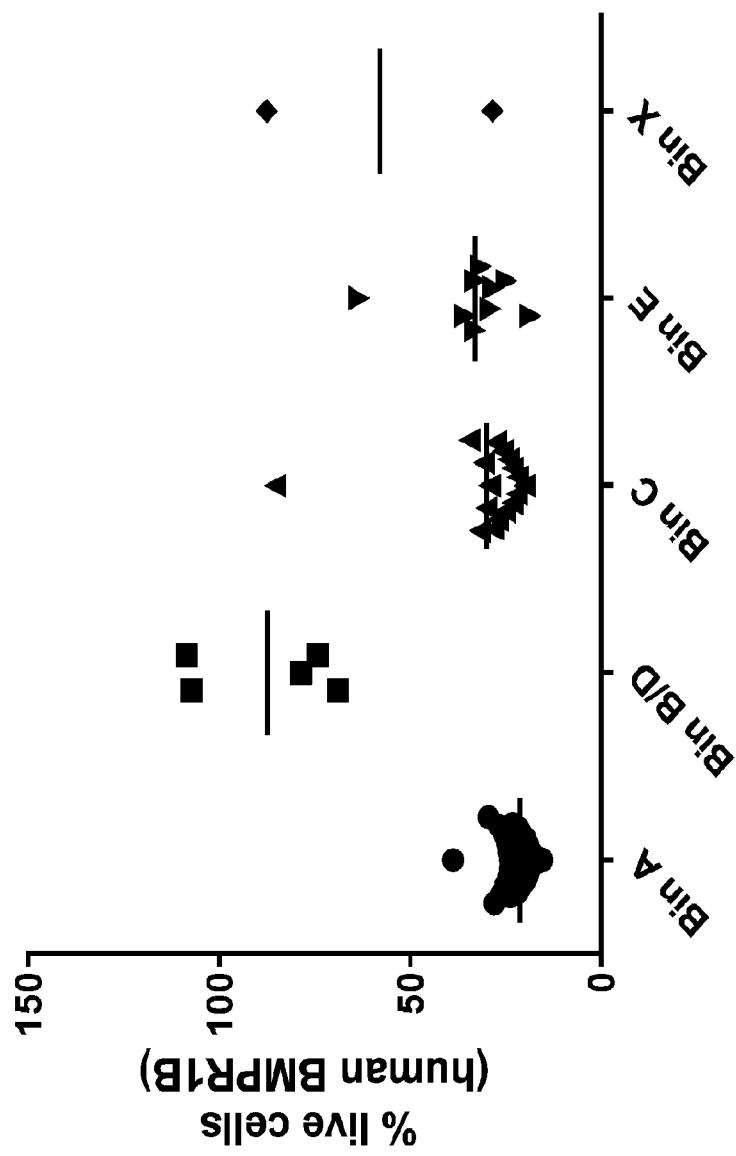

In order to determine whether epitope position plays a role in the ability of an antibody to mediate cell killing, the killing data set forth in FIGS. 7A and 7B for 293 cells expressing human BMPR1B was plotted by bin to provide FIGS. 7C and 7D. A review of FIGS. 7C and 7D shows that those antibodies mapped to bins A, C or E exhibit higher cell killing activity when used in conjunction with saporin as set forth above. These data indicate that antibodies in bins A, C or E may be particularly effective when used as a component of an antibody drug conjugate as disclosed herein.

Example 8

Cross Reactivity of Anti-BMPR1B Antibodies with BMPR1A

BMPR1B is a type 1B serine/threonine kinase receptor that shares 73% homology with the type 1A receptor, BMPR1A. In order to determine whether the antibodies of the invention cross reacted with BMPR1A, an ELISA assay was used.

With regard to the first screening antibodies were incubated at 0.1 ug/mL on plates previously coated over night with four different recombinant proteins: BMPR1B-his, BMPR1B-Fc, BMPR1A-Fc and an irrelevant Fc-tagged protein. Detection was achieved by use of goat anti-mouse antibodies conjugated to horse radish peroxidase. All antibodies were ELISA positive when tested on BMPR1B, both in his and Fc fusion format. As seen in FIG. 8A only a few clones showed weak binding to BMPR1A-Fc; this was suspected to be unspecific due to concurrent binding to an irrelevant Fc construct and to BMPR1B-his. These data were then correlated with Biacore (using substantially the conditions set forth above, data not shown) and a combination of the readings indicated that, of all the antibodies tested, only SC91.33 is somewhat cross-reactive to human BMPR1A.

Similarly, antibodies from screen 2 were incubated at 0.1 ug/mL on two plates previously coated over night with recombinant human BMPR-1A/ALK-3-Fc Chimera (R&D systems Catolog: 315-BR) at 0.3 ug/mL. Each plate consisted of control wells containing murine anti-his and anti-fc primary antibodies. Detection was achieved by use of goat anti-mouse antibodies conjugated to horse radish peroxidase. All anti-his antibodies were ELISA positive while all anti-fc antibodies were below background when tested against rhBMPR-1A/ALK-3-Fc chimera. This was expected due to the 6-his tag on the C terminus of the protein. As shown in FIG. 8B of the 92 mouse anti-BMPR1B antibodies that were tested, 16 are cross-reactive to human BMPR1A.

Taken together these data indicate that immunospecific BMPR1B antibodies may readily be generated and selected for to provide therapeutically effective ADCs in accordance with the teachings herein.

Example 9

Sequencing of BMPR1B Antibodies

The anti-BMPR1B mouse antibodies that were generated in Example 6 were sequenced as described below. Total RNA was purified from selected hybridoma cells using the RNeasy Miniprep Kit (Qiagen) according to the manufacturer's instructions. Between $10^4$ and $10^5$ cells were used per sample. Isolated RNA samples were stored at −80° C. until used.

The variable region of the Ig heavy chain of each hybridoma was amplified using two 5' primer mixes comprising eighty-six mouse specific leader sequence primers designed to target the complete mouse VH repertoire in combination with a 3' mouse Cγ primer specific for all mouse Ig isotypes. Similarly, two primer mixes containing sixty-four 5' Vκ leader sequences designed to amplify each of the Vκ mouse families was used in combination with a single reverse primer specific to the mouse kappa constant region in order to amplify and sequence the kappa light chain. The VH and VL transcripts were amplified from 100 ng total RNA using the Qiagen One Step RT-PCR kit as follows. A total of four RT-PCR reactions were run for each hybridoma, two for the Vκ light chain and two for the VH heavy chain. PCR reaction mixtures included 1.5 μL of RNA, 0.4 μL of 100 μM of either heavy chain or kappa light chain primers (custom synthesized by Integrated DNA Technologies), 5 μL of 5× RT-PCR buffer, 1 μL dNTPs, and 0.6 μL of enzyme mix containing reverse transcriptase and DNA polymerase. The thermal cycler program was RT step 50° C. for 60 min., 95° C. for 15 min. followed by 35 cycles of (94.5° C. for 30 seconds, 57° C. for 30 seconds, 72° C. for 1 min.). There was then a final incubation at 72° C. for 10 min.

The extracted PCR products were sequenced using the same specific variable region primers as described above for the amplification of the variable regions. PCR products were sent to an external sequencing vendor (MCLAB) for PCR purification and sequencing services. Nucleotide sequences were analyzed using the IMGT sequence analysis tool (http://www.imgt.org/IMGTmedical/sequence_analysis.html) to identify germline V, D and J gene members with the highest sequence homology. The derived sequences were compared to known germline DNA sequences of the Ig V- and J-regions by alignment of VH and VL genes to the mouse germline database using a proprietary antibody sequence database.

FIG. 9A depicts the contiguous amino acid sequences of several novel murine light chain variable regions from anti-BMPR1B antibodies while FIG. 9B depicts the contiguous amino acid sequences of novel murine heavy chain variable regions from the same anti-BMPR1B antibodies. Taken together murine light and heavy chain variable region amino acid sequences are provided in SEQ ID NOS: 21-55 odd numbers with SEQ ID NO: 53 reserved.

More particularly FIGS. 9A and 9B provide the annotated amino acid sequences of several murine anti-BMPR1B antibodies, termed SC91.1, having a VL of SEQ ID NO: 21 and VH of SEQ ID NO: 23; SC91.3, having a VL of SEQ ID NO: 25 and a VH of SEQ ID NO: 27; SC91.9, having a VL of SEQ ID NO: 29 and a VH of SEQ ID NO: 31; SC91.11, having a VL of SEQ ID NO: 33 and a VH of SEQ ID NO: 35; SC91.14, having a VL of SEQ ID NO: 37 and a VH of SEQ ID NO: 39; SC91.15 having a VL of SEQ ID NO: 41 and a VH of SEQ ID NO: 43; SC91.19, having a VL of SEQ ID NO: 45 and a VH of SEQ ID NO: 47; SC91.111, having a VL of SEQ ID NO: 49 and a VH of SEQ ID NO: 51; SC91.119, having a VL of SEQ ID NO: 53 and a VH of SEQ ID NO: 55; SC91.129, having a VL of SEQ ID NO: 57 and a VH of SEQ ID NO: 59; SC91.138, having a VL of SEQ ID NO: 61 and a VH of SEQ ID NO: 63; SC91.146 having a VL of SEQ ID NO: 65 and a VH of SEQ ID NO: 67; SC91.149, having a VL of SEQ ID NO: 69 and a VH of SEQ ID NO: 71; SC91.155, having a VL of SEQ ID NO: 73 and a VH of SEQ ID NO: 75; SC91.160, having a VL of SEQ ID NO: 77 and a VH of SEQ ID NO: 79; SC91.172, having a VL of SEQ ID NO: 81 and a VH of SEQ ID NO: 83; SC91.187, having a VL of SEQ ID NO: 85 and a VH of SEQ ID NO: 87; SC91.20, having a VL of SEQ ID NO: 89 and a VH of SEQ ID NO: 91; SC91.27, having a VL of SEQ ID NO: 89 and a VH of SEQ ID NO: 93; and SC91.186 having a VL of SEQ ID NO: 37 and a VH of SEQ ID NO: 95. Note that SC91.20 and SC91.27 have the same light chain variable region (i.e., SEQ ID NO: 89) paired with two unique heavy chain variable regions (SEQ ID NOS: 91 and 93). Similarly, SC91.186 comprises the same light chain as SC91.14 (SEQ ID NO: 37) though the antibodies comprise two unique heavy chains (SEQ ID NOS: 39 and 95).

A summary of the disclosed antibodies (or clones producing them), along with their respective variable region nucleic acid or amino acid SEQ ID NOS (see FIGS. 9A-9C) are shown immediately below in Table 5.

TABLE 5

|   | Clone | VL SEQ ID NO: NA/AA | VH SEQ ID NO: NA/AA |
|---|---|---|---|
| 1 | 91.1 | 20/21 | 22/23 |
| 2 | 91.3 | 24/25 | 26/27 |
| 3 | 91.9 | 28/29 | 30/31 |
| 4 | 91.11 | 32/33 | 34/35 |
| 5 | 91.14 | 36/37 | 38/39 |
| 6 | 91.15 | 40/41 | 42/43 |
| 7 | 91.19 | 44/45 | 46/47 |
| 8 | 91.111 | 48/49 | 50/51 |
| 9 | 91.119 | 52/53 | 54/55 |
| 10 | 91.129 | 56/57 | 58/59 |
| 11 | 91.138 | 60/61 | 62/63 |
| 12 | 91.146 | 64/65 | 66/67 |
| 13 | 91.149 | 68/69 | 70/71 |
| 14 | 91.155 | 72/73 | 74/75 |
| 15 | 91.160 | 76/77 | 78/79 |
| 16 | 91.172 | 80/81 | 82/83 |
| 17 | 91.187 | 84/85 | 86/87 |
| 18 | 91.20 | 88/89 | 90/91 |
| 19 | 91.27 | 88/89 | 92/93 |
| 20 | 91.186 | 36/37 | 94/95 |

The VL and VH amino acid sequences in FIGS. 9A and 9B are annotated to identify the framework regions (i.e. FR1-FR4) and the complementarity determining regions (i.e., CDRL1-CDRL3 in FIG. 9A or CDRH1-CDRH3 in FIG. 9B), defined as per Kabat et al. The variable region sequences were analyzed using a proprietary version of the Abysis database to provide the CDR and FR designations. Though the CDRs are defined as per Kabat et al., those skilled in the art will appreciate that the CDR and FR designations can also be defined according to Chothia, McCallum or any other accepted nomenclature system. In addition, FIG. 9C provides the nucleic acid sequences (SEQ ID NOS: 20-94, even numbers) encoding the amino acid sequences set forth in FIGS. 9A and 9B.

As seen in FIGS. 9A and 9B and Table 5 the SEQ ID NOS. of the heavy and light chain variable region amino acid sequences for each particular murine antibody are generally sequential odd numbers. Thus the monoclonal anti-BMPR1B antibody, SC91.1, comprises amino acid SEQ ID NOS: 21 and 23 for the light and heavy chain variable regions respectively; SC91.3 comprises SEQ ID NOS: 25 and 27; SC91.9 comprises SEQ ID NOS: 29 and 31, and so on. As noted above exceptions to the sequential numbering scheme set forth in FIGS. 9A and 9B are SC91.27 (SEQ ID NOS: 89 and 93) which comprises the same light chain variable region as that found in antibody SC91.20 (SEQ ID NOS: 89 and 91) and SC91.186 (SEQ ID NOS: 37 and 95) which comprises the same light chain variable region as that found in antibody SC91.14 (SEQ ID NOS: 37 and 39). In any event the corresponding nucleic acid sequence encoding the murine antibody amino acid sequence (set forth in FIG. 9C) has a SEQ ID NO: immediately preceding the corresponding amino acid SEQ ID NO. Thus, for example, the SEQ ID NOS: of the nucleic acid sequences of the VL and VH of the SC91.1 antibody are SEQ ID NOS: 20 and 22, respectively.

In addition to the annotated sequences in FIGS. 9A-9C, FIGS. 9F and 9G provide CDR designations for the light and heavy chain variable regions of SC91.1 and SC91.9 as determined using Kabat, Chothia, ABM and Contact methodology. Note that in FIG. 9G (SC91.1) there is an asterisk above the asparagine amino acid at position 55 of the VH chain. As discussed in more detail below the amino acid in this position may be mutated to glutamine (or any other amino acid) to impart additional molecular stability.

It will be appreciated that the CDR designations depicted in FIGS. 9F and 9G were derived using a proprietary version of the Abysis database as discussed above. As described herein, those of skill in the art will appreciate that the disclosed murine CDRs (optionally including selected mutations) may be grafted into human framework sequences to provide CDR grafted or humanized anti-BMPR1B antibodies in accordance with the instant invention. Moreover, in view of the instant disclosure one could easily determine the CDRs of any anti-BMPR1B antibody made and sequenced in accordance with the teachings herein and use the derived CDR sequences to provide CDR grafted or humanized anti-BMPR1B antibodies of the instant invention. This is particularly true of the antibodies with the heavy and light chain variable region sequences set forth in in FIGS. 9A-9B.

Example 10

Generation of Chimeric and Humanized Anti-BMPR1B Antibodies

Chimeric anti-BMPR1B antibodies were generated using art-recognized techniques as follows.

Total RNA was extracted from the hybridomas and PCR amplified. Data regarding V, D and J gene segments of the VH and VL chains of the following murine antibodies: SC91.1 and SC91.9 were obtained from an analysis of the subject nucleic acid sequences (see FIG. 9C for nucleic acid sequences). Primer sets specific to the framework sequence of the VH and VL chains of the antibodies were designed using the following restriction sites: AgeI and XhoI for the VH fragments, and XmaI and DraIII for the VL fragments. PCR products were purified with a Qiaquick PCR purification kit (Qiagen), followed by digestion with restriction enzymes AgeI and XhoI for the VH fragments and XmaI and DraIII for the VL fragments.

The VH and VL digested PCR products were purified and ligated into IgH or Igκ expression vectors, respectively. Ligation reactions were performed in a total volume of 10 µL with 200U T4-DNA Ligase (New England Biolabs), 7.5 µL of digested and purified gene-specific PCR product and 25 ng linearized vector DNA. Competent *E. coli* DH10B bacteria (Life Technologies) were transformed via heat shock at 42° C. with 3 µL ligation product and plated onto ampicillin plates at a concentration of 100 µg/mL. Following purification and digestion of the amplified ligation products, the VH fragment was cloned into the AgeI-XhoI restriction sites of the pEE6.4 expression vector (Lonza) comprising HuIgG1 and the VL fragment was cloned into the XmaI-DraIII restriction sites of the pEE12.4 expression vector (Lonza) comprising Hu-Kappa light constant region.

Chimeric antibodies comprising the entire murine heavy and light chain variable regions and human constant regions were expressed by co-transfection of CHO-S cells with Human IgG1 and Human kappa expression vectors and PEI as a transfection reagent. Supernatants were harvested three to six days after transfection. Culture supernatants containing recombinant chimeric antibodies were cleared from cell debris by centrifugation at 800×g for 10 mins. and stored at 4° C. Recombinant chimeric antibodies were purified with Protein A beads.

Murine anti-BMPR1B antibodies were also CDR grafted or humanized using a proprietary computer-aided CDR-grafting method (Abysis Database, UCL Business) and standard molecular engineering techniques as follows. Human framework regions of the variable regions were designed based on the highest homology between the framework sequences and CDR canonical structures of human germline antibody sequences, and the framework sequences and CDRs of the relevant mouse antibodies. For the purpose of the analysis the assignment of amino acids to each of the CDR domains was done in accordance with Kabat et al. numbering. In this regard FIGS. 9F and 9G show heavy and light CDRs derived using various analytical schemes for the murine antibodies SC91.1 and SC91.9. Once the variable regions comprising murine Kabat CDRs and the selected human frameworks were designed, they were generated from synthetic gene segments (Integrated DNA Technologies). Humanized antibodies were then cloned and expressed using the molecular methods described above for chimeric antibodies.

The VL and VH amino acid sequences of the humanized antibodies hSC91.1 (SEQ ID NOS: 101 and 103), hSC91.1 (N55Q) (SEQ ID NOS: 101 and 105), hSC91.1v2 (N55Q) (SEQ ID NOS: 101 and 127) and hSC91.9 (SEQ ID NOS: 107 and 109), are shown in FIG. 9D and are derived from the VL and VH sequences of the corresponding murine antibodies (e.g. hSC91.1 is derived from SC91.1). The corresponding nucleic acid sequences of the humanized VL and VH are also set forth in FIG. 9D (SEQ ID NOS: 100-108, even numbers and SEQ ID NO: 126). Table 6 below shows that selected framework changes were introduced to maintain the favorable properties of the selected antibodies and that one change was made in CDR2 of the hSC91.1 heavy chain.

More specifically during the humanization process, a prospective glycosylation site in CDRH2 of SC91.1 was removed through the use of an amino acid substitution, N55Q, in order to enhance the stability and homogeneity of the final humanized antibody. This substitution is included in the hSC91.1 derived antibodies and the site is underlined in FIG. 9D. As with the other humanized constructs (including certain site-specific constructs and MJ mutants discussed in more detail below), these particulars are set forth in Table 6 immediately below.

TABLE 6

| mAb | Isotype | human VH | human JH | VH FR changes | VH CDR Changes | human VK | human JK | VK FR changes | VK CDR Changes |
| --- | --- | --- | --- | --- | --- | --- | --- | --- | --- |
| hSC91.1 | IgG1/κ | IGHV5-51*01 | JH6 | None | None | IGKV4-1*01 | JK2 | None | None |
| hSC91.1MJ | IgG1 N297A/κ | IGHV5-51*01 | JH6 | None | N55Q | IGKV4-1*01 | JK2 | None | None |
| hSC91.1ss1 | IgG1 C220S/κ | IGHV5-51*01 | JH6 | None | N55Q | IGKV4-1*01 | JK2 | None | None |
| hSC91.1ss1MJ | IgG1 C220S N297A/κ | IGHV5-51*01 | JH6 | None | N55Q | IGKV4-1*01 | JK2 | None | None |
| hSC91.9 | IgG1/κ | IGHV1-46*01 | JH1 | T30I | None | IGKV1-39*01 | JK4 | None | None |
| hSC91.9MJ | IgG1 N297A/κ | IGHV1-46*01 | JH1 | T30I | None | IGKV1-39*01 | JK4 | None | None |
| hSC91.9ss1MJ | IgG1 C220S N297A/κ | IGHV1-46*01 | JH1 | T30I | None | IGKV1-39*01 | JK4 | None | None |

As set forth in the next Example, Table 6 also shows the composition of the exemplary site-specific antibodies (e.g., hSC91.1ss1) fabricated as described herein. Additionally, variants with the additional MJ mutation N297A were constructed to improve the properties of the humanized antibodies.

More particularly, as set forth in Example 11 site-specific constructs were fabricated using the humanized VL and VH sequences set forth in FIG. 9D. In addition a N297A mutation (EU numbering) was introduced into the humanized antibodies to reduce the binding of antibodies to Fc receptors, which is believed to be a source of off-target toxicity. As shown in Table 6 this modification could be introduced in either the ss1 or the wild type human IgG1 constructs. In this case the N297A modification was introduced into the wild-type hSC91.1 and site-specific hSC91.1ss1 antibodies as denoted by the MJ suffix (i.e., hSC91.1MJ and hSC91.1ss1MJ). Similarly the MJ mutation was introduced into the hSC91.9 antibody and the hSC91.9ss1 antibody to provide hSC91.9MJ and hSC91.9ss1MJ antibodies. In each case the mutation was introduced using the Quikchange mutagenesis kit (ThermoFisher Scientific) on the plasmid for heavy chain expression, and the antibody was expressed and purified using the same methods described above.

Besides the aforementioned constructs a chimeric humanized SC91.1 antibody comprising a chimeric N55Q heavy chain and a humanized light chain was synthesized. This hybrid antibody (hSC91.1v2) incorporates the murine SC91.1 VH (SEQ ID NO: 23) comprising the N55Q mutation (underlined in SEQ ID NO: 127 set forth in FIG. 9D) to remove the potential glycosylation site in CDRH2. This N55Q murine VH region was then operably associated (see Example 11) with a human IgG1 constant region comprising a C220S mutation (to provide hSC91.1v2ss1) and a human IgG1 constant region comprising a C220S mutation and an N297A mutation (to provide hSC91.1v2ss1MJ). In each embodiment the selected heavy chain construct was paired with the standard hSC91.1 light chain (SEQ ID NO: 110) to provide the intact antibodies. This chimeric construct, used to test the removal of the potential glycosylation site, was found to be highly comparable to the fully humanized hSC91.1 constructs upon testing (data not shown). Note that the amino acid and nucleic acid sequences for the murine SC91.1 N55Q VH region were included in FIGS. 9D and 9E despite the lack of a heavy chain variable region human framework.

In addition to the humanized VH and VL amino acid and nucleic acid sequences (FIG. 9D), FIG. 9E provides full length heavy and light chain amino acid sequences for the exemplary humanized antibody constructs set forth in Table 6. A summary of the nucleic and amino acid sequences associated with each of the humanized constructs are presented immediately below in Table 7. Note that a number of the constructs employ the same VL, VH or full length sequences in different arrangements.

TABLE 7

| Clone | VL SEQ ID NO: NA/AA | VH SEQ ID NO: NA/AA | Full Length SEQ ID NO: LC/HC |
|---|---|---|---|
| hSC91.1 | 100/101 | 102/103 | 110/111 |
| hSC91.1MJ (N55Q) | 100/101 | 102/105 | 110/113 |
| hSC91.1ss1 (N55Q) | 100/101 | 102/105 | 110/115 |
| hSC91.1ss1MJ (N55Q) | 100/101 | 102/105 | 100/117 |
| hSC91.1v2ss1 (N55Q) | 100/101 | 126/127 | —/— |

TABLE 7-continued

| Clone | VL SEQ ID NO: NA/AA | VH SEQ ID NO: NA/AA | Full Length SEQ ID NO: LC/HC |
|---|---|---|---|
| hSC91.1v2ss1MJ (N55Q) | 100/101 | 126/127 | —/— |
| hSC91.9 | 106/107 | 108/109 | 120/121 |
| hSC91.9MJ | 106/107 | 108/109 | 120/123 |
| hSC91.9ss1MJ | 106/107 | 108/109 | 120/125 |

The exemplary humanized antibodies set forth in this Example demonstrate that clinically compatible antibodies may be generated and derived as disclosed herein. In certain aspects of the instant invention such antibodies may be incorporated in BMPR1B ADCs to provide compositions comprising a favorable therapeutic index. Moreover, as discussed in the next Example, Table 7 also shows the sequence composition of selected site-specific antibodies (hSC91.1ss1) and selected site-specific MJ antibodies (hSC91.1ss1MJ and hSC91.9ss1MJ) fabricated as described herein.

Example 11

Generation of Site-Specific BMPR1B Antibodies

In addition to native humanized IgG1 anti-BMPR1B antibodies (hSC91.1 and hSC91.9) engineered human IgG1/kappa anti-BMPR1B site-specific antibodies were also constructed comprising a native light chain (LC) constant region and a heavy chain (HC) constant region mutated to provide an unpaired cysteine. In this respect cysteine 220 (C220) in the upper hinge region of the HC was substituted with serine (C220S) to provide hSC91.1ss1, hSC91.1ss1MJ, hSC91.1v2ss1, hSC91.1v2ss1MJ, and hSC91.9ss1MJ. When assembled, the HCs and LCs form an antibody comprising two free cysteines at the c-terminal ends of the light chain constant regions that are suitable for conjugation to a therapeutic agent. Unless otherwise noted all numbering of constant region residues is in accordance with the EU numbering scheme as set forth in Kabat et al. Finally, as described in the previous Example, the heavy chain constant region of certain site-specific antibodies were further engineered to incorporate the N297A mutation and provide hSC91.1ss1MJ and hSC91.9ss1MJ.

To generate humanized native IgG1 antibodies and site-specific constructs a VH nucleic acid was cloned onto an expression vector containing a HC constant region (e.g., SEQ ID NO: 2) or a C220S mutation of the same (e.g., SEQ ID NO: 3). Vectors encoding the native hSC91.1 HC (FIG. 9E, SEQ ID NO: 111), mutant C220S HC of hSC91.1 (FIG. 9E, SEQ ID NO: 115) or the C220S N297A mutant HC (FIG. 9E, SEQ ID NO: 117) were co-transfected in CHO-S cells with a vector encoding the selected VL (hSC91.1, SEQ ID NO: 100) operably associated with a wild-type IgG1 kappa LC (SEQ ID NO: 5) to provide the hSC91.1 LC (SEQ ID NO: 110) and expressed using a mammalian transient expression system. The resulting anti-BMPR1B site-specific antibody containing the C220S mutant HC was termed hSC91.1ss1 while the native version was termed hSC91.1 and the site-specific construct comprising the N297A mutation hSC91.1ss1MJ. In this regard the amino acid sequences of the full-length hSC91.1 site-specific antibody heavy and light chains are shown in FIG. 9E (along with native humanized antibody hSC91.1 and the N297A analog) where hSC91.1ss1 comprises an LC and HC of SEQ ID NOS: 110 and 115 respectively and hSC91.1 comprises an LC and HC of SEQ ID NOS: 110 and 111 and hSC91.1ss1MJ comprises an LC and HC of SEQ ID NOS: 110 and 117 respectively. Note that the hSC91.1 heavy chains comprising the MJ and ss1 mutations further include the N55Q mutation as set forth in SEQ ID NOS: 113, 115 and 117. In any event, substantially the same process was used to provide the hSC91.9 analogs shown in Table 7 using the appropriate sequences. The positions of the site-specific mutation, MJ mutation and N55Q mutation on the heavy chains are underlined, as applicable, in FIG. 9E for both sets of molecules.

The engineered anti-BMPR1B site-specific antibodies were characterized by SDS-PAGE to confirm that the correct mutants had been generated. SDS-PAGE was conducted on a pre-cast 10% Tris-Glycine mini gel from Life Technologies in the presence and absence of a reducing agent such as DTT (dithiothreitol). Following electrophoresis, the gels were stained with a colloidal coomassie solution (data not shown). Under reducing conditions, two bands corresponding to the free LCs and free HCs, were observed. This pattern is typical of IgG molecules in reducing conditions. Under non-reducing conditions, the band patterns were different from native IgG molecules, indicative of the absence of a disulfide bond between the HC and LC. A band around 98 kD corresponding to the HC-HC dimer was observed. In addition, a faint band corresponding to the free LC and a predominant band around 48 kD that corresponded to a LC-LC dimer was observed. The formation of some amount of LC-LC species is expected due to the free cysteines on the c-terminus of each LC.

Example 12

Preparation of Anti-BMPR1B Antibody-Drug Conjugates

Anti-BMPR1B ADCs were prepared according to the teachings herein for further in vitro and in vivo testing.

To this end selected drug linker candidates, including PBD drug linkers, were screened to determine which cytotoxic payloads may be particularly compatible for use in the disclosed compositions. Following the initial in vitro screening program payloads comprising PBD1 and PBD3 were selected for further analysis. To conduct this analysis the PBD payloads were conjugated to a test antibody (hN149) which binds to CD46, an antigen known to be highly expressed on certain tumors of interest including luminal B tumors. The conjugation was effected substantially as set forth below and the resulting ADCs (hN149.ss1.PBD1 and hN149.ss1.PBD3) were tested in an in vitro cell killing assay.

More particularly, a single cell suspension of luminal B PDX line, BR163 was plated at 25,000 cells per well into 96-well Corning Falcon Tissue Culture plates (Fisher Sciences). One day later, various concentrations of purified huN149 ADC or human IgG1 control antibody conjugated to PBD1 or PBD3 were added to the cultures. The cells were incubated for 1 week. After the incubation viable cells were enumerated using CellTiter-Glo® (Promega) as per the manufacturer's instructions. Raw luminescence counts using cultures containing non-treated cells were set as 100% reference values and all other counts were calculated as a percentage of the reference value. The results of the assay demonstrate that both PBD1 and PBD3 internalize and kill BR163 cells when conjugated to the hN149 test antibody (data not shown). Based on the results of the assay the PBD3 warhead was selected for further study.

In this regard selected humanized anti-BMPR1B antibodies (native, site-specific and site-specific N297A) from Examples 10 and 11 were conjugated to the pyrrolobenzodiazepine cytotoxin (PBD3) via a terminal maleimido moiety with a free sulfhydryl group to create exemplary antibody drug conjugates (ADCs).

The native antibody anti-BMPR1B ADCs were prepared as follows. The cysteine bonds of anti-BMPR1B antibodies were partially reduced with a pre-determined molar addition of mol tris(2-carboxyethyl)-phosphine (TCEP) per mol antibody for 90 min. at room temperature in phosphate buffered saline (PBS) with 5 mM EDTA. The resulting partially reduced preparations were then conjugated to PBD3 (the structure of PBD3 is provided above in the current specification) via a maleimide linker for a minimum of 30 mins. at room temperature. The reaction was then quenched with the addition of excess N-acetyl cysteine (NAC) compared to linker-drug using a 10 mM stock solution prepared in water. After a minimum quench time of 20 mins, the pH was adjusted to 6.0 with the addition of 0.5 M acetic acid. The preparations of the ADCs were buffer exchanged into diafiltration buffer by diafiltration using a 30 kDa membrane. The dialfiltered anti-BMPR1B ADCs were then formulated with sucrose and polysorbate-20 to the target final concentration. The resulting anti-BMPR1B ADCs were analyzed for protein concentration (by measuring UV), aggregation (SEC), drug to antibody ratio (DAR) by reverse-phase HPLC (RP-HPLC) and activity (in vitro cytotoxicity).

The site-specific humanized anti-BMPR1B ADCs (with and without the N297 mutation, e.g., hSC91.1ss1 and hSC91.1ss1MJ) were conjugated using a modified partial reduction process. The desired product is an ADC that is maximally conjugated on the unpaired cysteine (C214) on each LC constant region and that minimizes ADCs having a drug loading which is greater than 2 while maximizing ADCs having a drug loading of 2. In order to further improve the specificity of the conjugation, the antibodies were selectively reduced using a process comprising a stabilizing agent (e.g. L-arginine) and a mild reducing agent (e.g. glutathione) prior to conjugation with the linker-drug, followed by a diafiltration and formulation step.

More specifically a preparation of each antibody was partially reduced in a buffer containing 1M L-arginine/5 mM EDTA with a pre-determined concentration of reduced glutathione (GSH), pH 8.0 for a minimum of two hours at room temperature. All preparations were then buffer exchanged into a 20 mM Tris/3.2 mM EDTA, pH 7.0 buffer using a 30 kDa membrane (Millipore Amicon Ultra) to remove the reducing buffer. The resulting partially reduced preparations were then conjugated to PBD3 via a maleimide linker for a minimum of 30 mins. at room temperature. The reaction was then quenched with the addition of excess NAC compared to linker-drug using a 10 mM stock solution prepared in water. After a minimum quench time of 20 mins., the pH was adjusted to 6.0 with the addition of 0.5 M acetic acid. The preparations of the ADCs were buffer exchanged into diafiltration buffer by diafiltration using a 30 kDa membrane. The dialfiltered anti-BMPR1B ADC was then formulated with sucrose and polysorbate-20 to the target final concentration.

The resulting anti-BMPR1B ADCs were analyzed for protein concentration (by measuring UV), aggregation (SEC), drug to antibody ratio (DAR) by reverse-phase HPLC (RP-HPLC) and activity (in vitro cytotoxicity). They were then frozen and stored until use.

Example 13

BMPR1B Protein Expression in Tumors

Given the elevated BMPR1B mRNA transcript levels associated with various tumors described in Examples 1-3, work was undertaken to test whether BMPR1B protein expression was also elevated in PDX tumors. To detect and quantify BMPR1B protein expression, an electrochemiluminscence BMPR1B sandwich ELISA assay was developed using the MSD Discovery Platform (Meso Scale Discovery).

PDX tumors were excised from mice and flash frozen on dry ice/ethanol. Protein Extraction Buffer (Biochain Institute) was added to the thawed tumor pieces and tumors were pulverized using a TissueLyser system (Qiagen). Lysates were cleared by centrifugation (20,000 g, 20 min., 4° C.) and the total protein concentration in each lysate was quantified using bicinchoninic acid. The protein lysates were then normalized to 5 mg/mL and stored at −80° C. until used. Normal tissues were purchased from a commercial source.

The ELISA sandwich antibody pair used in the MSD assay consisted of SC91.9 capture and SC91.46 detection. BMPR1B protein concentrations from the lysate samples were determined by interpolating the values from a standard protein concentration curve that was generated using purified recombinant hBMPR1B-HIS protein, generated as described in Example 5 above. The BMPR1B protein standard curve and protein quantification assay were conducted as follows:

MSD standard plates were coated overnight at 4° C. with 15 μL of SC91.9 capture antibody at 2 μg/mL in PBS. Plates were washed in PBST and blocked in 35 μL MSD 3% Blocker A solution for one hour while shaking. Plates were again washed in PBST. 10 μL of 10× diluted lysate (or serially diluted recombinant BMPR1B standard) in MSD 1% Blocker A containing 10% Protein Extraction Buffer was also added to the wells and incubated for two hours while shaking. Plates were again washed in PBST. The SC91.46 detection antibody was then sulfo-tagged using an MSD® SULFO-TAG NHS Ester according to the manufacturer's protocol. 10 μL of the tagged SC91.46 antibody was added to the washed plates at 0.5 μg/mL in MSD 1% Blocker A for 1 hour at room temperature while shaking. Plates were washed in PBST. MSD Read Buffer T with surfactant was diluted to 1× in water and 35 μL was added to each well. Plates were read on an MSD Sector Imager 2400 using an integrated software analysis program to derive BMPR1B concentrations in PDX samples via interpolation from the standard curve. Values were then divided by total protein concentration to yield nanograms of BMPR1B per milligram of total lysate protein.

Figure 10:
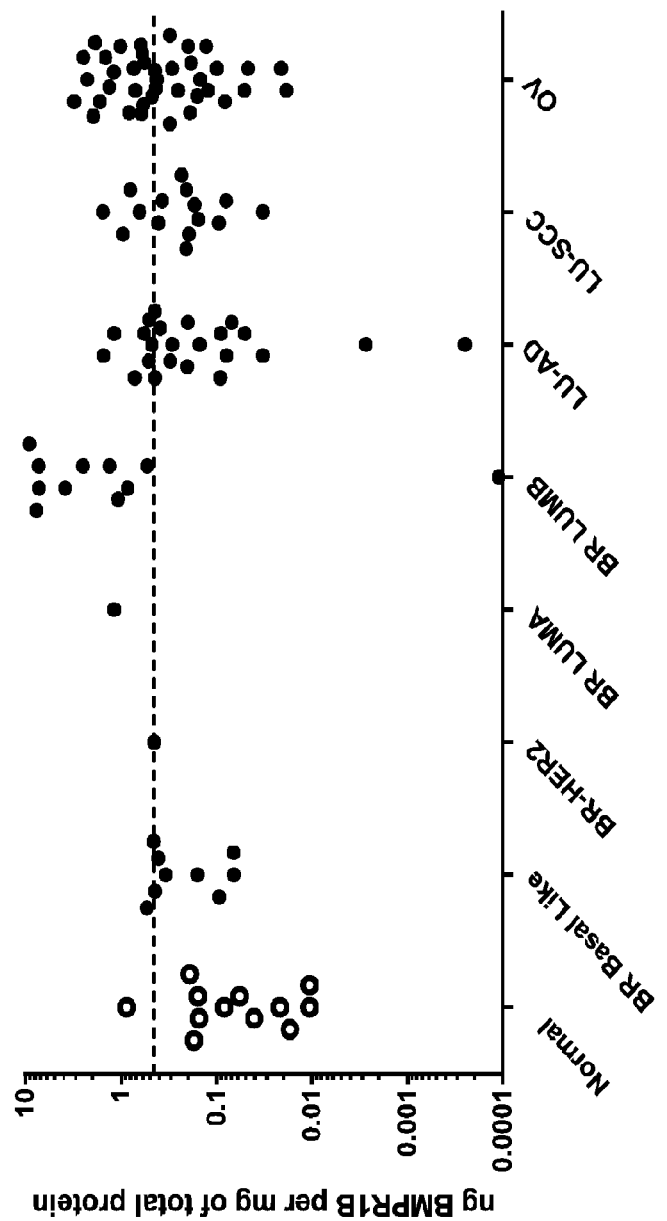
FIG. 10 illustrates the level of BMPR1B protein expression in a number of exemplary PDX tumor cell lines.

The resulting concentrations are set forth in FIG. 10 wherein each spot represents BMPR1B protein concentrations derived from a single PDX tumor line. While each spot is derived from a single PDX line, in most cases multiple biological samples were tested from the same PDX line and values were averaged to provide the data point.

FIG. 10 shows that representative samples of BR tumor samples exhibited high BMPR1B protein expression, particularly the luminal B subtype. Expression was also seen in a subset of LU-AD/SCC and OV samples. The levels of BMPR1B protein expression for each sample are given in ng/mg total protein and the median derived for each tumor type is indicated by the horizontal bar. Normal tissues that were tested include adrenal gland, artery, colon, esophagus, gall bladder, heart, kidney, liver, lung, peripheral and sciatic nerve, pancreas, skeletal muscle, skin, small intestine, spleen, stomach, trachea, red and white blood cells and platelets, bladder, brain, breast, eye, lymph node, ovary, pituitary gland, prostate and spinal cord. Only one normal tissue (prostate) was detected at levels above the lower limit of quantitation of the assay. These data, combined with the mRNA transcription data for BMPR1B expression set forth above strongly reinforce the proposition that BMPR1B is an attractive target for antibody-based therapeutic intervention.

Example 14

Immunohistochemistry of BMPR1B Protein Expression in Tumors

Immunohistochemistry (IHC) was performed on PDX tumor and primary human tumor tissue sections to assess the expression and location of BMPR1B in tumor cells. In order to identify an IHC-compatible anti-BMPR1B antibody, IHC was performed on HEK293T parental cell pellets or BMPR1B-expressing HEK293T cell pellets using a number of exemplary anti-BMPR1B antibodies.

Anti-BMPR1B antibodies SC91.15 and SC91.27 were able to specifically detect BMPR1B-overexpressing HEK293T cell pellets more effectively than other anti-BMPR1B antibodies of the invention that were tested (data not shown). The ability of these antibodies to specifically detect BMPR1B was confirmed by a competition experiment in which the relevant anti-BMPR1B antibody was mixed with a 5× molar ratio excess of hBMPR1B-Fc or irrelevant protein (SCRx91-Fc) and then incubated with BMPR1B-expressing HEK293T formalin fixed and paraffin embedded (FFPE) sections. The absence of positive staining demonstrated that the hBMPR1B-Fc protein interfered with the binding of the anti-BMPR1B antibody to the BMPR1B-overexpressing HEK293T cells (data not shown).

In addition to engineered 293 cells IHC was performed, as described below, on formalin fixed and paraffin embedded (FFPE) tissues (e.g., tumor samples) as is standard in the art. Planar sections of tissues were cut and mounted on glass microscope slides. After xylene de-paraffinization 5 μm sections were pre-treated with Antigen Retrieval Solution (Dako) for 20 mins. at 99° C., cooled to 75° C. and then treated with 0.3% hydrogen peroxide in PBS followed by Avidin/Biotin Blocking Solution (Vector Laboratories). FFPE slides were then blocked with 10% horse serum in 3% BSA in PBS buffer for 30 minute and then incubated with a primary anti-BMPR1B antibody of the invention, diluted to 10 μg/ml in 3% BSA/PBS, for 30 minute at room temperature. FFPE slides were incubated with biotin-conjugated horse anti-mouse antibody (Vector Laboratories), diluted to 2.5 μg/ml in 3% BSA/PBS, for 30 mins. at room temperature followed by incubation in streptavidin-HRP (ABC Elite Kit; Vector Laboratories). Chromogenic detection was developed with 3,3'-diaminobenzidine (Thermo Scientific) for 5 mins. at room temperature and tissues were counterstained with Meyer's hematoxylin (IHC World), washed with alcohol and immersed in xylene. Sections were then viewed by brightfield microscopy.

Expression was scored using an H-score algorithm which is calculated for membrane staining of tumor cells using the following formula; H-Score=(% staining intensity at 0)*0+(% staining intensity at 1+)*1+(% staining intensity at 2+)*2+(% staining intensity at 3+)*3. Thus, this score produces a continuous variable that ranges from 0 to 300. IHC expression is also scored in % positive cells taking into account all the cells that express the target at any intensity ranging from 1 (lowest) to 3+ (highest).

Figures 11B, 11C:
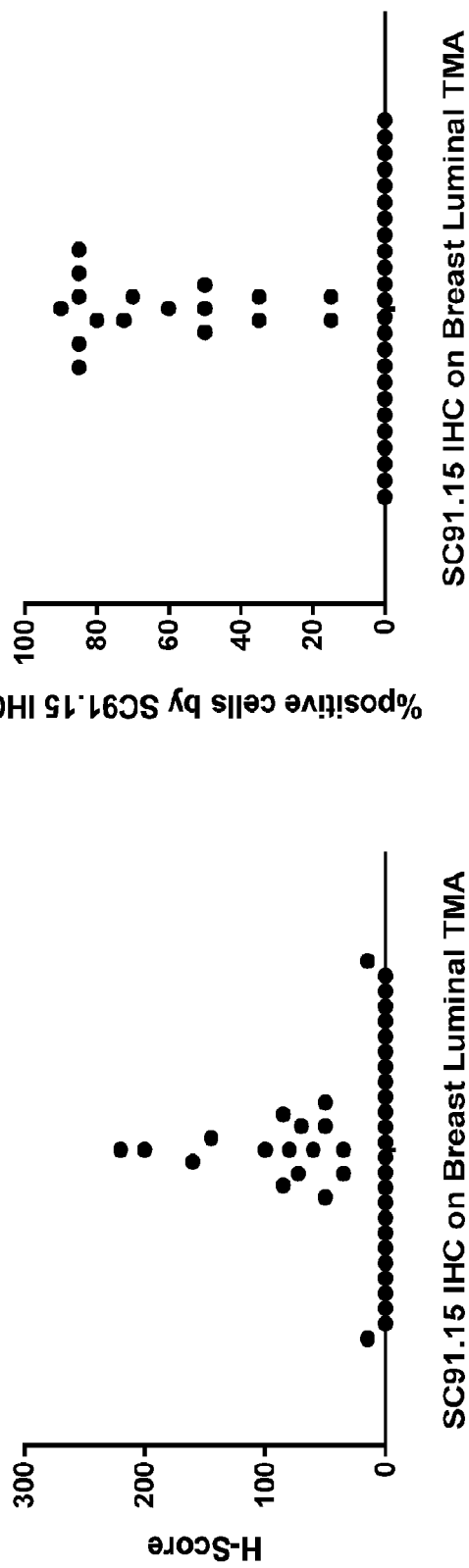

The results of the IHC testing are provided in FIGS. 11A-11G, wherein FIG. 11A shows the percentage and H-Score staining values for a number of BR-LUMB PDX lines. More specifically FIG. 11A summarizes the expression of BMPR1B in 13 BR-LumB PDX lines where BMPR1B was shown to have protein expression on 69% of BR-LumB PDX lines tested.

FIGS. 11B and 11C summarize the expression of BMPR1B on human luminal breast tumor microarray samples as H-score (FIG. 11B) and as percentage of positive cells (FIG. 11C). 33% of samples have an H-score higher than 50 and 40% of samples show positive percent of cells at any intensity.

Figures 11D, 11E:
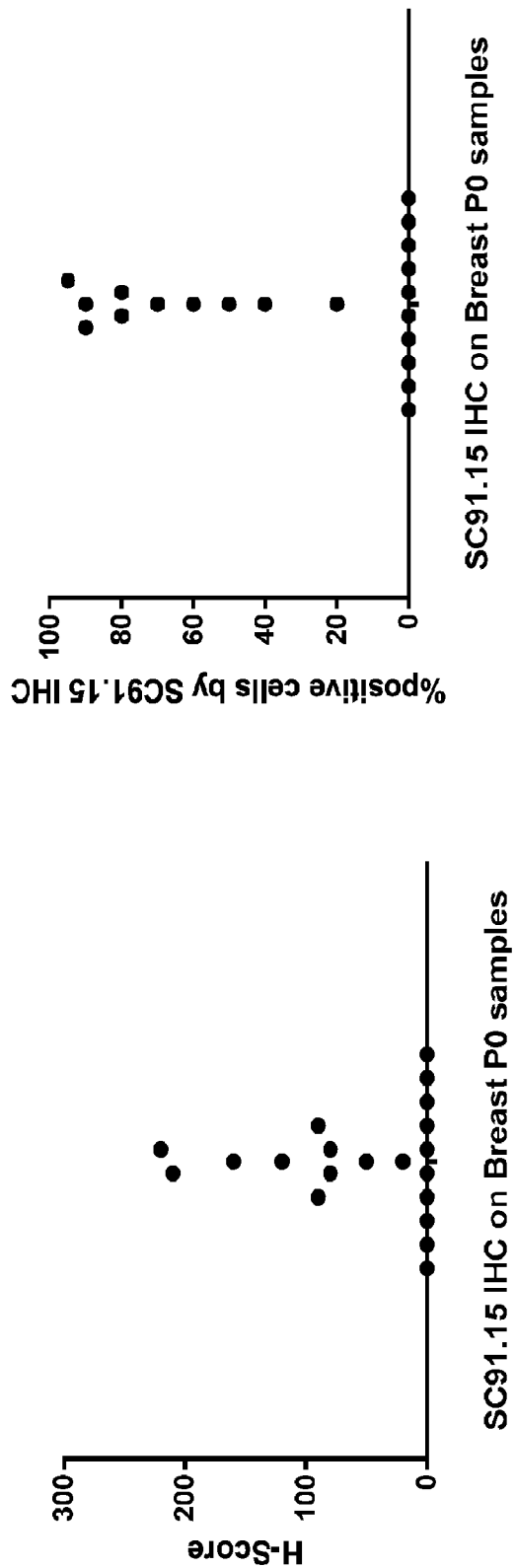

FIGS. 11D and 11E summarize the expression of BMPR1B on whole sections of primary luminal breast cancer tissue as H-score (FIG. 11D) and as percentage of positive cells (FIG. 11E). 40% of samples show H-score higher than 50 and 50% of samples have positive percent of cells at any intensity.

Figures 11F, 11G:
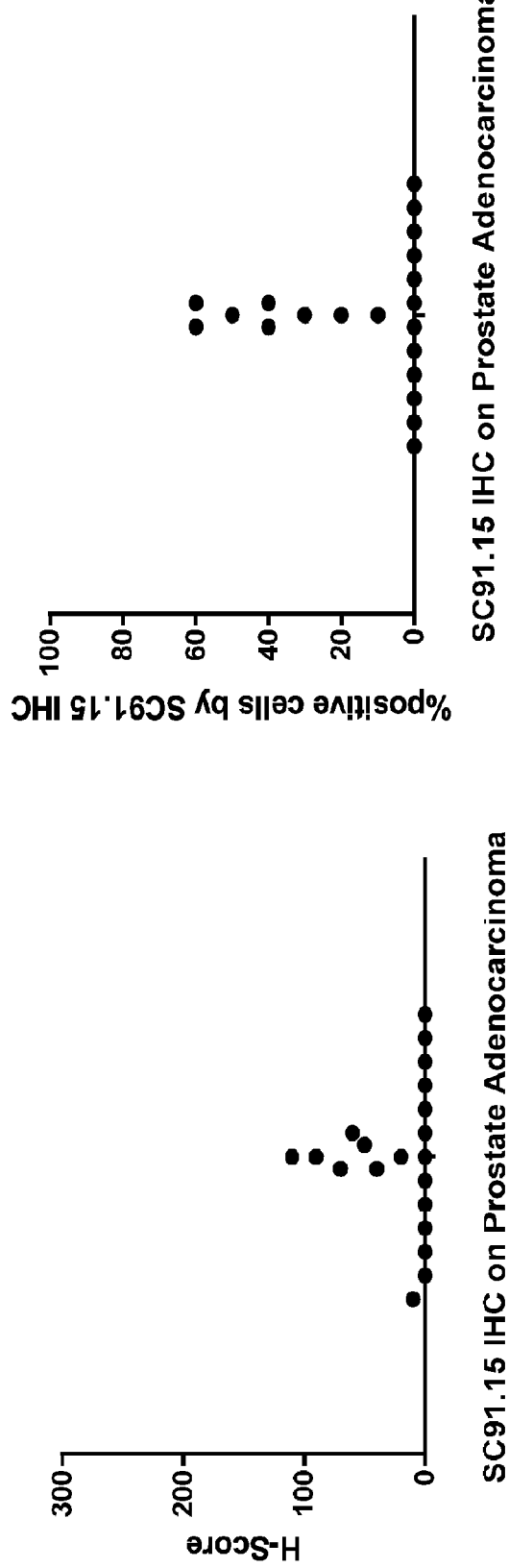

FIGS. 11F and 11G summarize the expression of BMPR1B on human prostate adenocarcinoma samples as H-score (FIG. 11F) and as percentage of positive cells (FIG. 11G). 25% of samples have an H-score higher than 50 and 40% of samples show positive percent of cells at any intensity.

The relatively high expression levels of BMPR1B antigen confirm the results of previous Examples set forth herein and further demonstrate the applicability of BMPR1B as a therapeutic target.

Example 15

Flow Cytometry Detection of BMPR1B Protein Expression in Tumors

Flow cytometry was used to assess the ability of the anti-BMPR1B antibodies of the invention to specifically detect the presence of human BMPR1B protein on the surface of luminal B PDX tumor cell lines. The luminal B PDX tumors were harvested and dissociated using art-recognized enzymatic tissue digestion techniques to obtain single cell suspensions of PDX tumor cells (see, for example, U.S.P.N. 2007/0292424). PDX tumor single cell suspensions were incubated with 4'6-diamidino-2-phenylindole (DAPI) to detect dead cells, anti-mouse CD45 and H-2K$^d$ antibodies to identify mouse cells and anti-human EPCAM antibodies to identify human carcinoma cells. The resulting single cell suspensions comprised a bulk sample of tumor cells including both NTG cells and CSCs. Bulk tumor cells were analyzed for hBMPR1B expression by flow cytometry using a BD FACS Canto II flow cytometer with SC91.3, an anti-BMPR1B antibody generated as set forth above.

Figure 12:
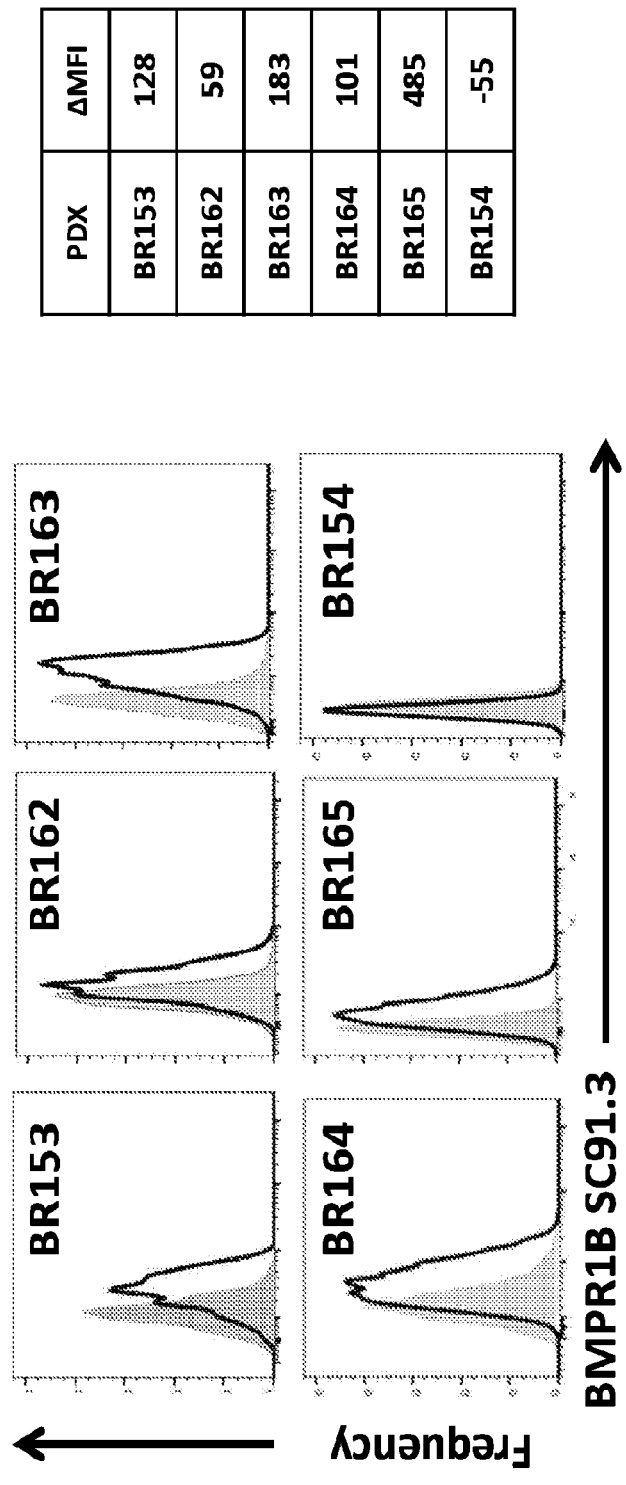
FIG. 12 shows BMPR1B protein expression on the surface of tumor cells as determined by flow cytometry with various breast cancer PDX cell lines where an exemplary antibody of the instant invention (black line) is compared to an isotype-control stained population (solid gray) along with related ΔMFI measurements.

FIG. 12 shows that the anti-hBMPR1B antibody SC91.3 detected expression of hBMPR1B on the surface of bulk luminal B PDX tumor cells. In all samples, except BR154, the anti-BMPR1B antibody (black line) detected increased BMPR1B expression compared to the IgG isotype control antibody (gray-filled). This demonstrates that BMPR1B is expressed on a number of luminal B tumors. Further, expression can be quantified as the change in geometric mean fluorescence intensity (ΔMFI) observed on the surface of tumor cells which have been stained with an anti-BMPR1B antibody compared to the same tumor that has been stained with an isotype control antibody. A table summarizing the ΔMFI of for each of the tumor cell lines that were analyzed is shown as an insert in FIG. 12.

This data confirms the IHC results in FIG. 11A, in which luminal B PDX lines, except for BR154 also show positive staining by IHC. BR154 did not show expression of hBMPR1B by flow cytometry, which was expected, based on the low RNA expression data provided in the Examples 1 to 3 above; and further demonstrates specificity of anti-BMPR1B antibody binding. Collectively, this data suggests that BMPR1B is expressed in a high percentage of luminal B PDX tumor cells and is a viable candidate for targeted therapy with anti-BMPR1B antibody drug conjugates.

Example 16

Enrichment of BMPR1B Expression in Cancer Stem Cell Populations

Tumor cells can be divided broadly into two types of cell subpopulations: non-tumorigenic cells (NTG) and tumor initiating cells or tumorigenic cells. Tumorigenic cells have the ability to form tumors when implanted into immuno-compromised mice, whereas non-tumorigenic cells do not. Cancer stem cells (CSCs) are a subset of tumorigenic cells and, as previously alluded to, are able to self-replicate indefinitely while maintaining the capacity for multilineage differentiation.

To determine whether BMPR1B expression in tumors could be correlated with enhanced tumorigenicity, the following study was conducted. Human luminal B PDX tumor samples were grown in immunocompromised mice and were resected after the tumor reached 800-2,000 mm$^3$. The tumors were dissociated into single cell suspensions using art-recognized enzymatic digestion techniques (see, for example, U.S.P.N. 2007/0292414). Human luminal B PDX tumor cells were stained with mouse anti-CD45 or anti-H2kD antibodies to differentiate between human tumor cells and mouse cells. The tumors were also stained with anti-BMPR1B antibody and then sorted using a FACSAria™ Flow Cytometer (BD Biosciences). The human luminal B PDX tumor cells were separated into cell populations expressing BMPR1B (BMPR1B-positive) and cell populations that did not express BMPR1B (BMPR1B-neg), as defined with a parallel isotype-stained control sample. Five female NOD/SCID immunocompromised mice were injected subcutaneously with 500 BMPR1B-positive luminal B tumor cells; and five mice were injected with 500 BMPR1B-neg luminal B tumor cells. Tumor volumes were measured on a weekly basis for five months.

Figure 13:
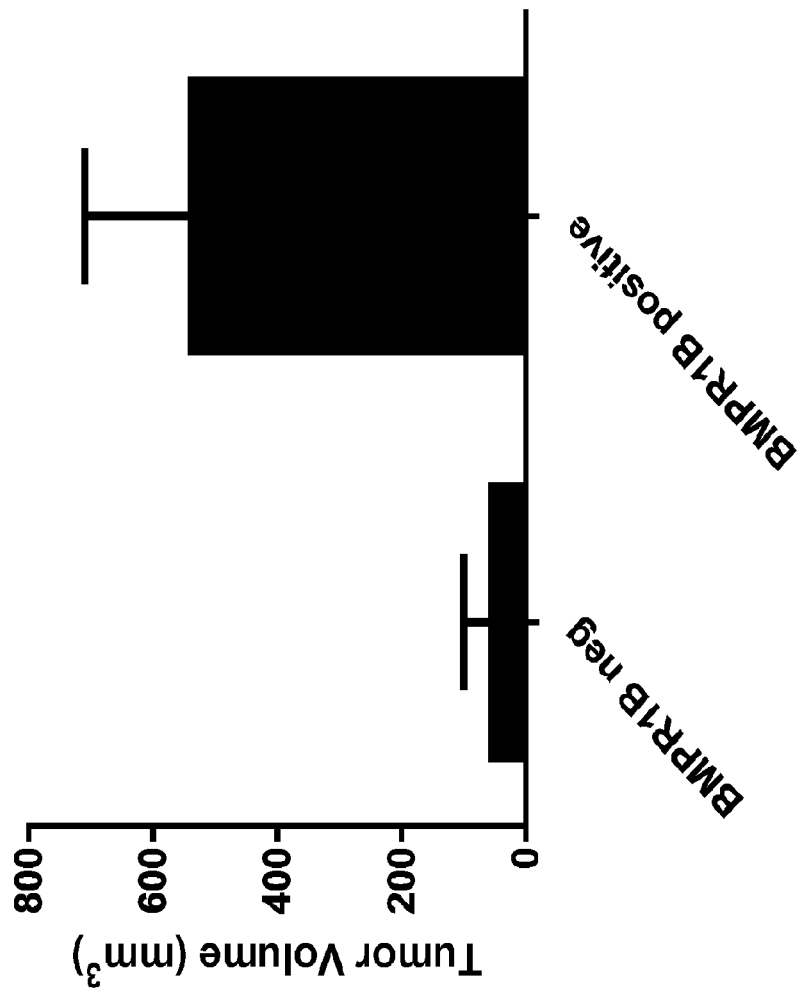
FIG. 13 demonstrates that BMPR1B is associated with tumorigenicity in that BMPR1B-positive tumor cells are able to regularly reconstitute tumors wherein BMPR1B-negative cells reconstitute tumors much less often.

Under these conditions BMPR1B-positive tumor cells are able to functionally and consistently reconstitute tumors in vivo, whereas BMPR1B-negative population only gave rise to one out of 5 injected tumors. More importantly, as shown in FIG. 13 the BMPR1B-neg derived tumor remained static for the entire five month incubation time while the BMPR1B-positive derived tumors grew continuously and substantially increased in volume. This indicates that tumor cells expressing BMPR1B were much more tumorigenic than those tumor cells that did not express BMPR1B strongly suggesting that the BMPR1B determinant may be used to define a tumorigenic subpopulation within human tumors. This finding, in turn, supports the concept that selected anti-BMPR1B ADCs can be used to target a tumorigenic cell subpopulations leading to significant tumor regression and prevention of tumor recurrence or metastasis.

Example 17

BMPR1B Expression Status and Somatic Mutations

The mutational status of various relevant genes in Breast Luminal B (BR-LumB) patient derived xenograft (PDX)

line may be determined by performing targeted re-sequencing of genomic DNA (gDNA). It has surprisingly been found that mutations in at least some of these genes may correlate with the expression of hBMPR1B protein on tumorigenic cells and may therefore be used as surrogate markers for patient selection.

In an exemplary embodiment, targeted re-sequencing of gDNA may be performed using gDNA from each BR-LumB PDX cell line to generate a library with the Ion AmpliSeq Library Kit 2.0 and a custom panel of AmpliSeq primers (Life Technologies) encompassing over 3000 amplicons of up to 250 bp, and covering coding and non-coding regions of multiple genes. Each sample may be ligated to an Ion Xpress Barcode Adapter (Life Technologies) to allow pooling of multiple samples for each sequencing run. Sequencing can then be performed on an Ion Torrent PGM machine (Life Technologies), and data analysis can be carried out to identify variations in sequence of BR-LumB-related genes that lead to changes at the gDNA, mRNA transcript and protein levels. As suggested above, the mutational status of certain BR-LumB-related genes can be used as surrogate biomarkers to determine whether the tumor cells are likely to express BMPR1B and be treatable with the anti-BMPR1B antibodies or ADCs of the invention. In other embodiments the mutational status of the BR-LumB-related genes can be used to determine whether there is a correlation between genetic mutations and the response to treatment with the anti-BMPR1B antibodies or ADCs of the invention. In further embodiments the mutational status of the BR-LumB-related genes can be used to determine effective combination therapies.

As to genes of interest the TP53 mutation status is well-described in hormone positive breast cancer and inactivating mutations in the TP53 correlate with disease progression. (Banerji et. al., 2012, PMID: 22722202). To determine the significance of mutations in TP53 that may correlate with expression of BMPR1B, BR-LumB, PDX tumors were evaluated for targeted re-sequencing of major cancer driver genes using Ion Ampliseq and Ion Torrent PGM technologies described above. BR-LumB tumors high and low in expression of BMPR1B were determined by microarray and used to correlate mutation data with BMPR1B expression. A mutation in TP53 is defined by any non-synonymous alteration occurring in the protein-coding region of the sequenced gene, including missense non-synonymous, insertions or deletions of codons, amplicon deletions or amplicon amplifications, nonsense non-synonymous, frameshift, and mutations that lead to altered splice-site variants of the gene sequenced. Selected TP53 mutations that may be used in conjunction with the teachings herein are set forth in Table 8 immediately below.

TABLE 8

| PDX | TP53 |
| --- | --- |
| BR153 | WT |
| BR162 | R248W |
| BR163 | C182* |
| BR164 | VVT |
| BR165 | I195T |
| BR154 | WT |

Figures 14A, 14B:
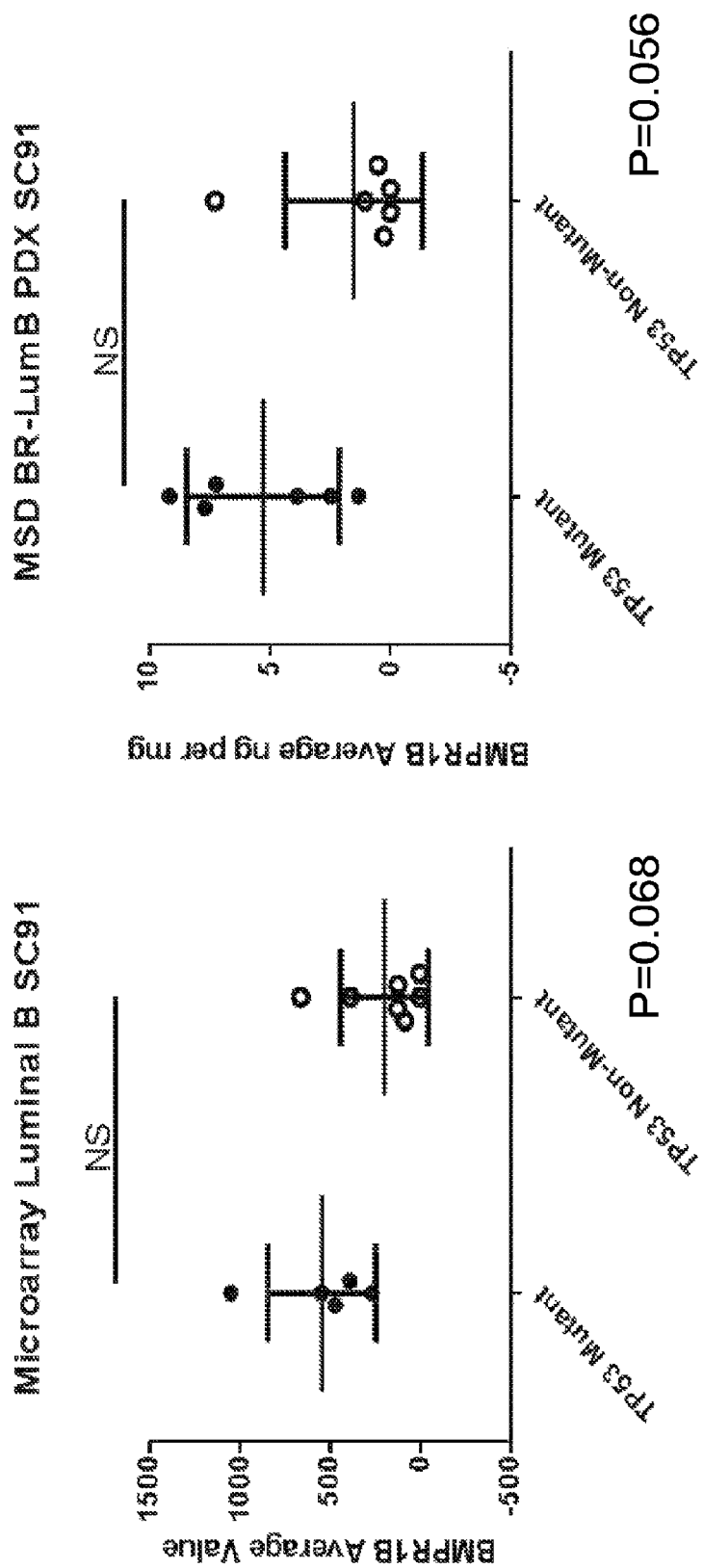
FIGS. 14A and 14B indicate that expression of BMPR1B protein correlates with known tumorigenic TP53 mutations as measured using microarray technology (FIG. 14A) and MSD (FIG. 14B)

In accordance with the invention BR-LumB PDX tumors with the TP53 mutations set forth in Table 8 (along with wild-type [WT] lines) were analyzed for BMPR1B expression. Upon review, BR-LumB PDX tumor lines containing a mutation in TP53 apparently demonstrate higher expression of BMPR1B in microarray and MSD datasets compared to wild-type PDX tumors as determined by Welch's T-test though the difference was not significant (FIGS. 14A and 14B). The lack of significance observed in the BR-LumB PDX datasets may be due to small sample size. In any event these data suggest that non-synonymous mutations detected in TP53 may correlate with expression or absence of expression of BMPR1B. Accordingly, such mutations may be useful as biomarkers to predict expression of BMPR1B in patient populations and more accurately guide treatment for these subsets of tumors.

Example 18

Anti-BMPR1B Antibody Drug Conjugates Facilitate Delivery of Cytotoxic Agents In Vitro To determine whether anti-BMPR1B ADCs of the invention are able to internalize in order to mediate the delivery of cytotoxic agents to live tumor cells, an in vitro cell killing assay was performed using the anti-BMPR1B ADCs, hSC91.1ss1MJ PBD3 (SEQ ID NOS: 110 and 117) and hSC91.9ss1MJ PBD3 (SEQ ID NOS: 120 and 125) produced as described in Example 12 above.

Figure 15:
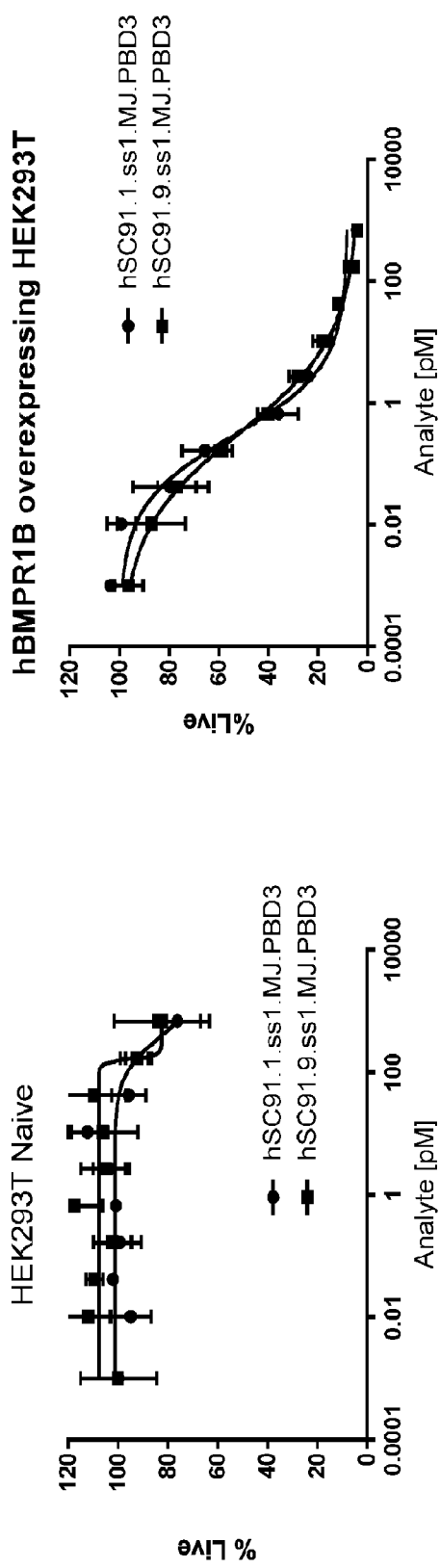
FIG. 15 depicts the ability of exemplary BMPR1B ADCs to internalize and kill HEK293T cells overexpressing BMPR1B protein in vitro.

Single cell suspensions of HEK293T cells overexpressing hBMPR1B or naïve HEK293T cells were plated at 500 cells per well into BD Tissue Culture plates (BD Biosciences). One day later, various concentrations of purified ADC or human IgG1 control antibody conjugated to PBD3 were added to the cultures. The cells were incubated for 96 hours. After the incubation, viable cells were enumerated using CellTiter-Glo® (Promega) as per the manufacturer's instructions. Raw luminescence counts using cultures containing non-treated cells were set as 100% reference values and all other counts were calculated as a percentage of the reference value. FIG. 15 shows that all treated HEK293 cells expressing hBMPR1B were sensitive to the anti-BMPR1B. Furthermore, the ADCs had very little effect on naive HEK293T cells that did not overexpress BMPR1B compared to the HEK293T cells overexpressing BMPR1B, demonstrating the specificity of the ADCs to the BMPR1B antigen (FIG. 15).

The above results demonstrate the ability of anti-BMPR1B ADCs to specifically mediate internalization and delivery of cytotoxic payloads to cells expressing BMPR1B.

Example 19

Anti-BMPR1B Antibody Drug Conjugates Suppress Tumor Growth In Vivo

Anti-BMPR1B ADCs, generated, for example, as described in Example 12 above, are tested using art-recognized techniques, essentially as described below, to demonstrate their ability to suppress human luminal B breast cancer (BR-LumB) tumor growth in immunodeficient mice.

PDX tumor lines (BR159, BR162 and BR164) expressing BMPR1B (e.g. BR-LumB PDX tumor lines) and control tumor lines which do not express BMPR1B are grown subcutaneously in the flanks of female NOD/SCID mice using art-recognized techniques. Tumor volumes and mouse weights are monitored once or twice per week. When tumor volumes reach 150-250 mm$^3$, mice are randomly assigned to treatment groups and injected intravenously with a single dose of 0.1 mg/kg hSC91.1v2ss1MJ PBD3 or 0.2 mg/kg hSC91.1v2ss1 PBD3 (FIGS. 16A and 16B) or a single dose of 0.2 mg/kg hSC91.1ss1MJ PBD3 or 0.2 mg/kg hSC91.9ss1MJ PBD3 (FIGS. 17A and 17B) along with a single dose of 0.2 mg/kg anti-hapten control human IgG ADC or vehicle control such as, for example, 0.9% saline. Following treatment, tumor volumes and mouse weights are monitored until tumors exceed 800 mm$^3$ or the mice become sick.

Figure 16A:
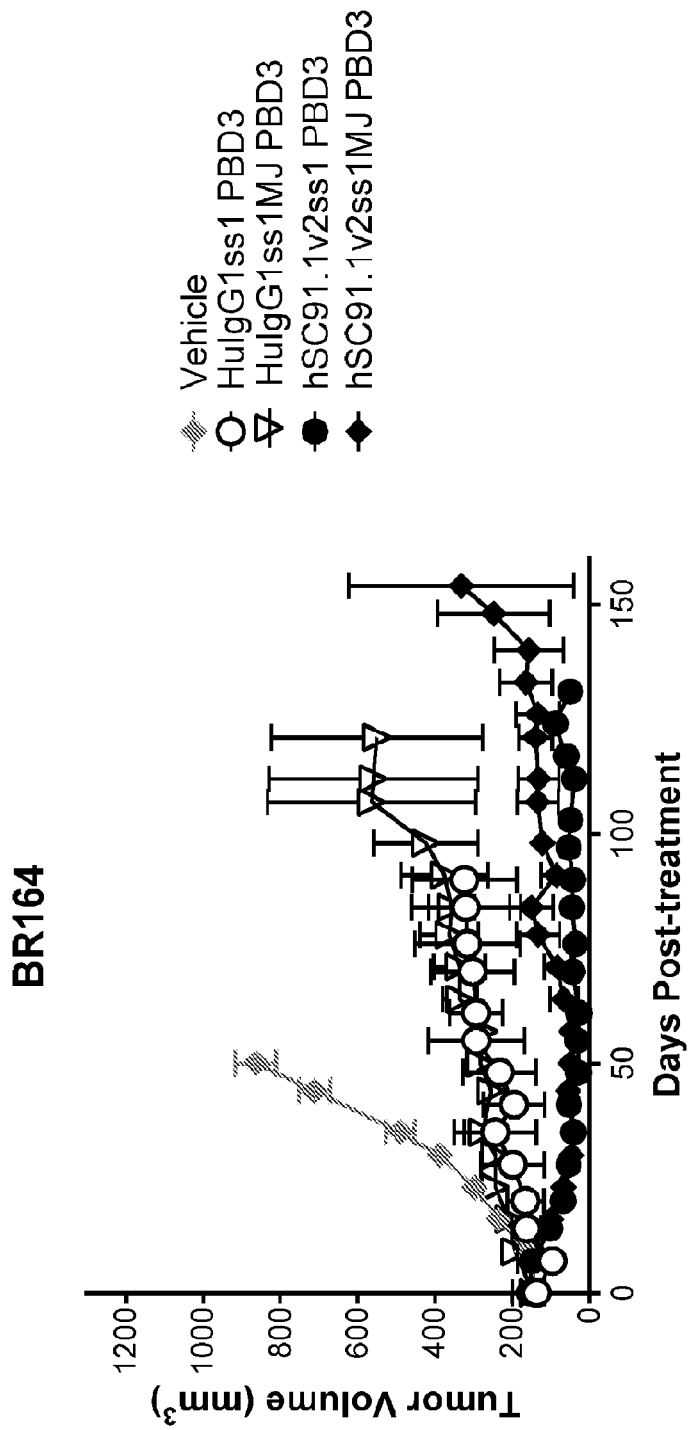
FIGS. 16A-16D demonstrate the capability of exemplary BMPR1B ADCs to suppress the growth of luminal B PDX tumors in vivo (FIGS. 16A and 16B) and to suppress the growth of peripheral (circulating tumor cells) and distant (lung metastasis) tumor burden in luminal B PDX tumors in vivo (FIGS. 16C and 16D respectively)
Figure 16B:
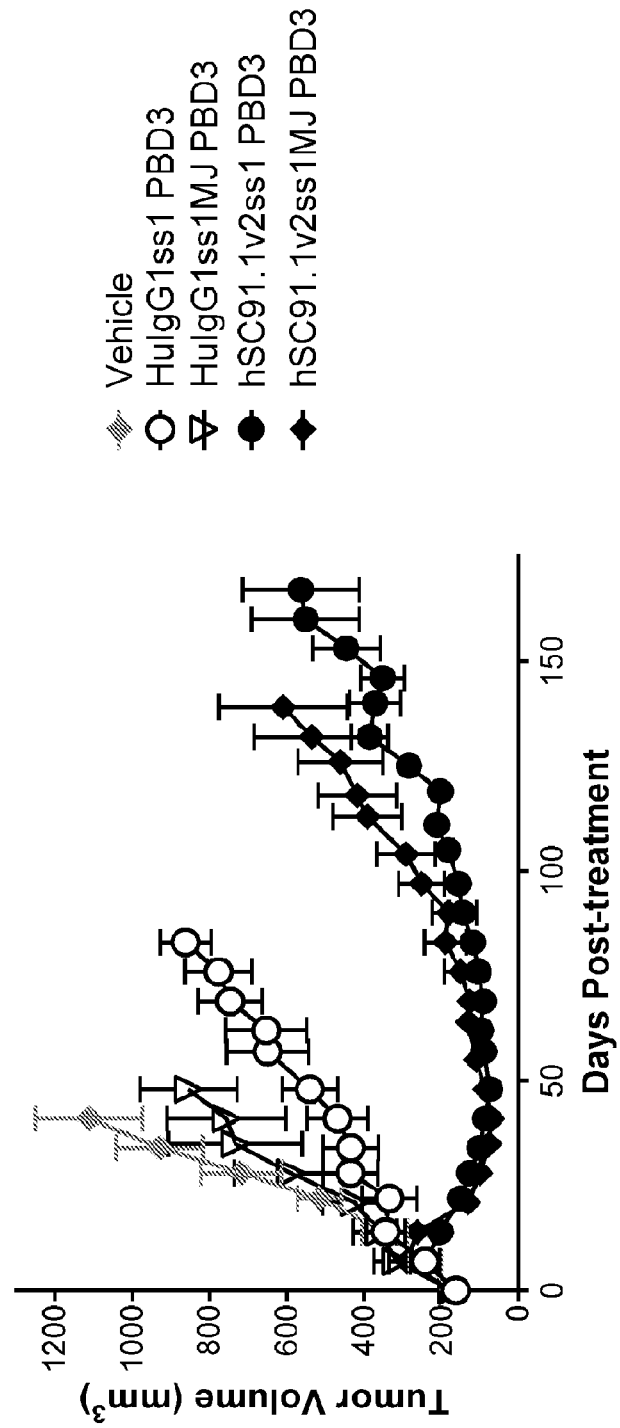
Figure 17A:
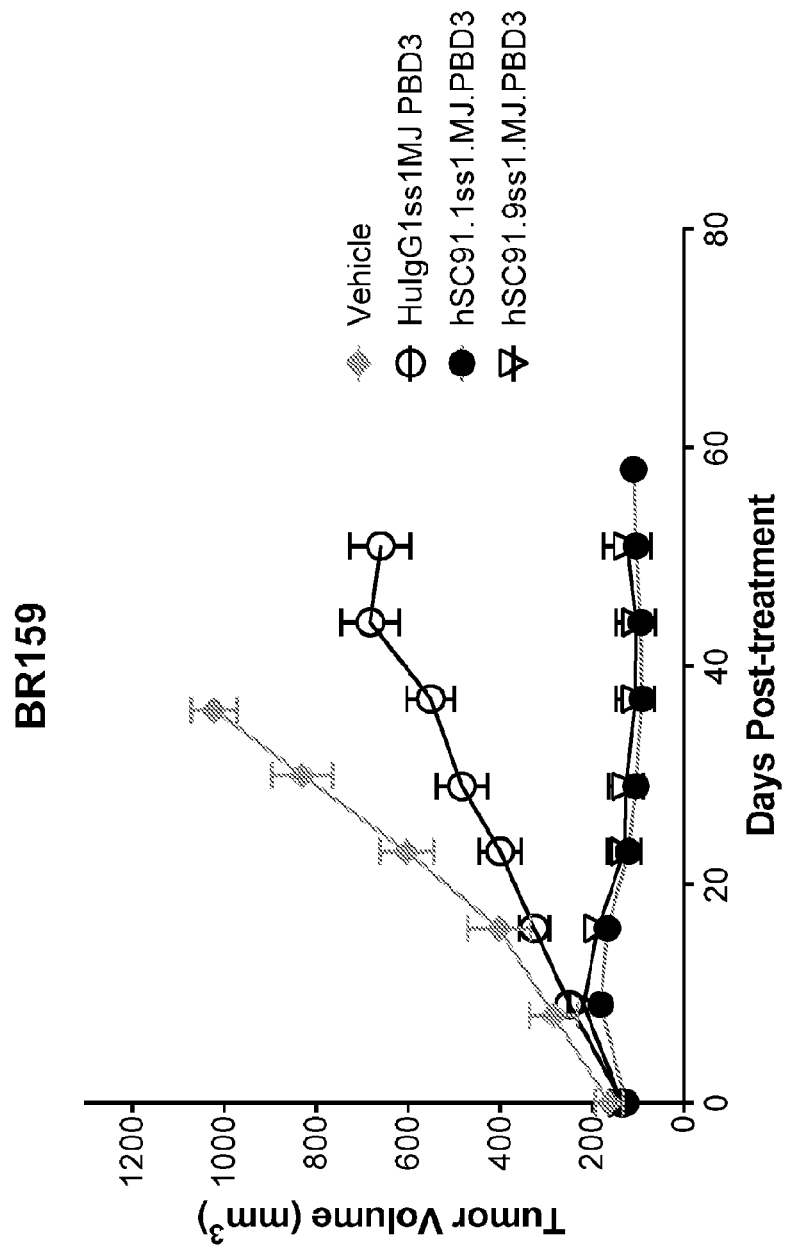
FIGS. 17A and 17B show that exemplary humanized BMPR1B ADCs effectively suppress luminal B tumor growth in vivo for the PDX cell lines BR159 (FIG. 17A) and BR162 (FIG. 17B)
Figure 17B:
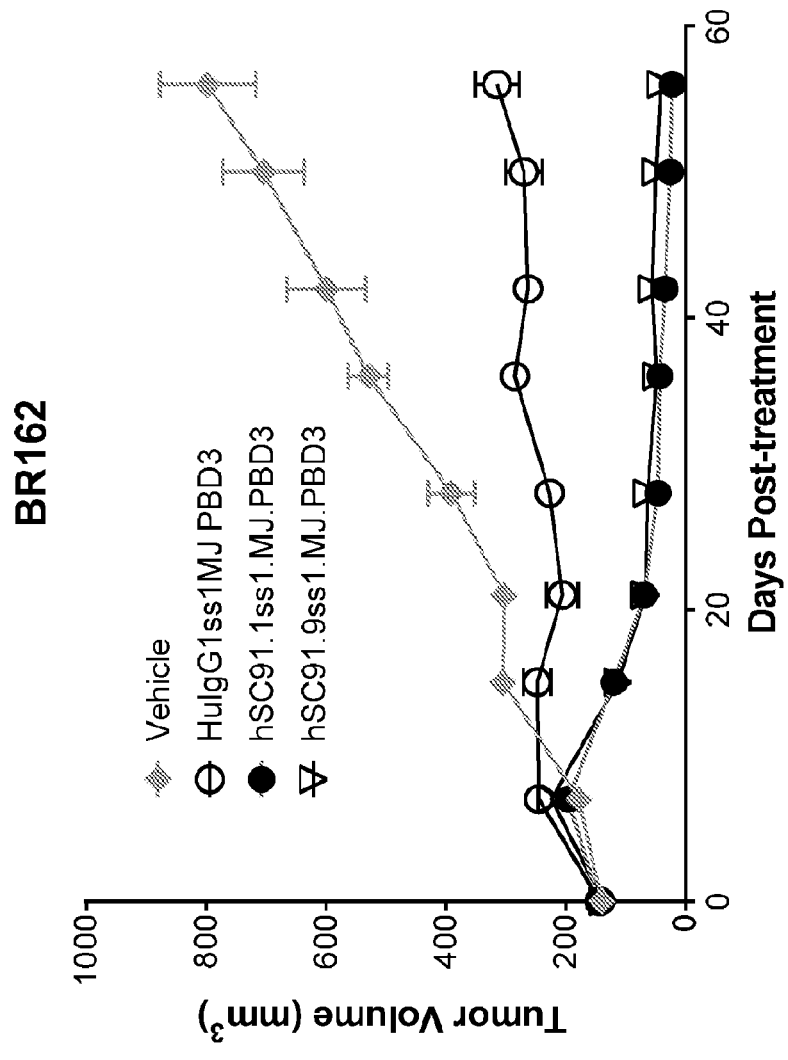

As shown in FIGS. 16A, 16B, 17A and 17B, the disclosed BMPR1B PBD3 ADCs substantially retard or suppress tumor growth in mice bearing luminal B breast tumors exhibiting BMPR1B expression. In this respect, treatment of BR164 with the exemplary BMPR1B ADCs hSC91.1v2ss1 PBD3 and hSC91.1v2ss1MJ PBD3, resulted in tumor shrinkage lasting 140 days (FIG. 16A). Similarly treatment of BR159, a different luminal B breast tumor, with exemplary antibodies hSC91.1v2ss1, hSC91.1v2ss1MJ, hSC91.1ss1MJ and hSC91.9ss1MJ, each conjugated to PBD3, resulted in tumor suppression lasting for extended periods. Both hSC91.1v2ss1 PBD3 and hSC91.1v2ss1MJ PBD3 provided responses on the order of a 100 days before tumor growth restarted (FIG. 16B). Similar results were observed when using hSC91.1ss1MJ PBD3 and hSC91.9ss1MJ PBD3 where tumor suppression on the order of at least 60 days were observed (FIG. 17A). In yet another example with a different luminal B breast tumor (BR162) both hSC91.1ss1MJ PBD3 and hSC91.9ss1MJ PBD3 produced lasting results on the order of at least 60 days with little to no tumor regrowth. Note that the studies shown in FIGS. 17A and 17B were ongoing at the time of filing.

Figures 16C, 16D:
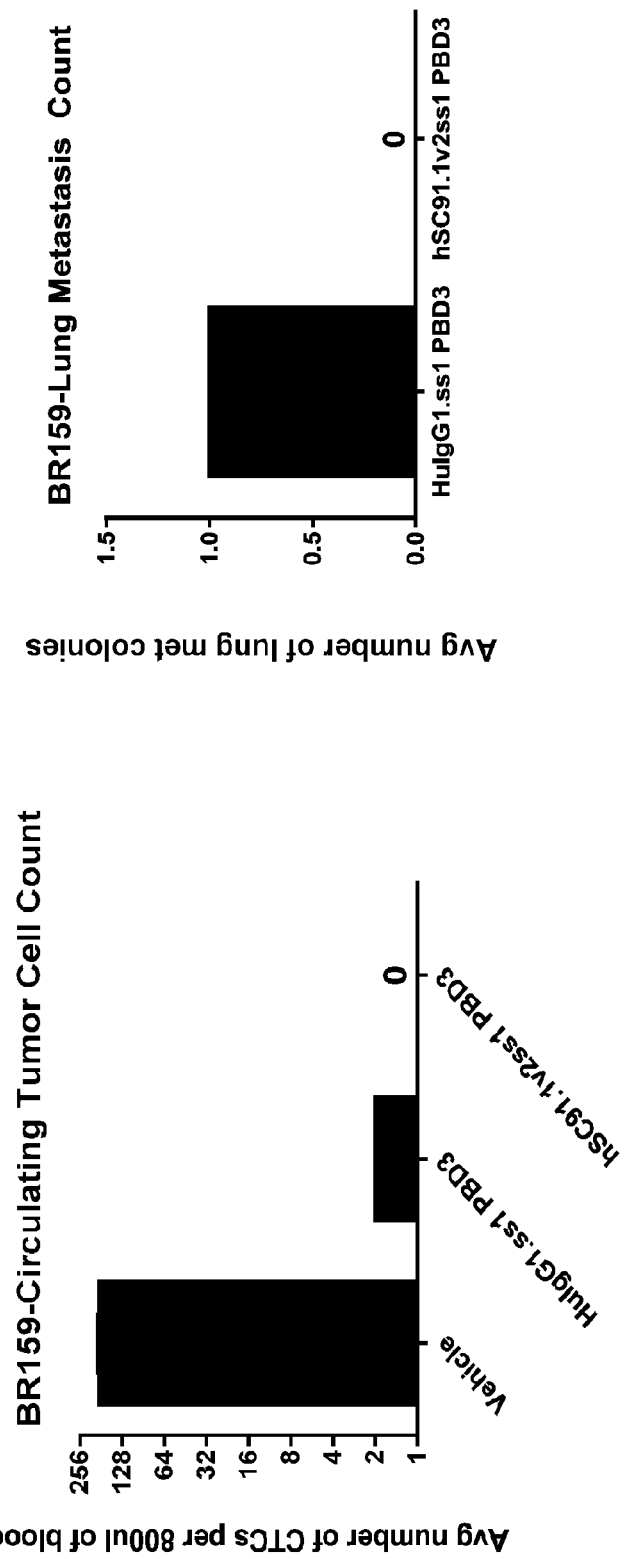

In addition to the suppression of primary tumor growth the exemplary ADC hSC91.1v2ss1 PBD3 demonstrated the ability to significantly deplete the peripheral tumor burden as early as one week after treatment (FIG. 16C). This reduction of the peripheral tumor burden is evidenced by a substantial decrease in the levels of circulating tumor cells (CTCs) in mouse blood obtained from the treated subjects in the above-referenced studies. Briefly blood was collected from the mice one week after treatment and interrogated for CTCs using the Cytefinder Instrument (Rarecyte, Inc) in accordance with the manufacturer's instructions. By way of contrast FIG. 16C shows that luminal B tumor bearing mice treated with vehicle control continued to exhibit relatively high levels of circulating tumor cells. These observations indicate that the disclosed ADCs may effectively be employed to reduce the chance of tumor recurrence or metastasis in addition to treating primary tumors.

The peripheral or distant tumor burden may also be gauged using lung metastasis in luminal B tumor bearing mice. At the same time the blood was collected from the mouse lung tissue was also obtained and stained using standard immunohistochemistry techniques. The lung tissue samples were then analyzed by trained pathologists to provide a count of lung met colonies per mouse. A review of the generated data showed that treatment with hSC91.1v2ss1 PBD3 resulted in the complete elimination of lung metastasis (at least to the extent observable in the study) whereas the human IgG ADC control treated luminal B tumors still had measurable lung metastasis (FIG. 16D). The data set forth in FIG. 16D, in addition to the data presented in FIGS. 16A-16C and FIGS. 17A and 17B, provides strong evidence that BMPR1B PBD ADCs significantly reduce primary and distant tumor burdens in luminal B tumor bearing mice.

Example 20

Reduction of Tumor Initiating Cell Frequency by Anti-BMPR1B Antibody-Drug Conjugates As demonstrated in the Examples above BMPR1B expression is associated with tumorigenicity and the disclosed BMPR1B ADCs effectively suppress or retard tumor growth. To show that treatment with anti-BMPR1B ADCs reduces the frequency of tumor initiating cells (TIC) that are known to be drug resistant and to fuel tumor recurrence and metastasis, in vivo limiting dilution assays (LDA) are performed essentially as described below.

PDX tumors (e.g. BR-LumB) are grown subcutaneously in immunodeficient mice. When tumor volumes average 150 mm$^3$-250 mm$^3$ in size, the mice are randomly segregated into two groups. One group was injected intraperitoneally with a human IgG1 control antibody conjugated to PBD3 as a negative control while the other group was injected intraperitoneally with the anti-BMPR1B ADC hSC91.1v2ss1 PBD3 (e.g., as prepared in Example 12). One week after dosing three representative mice from each group are euthanized and their tumors are harvested and dispersed to single-cell suspensions. The tumor cells from each treatment group are then harvested, pooled and disaggregated as previously described in Example 1. The cells are labeled with FITC conjugated anti-mouse H2kD and anti-mouse CD45 antibodies to detect mouse cells; EpCAM to detect human cells; and DAPI to detect dead cells. The resulting suspension is then sorted by FACS using a BD FACS Canto II flow cytometer and live human tumor cells are isolated and collected.

Four cohorts of mice are injected with either 875, 175, 35 or 7 sorted live, human cells from tumors treated with anti-BMPR1B ADC. As a negative control four cohorts of mice are transplanted with 625, 125, 25 or 5 sorted live, human cells from tumors that were untreated (Vehicle). Tumors in recipient mice are measured weekly, and individual mice are euthanized before tumors reach 1500 mm$^3$. Recipient mice are scored as having positive or negative tumor growth. Positive tumor growth is defined as growth of a tumor exceeding 100 mm$^3$. The results of these studies are presented in FIGS. 18A and 18B appended hereto.

Figure 18B:
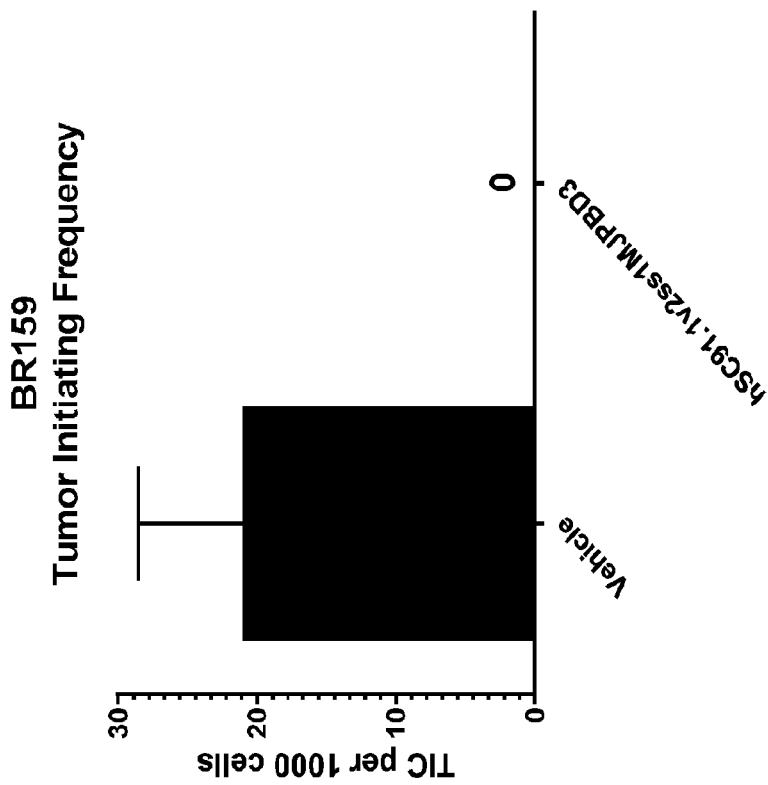
FIGS. 18A and 18B illustrate the ability of exemplary BMPR1B ADCs to reduce the frequency of tumor initiating cells by treating tumor bearing mice with the disclosed ADCs (FIG. 18A), subsequently implanting cells from the treated tumors (along with controls) in immunodeficient mice and measuring the frequency of tumor initiating cells in each subjective sample (FIG. 18B)
Figure 18A:
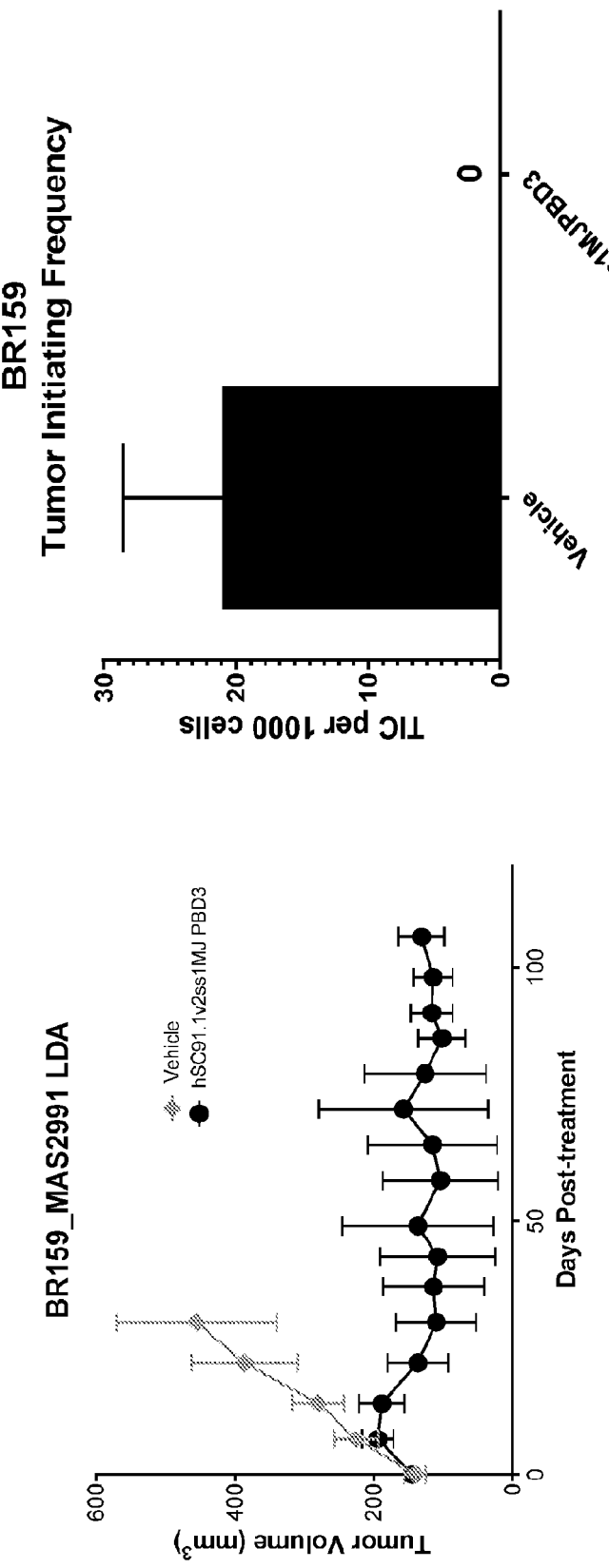

The data set forth in FIG. 18A shows that the tumor cells obtained from BMPR1B ADC treated luminal B PDX (BR159) tumor bearing mice fail to grow upon implantation. As detailed in FIG. 18A the implanted tumor cells actually had the same or less volume at 100 days than they had upon implantation. This indicates that the disclosed ADCs have the ability to suppress or eliminate tumorigenic cells (e.g., cancer stem cells) that have the capability to recapitulate and propagate the tumor. FIG. 18B supports this finding by showing that frequency of tumor initiating cells is essentially eliminated in mice treated with SC91.1ss1MJ PBD3 whereas the vehicle treated mice still show positive tumor growth. Those skilled in the art will appreciate that Poisson distribution statistics (L-Calc software, Stemcell Technologies) may be used to calculate the frequency of TICs in each population. Based on these calculations the disclosed BMPR1B ADCs reduce the frequency of tumor initiating cells beyond the limits of detection in this assay whereas the vehicle treated tumors still exhibit a cancer stem cell frequency on the order of 20 cells per 1000 tumor cells. It will be appreciated that the data shown in FIGS. 18A and 18B strongly support and confirm the results shown in FIGS. 16A-16D and 17A and 17B.

Example 21

Anti BMPR1B Antibodies Modulate Interactions Between BMPR1B and BMP2/4

As mentioned above, BMPR1B is also a receptor for BMP ligands, particularly BMP2 and BMP4. An ELISA assay using the Meso Scale Discovery (MSD) platform was performed to test the ability of the anti-BMPR1B antibodies generated in Example 6 to antagonize or agonize binding of BMPR1B (receptor) to BMP2 or BMP4 (ligand) (the "BMPR1B-BMP2/4 interaction"). In this respect, exemplary antibodies that modulate the BMPR1B-BMP2/4 interaction (e.g., functionally agonize or antagonize BMPR1B interactions with BMP2/4) are set forth in FIG. 19 appended hereto. A review of the data indicates that selected antibodies may inhibit or block the binding of the BMP2 or BMP4 ligand with its BMPR1B receptor.

More particularly the binding kinetics and affinities of human BMPR1B for human BMP2 and BMP4 were measured on a Biacore T200 instrument (GE Healthcare). In this regard BMP2 fused to a human Fc fragment was immobilized onto anti-human capture (AHC) chip and BMPR1B-his was injected at five different concentrations (2.5, 5, 10, 20, 40 µM) for kinetics parameter and equilibrium constant ($K_D$) determination. In another experiment, BMPR1B fused to human Fc fragment was immobilized onto anti-human capture (AHC) chip and BMP4-his was injected at five different concentrations (31.3, 62.5, 125, 250, 500 nM). In both cases sensograms were reference-subtracted and fit using a 1:1 binding model (data not shown). BMPR1B was found to bind BMP2 and BMP4 with $K_D$ values of 61 µM and 1.2 nM, respectively.

To determine the effects that exemplary antibodies of the instant invention may have on BMPR1B ligand binding MSD standard plates were coated with 30 µl of human BMPR1B at 100 ng/mL in PBS and incubated overnight at 4° C. After the plates were washed with PBS, 0.05% tween20 (PBST), they were blocked with 3% (w/v) BSA in PBS for 60 mins. at room temperature. The plates were washed in PBST and 25 µl of the selected murine BMPR1B antibody at 10 ug/mL in 1% (w/v) BSA in PBS+0.05% tween 20 (PBSA) was added to the plates and incubated for 60 mins. After washing with PBST, 25 uL of 10 ng/mL of BMP2 (R&D Systems, #355-BM-050) or BMP4 (R&D Systems, #314-BP-050) was added to the plates and incubated for 60 mins. During this incubation step, a goat anti human polyclonal anti-BMP2 detection antibody (R&D Systems, #AF355) and polyclonal anti-BMP4 detection antibody (R&D Systems, #AF757) was sulfo-tagged using an MSD® SULFO-TAG NHS Ester according to the manufacturer's protocol (Meso Scale Discovery, #R32AC-5). MSD SULFO-TAG NHS-Ester is an amine reactive, N-hydroxysuccinimide ester which readily couples to primary amine groups of proteins under mildly basic conditions to form a stable amide bond. After washing with PBST, 10 µL/well of sulfo tag-labeled goat anti-human polyclonal BMP2 or BMP4 antibody at 2 µg/ml in PBSTA was added for 1 hour at room temperature. Plates were washed in PBST and MSD Read Buffer T with surfactant was diluted to 1× in water and 150 µL was added to each well. Plates were read on an MSD Sector Imager 2400. Data was compared to control wells without anti-BMPR1B antibodies and the percent binding inhibition was calculated. The resulting inhibition data in shown in a tabular form in FIG. 19A.

A review of the data set forth in FIG. 19A shows that the tested antibodies tended to generally inhibit the binding of BMP4 more than the binding of BMP2 to BMPR1B. Moreover, while there is some variation in the percentage of binding inhibition, selected antibodies effectively blocked the binding of BMP4 and/or BMP2 (e.g., >50% in the case of BMP4 and >25% in the case of BMP2. That is, selected antibodies (including SC91.1 and SC91.9) were found to be antagonistic in that they inhibit the binding of the BMP2 and of BMP4 to the BMPR1B receptor.

Figures 19D, 19E:
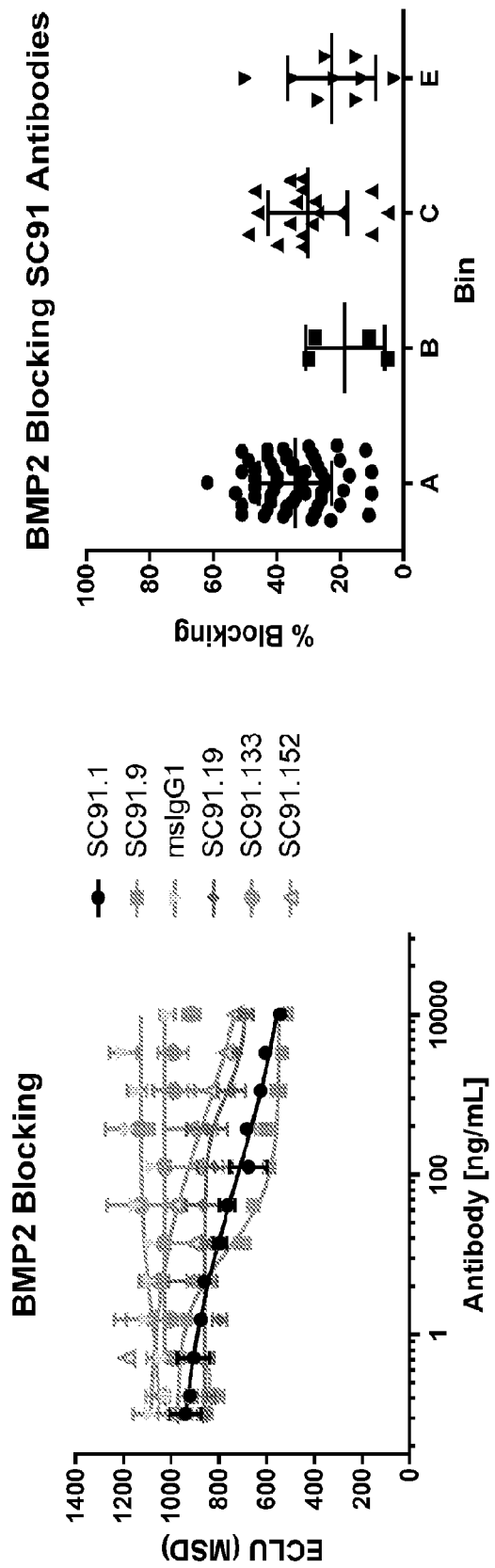

A second experiment was conducted essentially as set forth immediately above except that the concentration of the selected murine anti-BMPR1B antibodies was titrated to provide the ligand binding curves set forth in FIG. 19B (BMP4 blocking) and FIG. 19D (BMP2 blocking). As may be seen in FIGS. 19B and 19D these titration curves show that the exemplarly antibodies were generally more effective at blocking the binding of BMP4 than the blocking of BMP2 and that certain antibodies (e.g. SC91.1 and SC91.9) were particularly effective at blocking the binding of both ligands. Such findings are in accordance with the data set forth in FIG. 19A and confirm that antagonist anti-BMPR1B antibodies may be readily identified in view of the instant disclosure.

Finally, the ability of the disclosed antibodies to inhibit binding may be correlated with the bin in which the the antibody resides. More particularly FIGS. 19C and 19E plot the percent of binding inhibition (as set forth in FIG. 19A) exhibited by a selected antibody against the subject antibody bin determined as set forth in Example 7 above. The data set forth in FIG. 19C, directed to the inhibition of BMP4 binding, shows that the antibodies of bins A and C are likely to be particularly effective in blocking the binding of the ligand. Similarly, the data set forth in FIG. 19E, directed to the inhibition of BMP2 binding, shows that the antibodies in bins A and C tend to be more effective in blocking the binding of the ligand though not to the extent they block the binding of BMP4. Again, this data is consistent with the results shown in FIGS. 19A, 19B and 19D.

More surprisingly the data set forth in FIGS. 19A-19E also appears to correlate with the killing data generated and set forth in the Examples above. In this regard the ability of the antibodies in bins A and C to more effectively inhibit the binding of BMP4 and BMP2 strongly correlates with the ability of antibodies from the same bins to effectively kill cells as set forth in Example 7 above. This observation is easily substantiated by comparing FIGS. 19C and 19E (binding inhibition) with FIGS. 7C and 7D (cell killing) where the antibodies of bins A and C are generally more active than the antibodies of other bins.

Given the tumor suppression or elimination exhibited by such antagonistic antibodies (as evidenced by the Examples above) it may be that blocking BMPR1B ligand binding contributes to the observed activity of the disclosed compounds and enhances the potential therapeutic index of related compositions. Accoridngly, such antibodies or BMPR1B ADCs incorporating such antibodies may be particularly compatible for use in accordance with the teachings herein.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

The invention claimed is:

1. An isolated antibody that binds to BMPR1B and comprises:
   (a) a light chain variable region (VL) set forth as SEQ ID NO: 21 and a heavy chain variable region (VH) set forth as SEQ ID NO: 23; or
   (b) a VL set forth as SEQ ID NO: 41 and a VH set forth as SEQ ID NO: 43.

2. The isolated antibody of claim 1, wherein the antibody is conjugated to a payload.

3. A nucleic acid encoding all or part of the antibody of claim 1.

4. A vector comprising the nucleic acid of claim 3.

5. A host cell comprising the nucleic acid of claim 3.

6. The antibody of claim 1, wherein:
   (a) the antibody comprises residues 24-34 of SEQ ID NO: 21 for CDR-L1, residues 50-56 of SEQ ID NO: 21 for CDR-L2, residues 89-97 of SEQ ID NO: 21 for CDR-L3, residues 31-35 of SEQ ID NO: 23 for CDR-H1, residues 50-65 of SEQ ID NO: 23 for CDR-H2, and residues 95-102 of SEQ ID NO: 23 for CDR-H3, wherein the residues are numbered according to Kabat; or
   (b) the antibody comprises residues 24-34 of SEQ ID NO: 41 for CDR-L1, residues 50-56 of SEQ ID NO: 41 for CDR-L2, residues 89-97 of SEQ ID NO: 41 for CDR-L3, residues 31-35 of SEQ ID NO: 43 for CDR-H1, residues 50-65 of SEQ ID NO: 43 for CDR-H2, and residues 95-102 of SEQ ID NO: 43 for CDR-H3, wherein the residues are numbered according to Kabat.

7. The antibody of claim 1, wherein the antibody comprises a light chain variable region set forth as SEQ ID NO: 21 and a heavy chain variable region set forth as SEQ ID NO: 23.

8. The antibody of claim 1, wherein the antibody comprises a light chain variable region set forth as SEQ ID NO: 41 and a heavy chain variable region set forth as SEQ ID NO: 43.

9. The antibody of claim 1, wherein the antibody is a chimeric, CDR grafted, humanized, or human antibody, or an immunoreactive fragment thereof.

* * * * *